(12) United States Patent
Cho et al.

(10) Patent No.: US 6,538,126 B1
(45) Date of Patent: *Mar. 25, 2003

(54) HEPATITIS C DIAGNOSTICS AND VACCINES

(75) Inventors: Joong Myung Cho, Seoul (KR); Yong Beom Lee, Daejeon (KR); Young Woo Park, Deajeon (KR); Kook Jin Lim, Seoul (KR); Deog Young Choi, Daejeon (KR); Hong Seob So, Daejeon (KR); Chun Hyung Kim, Daejeon (KR); Sung Taek Kim, Daejeon (KR); Jae Young Yang, Daejeon (KR)

(73) Assignee: Lucky Limited (KR)

( * ) Notice: Subject to any disclaimer, the term of this patent is extended or adjusted under 35 U.S.C. 154(b) by 0 days.

This patent is subject to a terminal disclaimer.

(21) Appl. No.: 08/150,204

(22) PCT Filed: Jun. 8, 1992

(86) PCT No.: PCT/KR92/00022

§ 371 (c)(1),
(2), (4) Date: Apr. 20, 1994

(87) PCT Pub. No.: WO92/22655

PCT Pub. Date: Dec. 23, 1992

(30) Foreign Application Priority Data

Aug. 6, 1991 (KR) .............................................. 91-13601
Jun. 10, 1991 (KR) ................................................ 91-9510

(51) Int. Cl.$^7$ ........................... C07H 21/04; C12Q 1/70; C12Q 1/68; C12N 15/00

(52) U.S. Cl. ................................. 536/23.72; 536/24.32; 435/5; 435/6; 435/320.1; 435/326; 435/69.3; 435/69.7; 435/254.21; 435/252.33; 435/331; 435/339; 530/324; 530/388.3; 530/413; 530/826

(58) Field of Search .......................... 435/5, 7.1, 69.3, 435/91.1, 172.3, 240.27, 252.33, 255.1, 320.1, 6, 69.7, 331, 339; 436/501, 548; 536/23.1, 23.72; 930/223; 530/324, 325, 326, 388.1, 388.3, 387.1

(56) References Cited

U.S. PATENT DOCUMENTS 5,350,671 A * 9/1994 Houghton et al. .............. 435/5
5,372,928 A * 12/1994 Miyamura et al. ............. 435/5

FOREIGN PATENT DOCUMENTS

| EP | 318216 A1 | 5/1989 |
| EP | 388232 A1 | 9/1990 |
| EP | 0 419 182 A1 | 3/1991 |
| EP | 442394 A2 | 8/1991 |
| EP | 463848 A3 | 1/1992 |
| EP | 464287 A1 | 1/1992 |
| EP | 468657 | * 1/1992 |
| WO | WO92/03458 | 3/1992 |

OTHER PUBLICATIONS

Farci et al., Science, 258:135–140, Oct. 1992.*
Y.K. Shimizu et al., Proc. Natl. Acad. Sci. USA 87, 9524–9528 (1990).
N.Hayashi et al., Chemical Abstracts, vol. 116, No. 9, Abs. No. 77439W, 1991.
J.E. Chang et al., Chemical Abstracts, vol. 116, No. 21, Abs. No. 208921X 1991.
A. Takamizawa et al., J. of Virol. 65, 1105–1113 (1991).
Y.W. Lee, Biosis Previews, Biosis, Philadelphia, PA, USA, Abs. No. 94041213 1991.
H. Okamoto et al., Japan. J. Exp. Med. 60, 167–177 (1990).
Kato et al., "Molecular cloning of the human hepatitis C virsu genome from Japanese patients with non–A, non–B hepatitis", Proc. Natl. Acad. Sci 87, pp. 9524–9528 (Dec. 1990).*
Takamizawa et al., "Structure and Organization of the Hepatitis C Virus Genome Isolated from Human Carriers", J. Virol. 63 (3), pp. 1105–1113 (Mar. 1991).*
Schulz et al., Principles of Protein Structure, Springer–Verlag, New York, 1979, pp. 14–15.*
Enomoto et al., "There are Two Major Types of Hepatitis C Virus in Japan", Biochem. Biophys. Res. Commun. 170, 1021–1025 (1990).*
Takeuchi et al., "Hepatitus C viral cDNA clones isolated from a healthy carrier donor implicated in post–transfusion non–A, non–B hepatitis", Gene 9, 287–291 (1990).*
Reanney, The Evolution of RNA Viruses, Ann. Rev. Microbiol. 36, 47–73 (1982).*
Bukh et al., "Genetic Heterogeneityh of Hepatitis C Virus: Quasispecies and Genotypes", Semin. Liver Dis. 15, 41–63 (1995).*
Bachmair et al., "In Vitro Half–Life of a Protein Is a Function of Its Amino–Terminal Residue", Science 234, 178–186 (1986).*
Maina et al., "An Escherichia coli vector to express and purify fooreeign proteins by fusion to and separation from maltose–binding protein", Gene 74, 365–373 (1988).*
Lee, "Molecular Cloning of Korean Strains of Hepatitis C Virus", BIOSIS No. 94041213 (Nichidai Igaku Zasshi 51(3) 264–272 (1992).*

* cited by examiner

Primary Examiner—Anthony C. Caphta
Assistant Examiner—Brenda Brumback
(74) Attorney, Agent, or Firm—Rosenman & Colin LLP

(57) ABSTRACT

The present invention provides polynucleotides derived from cDNA of novel type of hepatitis C virus named Korean type hepatitis C virus (KHCV), polypeptides encoded therein, and antibodies directed against the polypeptides; and also provide diagnostics and vaccines employing any of the above materials as active ingredient(s).

36 Claims, 60 Drawing Sheets

```
           10         20         30         40         50         60
TGCCAGCCCCCGATTGGGGGCGACACTCCACCATAGATCACTCCCCTGTGAGGAACTACT
ACGGTCGGGGGCTAACCCCCGCTGTGAGGTGGTATCTAGTGAGGGGACACTCCTTGATGA 70         80         90        100        110        120
GTCTTCACGCAGAAAGCGTCTAGCCATGGCGTTAGTATGAGTGTCGTGCAGCCTCCAGGA
CAGAAGTGCGTCTTTCGCAGATCGGTACCGCAATCATACTCACAGCACGTCGGAGGTCCT 130        140        150        160        170        180
CCCCCCCTCCCGGGAGAGCCATAGTGGTCTGCGGAACCGGTGAGTACACCGGAATTGCCA
GGGGGGGAGGGCCCTCTCGGTATCACCAGACGCCTTGGCCACTCATGTGGCCTTAACGGT 190        200        210        220        230        240
GGACGACCGGGTCCTTTCTTGGATCAACCCGCTCAATGCCTGGAGATTTGGGCGTGCCCC
CCTGCTGGCCCAGGAAAGAACCTAGTTGGGCGAGTTACGGACCTCTAAACCCGCACGGGG 250        260        270        280        290        300
CGCGAGACTGCTAGCCGAGTAGTGTTGGGTCGCGAAAGGCCTTGTGGTACTGCCTGATAG
GCGCTCTGACGATCGGCTCATCACAACCCAGCGCTTTCCGGAACACCATGACGGACTATC 310        320        330        340        350        360
GGTGCTTGCGAGTGCCCCGGGAGGTCTCGTAGACCGTGCACCATGAGCACGAATCCTAAA
CCACGAACGCTCACGGGGCCCTCCAGAGCATCTGGCACGTGGTACTCGTGCTTAGGATTT
                                              M  S  T  N  P  K 370        380        390        400        410        420
CCTCAAAGAAAAACCAAACGTAACACCAACCGCCGCCCACAGGATATTAAGTTCCCGGGC
GGAGTTTCTTTTTGGTTTGCATTGTGGTTGGCGGCGGGTGTCCTATAATTCAAGGGCCCG
 P  Q  R  K  T  K  R  N  T  N  R  R  P  Q  D  I  K  F  P  G 430        440        450        460        470        480
GGTGGTCAGATCGTTGGTGGAGTTTACTTGTTGCCGCGCAGGGGCCCCAGGTTGGGTGTG
CCACCAGTCTAGCAACCACCTCAAATGAACAACGGCGCGTCCCCGGGGTCCAACCCACAC
 G  G  Q  I  V  G  G  V  Y  L  L  P  R  R  G  P  R  L  G  V 490        500        510        520        530        540
CGCGCGACTAGGAAGACTTCCGAGCGGTCGCAACCTCGTGGAAGGCGACAGCCTATCCCC
GCGCGCTGATCCTTCTGAAGGCTCGCCAGCGTTGGAGCACCTTCCGCTGTCGGATAGGGG
 R  A  T  R  K  T  S  E  R  S  Q  P  R  G  R  R  Q  P  I  P 550        560        570        580        590        600
AAGGCTCGCCGGCCCGAGGGCAGGGCCTGGGCTCAGCCCGGGTACCCTTGGCCCCTCTAT
TTCCGAGCGGCCGGGCTCCCGTCCCGGACCCGAGTCGGGCCCATGGGAACCGGGGAGATA
 K  A  R  R  P  E  G  R  A  W  A  Q  P  G  Y  P  W  P  L  Y
```

FIG. 2-1

```
         610       620       630       640       650       660
GGCAATGAGGGCTTGGGGTGGGCAGGATGGCTCCTGTCACCCCGCGGCTCCCGGCCTAGT
CCGTTACTCCCGAACCCCACCCGTCCTACCGAGGACAGTGGGGCGCCGAGGGCCGGATCA
  G  N  E  G  L  G  W  A  G  W  L  L  S  P  R  G  S  R  P  S 670       680       690       700       710       720
TGGGGCCCCACGGACCCCCGGCGTAAGTCGCGTAATTTGGGTAAGGTCATCGACACCCTC
ACCCCGGGGTGCCTGGGGGCCGCATTCAGCGCATTAAACCCATTCCAGTAGCTGTGGGAG
  W  G  P  T  D  P  R  R  K  S  R  N  L  G  K  V  I  D  T  L 730       740       750       760       770       780
ACATGCGGCTTCGCCGACCTCATGGGGTACATTCCGCTCGTCGGCGCCCCCCTAGGGGGC
TGTACGCCGAAGCGGCTGGAGTACCCCATGTAAGGCGAGCAGCCGCGGGGGGATCCCCCG
  T  C  G  F  A  D  L  M  G  Y  I  P  L  V  G  A  P  L  G  G 790       800       810       820       830       840
GTTGCCAGGGCCCTGGCACATGGTGTCCGGGTGCTGGAGGACGGCGTGAACTATGCAACA
CAACGGTCCCGGGACCGTGTACCACAGGCCCACGACCTCCTGCCGCACTTGATACGTTGT
  V  A  R  A  L  A  H  G  V  R  V  L  E  D  G  V  N  Y  A  T 850       860       870       880       890       900
GGGAATCTGCCCGGTTGCTCTTTCTCTATCTTCCTCTTGGCTCTGCTGTCTTGTTTGACC
CCCTTAGACGGGCCAACGAGAAAGAGATAGAAGGAGAACCGAGACGACAGAACAAACTGG
  G  N  L  P  G  C  S  F  S  I  F  L  L  A  L  L  S  C  L  T 910       920       930       940       950       960
ACCCCAGTTTCCGCTTATGAAGTGCGTAACGCGTCCGGGATGTACCATGTCACGAACGAC
TGGGGTCAAAGGCGAATACTTCACGCATTGCGCAGGCCCTACATGGTACAGTGCTTGCTG
  T  P  V  S  A  Y  E  V  R  N  A  S  G  M  Y  H  V  T  N  D 970       980       990      1000      1010      1020
TGCTCCAACTCAAGCATTGTGTATGAGGCAGCGGACATGATCATGCACACTCCCGGGTGC
ACGAGGTTGAGTTCGTAACACATACTCCGTCGCCTGTACTAGTACGTGTGAGGGCCCACG
  C  S  N  S  S  I  V  Y  E  A  A  D  M  I  M  H  T  P  G  C 1030      1040      1050      1060      1070      1080
GTGCCCTGCGTTCGGGAGGACAACTCCTCCCGTTGCTGGGTGGCACTTACTCCCACGCTC
CACGGGACGCAAGCCCTCCTGTTGAGGAGGGCAACGACCCACCGTGAATGAGGGTGCGAG
  V  P  C  V  R  E  D  N  S  S  R  C  W  V  A  L  T  P  T  L 1090      1100      1110      1120      1130      1140
GCGGCCAGGAATGCCAGCGTCCCCACTACGACATTGCGACGCCATGTCGACTTGCTCGTT
CGCCGGTCCTTACGGTCGCAGGGGTGATGCTGTAACGCTGCGGTACAGCTGAACGAGCAA
  A  A  R  N  A  S  V  P  T  T  T  L  R  R  H  V  D  L  L  V 1150      1160      1170      1180      1190      1200
GGGGTAGCTGCTTTCTGTTCCGCTATGTACGTGGGGGACCTCTGCGGATCTGTTTTCCTT
CCCCATCGACGAAAGACAAGGCGATACATGCACCCCCTGGAGACGCCTAGACAAAAGGAA
  G  V  A  A  F  C  S  A  M  Y  V  G  D  L  C  G  S  V  F  L
```

FIG. 2-2

```
        1210      1220      1230      1240      1250      1260
GTTTCCCAGCTGTTCACCTTTTCGCCTCGCCGGCATGAGACGGTACAGGACTGCAACTGC
CAAAGGGTCGACAAGTGGAAAAGCGGAGCGGCCGTACTCTGCCATGTCCTGACGTTGACG
 V  S  Q  L  F  T  F  S  P  R  R  H  E  T  V  Q  D  C  N  C 1270      1280      1290      1300      1310      1320
TCAATCTATCCCGGCCGCGTATCAGGTCACCGCATGGCCTGGGATATGATGATGAACTGG
AGTTAGATAGGGCCGGCGCATAGTCCAGTGGCGTACCGGACCCTATACTACTACTTGACC
 S  I  Y  P  G  R  V  S  G  H  R  M  A  W  D  M  M  M  N  W 1330      1340      1350      1360      1370      1380
TCGCCTACAACAGCCCTAGTGGTATCGCAGCTACTCCGGATCCCACAAGCTGTCGTGGAC
AGCGGATGTTGTCGGGATCACCATAGCGTCGATGAGGCCTAGGGTGTTCGACAGCACCTG
 S  P  T  T  A  L  V  V  S  Q  L  L  R  I  P  Q  A  V  V  D 1390      1400      1410      1420      1430      1440
ATGGTGACAGGGTCCCACTGGGGAATCCTGGCGGGCCTTGCCTACTATTCCATGGTGGGG
TACCACTGTCCCAGGGTGACCCCTTAGGACCGCCCGGAACGGATGATAAGGTACCACCCC
 M  V  T  G  S  H  W  G  I  L  A  G  L  A  Y  Y  S  M  V  G 1450      1460      1470      1480      1490      1500
AACTGGGCTAAGGTCTTAATTGCGATGCTACTCTTTGCCGGCGTTGACGGAACCACCCAC
TTGACCCGATTCCAGAATTAACGCTACGATGAGAAACGGCCGCAACTGCCTTGGTGGGTG
 N  W  A  K  V  L  I  A  M  L  L  F  A  G  V  D  G  T  T  H 1510      1520      1530      1540      1550      1560
GTGACAGGGGGGGCGCAAGGTCGGGCCGCTAGCTCGCTAACGTCCCTCTTTAGCCCTGGG
CACTGTCCCCCCCGCGTTCCAGCCCGGCGATCGAGCGATTGCAGGGAGAAATCGGGACCC
 V  T  G  G  A  Q  G  R  A  A  S  S  L  T  S  L  F  S  P  G 1570      1580      1590      1600      1610      1620
CCGGTTCAGCACCTCCAGCTCATAAACACCAACGGCAGCTGGCATATCAACAGGACCGCC
GGCCAAGTCGTGGAGGTCGAGTATTTGTGGTTGCCGTCGACCGTATAGTTGTCCTGGCGG
 P  V  Q  H  L  Q  L  I  N  T  N  G  S  W  H  I  N  R  T  A 1630      1640      1650      1660      1670      1680
CTGAGCTGCAATGACTCCCTCAACACTGGGTTTGTTGCCGCGCTGTTCTACAAATACAGG
GACTCGACGTTACTGAGGGAGTTGTGACCCAAACAACGGCGCGACAAGATGTTTATGTCC
 L  S  C  N  D  S  L  N  T  G  F  V  A  A  L  F  Y  K  Y  R 1690      1700      1710      1720      1730      1740
TTCAACGCGTCCGGGTGCCCGGAGCGCTTGGCCACGTGCCGCCCCATTGATACATTCGCG
AAGTTGCGCAGGCCCACGGGCCTCGCGAACCGGTGCACGGCGGGGTAACTATGTAAGCGC
 F  N  A  S  G  C  P  E  R  L  A  T  C  R  P  I  D  T  F  A 1750      1760      1770      1780      1790      1800
CAGGGGTGGGGTCCCATCACTTACACTGAGCCTCATGATTTGGATCAGAGGCCCTATTGC
GTCCCCACCCCAGGGTAGTGAATGTGACTCGGAGTACTAAACCTAGTCTCCGGGATAACG
 Q  G  W  G  P  I  T  Y  T  E  P  H  D  L  D  Q  R  P  Y  C
```

FIG. 2-3

```
         1810      1820      1830      1840      1850      1860
TGGCACTACGCGCCTCAACCGTGTGGTATTGTGCCCACGTTGCAGGTGTGTGGCCCAGTA
ACCGTGATGCGCGGAGTTGGCACACCATAACACGGGTGCAACGTCCACACACCGGGTCAT
 W  H  Y  A  P  Q  P  C  G  I  V  P  T  L  Q  V  C  G  P  V 1870      1880      1890      1900      1910      1920
TACTGCTTCACCCCGAGTCCTGTTGCGGTGGGGACTACCGATCGTTTCGGTGCCCCTACA
ATGACGAAGTGGGGCTCAGGACAACGCCACCCCTGATGGCTAGCAAAGCCACGGGGATGT
 Y  C  F  T  P  S  P  V  A  V  G  T  T  D  R  F  G  A  P  T 1930      1940      1950      1960      1970      1980
TACAGATGGGGGGCAAATGAGACGGACGTGCTGCTCCTTAACAACGCCGGGCCGCCGCAA
ATGTCTACCCCCCGTTTACTCTGCCTGCACGACGAGGAATTGTTGCGGCCCGGCGGCGTT
 Y  R  W  G  A  N  E  T  D  V  L  L  N  N  A  G  P  P  Q 1990      2000      2010      2020      2030      2040
GGCAACTGGTTCGGCTGTACATGGATGAATGGCACTGGGTTCACCAAGACATGTGGGGGC
CCGTTGACCAAGCCGACATGTACCTACTTACCGTGACCCAAGTGGTTCTGTACACCCCCG
 G  N  W  F  G  C  T  W  M  N  G  T  G  F  T  K  T  C  G  G 2050      2060      2070      2080      2090      2100
CCCCCGTGTAACATCGGGGGGGTCGGCAACAATACCTTGACCTGCCCCACGGACTGCTTC
GGGGGCACATTGTAGCCCCCCCAGCCGTTGTTATGGAACTGGACGGGGTGCCTGACGAAG
 P  P  C  N  I  G  G  V  G  N  N  T  L  T  C  P  T  D  C  F 2110      2120      2130      2140      2150      2160
CGAAAGCACCCCGGGGCCACTTACACCAAATGCGGTTCGGGGCCTTGGTTAACACCCAGG
GCTTTCGTGGGGCCCCGGTGAATGTGGTTTACGCCAAGCCCCGGAACCAATTGTGGGTCC
 R  K  H  P  G  A  T  Y  T  K  C  G  S  G  P  W  L  T  P  R 2170      2180      2190      2200      2210      2220
TGCTTAGTCGACTACCCGTACAGGCTCTGGCATTACCCCTGCACTGTCAACTTTACCATC
ACGAATCAGCTGATGGGCATGTCCGAGACCGTAATGGGGACGTGACAGTTGAAATGGTAG
 C  L  V  D  Y  P  Y  R  L  W  H  Y  P  C  T  V  N  F  T  I 2230      2240      2250      2260      2270      2280
TTTAAGGTTAGGATGTACGTGGGGGGCGCGGAGCACAGGCTCGACGCCGCATGCAACTGG
AAATTCCAATCCTACATGCACCCCCCGCGCCTCGTGTCCGAGCTGCGGCGTACGTTGACC
 F  K  V  R  M  Y  V  G  G  A  E  H  R  L  D  A  A  C  N  W 2290      2300      2310      2320      2330      2340
ACTCGGGGAGAGCGTTGTGACCTGGAGGACAGGGATAGGTCAGAGCTTAGCCCGCTGCTG
TGAGCCCCTCTCGCAACACTGGACCTCCTGTCCCTATCCAGTCTCGAATCGGGCGACGAC
 T  R  G  E  R  C  D  L  E  D  R  D  R  S  E  L  S  P  L  L 2350      2360      2370      2380      2390      2400
CTGTCTACAACAGAGTGGCAGGTACTGCCCTGTTCCTTCACAACCCTACCGGCTCTGTCC
GACAGATGTTGTCTCACCGTCCATGACGGGACAAGGAAGTGTTGGGATGGCCGAGACAGG
 L  S  T  T  E  W  Q  V  L  P  C  S  F  T  T  L  P  A  L  S
```

FIG. 2-4

```
      2410       2420       2430       2440       2450       2460
ACTGGTTTGATTCATCTCCATCAGAACATCGTGGACATACAATACCTGTACGGTATAGGG
TGACCAAACTAAGTAGAGGTAGTCTTGTAGCACCTGTATGTTATGGACATGCCATATCCC
 T  G  L  I  H  L  H  Q  N  I  V  D  I  Q  Y  L  Y  G  I  G 2470       2480       2490       2500       2510       2520
TCGGCGGTTGTCTCCTTTGCGATCAAATGGGAGTATATTGTGCTGCTCTTCCTTCTTCTG
AGCCGCCAACAGAGGAAACGCTAGTTTACCCTCATATAACACGACGAGAAGGAAGAAGAC
 S  A  V  V  S  F  A  I  K  W  E  Y  I  V  L  L  F  L  L  L 2530       2540       2550       2560       2570       2580
GCGGACGCGCGCGTCTGCGCTTGCTTGTGGATGATGCTGCTGGTAGCGCAAGCCGAGGCC
CGCCTGCGCGCGCAGACGCGAACGAACACCTACTACGACGACCATCGCGTTCGGCTCCGG
 A  D  A  R  V  C  A  C  L  W  M  M  L  L  V  A  Q  A  E  A 2590       2600       2610       2620       2630       2640
GCCTTAGAGAACCTGGTGGTCCTCAATGCAGCGTCCGTGGCCGGAGCGCATGGCATTCTT
CGGAATCTCTTGGACCACCAGGAGTTACGTCGCAGGCACCGGCCTCGCGTACCGTAAGAA
 A  L  E  N  L  V  V  L  N  A  A  S  V  A  G  A  H  G  I  L 2650       2660       2670       2680       2690       2700
TCCTTCATTGTGTTCTTCTGTGCTGCCTGGTACATCAAGGGCAGGCTGGTTCCCGGAGCG
AGGAAGTAACACAAGAAGACACGACGGACCATGTAGTTCCCGTCCGACCAAGGGCCTCGC
 S  F  I  V  F  F  C  A  A  W  Y  I  K  G  R  L  V  P  G  A 2710       2720       2730       2740       2750       2760
GCATACGCCCTCTATGGCGTATGGCCGCTGCTTCTGCTTCTGCTGGCGTTACCACCACGG
CGTATGCGGGAGATACCGCATACCGGCGACGAAGACGAAGACGACCGCAATGGTGGTGCC
 A  Y  A  L  Y  G  V  W  P  L  L  L  L  L  L  A  L  P  P  R 2770       2780       2790       2800       2810       2820
GCGTACGCCATGGACCGGGAGATGGCCGCATCGTGCGGAGGCGCGGTTTTTGTAGGTCTG
CGCATGCGGTACCTGGCCCTCTACCGGCGTAGCACGCCTCCGCGCCAAAAACATCCAGAC
 A  Y  A  M  D  R  E  M  A  A  S  C  G  G  A  V  F  V  G  L 2830       2840       2850       2860       2870       2880
GTACTCTTGACCTTGTCACCACACTATAAAGTGTTCCTTGCCAGGTTCATATGGTGGCTA
CATGAGAACTGGAACAGTGGTGTGATATTTCACAAGGAACGGTCCAAGTATACCACCGAT
 V  L  L  T  L  S  P  H  Y  K  V  F  L  A  R  F  I  W  W  L 2890       2900       2910       2920       2930       2940
CAATATCTCATCACCAGAACCGAAGCGCATCTGCAAGTGTGGGTCCCCCCTCTCAACGTT
GTTATAGAGTAGTGGTCTTGGCTTCGCGTAGACGTTCACACCCAGGGGGGAGAGTTGCAA
 Q  Y  L  I  T  R  T  E  A  H  L  Q  V  W  V  P  P  L  N  V 2950       2960       2970       2980       2990       3000
CGGGGGGGTCGCGATGCCATCATCCTCCTCACATGCGTGGTCCACCCAGAGCTAATCTTT
GCCCCCCCAGCGCTACGGTAGTAGGAGGAGTGTACGCACCAGGTGGGTCTCGATTAGAAA
 R  G  G  R  D  A  I  I  L  L  T  C  V  V  H  P  E  L  I  F
```

FIG. 2-5

```
      3010      3020      3030      3040      3050      3060
GACATCACAAAATATTTGCTCGCCATATTCGGCCCGCTCATGGTGCTCCAGGCCGGCATA
CTGTAGTGTTTTATAAACGAGCGGTATAAGCCGGGCGAGTACCACGAGGTCCGGCCGTAT
 D  I  T  K  Y  L  L  A  I  F  G  P  L  M  V  L  Q  A  G  I 3070      3080      3090      3100      3110      3120
ACTAGAGTGCCGTACTTCGTGCGCGCACAAGGGCTCATTCGTGCATGCATGTTGGCGCGG
TGATCTCACGGCATGAAGCACGCGCGTGTTCCCGAGTAAGCACGTACGTACAACCGCGCC
 T  R  V  P  Y  F  V  R  A  Q  G  L  I  R  A  C  M  L  A  R 3130      3140      3150      3160      3170      3180
AAAGTCGTGGGGGGTCATTACGTCCAAATGGTCTTCATGAAGCTGGCCGCACTAGCAGGT
TTTCAGCACCCCCCAGTAATGCAGGTTTACCAGAAGTACTTCGACCGGCGTGATCGTCCA
 K  V  V  G  G  H  Y  V  Q  M  V  F  M  K  L  A  A  L  A  G 3190      3200      3210      3220      3230      3240
ACGTACGTTTATGACCATCTTACTCCACTGCGAGATTGGGCTCACACGGGCTTACGAGAC
TGCATGCAAATACTGGTAGAATGAGGTGACGCTCTAACCCGAGTGTGCCCGAATGCTCTG
 T  Y  V  Y  D  H  L  T  P  L  R  D  W  A  H  T  G  L  R  D 3250      3260      3270      3280      3290      3300
CTTGCAGTGGCAGTAGAGCCCGTTGTCTTCTCTGACATGGAGACCAAAGTCATCACCTGG
GAACGTCACCGTCATCTCGGGCAACAGAAGAGACTGTACCTCTGGTTTCAGTAGTGGACC
 L  A  V  A  E  P  V  V  F  S  D  M  E  T  K  V  I  T  W 3310      3320      3330      3340      3350      3360
GGGGCAGACACCGCGGCGTGCGGGGACATCATCTTGGCCCTGCCTGCTTCCGCCCGAAGG
CCCCGTCTGTGGCGCCGCACGCCCCTGTAGTAGAACCGGGACGGACGAAGGCGGGCTTCC
 G  A  D  T  A  A  C  G  D  I  I  L  A  L  P  A  S  A  R  R 3370      3380      3390      3400      3410      3420
GGGAAGGAGATACTTCTGGGACCGGCCGATAGTCTTGAAGGACAGGGGTGGCGACTCCTT
CCCTTCCTCTATGAAGACCCTGGCCGGCTATCAGAACTTCCTGTCCCCACCGCTGAGGAA
 G  K  E  I  L  L  G  P  A  D  S  L  E  G  Q  G  W  R  L  L 3430      3440      3450      3460      3470      3480
GCGCCCATCACGGCCTACTCCCAACAAACGCGAGGCCTGCTTGGTTGCATCATCACTAGC
CGCGGGTAGTGCCGGATGAGGGTTGTTTGCGCTCCGGACGAACCAACGTAGTAGTGATCG
 A  P  I  T  A  Y  S  Q  Q  T  R  G  L  L  G  C  I  I  T  S 3490      3500      3510      3520      3530      3540
CTTACAGGCCGGGACAAGAACCAGGTTGAGGGGGAGGTTCAAGTGGTTTCCACCGCAACA
GAATGTCCGGCCCTGTTCTTGGTCCAACTCCCCCTCCAAGTTCACCAAAGGTGGCGTTGT
 L  T  G  R  D  K  N  Q  V  E  G  E  V  Q  V  V  S  T  A  T 3550      3560      3570      3580      3590      3600
CAATCTTTCCTGGCGACCTGCATCAATGGCGTGTGTTGGACTGTCTTCCACGGCGCCGGC
GTTAGAAAGGACCGCTGGACGTAGTTACCGCACACAACCTGACAGAAGGTGCCGCGGCCG
 Q  S  F  L  A  T  C  I  N  G  V  C  W  T  V  F  H  G  A  G
```

FIG. 2-6

```
       3610      3620      3630      3640      3650      3660
TCAAAGACCCTAGCCGGCCCAAAGGGTCCAATCACCCAAATGTACACCAATGTAGACCAG
AGTTTCTGGGATCGGCCGGGTTTCCCAGGTTAGTGGGTTTACATGTGGTTACATCTGGTC
 S   K   T   L   A   G   P   K   G   P   I   T   Q   M   Y   T   N   V   D   Q 3670      3680      3690      3700      3710      3720
GACCTTGTTGGCTGGCCGGCACCTCCTGGGGCGCGTTCCCTGACACCATGCACTTGCGGC
CTGGAACAACCGACCGGCCGTGGAGGACCCCGCGCAAGGGACTGTGGTACGTGAACGCCG
 D   L   V   G   W   P   A   P   P   G   A   R   S   L   T   P   C   T   C   G 3730      3740      3750      3760      3770      3780
TCCTCGGACCTTTACCTGGTCACGAGACATGCTGATGTCATTCCGGTGCGCCGGCGGGGT
AGGAGCCTGGAAATGGACCAGTGCTCTGTACGACTACAGTAAGGCCACGCGGCCGCCCCA
 S   S   D   L   Y   L   V   T   R   H   A   D   V   I   P   V   R   R   R   G 3790      3800      3810      3820      3830      3840
GACGGTAGGGGGAGCCTACTCCCCCCCAGGCCTGTCTCCTACTTGAAGGGCTCCTCGGGT
CTGCCATCCCCCTCGGATGAGGGGGGGTCCGGACAGAGGATGAACTTCCCGAGGAGCCCA
 D   G   R   G   S   L   L   P   P   R   P   V   S   Y   L   K   G   S   S   G 3850      3860      3870      3880      3890      3900
GGTCCACTGCTCTGCCCTTCGGGGCACGCTGTCGGCATACTTCCGGCTGCTGTATGCACC
CCAGGTGACGAGACGGGAAGCCCCGTGCGACAGCCGTATGAAGGCCGACGACATACGTGG
 G   P   L   L   C   P   S   G   H   A   V   G   I   L   P   A   A   V   C   T 3910      3920      3930      3940      3950      3960
CGGGGGGTTGCCATGGCGGTGGAATTCATACCCGTTGAGTCTATGGAAACTACTATGCGG
GCCCCCCAACGGTACCGCCACCTTAAGTATGGGCAACTCAGATACCTTTGATGATACGCC
 R   G   V   A   M   A   V   E   F   I   P   V   E   S   M   E   T   T   M   R 3970      3980      3990      4000      4010      4020
TCTCCGGTCTTCACGGACAATCCGTCTCCCCCGGCTGTACCGCAGACATTCCAAGTGGCC
AGAGGCCAGAAGTGCCTGTTAGGCAGAGGGGGCCGACATGGCGTCTGTAAGGTTCACCGG
 S   P   V   F   T   D   N   P   S   P   P   A   V   P   Q   T   F   Q   V   A 4030      4040      4050      4060      4070      4080
CACTTACACGCTCCCACCGGCAGCGGCAAGAGCACTAGGGTGCCGGCTGCATATGCAGCC
GTGAATGTGCGAGGGTGGCCGTCGCCGTTCTCGTGATCCCACGGCCGACGTATACGTCGG
 H   L   H   A   P   T   G   S   G   K   S   T   R   V   P   A   A   Y   A   A 4090      4100      4110      4120      4130      4140
CAAGGGTACAAGGTGCTCGTCCTAAATCCGTCCGTCGCCGCCACCTTGGGTTTTGGGGCG
GTTCCCATGTTCCACGAGCAGGATTTAGGCAGGCAGCGGCGGTGGAACCCAAAACCCCGC
 Q   G   Y   K   V   L   V   L   N   P   S   V   A   A   T   L   G   F   G   A 4150      4160      4170      4180      4190      4200
TATATGTCCAAGGCACATGGTATCGACCCCAACCTTAGAACTGGGGTAAGGACCATCACC
ATATACAGGTTCCGTGTACCATAGCTGGGGTTGGAATCTTGACCCCATTCCTGGTAGTGG
 Y   M   S   K   A   H   G   I   D   P   N   L   R   T   G   V   R   T   I   T
```

FIG. 2-7

```
       4210      4220      4230      4240      4250      4260
ACAGGTGCCCCTATCACATACTCCACCTATGGCAAGTTCCTTGCCGACGGTGGCGGCTCC
TGTCCACGGGGATAGTGTATGAGGTGGATACCGTTCAAGGAACGGCTGCCACCGCCGAGG
 T  G  A  P  I  T  Y  S  T  Y  G  K  F  L  A  D  G  G  S 4270      4280      4290      4300      4310      4320
GGGGGCGCCTATGACATCATAATGTGTGATGAGTGCCACTCAACTGACTCGACTACCATT
CCCCCGCGGATACTGTAGTATTACACACTACTCACGGTGAGTTGACTGAGCTGATGGTAA
 G  G  A  Y  D  I  I  M  C  D  E  C  H  S  T  D  S  T  T  I 4330      4340      4350      4360      4370      4380
TATGGCATCGGCACAGTCCTGGACCAAGCGGAGACGGCTGGAGCGCGGCTCGTGGTGCTC
ATACCGTAGCCGTGTCAGGACCTGGTTCGCCTCTGCCGACCTCGCGCCGAGCACCACGAG
 Y  G  I  G  T  V  L  D  Q  A  E  T  A  G  A  R  L  V  V  L 4390      4400      4410      4420      4430      4440
TCCACCGCTACGCCTCCGGGATCGGTCACCGTGCCACACCTCAATATCGAGGAGGTGGCC
AGGTGGCGATGCGGAGGCCCTAGCCAGTGGCACGGTGTGGAGTTATAGCTCCTCCACCGG
 S  T  A  T  P  P  G  S  V  T  V  P  H  L  N  I  E  E  V  A 4450      4460      4470      4480      4490      4500
CTGTCTAATACTGGAGAGATCCCCTTCTACGGCAAAGCCATTCCCATCGAGGCTATCAAG
GACAGATTATGACCTCTCTAGGGGAAGATGCCGTTTCGGTAAGGGTAGCTCCGATAGTTC
 L  S  N  T  G  E  I  P  F  Y  G  K  A  I  P  I  E  A  I  K 4510      4520      4530      4540      4550      4560
GGGGGAAGGCATCTCATTTTCTGCCATTCCAAGAAGAAGTGTGACGAACTCGCCGCAAAG
CCCCCTTCCGTAGAGTAAAAGACGGTAAGGTTCTTCTTCACACTGCTTGAGCGGCGTTTC
 G  G  R  H  L  I  F  C  H  S  K  K  K  C  D  E  L  A  A  K 4570      4580      4590      4600      4610      4620
CTGTCAGGCCTCGGACTCAATGCCGTAGCGTATTACCGGGGTCTTGACGTGTCCGTCATA
GACAGTCCGGAGCCTGAGTTACGGCATCGCATAATGGCCCCAGAACTGCACAGGCAGTAT
 L  S  G  L  G  L  N  A  V  A  Y  Y  R  G  L  D  V  S  V  I 4630      4640      4650      4660      4670      4680
CCGACCAGCGGAGACGTTGTTGTCGTGGCGACGGACGCTCTAATGACGGGCTTTACCGGC
GGCTGGTCGCCTCTGCAACAACAGCACCGCTGCCTGCGAGATTACTGCCCGAAATGGCCG
 P  T  S  G  D  V  V  V  V  A  T  D  A  L  M  T  G  F  T  G 4690      4700      4710      4720      4730      4740
GACTTTGACTCAGTGATCGACTGTAATACGTGTGTCACCCAGACAGTCGATTTCAGCTTG
CTGAAACTGAGTCACTAGCTGACATTATGCACACAGTGGGTCTGTCAGCTAAAGTCGAAC
 D  F  D  S  V  I  D  C  N  T  C  V  T  Q  T  V  D  F  S  L 4750      4760      4770      4780      4790      4800
GACCCCACCTTCACCATTGAGACGACGACCGTGCCCCAAGACGCAGTGTCGCGCTCGCAG
CTGGGGTGGAAGTGGTAACTCTGCTGCTGGCACGGGGTTCTGCGTCACAGCGCGAGCGTC
 D  P  T  F  T  I  E  T  T  T  V  P  Q  D  A  V  S  R  S  Q
```

FIG. 2-8

```
      4810       4820       4830       4840       4850       4860
AGGCGAGGCAGGACTGGTAGGGGCAGGGCTGGCATATACAGGTTTGTGACTCCAGGAGAA
TCCGCTCCGTCCTGACCATCCCCGTCCCGACCGTATATGTCCAAACACTGAGGTCCTCTT
  R  R  G  R  T  G  R  G  R  A  G  I  Y  R  F  V  T  P  G  E 4870       4880       4890       4900       4910       4920
CGGCCCTCGGGCATGTTCGATTCTTCGGTCCTGTGTGAGTGTTATGACGCGGGTTGTGCG
GCCGGGAGCCCGTACAAGCTAAGAAGCCAGGACACACTCACAATACTGCGCCCAACACGC
  R  P  S  G  M  F  D  S  S  V  L  C  E  C  Y  D  A  G  C  A 4930       4940       4950       4960       4970       4980
TGGTACGAACTCACGCCCGCTGAGACCTCGGTTAGGTTGCGGGCGTACCTAAACACACCA
ACCATGCTTGAGTGCGGGCGACTCTGGAGCCAATCCAACGCCCGCATGGATTTGTGTGGT
  W  Y  E  L  T  P  A  E  T  S  V  R  L  R  A  Y  L  N  T  P 4990       5000       5010       5020       5030       5040
GGGTTGCCCGTCTGCCAGGACCATCTGGAGTTCTCGGAGGGTGTCTTCACAGGCCTCACC
CCCAACGGGCAGACGGTCCTGGTAGACCTCAAGAGCCTCCCACAGAAGTGTCCGGAGTGG
  G  L  P  V  C  Q  D  H  L  E  F  S  E  G  V  F  T  G  L  T 5050       5060       5070       5080       5090       5100
CACATAGATGCCCACTTCTTATCCCAGACTAAACAGGCAGGAGAGAACTTCCCCTACTTG
GTGTATCTACGGGTGAAGAATAGGGTCTGATTTGTCCGTCCTCTCTTGAAGGGGATGAAC
  H  I  D  A  H  F  L  S  Q  T  K  Q  A  G  E  N  F  P  Y  L 5110       5120       5130       5140       5150       5160
GTAGCATACCAGGCTACAGTGTGCGCCAGGGCTCAAGCCCCACCTCCATCGTGGGATGAA
CATCGTATGGTCCGATGTCACACGCGGTCCCGAGTTCGGGGTGGAGGTAGCACCCTACTT
  V  A  Y  Q  A  T  V  C  A  R  A  Q  A  P  P  S  W  D  E 5170       5180       5190       5200       5210       5220
ATGTGGAGGTGTCTCATACGGCTGAAACCTACGCTGCACGGGCCAACACCCCTGCTGTAT
TACACCTCCACAGAGTATGCCGACTTTGGATGCGACGTGCCCGGTTGTGGGGACGACATA
  M  W  R  C  L  I  R  L  K  P  T  L  H  G  P  T  P  L  L  Y 5230       5240       5250       5260       5270       5280
AGGTTAGGAGCCGTCCAAAATGAGGTCACCCTCACACACCCCATAACCAAATTCATCATG
TCCAATCCTCGGCAGGTTTTACTCCAGTGGGAGTGTGTGGGGTATTGGTTTAAGTAGTAC
  R  L  G  A  V  Q  N  E  V  T  L  T  H  P  I  T  K  F  I  M 5290       5300       5310       5320       5330       5340
ACATGTATGTCGGCTGACCTGGAGGTCGTCACCAGCACCTGGGTGCTGGTAGGCGGAGTC
TGTACATACAGCCGACTGGACCTCCAGCAGTGGTCGTGGACCCACGACCATCCGCCTCAG
  T  C  M  S  A  D  L  E  V  V  T  S  T  W  V  L  V  G  G  V 5350       5360       5370       5380       5390       5400
CTCGCAGCTCTGGCCGCGTACTGCCTGACAACAGGCAGCGTGGTCATTGTGGGCAGGATC
GAGCGTCGAGACCGGCGCATGACGGACTGTTGTCCGTCGCACCAGTAACACCCGTCCTAG
  L  A  A  L  A  A  Y  C  L  T  T  G  S  V  V  I  V  G  R  I
```

FIG. 2-9

```
      5410       5420       5430       5440       5450       5460
ATCCTGTCCGGGAAGCCGGCTATCATCCCCGATAGGGAAGTTCTCTACCAGGAGTTCGAC
TAGGACAGGCCCTTCGGCCGATAGTAGGGGCTATCCCTTCAAGAGATGGTCCTCAAGCTG
 I  L  S  G  K  P  A  I  I  P  D  R  E  V  L  Y  Q  E  F  D 5470       5480       5490       5500       5510       5520
GAGATGGAGGAGTGTGCCTCACACCTCCCTTACTTCGAACAGGGAATGCAGCTCGCCGAG
CTCTACCTCCTCACACGGAGTGTGGAGGGAATGAAGCTTGTCCCTTACGTCGAGCGGCTC
 E  M  E  E  C  A  S  H  L  P  Y  F  E  Q  G  M  Q  L  A  E 5530       5540       5550       5560       5570       5580
CAATTCAAACAGAAGGCGCTCGGGTTGCTGCAAACAGCCACCAAGCAGGCGGAGGCTGCT
GTTAAGTTTGTCTTCCGCGAGCCCAACGACGTTTGTCGGTGGTTCGTCCGCCTCCGACGA
 Q  F  K  Q  K  A  L  G  L  L  Q  T  A  T  K  Q  A  E  A  A 5590       5600       5610       5620       5630       5640
GCTCCCGTGGTGGAGTCCAAGTGGCGAGCCCTTGAGACCTTCTGGGCGAAGCACATGTGG
CGAGGGCACCACCTCAGGTTCACCGCTCGGGAACTCTGGAAGACCCGCTTCGTGTACACC
 A  P  V  V  E  S  K  W  R  A  L  E  T  F  W  A  K  H  M  W 5650       5660       5670       5680       5690       5700
AACTTCATTAGTGGGATACAGTACTTGGCAGGCTTGTCCACTCTGCCTGGGAACCCCGCA
TTGAAGTAATCACCCTATGTCATGAACCGTCCGAACAGGTGAGACGGACCCTTGGGGCGT
 N  F  I  S  G  I  Q  Y  L  A  G  L  S  T  L  P  G  N  P  A 5710       5720       5730       5740       5750       5760
ATACGATCACCGATGGCATTCACAGCCTCCATCACCAGCCCGCTCACCACCCAGCATACC
TATGCTAGTGGCTACCGTAAGTGTCGGAGGTAGTGGTCGGGCGAGTGGTGGGTCGTATGG
 I  R  S  P  M  A  F  T  A  S  I  T  S  P  L  T  T  Q  H  T 5770       5780       5790       5800       5810       5820
CTCTTGTTTAACATCTTGGGGGGATGGGTGGCTGCCCAACTCGCCCCCCCCAGCGCTGCC
GAGAACAAATTGTAGAACCCCCCTACCCACCGACGGGTTGAGCGGGGGGGTCGCGACGG
 L  L  F  N  I  L  G  G  W  V  A  A  Q  L  A  P  P  S  A  A 5830       5840       5850       5860       5870       5880
TCAGCTTTCGTGGGCGCCGGCATCGCTGGAGCCGCTGTTGGCACGATAGGCCTTGGGAAG
AGTCGAAAGCACCCGCGGCCGTAGCGACCTCGGCGACAACCGTGCTATCCGGAACCCTTC
 S  A  F  V  G  A  G  I  A  G  A  A  V  G  T  I  G  L  G  K 5890       5900       5910       5920       5930       5940
GTGCTTGTGGACATTCTGGCAGGTTATGGAGCAGGGGTGGCGGGCGCACTTGTGGCCTTT
CACGAACACCTGTAAGACCGTCCAATACCTCGTCCCCACCGCCCGCGTGAACACCGGAAA
 V  L  V  D  I  L  A  G  Y  G  A  G  V  A  G  A  L  V  A  F 5950       5960       5970       5980       5990       6000
AAGATCATGAGCGGCGAGATGCCTTCAGCCGAGGACATGGTCAACTTACTCCCTGCCATC
TTCTAGTACTCGCCGCTCTACGGAAGTCGGCTCCTGTACCAGTTGAATGAGGGACGGTAG
 K  I  M  S  G  E  M  P  S  A  E  D  M  V  N  L  L  P  A  I
```

FIG. 2-10

```
       6010      6020      6030      6040      6050      6060
CTTTCTCCCGGTGCCCTGGTCGTCGGGATTGTGTGTGCAGCAATACTGCGTCGGCATGTG
GAAAGAGGGCCACGGGACCAGCAGCCCTAACACACACGTCGTTATGACGCAGCCGTACAC
 L   S   P   G   A   L   V   V   G   I   V   C   A   A   I   L   R   R   H   V 6070      6080      6090      6100      6110      6120
GGCCCAGGGGAAGGGGCTGTGCAGTGGATGAACCGGCTGATAGCGTTCGCCTCGCGGGGT
CCGGGTCCCCTTCCCCGACACGTCACCTACTTGGCCGACTATCGCAAGCGGAGCGCCCCA
 G   P   G   E   G   A   V   Q   W   M   N   R   L   I   A   F   A   S   R   G 6130      6140      6150      6160      6170      6180
AACCACGTCTCCCCCAGGCACTATGTGCCAGAGAGCGAGCCTGCAGCGCGTGTTACCCAG
TTGGTGCAGAGGGGGTCCGTGATACACGGTCTCTCGCTCGGACGTCGCGCACAATGGGTC
 N   H   V   S   P   R   H   Y   V   P   E   S   E   P   A   A   R   V   T   Q 6190      6200      6210      6220      6230      6240
ATCCTTTCCAGCCTCACCATCACTCAGCTGTTGAAGAGACTCCACCAGTGGATTAATGAG
TAGGAAAGGTCGGAGTGGTAGTGAGTCGACAACTTCTCTGAGGTGGTCACCTAATTACTC
 I   L   S   S   L   T   I   T   Q   L   L   K   R   L   H   Q   W   I   N   E 6250      6260      6270      6280      6290      6300
GACTGCTCTACGCCATGCTCCAGCTCGTGGCTAAGGGAGATTTGGGACTGGATCTGCACG
CTGACGAGATGCGGTACGAGGTCGAGCACCGATTCCCTCTAAACCCTGACCTAGACGTGC
 D   C   S   T   P   C   S   S   W   L   R   E   I   W   D   W   I   C   T 6310      6320      6330      6340      6350      6360
GTGTTGACTGACTTCAAGACCTGGCTCCAGTCCAAGCTCCTGCCGCGATTACCGGGAGTC
CACAACTGACTGAAGTTCTGGACCGAGGTCAGGTTCGAGGACGGCGCTAATGGCCCTCAG
 V   L   T   D   F   K   T   W   L   Q   S   K   L   L   P   R   L   P   G   V 6370      6380      6390      6400      6410      6420
CCTTTTTTCTCATGCCAACGCGGGTATAAGGGAGTCTGGCGGGGGGACGGCATCATGCAC
GGAAAAAAGAGTACGGTTGCGCCCATATTCCCTCAGACCGCCCCCCTGCCGTAGTACGTG
 P   F   F   S   C   Q   R   G   Y   K   G   V   W   R   G   D   G   I   M   H 6430      6440      6450      6460      6470      6480
ACCACCTGCCCATGCGGAGCACAGATCACCGGACACGTCAAAAACGGTTCCATGAGGATC
TGGTGGACGGGTACGCCTCGTGTCTAGTGGCCTGTGCAGTTTTTGCCAAGGTACTCCTAG
 T   T   C   P   C   G   A   Q   I   T   G   H   V   K   N   G   S   M   R   I 6490      6500      6510      6520      6530      6540
GTTGGGCCTAAAACCTGCAGCAACACGTGGTACGGGACATTCCCCATCAACGCGTACACC
CAACCCGGATTTTGGACGTCGTTGTGCACCATGCCCTGTAAGGGGTAGTTGCGCATGTGG
 V   G   P   K   T   C   S   N   T   W   Y   G   T   F   P   I   N   A   Y   T 6550      6560      6570      6580      6590      6600
ACGGGCCCCTGCACACCCTCCCCGGCGCCAAACTATTCCAAGGCATTGTGGAGAGTGGCC
TGCCCGGGGACGTGTGGGAGGGGCCGCGGTTTGATAAGGTTCCGTAACACCTCTCACCGG
 T   G   P   C   T   P   S   P   A   P   N   Y   S   K   A   L   W   R   V   A
```

FIG. 2-11

```
      6610      6620      6630      6640      6650      6660
GCTGAGGAGTACGTGGAGGTCACGCGGGTGGGAGATTTTCACTACGTGACGGGCATGACC
CGACTCCTCATGCACCTCCAGTGCGCCCACCCTCTAAAAGTGATGCACTGCCCGTACTGG
 A  E  E  Y  V  E  V  T  R  V  G  D  F  H  Y  V  T  G  M  T 6670      6680      6690      6700      6710      6720
ACTGACAACGTGAAGTGTCCATGCCAGGTTCCGGCCCCCGAATTCTTCACGGAGGTGGAT
TGACTGTTGCACTTCACAGGTACGGTCCAAGGCCGGGGGCTTAAGAAGTGCCTCCACCTA
 T  D  N  V  K  C  P  C  Q  V  P  A  P  E  F  F  T  E  V  D 6730      6740      6750      6760      6770      6780
GGAGTGCGGTTGCACAGGTACGCTCCGGCGTGCAGACCTCTCCTACGGGAGGAGGTCGTA
CCTCACGCCAACGTGTCCATGCGAGGCCGCACGTCTGGAGAGGATGCCCTCCTCCAGCAT
 G  V  R  L  H  R  Y  A  P  A  C  R  P  L  L  R  E  E  V  V 6790      6800      6810      6820      6830      6840
TTCCAGGTCGGGCTCCACCAGTACCTGGTCGGGTCACAGCTCCCATGCGAGCCCGAACCG
AAGGTCCAGCCCGAGGTGGTCATGGACCAGCCCAGTGTCGAGGGTACGCTCGGGCTTGGC
 F  Q  V  G  L  H  Q  Y  L  V  G  S  Q  L  P  C  E  P  E  P 6850      6860      6870      6880      6890      6900
GATGTAGCAGTGCTCACTTCCATGCTCACTGACCCCTCCCACATTACAGCAGAGACGGCT
CTACATCGTCACGAGTGAAGGTACGAGTGACTGGGGAGGGTGTAATGTCGTCTCTGCCGA
 D  V  A  V  L  T  S  M  L  T  D  P  S  H  I  T  A  E  T  A 6910      6920      6930      6940      6950      6960
AAGCGTAGGCTGGCCAGGGGGTCTCCCCCCTCCTTGGCCAGCTCTTCAGCTAGCCAGTTG
TTCGCATCCGACCGGTCCCCCAGAGGGGGGAGGAACCGGTCGAGAAGTCGATCGGTCAAC
 K  R  R  L  A  R  G  S  P  P  S  L  A  S  S  S  A  S  Q  L 6970      6980      6990      7000      7010      7020
TCTGCGCCTTCCTTGAAGGCGACATGCACTACCCATCATGACTCCCCGGACGCTGACCTC
AGACGCGGAAGGAACTTCCGCTGTACGTGATGGGTAGTACTGAGGGGCCTGCGACTGGAG
 S  A  P  S  L  K  A  T  C  T  T  H  H  D  S  P  D  A  D  L 7030      7040      7050      7060      7070      7080
ATTGAGGCCAACCTCTTGTGGCGGCAAGAGATGGGCGGGAACATCACCCGCGTGGAGTCA
TAACTCCGGTTGGAGAACACCGCCGTTCTCTACCCGCCCTTGTAGTGGGCGCACCTCAGT
 I  E  A  N  L  L  W  R  Q  E  M  G  G  N  I  T  R  V  E  S 7090      7100      7110      7120      7130      7140
GAGAATAAGGTGGTAATCCTGGACTCTTTCGACCCGCTCCGAGCGGAGGATGATGAGGGG
CTCTTATTCCACCATTAGGACCTGAGAAAGCTGGGCGAGGCTCGCCTCCTACTACTCCCC
 E  N  K  V  V  I  L  D  S  F  D  P  L  R  A  E  D  D  E  G 7150      7160      7170      7180      7190      7200
GAAATATCCGTTCCGGCGGAGATCCTGCGGAAATCCAGGAAATTCCCCCCAGCGCTGCCC
CTTTATAGGCAAGGCCGCCTCTAGGACGCCTTTAGGTCCTTTAAGGGGGGTCGCGACGGG
 E  I  S  V  P  A  E  I  L  R  K  S  R  K  F  P  P  A  L  P
```

FIG. 2-12

```
      7210      7220      7230      7240      7250      7260
ATATGGCGCCGCCGGATTACAACCCTCCGCTGCTAGAGTCCTGGAAGGACCCGGACTAC
TATACCCGCGGCGGCCTAATGTTGGGAGGCGACGATCTCAGGACCTTCCTGGGCCTGATG
 I  W  A  P  P  D  Y  N  P  P  L  L  E  S  W  K  D  P  D  Y 7270      7280      7290      7300      7310      7320
GTTCCTCCGGTGGTACACGGGTGCCCGTTGCCGCCCACCAAGGCCCCTCCAATACCACCT
CAAGGAGGCCACCATGTGCCCACGGGCAACGGCGGGTGGTTCCGGGGAGGTTATGGTGGA
 V  P  P  V  V  H  G  C  P  L  P  P  T  K  A  P  P  I  P  P 7330      7340      7350      7360      7370      7380
CCACGGAGGAAGAGGACGGTTGTCCTGACAGAATCCACCGTGTCTTCTGCCTTGGCGGAG
GGTGCCTCCTTCTCCTGCCAACAGGACTGTCTTAGGTGGCACAGAAGACGGAACCGCCTC
 P  R  R  K  R  T  V  V  L  T  E  S  T  V  S  S  A  L  A  E 7390      7400      7410      7420      7430      7440
CTCGCTACTAAGACCTTCGGCAGCTCCGGATCGTCGGCCATCGACAGCGGTACGGCGACC
GAGCGATGATTCTGGAAGCCGTCGAGGCCTAGCAGCCGGTAGCTGTCGCCATGCCGCTGG
 L  A  T  K  T  F  G  S  S  G  S  S  A  I  D  S  G  T  A  T 7450      7460      7470      7480      7490      7500
GCCCCTCCTGACCAAGCCTCCGGTGACGGCGACAGAGAGTCCGACGTTGAGTCGTTCTCC
CGGGGAGGACTGGTTCGGAGGCCACTGCCGCTGTCTCTCAGGCTGCAACTCAGCAAGAGG
 A  P  P  D  Q  A  S  G  D  G  D  R  E  S  D  V  E  S  F  S 7510      7520      7530      7540      7550      7560
TCCATGCCCCCCCTTGAGGGAGAGCCGGGGGACCCCGATCTCAGCGACGGATCTTGGTCC
AGGTACGGGGGGGAACTCCCTCTCGGCCCCCTGGGGCTAGAGTCGCTGCCTAGAACCAGG
 S  M  P  P  L  E  G  E  P  G  D  P  D  L  S  D  G  S  W  S 7570      7580      7590      7600      7610      7620
ACCGTGAGCGAGGAGGCTAGTGAGGACGTCGTCTGCTGTTCGATGTCCTACACATGGACA
TGGCACTCGCTCCTCCGATCACTCCTGCAGCAGACGACAAGCTACAGGATGTGTACCTGT
 T  V  S  E  E  A  S  E  D  V  V  C  C  S  M  S  Y  T  W  T 7630      7640      7650      7660      7670      7680
GGCGCCCTGATCACGCCATGCGCTGCGGAGGAAAGCAAGTTGCCCATCAACCCGTTGAGC
CCGCGGGACTAGTGCGGTACGCGACGCCTCCTTTCGTTCAACGGGTAGTTGGGCAACTCG
 G  A  L  I  T  P  C  A  A  E  E  S  K  L  P  I  N  P  L  S 7690      7700      7710      7720      7730      7740
AATTCTTTGCTACGTCACCACAACATGGTCTATGCTACAACATCCCGCAGCGCAGGCCTG
TTAAGAAACGATGCAGTGGTGTTGTACCAGATACGATGTTGTAGGGCGTCGCGTCCGGAC
 N  S  L  L  R  H  H  N  M  V  Y  A  T  T  S  R  S  A  G  L 7750      7760      7770      7780      7790      7800
CGGCAGAAGAAGGTCACCTTTGACAGACTGCAAGTCCTGGACGACCACTACCGGGACGTG
GCCGTCTTCTTCCAGTGGAAACTGTCTGACGTTCAGGACCTGCTGGTGATGGCCCTGCAC
 R  Q  K  K  V  T  F  D  R  L  Q  V  L  D  D  H  Y  R  D  V
```

FIG. 2-13

```
      7810        7820        7830        7840        7850        7860
CTTAAGGAGATGAAGGCGAAGGCGTCCACAGTTAAGGCTAAACTTCTATCTGTAGAAGAA
GAATTCCTCTACTTCCGCTTCCGCAGGTGTCAATTCCGATTTGAAGATAGACATCTTCTT
 L  K  E  M  K  A  K  A  S  T  V  K  A  K  L  L  S  V  E  E 7870        7880        7890        7900        7910        7920
GCCTGCAAACTGACGCCCCACATTCGGCCAAATCCAAATTTGGCTACGGGGCGAAGGAC
CGGACGTTTGACTGCGGGGGTGTAAGCCGGTTTAGGTTTAAACCGATGCCCCGCTTCCTG
 A  C  K  L  T  P  P  H  S  A  K  S  K  F  G  Y  G  A  K  D 7930        7940        7950        7960        7970        7980
GTCCGGAGCCTATCCAGCAGGGCCGTTACCCACATCCGCTCCGTGTGGAAGGACCTGCTG
CAGGCCTCGGATAGGTCGTCCCGGCAATGGGTGTAGGCGAGGCACACCTTCCTGGACGAC
 V  R  S  L  S  S  R  A  V  T  H  I  R  S  V  W  K  D  L  L 7990        8000        8010        8020        8030        8040
GAAGACACTGAAACACCAATTAGCACTACCATCATGGCAAAAAATGAGGTTTTCTGTGTC
CTTCTGTGACTTTGTGGTTAAT
CGTGATGGTAGTACCGTTTTTTACTCCAAAAGACACAG
 E  D  T  E  T  P  I  S  T  T  I  M  A  K  N  E  V  F  C  V 8050        8060        8070        8080        8090        8100
CAACCAGAGAAGGGAGGCCGCAAGCCAGCTCGCCTTATCGTGTTCCCAGATCTGGGAGTT
GTTGGTCTCTTCCCTCCGGCGTTCGGTCGAGCGGAATAGCACAAGGGTCTAGACCCTCAA
 Q  P  E  K  G  G  R  K  P  A  R  L  I  V  F  P  D  L  G  V 8110        8120        8130        8140        8150        8160
CGTGTATGCGAGAAGATGGCCCTTTATGACGTGGTCTCCACCCTTCCTCAGGCCGTGATG
GCACATACGCTCTTCTACCGGGAAATACTGCACCAGAGGTGGGAAGGAGTCCGGCACTAC
 R  V  C  E  K  M  A  L  Y  D  V  V  S  T  L  P  Q  A  V  M 8170        8180        8190        8200        8210        8220
GGCTCCTCATACGGATTCCAGTACTCTCCTAAGCAGCGGGTCGAGTTCCTGGTGAATACC
CCGAGGAGTATGCCTAAGGTCATGAGAGGATTCGTCGCCCAGCTCAAGGACCACTTATGG
 G  S  S  Y  G  F  Q  Y  S  P  K  Q  R  V  E  F  L  V  N  T 8230        8260        8270        8260        8270        8280
TGGAAATCAAAGAAATGCCCCATGGGCTTCTCATATGACACCCGCTGTTTTGACTCAACG
ACCTTTAGTTTCTTTACGGGGTACCCGAAGAGTATACTGTGGGCGACAAAACTGAGTTGC
 W  K  S  K  K  C  P  M  G  F  S  Y  D  T  R  C  F  D  S  T 8290        8300        8310        8320        8330        8340
GTCACTGAGAATGACATCCGTGTTGAGGAGTCAATTTACCAATGTTGTGACTTGGCCCCC
CAGTGACTCTTACTGTAGGCACAACTCCTCAGTTAAATGGTTACAACACTGAACCGGGGG
 V  T  E  N  D  I  R  V  E  E  S  I  Y  Q  C  C  D  L  A  P 8350        8360        8370        8380        8390        8400
GAAGCCAAACTGGCCATAAAGTCGCTCACAGAGCGGCTCTATATCGGGGGTCCCCTGACT
CTTCGGTTTGACCGGTATTTCAGCGAGTGTCTCGCCGAGATATAGCCCCCAGGGGACTGA
 E  A  K  L  A  I  K  S  L  T  E  R  L  Y  I  G  G  P  L  T
```

FIG. 2-14

```
                8410        8420        8430        8440        8450        8460
         AATTCAAAAGGGCAGAACTGCGGTTACCGCCGGTGCCGCGCGAGCGGCGTGCTGACGACT
         TTAAGTTTTCCCGTCGTTGACGCCAATGGCGGCCACGGCGCGCTCGCCGCACGACTGCTGA
           N  S  K  G  Q  N  C  G  Y  R  R  C  R  A  S  G  V  L  T  T 8470        8480        8490        8500        8510        8520
         AGCTGCGGTAATACCCTCACATGTTACCTGAAAGCCACTGCGGCCTGTCGAGCTGCGAAG
         TCGACGCCATTATGGGAGTGTACAATGGACTTTCGGTGACGCCGGACAGCTCGACGCTTC
           S  C  G  N  T  L  T  C  Y  L  K  A  T  A  A  C  R  A  A  K 8530        8540        8550        8560        8570        8580
         CTCCGGGACTGCACGATGCTCGTGAACGGAGACGACCTTGTCGTTATCTGTGAAAGCGCG
         GAGGCCCTGACGTGCTACGAGCACTTGCCTCTGCTGGAACAGCAATAGACACTTTCGCGC
           L  R  D  C  T  M  L  V  N  G  D  D  L  V  V  I  C  E  S  A 8590        8600        8610        8620        8630        8640
         GGAACCCAAGAGGATGCGGCGAGCCTACGAGTCTTCACGGAGGCTATGACTAGGTACTCT
         CCTTGGGTTCTCCTACGCCGCTCGGATGCTCAGAAGTGCCTCCGATACTGATCCATGAGA
           G  T  Q  E  D  A  A  S  L  R  V  F  T  E  A  M  T  R  Y  S 8650        8660        8670        8680        8690        8700
         GCCCCCCCTGGGGACCCGCCTCAACCGGAATACGACTTGGAGTTGATAACATCATGTTCC
         CGGGGGGGACCCCTGGGCGGAGTTGGCCTTATGCTGAACCTCAACTATTGTAGTACAAGG
           A  P  P  G  D  P  P  Q  P  E  Y  D  L  E  L  I  T  S  C  S 8710        8720        8730        8740        8750        8760
         TCCAATGTGTCGGTCGCACACGATGCATCTGGTAAAAGGGTGTACTACCTCACCCGTGAC
         AGGTTACACAGCCAGCGTGTGCTACGTAGACCATTTTCCCACATGATGGAGTGGGCACTG
           S  N  V  S  V  A  H  D  A  S  G  K  R  V  Y  Y  L  T  R  D 8770        8780        8790        8800        8810        8820
         CCTACCACCCCCCTTGCACGGGCTGCGTGGGAGACAGCTAGACACACTCCAGTCAACTCC
         GGATGGTGGGGGGAACGTGCCCGACGCACCCTCTGTCGATCTGTGTGAGGTCAGTTGAGG
           P  T  T  P  L  A  R  A  A  W  E  T  A  R  H  T  P  V  N  S 8830        8860        8870        8860        8870        8880
         TGGCTAGGCAACATCATCATGTATGCGCCCACCTTATGGGCAAGGATGATTCTGATGACT
         ACCGATCCGTTGTAGTAGTACATACGCGGGTGGAATACCCGTTCCTACTAAGACTACTGA
           W  L  G  N  I  I  M  Y  A  P  T  L  W  A  R  M  I  L  M  T 8890        8900        8910        8920        8930        8940
         CATTTCTTCTCCATCCTTCTAGCTCAGGAGCAACTTGAAAAAACCCTAGATTGTCAGATC
         GTAAAGAAGAGGTAGGAAGATCGAGTCCTCGTTGAACTTTTTTGGGATCTAACAGTCTAG
           H  F  F  S  I  L  L  A  Q  E  Q  L  E  K  T  L  D  C  Q  I 8950        8960        8970        8980        8990        9000
         TACGGGGCCTGTTACTCCATTGAACCACTTGATCTACCTCAGATCATTGAGCGACTCCAT
         ATGCCCCGGACAATGAGGTAACTTGGTGAACTAGATGGAGTCTAGTAACTCGCTGAGGTA
           Y  G  A  C  Y  S  I  E  P  L  D  L  P  Q  I  I  E  R  L  H
```

FIG. 2-15

```
      9010       9020       9030       9040       9050       9060
GGTCTTAGCGCATTTTCACTCCATAGTTACTCTCCAGGCGAGATCAATAGGGTGGCTTCA
CCAGAATCGCGTAAAAGTGAGGTATCAATGAGAGGTCCGCTCTAGTTATCCCACCGAAGT
  G  L  S  A  F  S  L  H  S  Y  S  P  G  E  I  N  R  V  A  S 9070       9080       9090       9100       9110       9120
TGCCTCAGAAAACTTGGGGTACCACCCTTGCGAGCCTGGAGACATCGGGCCAGAAGTGTC
ACGGAGTCTTTTGAACCCCATGGTGGGAACGCTCGGACCTCTGTAGCCCGGTCTTCACAG
  C  L  R  K  L  G  V  P  P  L  R  A  W  R  H  R  A  R  S  V 9130       9140       9150       9160       9170       9180
CGCGCTAAGCTACTGTCCCAGGGGGGGAGGGCCGCCACTTGTGGCAAGTACCTCTTCAAC
GCGCGATTCGATGACAGGGTCCCCCCCTCCCGGCGGTGAACACCGTTCATGGAGAAGTTG
  R  A  K  L  L  S  Q  G  G  R  A  A  T  C  G  K  Y  L  F  N 9190       9200       9210       9220       9230       9240
TGGGCGGTGAGGACCAAGCTCAAACTCACTCCAATCCCAGCCGCGTCCCGGTTGGACTTG
ACCCGCCACTCCTGGTTCGAGTTTGAGTGAGGTTAGGGTCGGCGCAGGGCCAACCTGAAC
  W  A  V  R  T  K  L  K  L  T  P  I  P  A  A  S  R  L  D  L 9250       9260       9270       9280       9290       9300
TCCGGCTGGTTCGTTGCTGGTTACAGCGGGGGAGACATATATCACAGCCTGTCTCGTGCC
AGGCCGACCAAGCAACGACCAATGTCGCCCCCTCTGTATATAGTGTCGGACAGAGCACGG
  S  G  W  F  V  A  G  Y  S  G  G  D  I  Y  H  S  L  S  R  A 9310       9320       9330       9340       9350       9360
CGACCCCGCTGGTTCATGTTGTGCCTACTCCTACTTTCCGTGGGGGTAGGCATCTACCTG
GCTGGGGCGACCAAGTACAACACGGATGAGGATGAAAGGCACCCCCATCCGTAGATGGAC
  R  P  R  W  F  M  L  C  L  L  L  L  S  V  G  V  G  I  Y  L 9370       9380       9390       9400       9410       9420
CTCCCCAACCGATGAATGGGGAGCTAAACACTCCAGGCCAATAGGCCGTTTCTCTTTTTT
GAGGGGTTGGCTACTTACCCCTCGATTTGTGAGGTCCGGTTATCCGGCAAAGAGAAAAAA
  L  P  N  R 9430       9460       9470       9460       9470
TTTTTTTTTTTTTTTTTTTTTTTTTTTTTTTTTTTTTTTTTTTTTTTTTTTT
AAAAAAAAAAAAAAAAAAAAAAAAAAAAAAAAAAAAAAAAAAAAAAAAAAAA
```

FIG. 2-16

| NAME OF cDNA CLONE | POSITION IN KHCV-LBC1 (NUCLEOTIDE NUMBER) |
|---|---|
| KHCV 426 | FROM 301 TO 726 |
| KHCV 652 | FROM 3928 TO 4563 |
| KHCV 403 | FROM 6649 TO 7050 |
| KHCV 752 | FROM 3208 TO 3960 |
| KHCV 675 | FROM 4264 TO 4938 |
| KHCV 240 | FROM 616 TO 855 |
| KHCV 513 | FROM 814 TO 1326 |
| KHCV 810 | FROM 1201 TO 2016 |
| KHCV 798 | FROM 1945 TO 2742 |
| KHCV 932 | FROM 6892 TO 7824 |
| KHCV 496 | FROM 7642 TO 8136 |
| KHCV 847 | FROM 7969 TO 8814 |
| KHCV 494 | FROM 8722 TO 9216 |
| KHCV 570 | FROM 2686 TO 3300 |
| KHCV 1774 | FROM 4903 TO 6677 |
| KHCV 226 | FROM 9160 TO 9472 |
| KHCV 366 | FROM 1 TO 366 |

FIG. 3

| | | |
|---|---|---|
| KHCV366 | 1 | gGCCAGCCCCCgaTTGGGGGCGACACTCCACCATAGATCACTCCCTGTGAGGAACTACT |
| HCPT-CHIRON | 1 | GCCAGCCCCCTgaTGGGGGCGACACTCCACCATgaATCACTCCCTGTGAGGAACTACT |
| JHCV-NCI | | TTGGGGGCGACACTCCACCATAGATCACTCCCCTGTGAGGAACTACT |
| KHCV366 | 61 | GTCTTCACGCAGAAAGCGTCTAGCCATGGCGTTAGTATGAGTGTCGTGCAGCCTCCAGGA |
| HCPT-CHIRON | 60 | GTCTTCACGCAGAAAGCGTCTAGCCATGGCGTTAGTATGAGTGTCGTGCAGCCTCCAGGA |
| JHCV-NCI | 48 | GTCTTCACGCAGAAAGCGTCTAGCCATGGCGTTAGTATGAGTGTtGTGCAGCCTCCAGGA |
| KHCV366 | 121 | CCCCCCCTCCCGGGAGAGCCATAGTGGTCTGCGAACCGGTGAGTACACCGGAATTGCCA |
| HCPT-CHIRON | 120 | CCCCCCCTCCCGGGAGAGCCATAGTGGTCTGCGAACCGGTGAGTACACCGGAATTGCCA |
| JHCV-NCI | 108 | CCCCCCCCTCCCGGGAGAGCCATAGTGGTCTGCGAACCGGTGAGTACACCGGAATTGCCA |
| KHCV366 | 181 | GGACGACCGGGTCCTTTCTTGGATCAACCCGCTCAATGCCTGGAGATTTGGGCGTGCCCC |
| HCPT-CHIRON | 180 | GGACGACCGGGTCCTTTCTTGGATCAACCCGCTCAATGCCTGGAGATTTGGGCGTGCCCC |
| JHCV-NCI | 168 | GGACGACCGGGTCCTTTCTTTGATCAACgCGCTCAATGCCTGGAGATTTGGGCGTGCCCC |
| KHCV366 | 241 | CGCGAGACTGCTAGCCGAGTAGTGTTGGGTCGCGAAAGGCCTTGTGGTACTGCCTGATAG |
| HCPT-CHIRON | 240 | CGCaAGACTGCTAGCCGAGTAGTGTTGGG

```
         10        20        30        40        50        60
          |         |         |         |         |         |
CTCTTTACCCTGTCACCACACTACAAAGTGTTCCTCGCTAGGCTCATATGGTGGTTACAG
LeuPheThrLeuSerProHisTyrLysValPheLeuAlaArgLeuIleTrpTrpLeuGln 70        80        90       100       110       120
          |         |         |         |         |         |
TATTTTATCACCAGGGCCGAAGCGCACCTGCAAGTGTGGATCCCCCCCCTCAACGTTCGG
TyrPheIleThrArgAlaGluAlaHisLeuGlnValTrpIleProProLeuAsnValArg 130       140       150       160       170       180
          |         |         |         |         |         |
GGGGGCCGCGATGCCATCATCCTCCTCACGTGTGCGGTCCACTCAGAGCTGATTTTTGAC
GlyGlyArgAspAlaIleIleLeuLeuThrCysAlaValHisSerGluLeuIlePheAsp 190       200       210       220       230       240
          |         |         |         |         |         |
ATCACCAAGATCTTGCTCGCCATACTTGGTCCGCTCATGGTACTCCAGGCTGGCCTAACC
IleThrLysIleLeuLeuAlaIleLeuGlyProLeuMETValLeuGlnAlaGlyLeuThr 250       260       270
          |         |         |
AGAGTGCCGTACTTTGTCAGCGCTCAAGGGCTCATCC
ArgValProTyrPheValSerAlaGlnGlyLeuIle
```

FIG. 7

```
         10        20        30        40        50        60
          |         |         |         |         |         |
CTCTTGACCTTGTCACCATACTATAAAGTGTTCCTCGCTAGGCTCATATGGTGGTTGCAA
LeuLeuThrLeuSerProTyrTyrLysValPheLeuAlaArgLeuIleTrpTrpLeuGln 70        80        90       100       110       120
          |         |         |         |         |         |
TATTTTATCACCAGAGCCGAGGCGCACTTGCAAGTGTGGATCCCCCCTCTCAACGTCCGG
TyrPheIleThrArgAlaGluAlaHisLeuGlnValTrpIleProProLeuAsnValArg 130       140       150       160       170       180
          |         |         |         |         |         |
GGAGGCCGTGATGCAATCATCCTCCTGGCGTGTGCGGTCCACCCAGAGCCGATCTTTGAC
GlyGlyArgAspAlaIleIleLeuLeuAlaCysAlaValHisProGluProIlePheAsp 190       200       210       220       230       240
          |         |         |         |         |         |
ATCACAAAATATTTGCTCGCCATATTCGGCCCGCTCATGGTGCTCCAGGCCGGCATAACT
IleThrLysTyrLeuLeuAlaIlePheGlyProLeuMETValLeuGlnAlaGlyIleThr 250       260       270       280       290       300
          |         |         |         |         |         |
AGAGTGCCGTACTTCTGGCGCGCACAAGGGCTCATTCGTGCATGCATGTTGGCGCGGAAA
ArgValProTyrPheTrpArgAlaGlnGlyLeuIleArgAlaCysMETLeuAlaArgLys

310
          |
GTCGCTGGGGGTCATTAC
ValAlaGlyGlyHisTyr
```

FIG. 8

```
        10        20        30        40        50        60
         |         |         |         |         |         |
CTCTTGACCTTGTCACCACACTATAAAGTGTTCCTTGCCAGGTTCATATGGTGGCTACAA
LeuLeuThrLeuSerProHisTyrLysValPheLeuAlaArgPheIleTrpTrpLeuGln 70        80        90       100       110       120
         |         |         |         |         |         |
TATCTCATCACCAGAACCGAAGCGCATCTGCAAGTGTGGGTCCCCCCTCTCAACGTTCGA
TyrLeuIleThrArgThrGluAlaHisLeuGlnValTrpValProProLeuAsnValArg 130       140       150       160       170       180
         |         |         |         |         |         |
GGAGGCCGTGATGCCGTCATCCTCCTCACGTGCGCAGTCTACCCAGAGCTAATCTTTGAC
GlyGlyArgAspAlaValIleLeuLeuThrCysAlaValTyrProGluLeuIlePheAsp 190       200       210       220       230       240
         |         |         |         |         |         |
ATCACCAAACTCCTGCTTGCCACACTCGGTCCGCTCATGGTGCTCCAGGCTGGCTTAATT
IleThrLysLeuLeuLeuAlaThrLeuGlyProLeuMETValLeuGlnAlaGlyLeuIle 250       260       270       280       290       300
         |         |         |         |         |         |
AGAGTGCCGTACTTCGTACGCTCAGGGCTCATTCGTGCATGCATGTTGGTGCGGAAAGTT
ArgValProTyrPheValArgSerGlyLeuIleArgAlaCysMETLeuValArgLysVal

310
         |
GCTGGGGGTCATTAT
AlaGlyGlyHisTyr
```

FIG. 9

```
          10        20        30        40        50        60
          |         |         |         |         |         |
CTCTTGACCCTGTCACCACACTATAAAGTGTTCCTCGCTAGGCTCATGTGGTGGTTACAA
LeuLeuThrLeuSerProHisTyrLysValPheLeuAlaArgLeuMETTrpTrpLeuGln 70        80        90       100       110       120
          |         |         |         |         |         |
TACTTCCTCACCAGAGCCGAAGCGCACTTGCAAGTGTGGGTCCCCTCTCTCAACGTTCGA
TyrPheLeuThrArgAlaGluAlaHisLeuGlnValTrpValProSerLeuAsnValArg 130       140       150       160       170       180
          |         |         |         |         |         |
GGAGGCCGCGATGCCATCATCCTCCTCACGTGCGCAGTCTACCCAGAGCTAATCTTTGAC
GlyGlyArgAspAlaIleIleLeuLeuThrCysAlaValTyrProGluLeuIlePheAsp 190       200       210       220       230       240
          |         |         |         |         |         |
ATCACCAAACTCTTGCTTGCCACACTCGGCCCGCTCATGGTGCTCCAGGCTGGCTTAACT
IleThrLysLeuLeuLeuAlaThrLeuGlyProLeuMETValLeuGlnAlaGlyLeuThr 250       260       270       280       290       300
          |         |         |         |         |         |
AGAGTGCCGTACTTTGTGCGCGCCCAGGGGCTCATTCGTGCGTGCATGTTGGTGCGGAAA
ArgValProTyrPheValArgAlaGlnGlyLeuIleArgAlaCysMETLeuValArgLys

310
          |
GTTGTGGGGGGCCATTAT
ValValGlyGlyHisTyr
```

FIG. 10

```
         10        20        30        40        50        60
          |         |         |         |         |         |
CTCTTGACCTTGTCACCACACTATAAAGTGTTCCTTGCCAGGTTCATATGGTGGCTACAA
LeuLeuThrLeuSerProHisTyrLysValPheLeuAlaArgPheIleTrpTrpLeuGln 70        80        90       100       110       120
          |         |         |         |         |         |
TATCTCATCACCAGAACCGAAGCGCATCTGCAAGTGTGGGTCCCCCCTCTCAACGTTCGG
TyrLeuIleThrArgThrGluAlaHisLeuGlnValTrpValProProLeuAsnValArg 130       140       150       160       170       180
          |         |         |         |         |         |
GGGGGTCGCGATGCCATCATCCTCCTCGCGTGTGCGGTCCACCCAGAGCTGATCTTTGAC
GlyGlyArgAspAlaIleIleLeuLeuAlaCysAlaValHisProGluLeuIlePheAsp 190       200       210       220       230       240
          |         |         |         |         |         |
ATCACCAAACTCTTGCTCGCCATACTCGGTCCGCTCATGGTGCTCCAGGCTAGCATAATT
IleThrLysLeuLeuLeuAlaIleLeuGlyProLeuMETValLeuGlnAlaSerIleIle 250       260       270       280       290       300
          |         |         |         |         |         |
CGAGTGCCGTACTCCGTGCGCGCTCAAGGCCTCATTCGTGCATGCATGTTGGTGCGGAAA
ArgValProTyrSerValArgAlaGlnGlyLeuIleArgAlaCysMETLeuValArgLys

310
          |
GCCGCCGGGGGTCATTAT
AlaAlaGlyGlyHisTyr
```

FIG. 11

```
         10        20        30        40        50        60
         |         |         |         |         |         |
CTCTTGACCTTGTCACCATACTATAAGGTGCTCCTCGCTAGGCTCATATGGTGGTTGCAA
LeuLeuThrLeuSerProTyrTyrLysValLeuLeuAlaArgLeuIleTrpTrpLeuGln 70        80        90       100       110       120
         |         |         |         |         |         |
TATTTTATCACCAGAGCCGAGGCGCACTTGCAAGTGTGGGCTCCCCCCCTTAACGTTCGG
TyrPheIleThrArgAlaGluAlaHisLeuGlnValTrpAlaProProLeuAsnValArg 130       140       150       160       170       180
         |         |         |         |         |         |
GGGGGCCGCGATGCCATCATCCTCCTCATGTGTGTAGTTCACCCGGAGCTAATCTTTGAC
GlyGlyArgAspAlaIleIleLeuLeuMETCysValValHisProGluLeuIlePheAsp 190       200       210       220       230       240
         |         |         |         |         |         |
ATCACAAAAATCCTGCTCGCCGTGCTCGGTCCGCTCACGGTGCTCCAGGCTGGCATAACC
IleThrLysIleLeuLeuAlaValLeuGlyProLeuThrValLeuGlnAlaGlyIleThr 250       260       270       280       290       300
         |         |         |         |         |         |
CGAGTGCCGTACTTTGTGCGCGCTCAATGGCTCATTCGTGCGTGCATGTTGGTGCGGAAC
ArgValProTyrPheValArgAlaGlnTrpLeuIleArgAlaCysMETLeuValArgAsn

310
         |
ATCGCTGGGGGTCATTAT
IleAlaGlyGlyHisTyr
```

FIG. 12

```
          10         20         30         40         50         60
           |          |          |          |          |          |
CTCTTGACCTTGTCACCACACTATAAAGTGTTCCTTGCCAGGTTCATATGGTGGCTACAA
LeuLeuThrLeuSerProHisTyrLysValPheLeuAlaArgPheIleTrpTrpLeuGln 70         80         90        100        110        120
           |          |          |          |          |          |
TATCTCATCACCAGAACCGAAGCGCATCTGCAAGTGTGGGTCCCCCCTCTCAACGTTCGG
TyrLeuIleThrArgThrGluAlaHisLeuGlnValTrpValProProLeuAsnValArg 130        140        150        160        170        180
           |          |          |          |          |          |
GGGGGTCGCGATGCCATCATCCTCCTCACATGCGTGGTCCACCCAGAGCTAATCTTTGAC
GlyGlyArgAspAlaIleIleLeuLeuThrCysValValHisProGluLeuIlePheAsp 190        200        210        220        230        240
           |          |          |          |          |          |
ATCACCAAACTCTTGCTCGCCATACTCGGTCCGCTCATGGTGCTCCAGGCTAGCATAATT
IleThrLysLeuLeuLeuAlaIleLeuGlyProLeuMETValLeuGlnAlaSerIleIle 250        260        270        280        290        300
           |          |          |          |          |          |
CGAGTGCCGTACTTTGTGCGCGCTCAAGGCCTCATTCGTGCATGTATGTTGGTGCGGAAA
ArgValProTyrPheValArgAlaGlnGlyLeuIleArgAlaCysMETLeuValArgLys

310
           |
GTTGCTGGGGGTCATTAT
ValAlaGlyGlyHisTyr
```

FIG. 13

```
           10        20        30        40        50        60
            |         |         |         |         |         |
CTCTTGACTCTGTCGCCACACTATAAAGTGTTCCTCGCTAGCCTCATGTGGTGGTTACAA
LeuLeuThrLeuSerProHisTyrLysValPheLeuAlaSerLeuMETTrpTrpLeuGln 70        80        90       100       110       120
            |         |         |         |         |         |
TACTTCCTCACCAGAGCCGAAGCGCACTTGCAAGTGTGGGTCCCCTCTCTCAACGTTCGA
TyrPheLeuThrArgAlaGluAlaHisLeuGlnValTrpValProSerLeuAsnValArg 130       140       150       160       170       180
            |         |         |         |         |         |
GGAGGCCGCGATGCCATCATCCTCCTCACGTGCGCAGTCTACCCAGAGCTAATCTTAGAC
GlyGlyArgAspAlaIleIleLeuLeuThrCysAlaValTyrProGluLeuIleLeuAsp 190       200       210       220       230       240
            |         |         |         |         |         |
ATCACCAAACTCTTGCTCGCCATACTCGGTCCGCTCATGGTGCTCCAGGCTAGCATAATT
IleThrLysLeuLeuLeuAlaIleLeuGlyProLeuMETValLeuGlnAlaSerIleIle 250       260       270       280       290       300
            |         |         |         |         |         |
CGAGTGCCGTACTTCGTACGCGCTCAAGGCCTCATTCGTGCATGCATGTTGGTGCGGAAA
ArgValProTyrPheValArgAlaGlnGlyLeuIleArgAlaCysMETLeuValArgLys

310
            |
GCCGCCGGGGGTCATTAT
AlaAlaGlyGlyHisTyr
```

FIG. 14

```
          10        20        30        40        50        60
           |         |         |         |         |         |
CTCTTGACCCTGTCACCGCACTATAAAGTGTTCCTCGCTAGGCTCACGTGGTGGTTACAA
LeuLeuThrLeuSerProHisTyrLysValPheLeuAlaArgLeuThrTrpTrpLeuGln 70        80        90       100       110       120
           |         |         |         |         |         |
TACTTCCTCACCAGAGCCGAAGCGCACTTGCAAGTGTGGGTCCCCTCTCTCAACGTTCGA
TyrPheLeuThrArgAlaGluAlaHisLeuGlnValTrpValProSerLeuAsnValArg 130       140       150       160       170       180
           |         |         |         |         |         |
GGAGGCCGCGATGCCATCATCCTCCTCACGTGCGCAGTCTACCCAGAGCTGATCTTTGAC
GlyGlyArgAspAlaIleIleLeuLeuThrCysAlaValTyrProGluLeuIlePheAsp 190       200       210       220       230       240
           |         |         |         |         |         |
ATCACCAAACTCTTGCTTGCCACACTCGGCCCGCTCATGGTGCTCCAGGCTGGCTTAACT
IleThrLysLeuLeuLeuAlaThrLeuGlyProLeuMETValLeuGlnAlaGlyLeuThr 250       260       270       280       290       300
           |         |         |         |         |         |
AGAGTGCCGTACTTTGTGCGCGCCCAGGGGCTCATTCGTGCGTGCATGTTGGTGCGGAAA
ArgValProTyrPheValArgAlaGlnGlyLeuIleArgAlaCysMETLeuValArgLys

310
           |
GTTGCTGGGGGCCATTAT
ValAlaGlyGlyHisTyr
```

FIG. 15

```
         10        20        30        40        50        60
          |         |         |         |         |         |
CTCTTGACCTTGTCACCATACTATAAAGTGTTCCTCGCTAGGCTCATATGGTGGTTGCAA
LeuLeuThrLeuSerProTyrTyrLysValPheLeuAlaArgLeuIleTrpTrpLeuGln 70        80        90       100       110       120
          |         |         |         |         |         |
TATTTTATCACCAGAGCCGAAGCGCACTTGCAAGTGTGGGTCCCCCCTCTCAACGTTCGA
TyrPheIleThrArgAlaGluAlaHisLeuGlnValTrpValProProLeuAsnValArg 130       140       150       160       170       180
          |         |         |         |         |         |
GGAGGCCGTGATGCTATCATCCTCCTCACGTGCGCAGTCTACCCAGAGCTAATCTTTGAC
GlyGlyArgAspAlaIleIleLeuLeuThrCysAlaValTyrProGluLeuIlePheAsp 190       200       210       220       230       240
          |         |         |         |         |         |
ATCACCAAACTCTTGCTTGCCATACTCGGTCCGCTCATGGTGCTCCAGGCTAGCATAATT
IleThrLysLeuLeuLeuAlaIleLeuGlyProLeuMETValLeuGlnAlaSerIleIle 250       260       270       280       290       300
          |         |         |         |         |         |
CGAGTGCCGTACTTCGTACGCGCTCAAGGCCTCATTCGTGCATGCATGTTGGTGCGGAAA
ArgValProTyrPheValArgAlaGlnGlyLeuIleArgAlaCysMETLeuValArgLys

310
          |
GCCGCCGGGGTCAATTAT
AlaAlaGlyValAsnTyr
```

FIG. 16

```
          10        20        30        40        50        60
           |         |         |         |         |         |
CTCTTTACCCTGTCACCACACTGCAAAGTGTTCCTCGCTAGGCTCATATGGTGGTTACAG
LeuPheThrLeuSerProHisCysLysValPheLeuAlaArgLeuIleTrpTrpLeuGln 70        80        90       100       110       120
           |         |         |         |         |         |
TATTTTATCACCAGGGCCGAAGCGCACCTGCAAGTGTGGATCCCCCCCCTCAACGTTCGG
TyrPheIleThrArgAlaGluAlaHisLeuGlnValTrpIleProProLeuAsnValArg 130       140       150       160       170       180
           |         |         |         |         |         |
GGGGGCCGTGATGCCATCATCCTCCTCGCATGTGCGGTCCACCCAGAGCTGATCTTCGAC
GlyGlyArgAspAlaIleIleLeuLeuAlaCysAlaValHisProGluLeuIlePheAsp 190       200       210       220       230       240
           |         |         |         |         |         |
ATCACCAAACTCTTGCTCGCCATACTCGGTCCGCTCATGGTGCTCCAGGCTAGCATAATT
IleThrLysLeuLeuLeuAlaIleLeuGlyProLeuMETValLeuGlnAlaSerIleIle 250       260       270       280       290       300
           |         |         |         |         |         |
CGAGTGCCGTACTTGTACCGCGCTCAAGGCCTCATTCGTGCATGCATGTTGGTGCGGAAA
ArgValProTyrLeuTyrArgAlaGlnGlyLeuIleArgAlaCysMETLeuValArgLys

310
           |
GCCGCCGGGGGTCATTAT
AlaAlaGlyGlyHisTyr
```

FIG. 17

```
         10        20        30        40        50        60
         |         |         |         |         |         |
CTCTTTAACCTGTCACCACACTACAAAGTGTTCCTCGCTAGGCTCATATGGTGGTTACAG
LeuPheAsnLeuSerProHisTyrLysValPheLeuAlaArgLeuIleTrpTrpLeuGln 70        80        90       100       110       120
         |         |         |         |         |         |
TATTTTATCACCAGGGCCGAAGCGCACCTGCAAGTGTGGATCCCCCCCCTCAACGTTCAG
TyrPheIleThrArgAlaGluAlaHisLeuGlnValTrpIleProProLeuAsnValGln 130       140       150       160       170       180
         |         |         |         |         |         |
GGGGGCCGTGATGCCATCATCCTCCTCGCATGTGCGGTCCACCCAGAGCTGATCTTTGAC
GlyGlyArgAspAlaIleIleLeuLeuAlaCysAlaValHisProGluLeuIlePheAsp 190       200       210       220       230       240
         |         |         |         |         |         |
ATCACCAAACTCTTGCTCGCCATACTCGGTCCGCTCATGGTGCTCCAGGCTAGCATAATT
IleThrLysLeuLeuLeuAlaIleLeuGlyProLeuMETValLeuGlnAlaSerIleIle 250       260       270       280       290       300
         |         |         |         |         |         |
CGAGTGCCGTACTTCGTACGCGCTCAAGGCCTCATTCGTGCATGCATGTTGGTGCGGAAA
ArgValProTyrPheValArgAlaGlnGlyLeuIleArgAlaCysMETLeuValArgLys

310
         |
GCCGCCGGGGGTCATTAT
AlaAlaGlyGlyHisTyr
```

FIG. 18

```
         10          20          30         40          50         60
          |           |           |          |           |          |
CTCTTGACCTTGTCACCACACTATAAAGTGTTCCTTGCCAGGTTCGTATGGTGGCTACAA
LeuLeuThrLeuSerProHisTyrLysValPheLeuAlaArgPheValTrpTrpLeuGln 70          80          90        100         110        120
          |           |           |          |           |          |
TATCTCATCACCAGAACCGAAGCGCATCTGCAAGTGTGGGTCCCCCCTCTCAACGTTCGG
TyrLeuIleThrArgThrGluAlaHisLeuGlnValTrpValProProLeuAsnValArg 130         140         150        160         170        180
          |           |           |          |           |          |
GGGGGTCGCGATGCCATCACCCTCCTCACATGCGTGGTCCACCCAGAGCTAATCTTCGAC
GlyGlyArgAspAlaIleThrLeuLeuThrCysValValHisProGluLeuIlePheAsp 190         200         210        220         230        240
          |           |           |          |           |          |
ATCACAAAATATTTGCTCGCCATATTCGGCCCGCTCATGGTGCTCCAGGCCGGCATAACT
IleThrLysTyrLeuLeuAlaIlePheGlyProLeuMETValLeuGlnAlaGlyIleThr 250         260         270        280         290        300
          |           |           |          |           |          |
AGAGTGCCGTACTTCGTGCGCGCACAAGGGCTCATTCGTGCATGCATGTTGGTGCGGAAA
ArgValProTyrPheValArgAlaGlnGlyLeuIleArgAlaCysMETLeuValArgLys

310
          |
GTTGCTGGGGGCCATTAT
ValAlaGlyGlyHisTyr
```

FIG. 19

```
          10         20         30         40         50         60
          |          |          |          |          |          |
CCGTGTTGAGGAGTCAATTTACCAATGTTGTGACTTGGCCCCCGAAGCCAAACTGGCCAT
 ArgValGluGluSerIleTyrGlnCysCysAspLeuAlaProGluAlaLysLeuAlaIle 70         80         90        100        110        120
          |          |          |          |          |          |
AAAGTCGCCCACAGAGCGGCTCTATATCGGGGGTCCCCTGACTAATTCAAAAGGGCAGAA
 LysSerProThrGluArgLeuTyrIleGlyGlyProLeuThrAsnSerLysGlyGlnAsn 130        140        150        160        170        180
          |          |          |          |          |          |
CTGCGGTTACTGCCGGTGCCGCGCGAGCCTGCTGACGACTAGCTGCGGTAATACCCTCAC
 CysGlyTyrCysArgCysArgAlaSerLeuLeuThrThrSerCysGlyAsnThrLeuThr 190        200        210        220        230        240
          |          |          |          |          |          |
ATGTCACCTGAAAGCCACTGCGGCCTGTCGAGCTGCGAAGCTCCAGGACTGCACGATGCT
 CysHisLeuLysAlaThrAlaAlaCysArgAlaAlaLysLeuGlnAspCysThrMETLeu 250        260        270        280        290        300
          |          |          |          |          |          |
CGTGAACGGAGACGACCTTGTCGTTATCTGTGAAAGCGCGGGGACCCAGGAGGACGCGGC
 ValAsnGlyAspAspLeuValValIleCysGluSerAlaGlyThrGlnGluAspAlaAla

310
          |
GAGCCTACGAGTC
 SerLeuArgVal
```

FIG. 20

```
         10        20        30        40        50        60
          |         |         |         |         |         |
CCGTGTTGAGGAGTCAATTTACCAATGTTGTGACTTGGCCCCCGAAGCCAAACTGGCCAT
 ArgValGluGluSerIleTyrGlnCysCysAspLeuAlaProGluAlaLysLeuAlaIle 70        80        90       100       110       120
          |         |         |         |         |         |
AAAGTCGCCCACAGAGCGGCTCTATATCGGGGGTCCCCTGACTAATTCAAAAGGGCAGAA
 LysSerProThrGluArgLeuTyrIleGlyGlyProLeuThrAsnSerLysGlyGlnAsn 130       140       150       160       170       180
          |         |         |         |         |         |
CTGCGGTTACTGCCGGTGCCGCGCGAGCCTGCTGACGACTAGCTGCGGTAATACCCTCAC
 CysGlyTyrCysArgCysArgAlaSerLeuLeuThrThrSerCysGlyAsnThrLeuThr 190       200       210       220       230       240
          |         |         |         |         |         |
ATGTCACCTGAAAGCCACTGCGGCCTGTCGAGCTGCGAAGCTCCAGGACTGCACGATGCT
 CysHisLeuLysAlaThrAlaAlaCysArgAlaAlaLysLeuGlnAspCysThrMETLeu 250       260       270       280       290       300
          |         |         |         |         |         |
CGTGAACGGAGACGACCTTGTCGTTATCTGTGAAAGCGCGGGGACCCAGGAGGACGCGGC
 ValAsnGlyAspAspLeuValValIleCysGluSerAlaGlyThrGlnGluAspAlaAla

310
          |
GAGCCTACGAGTC
 SerLeuArgVal
```

FIG. 21

```
          10        20        30        40        50        60
          |         |         |         |         |         |
CCGTGTTGAGGAGTCAATTTACCAATGTTGTGACTTGGCCCCCGAAGCCAAACTGGCCAT
 ArgValGluGluSerIleTyrGlnCysCysAspLeuAlaProGluAlaLysLeuAlaIle 70        80        90       100       110       120
          |         |         |         |         |         |
AAAGTCGCTCACAGAGCGGCTCTATATCGGGGGTCCCCTGACTAATTCAAAAGGGCAGAA
 LysSerLeuThrGluArgLeuTyrIleGlyGlyProLeuThrAsnSerLysGlyGlnAsn 130       140       150       160       170       180
          |         |         |         |         |         |
CTGCGGTTACCGCCGGTGCCACGCGAGCGGCGTGCTGACGACTAGCTGCGGTAATACCCT
 CysGlyTyrArgArgCysHisAlaSerGlyValLeuThrThrSerCysGlyAsnThrLeu 190       200       210       220       230       240
          |         |         |         |         |         |
CACATGTCACCTGAAAGCCACTGCGGCCTGTCGAGCTGCGAAGCTCCGGGACTGCACGAT
 ThrCysHisLeuLysAlaThrAlaAlaCysArgAlaAlaLysLeuArgAspCysThrMET 250       260       270       280
          |         |         |         |
GCTCGTGAACGGAGATGACCTTGTCGTTATCTGTGAAAGCGCGGG
 LeuValAsnGlyAspAspLeuValValIleCysGluSerAla
```

FIG. 22

```
          10        20        30        40        50        60
          |         |         |         |         |         |
CCGTGTTGAGGAGTCAATTTACCAATGTTGTGACTTGGCCCCCGAAGCCAAACTGGCCAT
ArgValGluGluSerIleTyrGlnCysCysAspLeuAlaProGluAlaLysLeuAlaIle 70        80        90       100       110       120
          |         |         |         |         |         |
AAAGTCGCTCACAGAGCGGCTCTATATCGGGGGTCCCCTGACTAATTCAAAAGGGCAGAA
LysSerLeuThrGluArgLeuTyrIleGlyGlyProLeuThrAsnSerLysGlyGlnAsn 130       140       150       160       170       180
          |         |         |         |         |         |
CTGCGGTTACCGCCGGTGCCGCGCGAGCCTGCTGACGACTAGCTGCGGTAATACCCTCAC
CysGlyTyrArgArgCysArgAlaSerLeuLeuThrThrSerCysGlyAsnThrLeuThr 190       200       210       220       230       240
          |         |         |         |         |         |
ATGTCACCTGAAAGCCACTGCGGCCTGTCGAGCTGCGAAGCTCCGGGACTGCACGATGCT
CysHisLeuLysAlaThrAlaAlaCysArgAlaAlaLysLeuArgAspCysThrMETLeu 250       260       270       280
          |         |         |         |
CGTGAACGGAGACGACCTTGTCGTTATCTGTGAAAGCGCGGG
ValAsnGlyAspAspLeuValValIleCysGluSerAla
```

FIG. 23

```
          10        20        30        40        50        60
           |         |         |         |         |         |
CCGTGTTGAGGAGTCAATTTACCAATGTTGTGACTTGGCCCCCGAAGCCAAACTGGCCAT
 ArgValGluGluSerIleTyrGlnCysCysAspLeuAlaProGluAlaLysLeuAlaIle 70        80        90       100       110       120
           |         |         |         |         |         |
AAAGTCGCTCACAGAGCGGCTCTATATCGGGGGTCCCCTGACTAATTCAAAAGGGCAGAA
 LysSerLeuThrGluArgLeuTyrIleGlyGlyProLeuThrAsnSerLysGlyGlnAsn 130       140       150       160       170       180
           |         |         |         |         |         |
CTGCGGTTACCGCCGGTGCCACGCGAGCGGCGTGCTGACGACTAGCTGCGGTAATACCCT
 CysGlyTyrArgArgCysHisAlaSerGlyValLeuThrThrSerCysGlyAsnThrLeu 190       200
           |         |
CACATGTCACCTGAAAGCCACTGCGGCC
 ThrCysHisLeuLysAlaThrAlaAla
```

FIG. 24

```
         10         20         30         40         50         60
          |          |          |          |          |          |
CCGTGTTGAGGAGTCAATTTACCAATGTTGTGACTTGGCCCCCGAAGCCAAACTGGCCAT
 ArgValGluGluSerIleTyrGlnCysCysAspLeuAlaProGluAlaLysLeuAlaIle 70         80         90        100        110        120
          |          |          |          |          |          |
AAAGTCGCTCACAGAGCGGCTCTATATCGGGGGTCCCCTGACTAATTCAAAAGGGCAGAA
 LysSerLeuThrGluArgLeuTyrIleGlyGlyProLeuThrAsnSerLysGlyGlnAsn 130        140        150        160        170        180
          |          |          |          |          |          |
CTGCGGTTACCGCCGGTGCCACGCGAGCGGCGTGCTGACGACTAGCTGCGGTAATACCCT
 CysGlyTyrArgArgCysHisAlaSerGlyValLeuThrThrSerCysGlyAsnThrLeu 190        200        210        220        230        240
          |          |          |          |          |          |
CACATGTCGCCTGAAAGCCACTGCGGCCTGTCGAGCTGCGAAGCTCCGGGACTGCACGAT
 ThrCysArgLeuLysAlaThrAlaAlaCysArgAlaAlaLysLeuArgAspCysThrMET 250        260        270        280        290        300
          |          |          |          |          |          |
GCTCGTGAACGGAGATGACCTTGTCGTTATCTGTGAAAGCGCGGGGACCCAGGAGGACGC
 LeuValAsnGlyAspAspLeuValValIleCysGluSerAlaGlyThrGlnGluAspAla

310
          |
GGCGAGCCTACGAGTC
 AlaSerLeuArgVal
```

FIG. 25

```
              828           842    849 853                           880
KHCV-LBC1   LLTLSPHYKVFLARFIWWLQYLITRTEAHLQVWVPPLNVRGGRDAIILLTCVV
KHCV-LBC23  --------------F------L---T----------------------A-A-
KHCV-LBC26  --------------F------L---T--------------------------
KHCV-LBC20  --------------F------L---T------------------V-----A-

KHCV-LBC2   -F-------------------L------F---A-------I-----------A-
KHCV-LBC3   -F----Y--------------L------F---A-------I-----------A-A-
KHCV-LBC25  -F----Y---L----L------F---A-------A-----------M---
KHCV-LBC21  --------------LM-----FL--A---------S---------------A-
KHCV-LBC27  --------------LM-----FL--A---------S---------------A-
KHCV-LBC28  --------------LM-----FL--A----R----S---------------A-
JHCV-NCI    ------Y--------------L------F---A-------------------A-
JHCV-OSAKA  ------Y--------------L------FT--A--D-H--I----A---------M-A-

HCPT-CHIRON A--------RYISWCL------L--V--Q-H--I-----------V---M-A-

933
KHCV-LBC1   HPELIFDITKYLLAIFGPLMVLQAGITRVPYFVRAQGLIRACMLARKVVGGHY
KHCV-LBC23  -----------L----L---------S-I----S-----------V--AA----
KHCV-LBC26  -----------L----L--P-----S-I------------------V---A----
KHCV-LBC20  Y----------L---TL---------LI-------S --------V---A----

KHCV-LBC2   -S--------I----L---------L-------S-----
KHCV-LBC3   ---P----------------------------W---------------A----
KHCV-LBC25  ----------I---VL---T-------------W-------V-NIA----
KHCV-LBC21  Y----------L---TL---------L-----------------V--------
KHCV-LBC27  Y----L----L----L--------S-I-----------------V--AA----
KHCV-LBC28  Y----------L---TL---------L------------------V---A----
JHCV-NCI    ---------L----L-----------------------------V---A----
JHCV-OSAKA  ---------L-I--L----------------------H----V---A----

HCPT-CHIRON --T-V-----L---V----WI---SLLK------V---L-F-A----MI----
```

```
NS5B-LBC1   CCGTGTTGAGGAGTCAATTTACCAATGTTGTGACTTGGCCCCCGAAGCCAAACTGGCCATAAAGTCGCTCACAGAGCGGC
NS5B-20     --------------------------------------------------------------------C-----------
NS5B-23     --------------------------------------------------------------------------------
NS5B-24     --------------------------A-----------------------------------------C-----------
NS5B-25     --------------------------------------------------------------------------------
NS5B-27     --------------------------------------------------------------------C-----------
NS5B-28     --------------------------------------------------------------------------------

NS5B-LBC1   TCTATATCGGGGGTCCCCTGACTAATTCAAAAGGGCAGAACTGCGGTTACCGCCGGTGCCGCGCGAGCGGCGTGCTGACGA
NS5B-LBC20  ------------------------------------T-------------T---------------  --C----------
NS5B-LBC23  -----------------------------------------------------------A---------------------
NS5B-LBC24  ------------------------------------------------------------------  C------------
NS5B-LBC25  ------------------------------------------------------------------  --C----------
NS5B-LBC27  -----------------------------------------------------------A---------------------
NS5B-LBC28  -----------------------------------------------------------A---------------------

NS5B-LBC1   CTAGCTGCGGTAATACCCTCACATGTTACCTGAAAGCCACTGCGGCCTGTCGAGCTGCGAAGCTCCGGGACTGCACGATGC
NS5B-LBC20  --------------------------C---------------------------------------A--------------
NS5B-LBC23  --------------------------C------------------------------------------------------
NS5B-LBC24  --------------------------C----------------------------------A-------------------
NS5B-LBC25  --------------------------C------------------------------------------------------
NS5B-LBC27   --------------------------C---------------------
NS5B-LBC28  --------------------------CG-----------------------------------------------------

NS5B-LBC1   TCGTGAACGGAGACGACCTTGTCGTTATCTGTGAAAGCGCGGGAACCCAAGAGGATGCGGCGAGCCTACGAGTC
NS5B-LBC20  -------------------------------------------G-----G-----C------------------
NS5B-LBC23  ----------------T-----------------------
NS5B-LBC24  ----------------------------------------
NS5B-LBC25  ----------------------------------------
NS5B-LBC27
NS5B-LBC28  ----------------T--------------------------G-----G-----C------------------
```

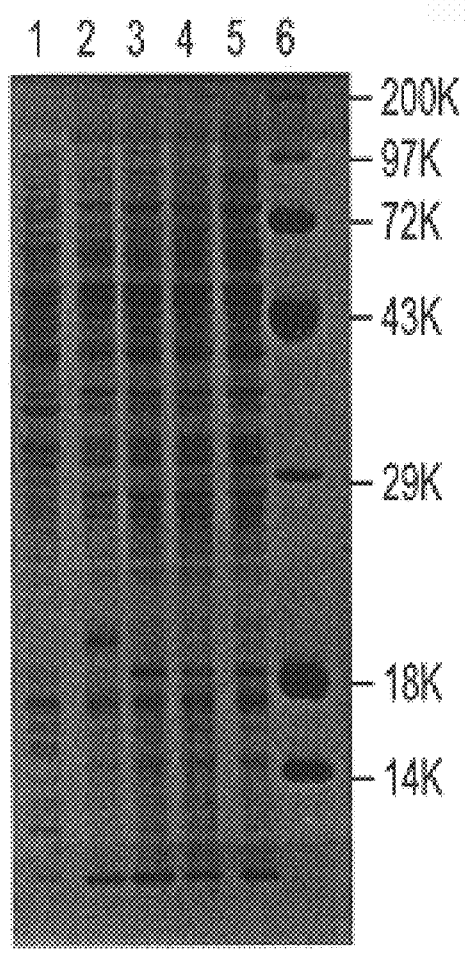
FIG. 32A
FIG. 32B

```
          10         20         30         40         50         60
ATGCAAATTT TCGTCAAAAC TCTAACAGGG AAGACTATAA CCCTAGAGGT TGAATCTTCC
TACGTTTAAA AGCAGTTTTG AGATTGTCCC TTCTGATATT GGGATCTCCA ACTTAGAAGG 70         80         90        100        110        120
GACACTATTG ACAACGTCAA AAGTAAAATT CAAGATAAAG AAGGTATCCC TCCGGATCAG
CTGTGATAAC TGTTGCAGTT TTCATTTTAA GTTCTATTTC TTCCATAGGG AGGCCTAGTC 130        140        150        160        170        180
CAGAGATTGA TTTTTGCTGG TAAGCAACTA GAAGATGGTA GAACCTTGTC TGACTACAAC
GTCTCTAACT AAAAACGACC ATTCGTTGAT CTTCTACCAT CTTGGAACAG ACTGATGTTG 190        200        210        220
ATCCAAAAGG AATCTACTCT TCACTTGGTG TTGAGACTCC GCGGTGGT
TAGGTTTTCC TTAGATGAGA AGTGAACCAC AACTCTGAGG CGCCACCA
```

FIG. 33

HEPATITIS C DIAGNOSTICS AND VACCINES

FIELD OF THE INVENTION

The present invention relates to polynucleotides derived from cDNA of a novel type of hepatitis C virus Korean type hepatitis C virus (KHCV), polypeptides encoded therein and antibodies directed against the polypeptides; and to diagnostics and vaccines employing any of these reagents, i.e., said polynucleotides, polypeptides and antibodies, as an active ingredient.

BACKGROUND OF THE INVENTION

In general, virus-induced hepatitis has been known to be caused by various hepatitis viruses including hepatitis A virus, hepatitis B virus, hepatitis delta virus, hepatitis E virus, Cytomegalo virus and Esptein-Barr virus; and the genotypes of the viruses have been discovered since 1980, facilitating the development of diagnostics, vaccines and therapeutic agents.

Further, it has been discovered that a new type of hepatitis nicknamed as non-A non-B or C hepatitis, accounts for 80 to 90% of hepatitis caused by blood transfusion (Lancet, 2, 838–841 (1975)); and such post-transfusion hepatitis frequently progresses to cirrhosis or hepatocellular carcinoma up to about 50%.

The number of hepatitis C virus (HCV) present in patient's blood is generally very small and the identity or specificity of the antigen and antibody systems associated with HCV has not been completely understood; and therefore, there have been many difficulties for developing therapeutic or diagnostic agents.

Consequently, the study on HCV has attracted a great deal of attention from numerous researchers (see, e.g., Alter, H. J. et al., Lancet, 459–463(1978); Tabor, E. et al., Lancet, 463–466 (1978); Hollinger, F. B. et al., Intervirology, 10, 60–68(1978); Wyke, R. J. et al., Lancet, 520–524(1979); Bradley, D. W. et al., J. Med. Virol., 9, 253–269(1979)).

Bradley et al., as discribed in Gastroenterology, 88, 773–779(1985), were able to determine the biochemical and biophysical characteristics of HCV by: infecting a champanzee with the serum of a hepatitis C patient; obtaining quantities of serum therefrom; extracting HCV from the serum; and analysing and studying HCV therewith.

Thereafter, many new studies were made with the HCV viruses isolated by employing the Bradley method for the development of agents to diagnose, prevent and/or treat hepatitis C.

Choo et al. cloned a partial cDNA fragment of HCV extracted from the serum of champanzee which had been infected with the serum of a hepatitis C patient; and proved that the protein produced by expressing the cDNA fragment in E. coli and yeast cell was immunologically reactive with the antibodies obtained from the serum of hepatitis C patients (Science 244, 359–362(1989).

Kuo et al. disclosed in Science, 244, 362–364(1989) that C100-3 protein prepared by expressing a partial HCV cDNA fragment, which was identified by Chiron Co. in U.S.A., fused with superoxide dismutase (SOD) gene in yeast was immunoreactive with the serum of hepatitis C patients and with 70% of the serum from those patients with post-transfusion hepatitis.

Further, Houghton et al. described the usefulness of HCV antigens, especially C100-3, encoded in HCV genomic sequence isolated from a champanzee contracted with hepatitis C (hereinafter, it is referred to as "American type HCV") for the preparation of vaccines and diagnostic agents capable of detecting anti-HCV antibodies (PCT WO 89/04669; WO 90/11089); and, established a diagnostic method employing enzyme immuno assay with said antigens, e.g., C100-3.

On the basis of the above invention, Ortho Diagnostic Systems Inc. of U.S.A. developed and distributed diagnostic agents for detecting anti-HCV antibodies in 1990. However, said C100-3 antigen used as the active ingredient for the diagnostic agents reacts only with the antibodies of patients with chronic hepatitis C, not with those of patients with acute hepatitis C especially during the early stage of the disease; and, further, it often exhibits false positive results due to the reaction of the fused protein, SOD (Shimizu, Y. K. et al., Proc. Natl. Acad. Sci. U.S.A., 87, 6441 (1990)).

On the other hand, partial HCV cDNA clones were prepared by employing the same method as of Houghton et al. from HCV taken from the serum collected from Japanese hepatitis C patients, including 5'-terminal region and structural genes encoding the core protein and the envelope protein; and the nucleotide sequence of the cDNA clones was determined from which it was discovered that the sequence is different from that of American type HCV about 10~15%, whereby the existence of a new type, what is called as Japaness type, of HCV was proven (Kubo, Y. et al., Nucl. Acid. Res., 17, 10367–10372(1989); Kato, N. et al., Proc. Japan. Acad., 65, 219–223(1990); Kaneko, S. et al., Lancet, 335, 976(1990); Takeuchi, K. et al., Gene, 91, 287–291 (1990); Takenchi, K. et al., Nucl. Acid. Res., 18, 4626 (1990); Takamizawa, A. et al., J. Virol., 65, 1105–1113 (1991)); and, the specificity of the antigens derived from Japanese type HCV for preparing vaccines and diagnostic agents against Japanese type HCV was described by Okamoto, H. et al. in Japan. J. Exp. Med., 60, 167–177 (1990).

Harada et al. further reported in J. Virol. 65, 3015 (1991) that when the core protein encoded in 5'-terminal portion of the structural gene was used for the antigen to diagnose anti-HCV antibodies which may be present in samples taken from putative patients, the antibodies could be detected 6 to 8 weeks earlier from the time of infection than the case of using C100-3 protein.

Lesniewski et al. also disclosed in Europen Patent Publication No. 725354 (1990) an improved diagnostic method using multiple antigens which was more sensitive and specific than the method of using C100-3 antigen alone; and Wang described in EP Publiction No. 442394 (1991) another diagnostic method wherein polypeptides consisting of 15~65 amino acids with epitope(s) selected from 10 different HCV epitopes were employed as antigens for detecting anti-HCV antibodies.

The above disclosures show that HCV diagnosis can be improved by empolying a mixture of polypeptides with different epitope(s) instead of using only one kind of antigen.

Furthermore, envelope proteins which exist on the surface of virus in the form of glycoproteins have been surfaced as a possible means for the development of vaccines as well as diagnostic agents. In the case of flavivirus which is very similar to HCV, it has been known that envelope proteins and non-structural protein 1(NS 1) play an important role in the induction of an immuno reaction of a host cell, and in binding itself to the receptors of host cell (F. Preugschart, J. Virol., 65, 4749–4758 (1991)). In addition, it has been reported that the formation of antibodies against envelope proteins is closely connected to recovery from hepatitis C (Lesniewski, R. et al., p 59; Watanabe et al., p 82, The 3rd International HCV Symposium, Strasbourg, France (1991)).

Further, Houghton et al. suggested the possibility that envelope 2(E2). Protein may prove to be an important antigen for preparing hepatitis C vaccines for the reason that said E2 protein is supposed to have a close relationship with immunoreaction mechanism since the amino terminal region of the E2 protein exhibits a conspicuous species heterogeneity (The 3rd International HCV Symposium, p 20, Strasbourg, France, 1991); and a comparison of the nucleotide sequences between the Japanese type HCV genome and the American type HCV genome has revealed that, while the nucleotide sequences encoding core proteins have a homology of about 91%, those encoding envelope proteins have a homology of about 74% (Takeuchi, K. et al., J. Gen. Vir., 71, 3027–3033(1990)).

SUMMARY OF THE INVENTION

As shown above, HCVs discovered in different countries may exhibit heterogeneity in various regions; and such heterogeneity may be a critical factor in deciding the effectiveness of vaccines and the sensitivity and accuracy of diagnostic agents.

Accordingly, the present invention pertains to the isolation and characterization of a novel type of HCV which is isolated from Korean hepatitis C patients (KHCV) and different from the already discovered HCVs including the American type and the Japanese type.

More specifically, the present invention provides a fully sequenced cDNA of said KHCV and partially sequenced cDNAs of several HCV varieties. Portions of the cDNA sequences derived from KHCV are useful as probes or primers to diagnose the presence of the virus in putative samples; and, diagnostic kits and methods utilizing such nucloeotide sequences also constitute further aspects of the invention.

In addition, the present invention provides polypeptides encoded in the above cDNA which are useful as reagents in diagnostic tests and/or as components of vaccines.

Said polypeptides encompass various polypeptides comprising a KHCV epitope including recombinant polypeptides such as fused polypeptides with a non-HCV protein; and purified forms thereof.

An additional aspect of the invention pertains to a recombinant expression vector comprising an open reading frame (ORF) of KHCV cDNA wherein said ORF is operably linked to a regulatory sequence compatible with a desired host organism and such vector may comprise: a nucleotide sequence encoding a non-KHCV protein for the preparation of a fused polypeptide of a polypeptide derived from KHCV and other type(s) of protein or polypeptide(s); a host cell transformed with the recombinant expression vector; and a polypeptide produced therefrom.

A further aspect of the present invention is a method for producing a polypeptide containing a KHCV epitope comprising: culturing host cells transformed with an expression vector containing a sequence encoding a polypeptide containing a KHCV epitope; and a polypeptide containing a KHCV epitope produced thereby.

Another aspect of the invention includes monoclonal antibody directed against a KHCV epitope.

A still additional aspect of the invention is directed to a hybridoma cell producing such monoclonal antibody.

Still further aspects of the invention are a diagnostic agent comprising one or more polypeptides which contain one or more KHCV epitopes as (an) active component(s) for detecting anti-KHCV antibodies in putative samples; and a diagnostic kit comprising such agent.

Still other aspects of the invention are a diagnostic agent comprising one or more monoclonal antibodies directed against the KHCV antigen to be detected as (an) active component(s) for dectecting HCV antigens in putative samples; and a diagnostic kit comprising such agent.

Even further aspect of the invention is a vaccine for the treatment and/or prevention of HCV infection comprising a polypeptide containing a KHCV epitope, and an inactivated or attenuated HCV.

BRIEF DESCRIPTION OF THE DRAWINGS

The invention can be more readily understood by reference to the accompanying drawings, wherein:

FIGS. 2-1 to 2-16 show the nucleotide sequcence of KHCV-LBC1 (SEQ ID NO: 96) and the amino acid sequcence of the polypeptide encoded therein;

FIG. 3 shows the starting nucleotide number and the ending nucleotide number of each cDNA clone on KHCV-LBC1;

| Name of CDNA clone | Position in KHCV-LBC1 (Nucleotide Number) |
|---|---|
| KHCV 426 | from 301 to 726 |
| KHCV 652 | from 3928 to 4563 |
| KHCV 403 | from 6649 to 7050 |
| KHCV 752 | from 3208 to 3960 |
| KHCV 675 | from 4264 to 4938 |
| KHCV 240 | from 616 to 855 |
| KHCV 513 | from 814 to 1326 |
| KHCV 810 | from 1201 to 2016 |
| KHCV 798 | from 1945 to 2742 |
| KHCV 932 | from 6892 to 7824 |
| KHCV 496 | from 7642 to 8136 |
| KHCV 847 | from 7969 to 8814 |
| KHCV 494 | from 8722 to 9216 |
| KHCV 570 | from 2686 to 3300 |
| KHCV 1774 | from 4903 to 6677 |
| KHCV 266 | from 9160 to 9472 |
| KHCV 366 | from 1 to 366 |

Figure 4:
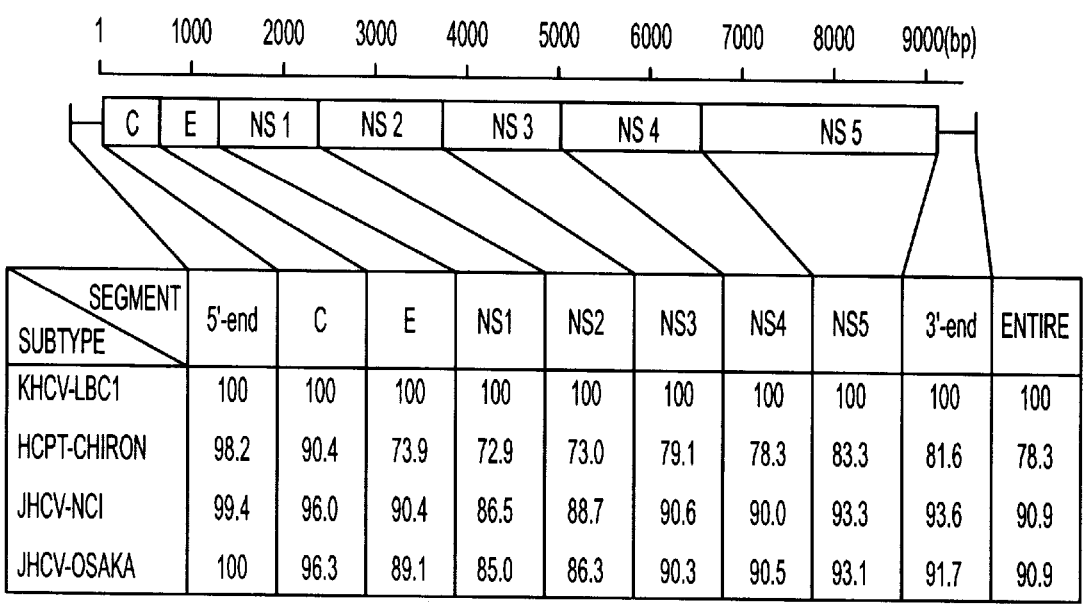
Figure 5:
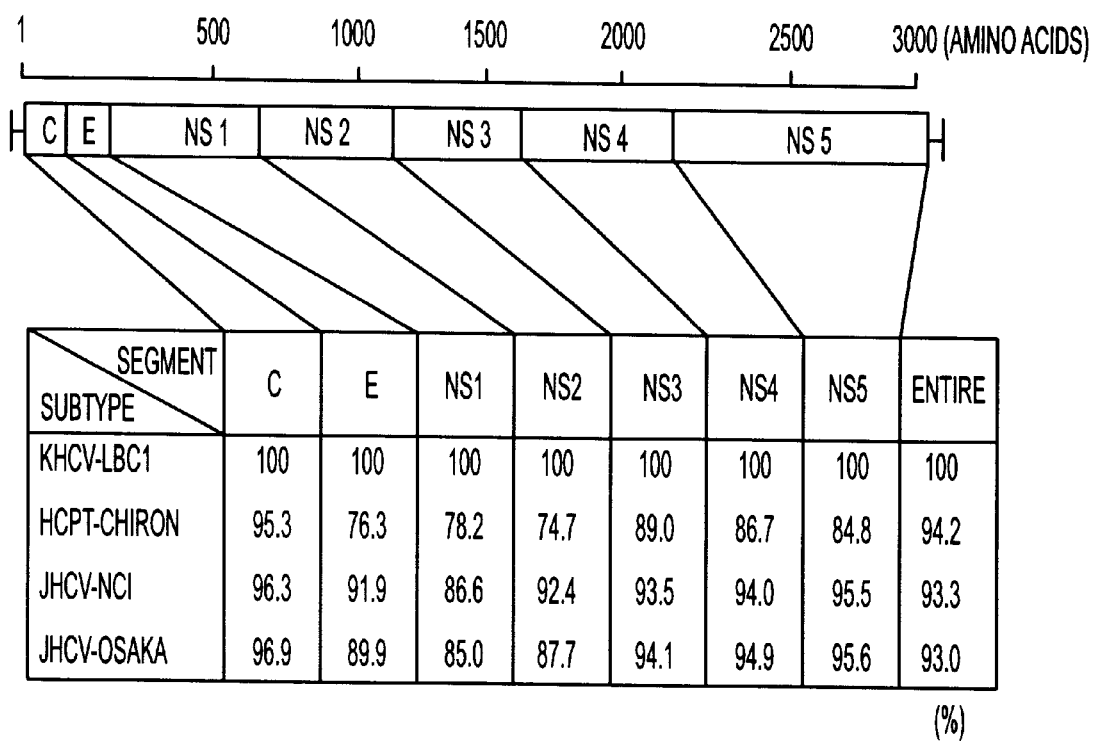
Figure 30:
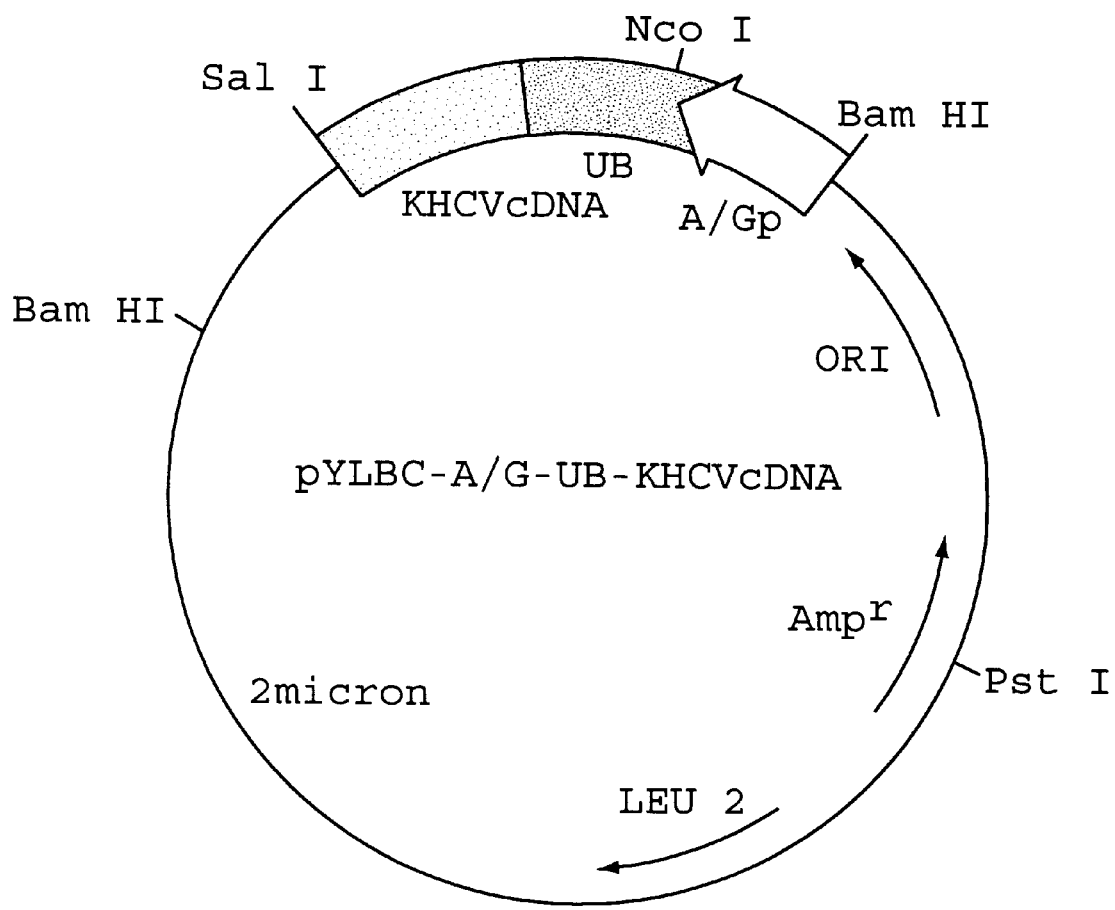
Figure 31A:
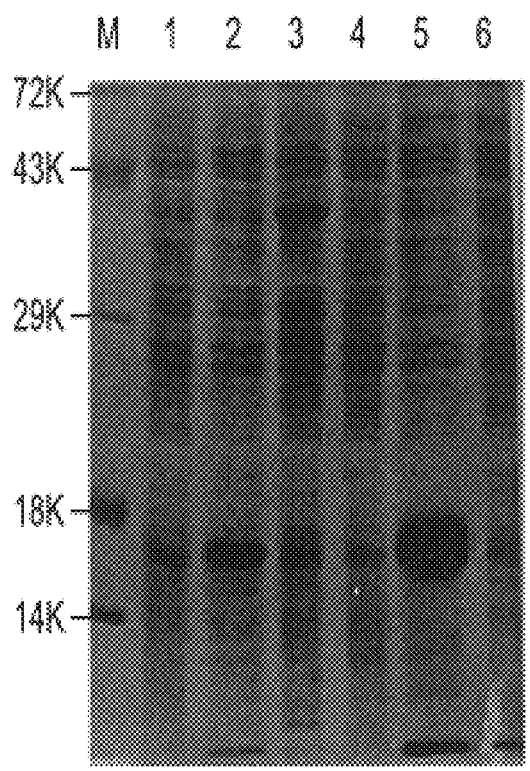
Figure 31B:
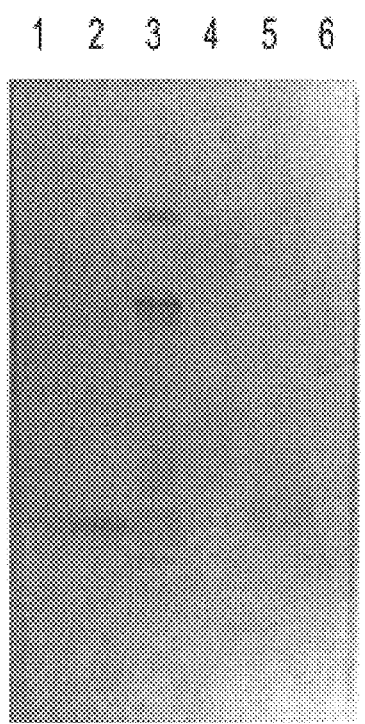
Figure 34:
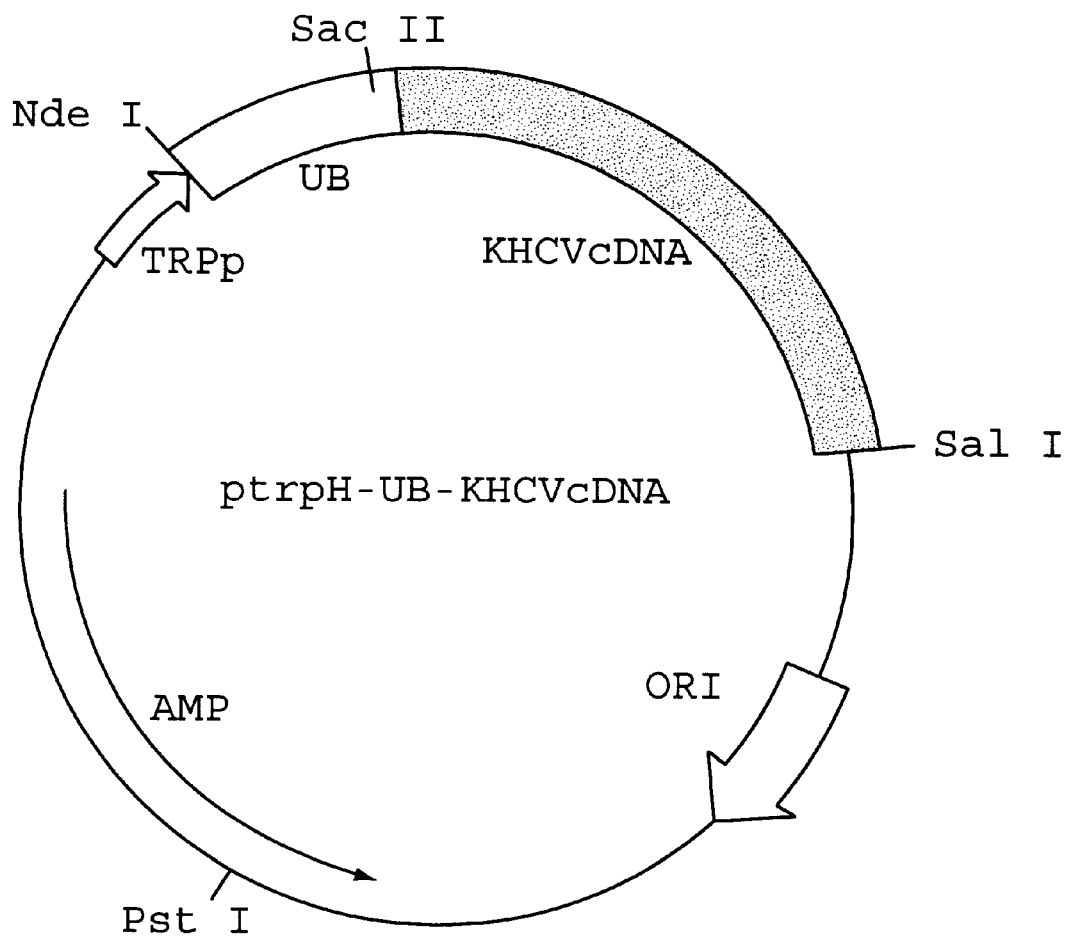
Figure 35:
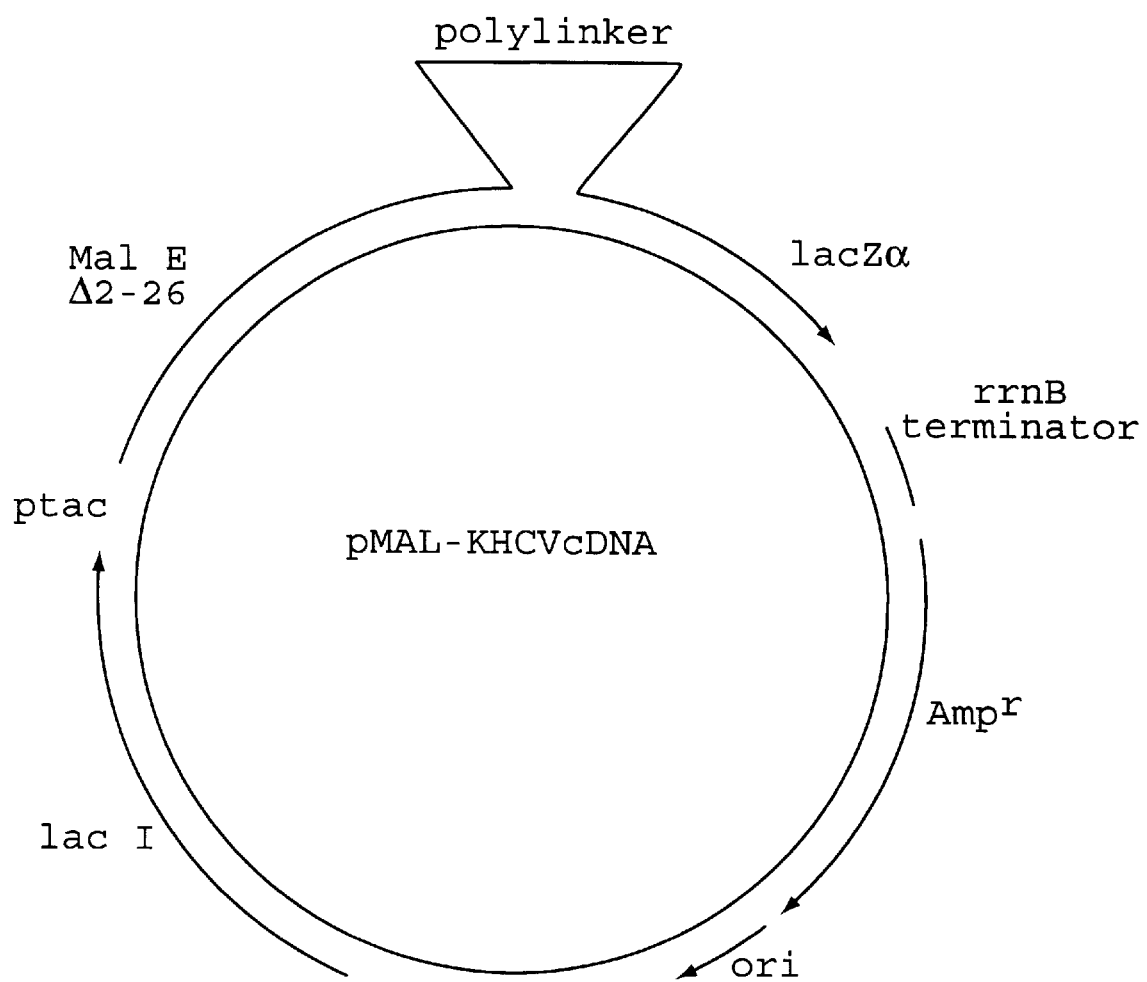
Figure 36:
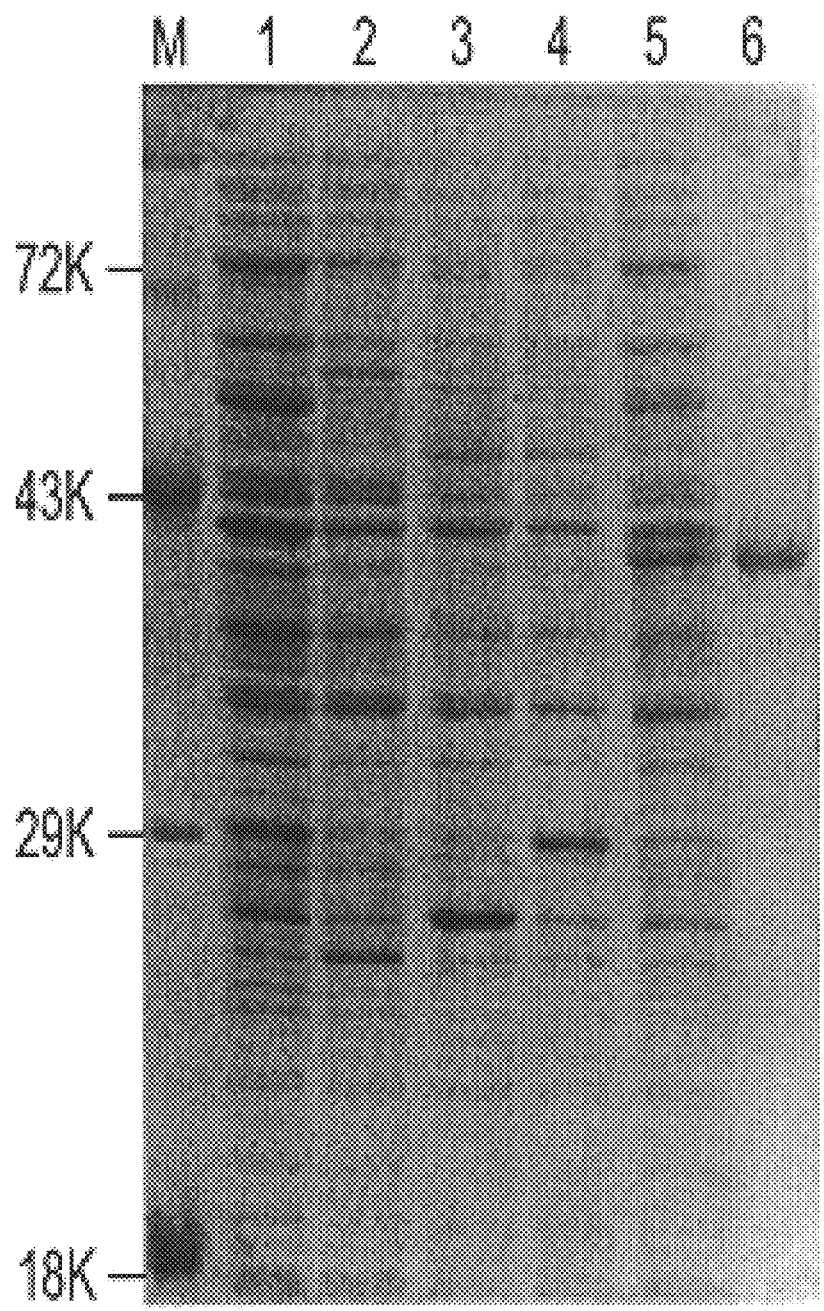
Figure 37:
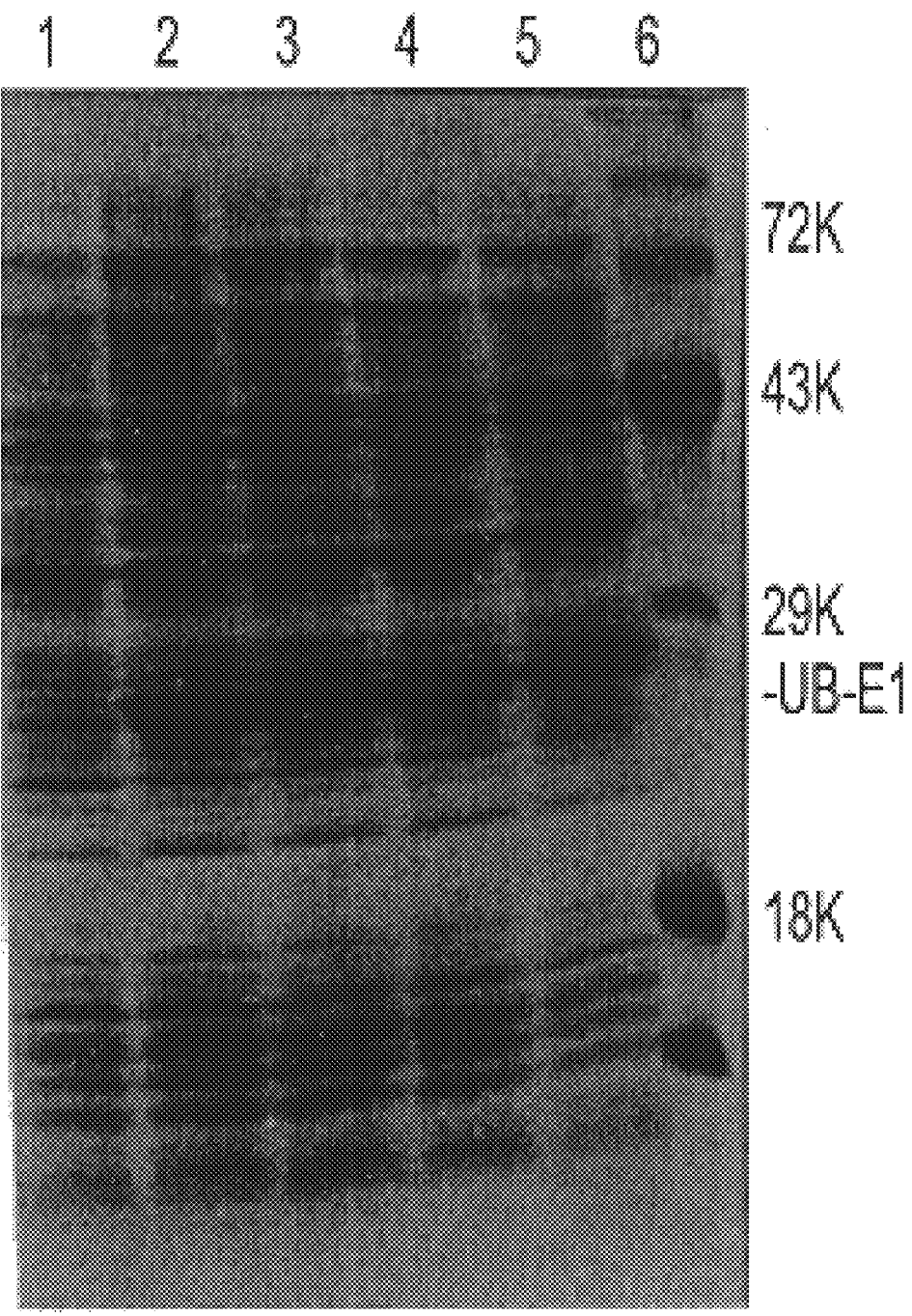

FIG. 4 shows the comparative analysis of the nucleotide sequences of KHCV-LBC1 and of genomes of American type HCV and Japanese type HCV;

FIG. 5 shows the comparative analysis of the amino acid sequences encoded in KHCV-LBC1, the American type HCV and the Japanese type HCV;

FIG. 6 shows the comparative analysis of the nucleotide sequences of 5'-terminal region of KHCV-LBC1 (SEQ ID NO: 98) and genomes of the American type HCV (SEQ ID NO: 99) and the Japanese type HCV (SEQ ID NO: 100);

FIG. 7 shows the nucleotide sequcence of cDNA fragment NS2-LBC2 (SEQ ID NO: 97) and the amino acid sequence of the polypeptide encoded therein;

FIG. 8 shows the nucleotide sequcence of cDNA fragment NS2-LBC3 (SEQ ID NO: 101) and the amino acid sequence of the polypeptide encoded therein;

FIG. 9 shows the nucleotide sequcence of cDNA fragment NS2-LBC20 (SEQ ID NO: 102) and the amino acid sequence of the polypeptide encoded therein;

FIG. 10 shows the nucleotide sequence of cDNA fragment NS2-LBC21 (SEQ ID NO: 103) and the amino acid sequence of the polypeptide encoded therein;

FIG. 11 shows the nucleotide sequence of cDNA fragment NS2-LBC23 (SEQ ID NO: 104) and the amino acid sequence of the polypeptide encoded therein;

FIG. 12 shows the nucleotide sequence of cDNA fragment NS2-LBC25 (SEQ ID NO: 105) and the amino acid sequence of the polypeptide encoded therein;

FIG. 13 shows the nucleotide sequence of cDNA fragment NS2-LBC26 (SEQ ID NO: 106) and the amino acid sequence of the polypeptide encoded therein;

FIG. 14 shows the nucleotide sequence of cDNA fragment NS2-LBC27 (SEQ ID NO: 107) and the amino acid sequence of the polypeptide encoded therein;

FIG. 15 shows the nucleotide sequence of cDNA fragment NS2-LBC28 (SEQ ID NO: 108) and the amino acid sequence of the polypeptide encoded therein;

FIG. 16 shows the nucleotide sequence of cDNA fragment NS2-LBC29 (SEQ ID NO: 109) and the amino acid sequence of the polypeptide encoded therein;

FIG. 17 shows the nucleotide sequence of cDNA fragment NS2-LBC30 (SEQ ID NO: 110) and the amino acid sequence of the polypeptide encoded therein;

FIG. 18 shows the nucleotide sequence of cDNA fragment NS2-LBC31 (SEQ ID NO: 111) and the amino acid sequence of the polypeptide encoded therein;

FIG. 19 shows the nucleotide sequence of cDNA fragment NS2-LBC32 (SEQ ID NO: 112) and the amino acid sequence of the polypeptide encoded therein;

FIG. 20 shows the nucleotide sequence of cDNA fragment NS5-LBC20 (SEQ ID NO: 113) and the amino acid sequence of the polypeptide encoded therein;

FIG. 21 shows the nucleotide sequence of cDNA fragment NS5-LBC21 (SEQ ID NO: 114) and the amino acid sequence of the polypeptide encoded therein;

FIG. 22 shows the nucleotide sequence of cDNA fragment NS5-LBC23 (SEQ ID NO: 115) and the amino acid sequence of the polypeptide encoded therein;

FIG. 23 shows the nucleotide sequence of cDNA fragment NS5-LBC25 (SEQ ID NO: 116) and the amino acid sequence of the polypeptide encoded therein;

FIG. 24 shows the nucleotide sequence of cDNA fragment NS5-LBC27 (SEQ ID NO: 117) and the amino acid sequence of the polypeptide encoded therein;

FIG. 25 shows the nucleotide sequence of cDNA fragment NS5-LBC28 (SEQ ID NO: 118) and the amino acid sequence of the polypeptide encoded therein;

FIG. 26 shows the comparative analysis of the amino acid sequences of polypeptides encoded in NS2 region of cDNA of KHCV variants (SEQ ID NO: 97), (SEQ ID NO: 101), (SEQ ID NO: 102), (SEQ ID NO: 103), (SEQ ID NO: 104), (SEQ ID NO: 105), (SEQ ID NO: 106), (SEQ ID NO: 107), (SEQ ID NO: 108), (SEQ ID NO: 119), (SEQ ID NO: 120), (SEQ ID NO: 119), (SEQ ID NO: 120), (SEQ ID NO: 121) and (SEQ ID NO: 122), respectively included in subtype KHCV-L1 or KHCV-L2;

Figure 27:
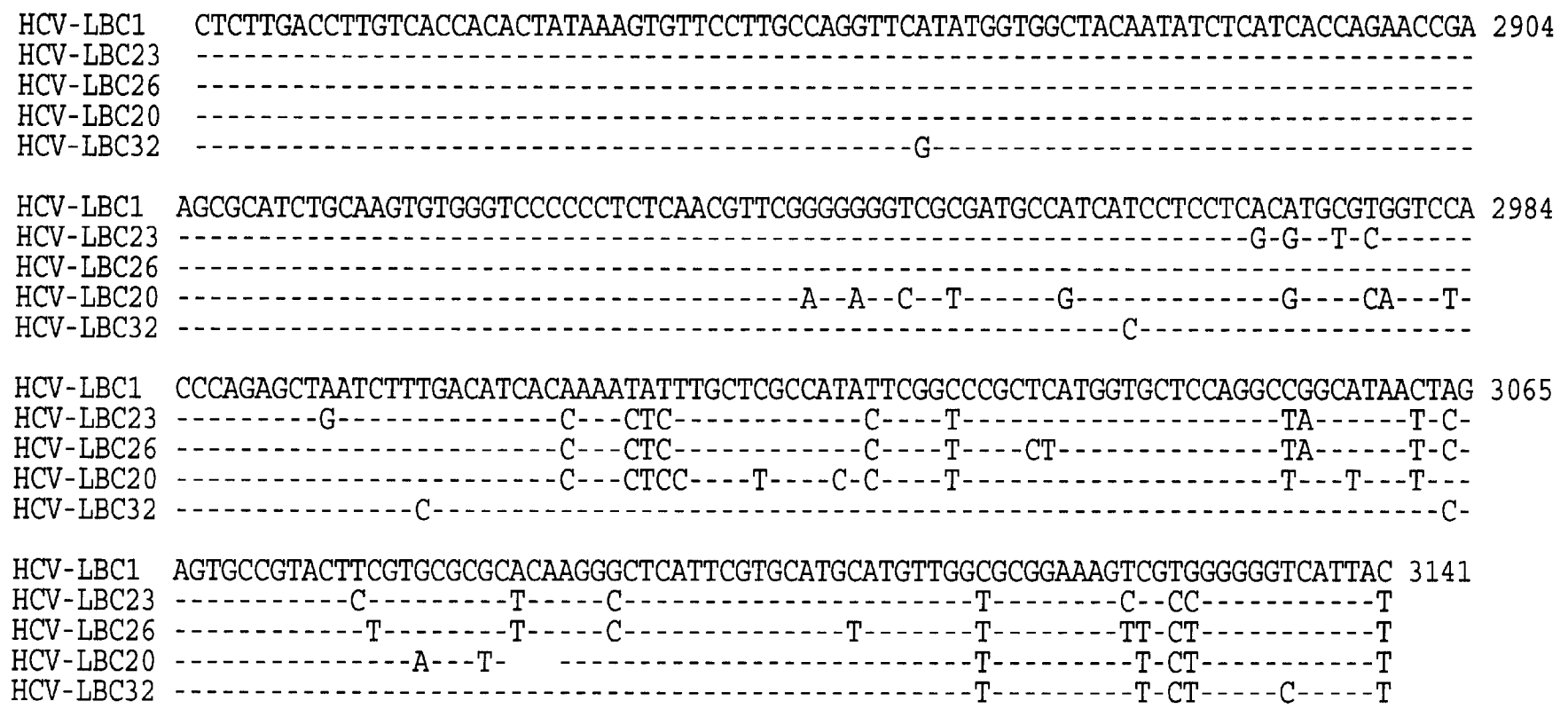

FIG. 27 shows the comparative analysis of the nucleotide sequeces of NS2 region of cDNA of KHCV variants (SEQ ID NO: 102), (SEQ ID NO: 104), (SEQ ID NO: 106), (SEQ ID NO: 112) and (SEQ ID NO: 119), respectively included in subtype KHCV-L1;

Figure 28:
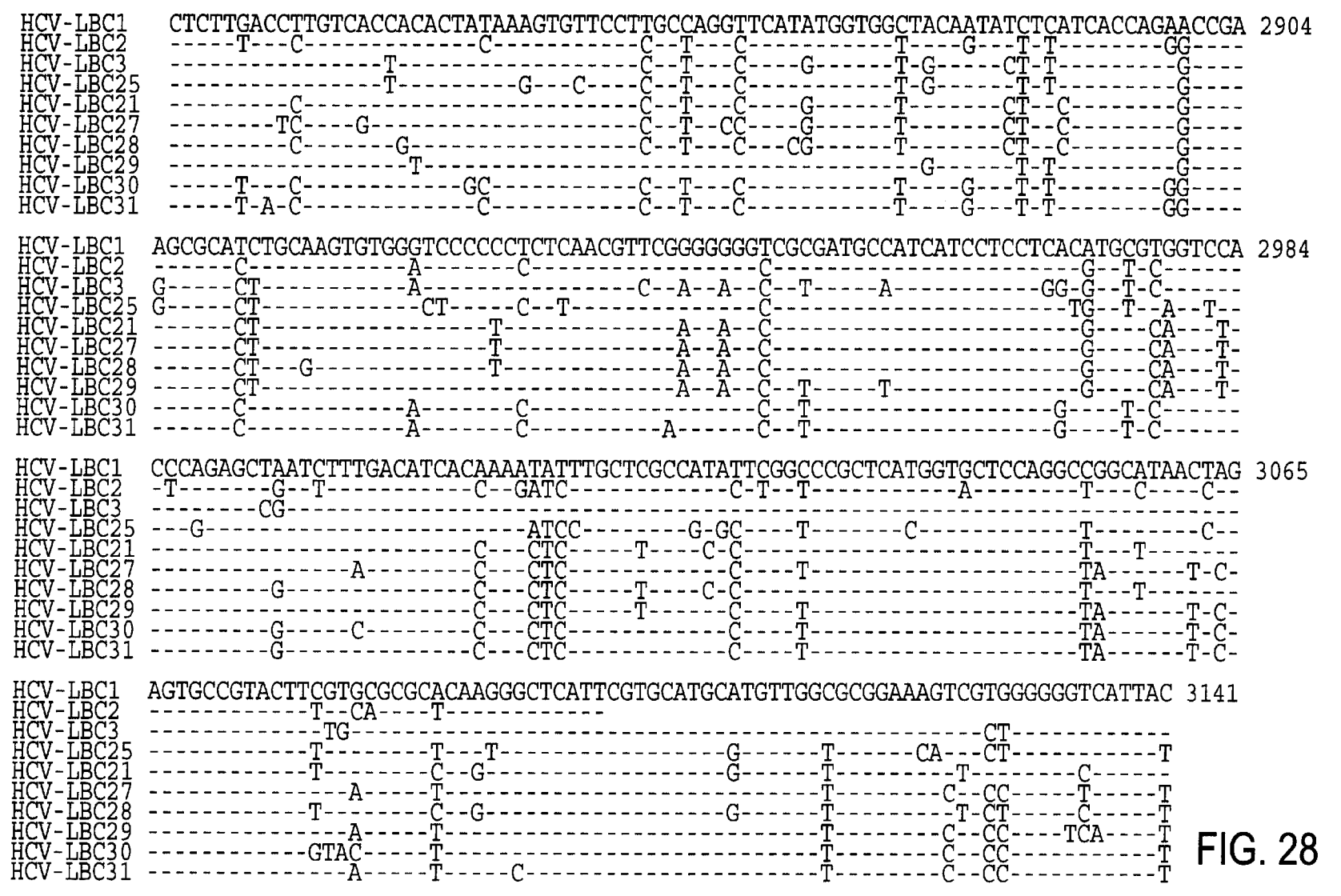

FIG. 28 shows the comparative analysis of the nucleotide sequences of NS2 region of cDNA of KHCV variants (SEQ ID NO: 97), (SEQ ID NO: 101), (SEQ ID NO: 103), (SEQ ID NO: 105), (SEQ ID NO: 107), (SEQ ID NO: 108), (SEQ ID NO: 109), (SEQ ID NO: 110), (SEQ ID NO: 111) and (SEQ ID NO: 119), respectively included in subtype KHCV-L2;

FIG. 29 shows the comparative analysis of the nucleotide sequences of NS5 region of cDNA of KHCV variants (SEQ ID NO: 113), (SEQ ID NO: 115), (SEQ ID NO: 116), (SEQ ID NO: 117), (SEQ ID NO: 118) and (SEQ ID NO: 123), respectively included in subtype KHCV-L1 and KHCV-L2, respectively;

FIG. 30 shows an expression vector constructed for the purpose of expressing a KHCV cDNA fragment in yeast cells;

FIGS. 31A and B show the result of SDS polyacrylamide gel electrophoresis (SDS-PAGE) after the expression of a KHCV cDNA fragment in yeast cells, and FIG. 31B shows the result of western blotting analysis with the gel of FIG. 31A;

FIGS. 32A and B show the results of SDS-PAGE (FIG. 31A) and western blotting analysis (FIG. 31B) exhibiting the production of KHCV E2N and E2C polypeptides in yeast cells;

FIG. 33 shows the nucleotide sequence of a chemically synthesized ubiquitin gene (SEQ ID NO: 124);

FIG. 34 shows the expression vector comprising trp promoter for the expression of a KHCV cDNA fragment in *E. coli* cells;

FIG. 35 shows the expression vector comprising tac promoter for the expression of a KHCV cDNA fragment in *E. coli* cells;

FIGS. 36 to 38 show the results of SDS-PAGE after the expression of a KHCV cDNA fragment in *E. coli* cells;

FIGS. 39 to 41 show the results of western blotting analyses with the gels of FIGS. 36 to 38;

FIG. 42 shows the result of SDS-PAGE after the expression of a KHCV cDNA fragment fused with an MBP gene under the control of tac promoter in *E. coli* cells;

FIG. 43 shows the result of western blotting analysis with the gel of FIG. 42;

FIG. 44 shows standard curves for enzyme immuno assay (EIA) varying with the concentration of KHCV antigen(s) used for the detection of anti-HCV antibodies in samples; and FIG. 45 shows a standard curve for EIA with monoclonal antibodies as a function of the concentration of KHCV antigen present in samples.

DETAILED DESCRIPTION OF THE INVENTION

All references cited herein are hereby incorporated in their entirety by reference.

As used herein, the following terms shall have the following meanings:

The term "hepatitis C virus" refers to a virus causative of non-A non-B hepatitis or hepatitis C. The terms HCV and NANBV, and the terms NANB hepatitis (NANBH) and hepatitis C are used interchangeably herein, respectively.

The term "Korean type of hepatitis C virus" or "KHCV" refers to a novel type of HCV which is isolated from Korean hepatitis C patients; and whose cDNA has an open reading frame of a nucleotide sequence encoding the amino acid sequence wherein the amino acids whose numbers are 842, 849 and 853 are phenylalanine, leucine and threonine, respectively; or leucine, phenylalanine and alanine, respectively.

The term "epitope" refers to an antigenic determinant of a polypeptide which is capable of eliciting an immune response in an immunologically competent host organism and/or is capable of specifically binding itself to a complementary antibody. An epitope of the present invention generally consists of at least 6 amino acids, preferably 7 or 8 amino acids.

The term "fragment" means a polynucleotide or polypeptide comprising a subsequence of one of the cDNAs or proteins of the invention. Such fragments can be produced by an enzymatic cleavage of larger molecules, using restriction endonucleases for the DNA and proteases for the proteins. The fragments of the invention, however, are not limited to the products from any particular form of enzymatic cleavage; and may include subsequences, the termini of which do not correspond to any enzymatic cleavage points. Such fragments can be made, e.g., by chemical synthesis, using the sequence data provided herein. Protein fragments can also be produced by expressing DNA fragments encoding the protein fragments. Such protein fragments can be useful in the present invention if they contain a sufficient number of amino acid residues to constitute an immunoreactive and/or antigenic determinant.

The term "open reading frame" refers to a region of a polynucleotide sequence where successive nucleotide triplets may be read as codons specifying amino acids to encode a polypeptide.

The term "expression vector" refers to a cloning vehicle designed to promote the expression of polynucleotide inserts.

The term "regulatory sequence" means a DNA sequence involved in regulating the expression of a polynucleotide sequence, which comprises, for example, promoter, ribosomal binding site, and terminator.

The term "recombinant KHCV polypeptide" refers to a polypeptide which contains at least a 6 amino acid sequence encoded in KHCV cDNAs of FIGS. 2-1 to 2-16 and FIGS. 7 to 25 and is linked to (an) amino acid(s) other than that to which it is linked in the polypeptide encoded in the KHCV cDNAs.

The term "purified KHCV polypeptide" refers to a KHCV polypeptide or a fragment thereof which is substantially pure and homogenous, and separated from cellular components which naturally accompany it. Generally, a purified KHCV polypeptide comprises over about 70 to 90% of the polypeptide, and more preferably at least 95% of the polypeptide.

The other terms used herein have normal and conventional meanings as used in the art.

The present invention will be more specifically illustrated hereinbelow.

Cloning of KHCV cDNA

KHCV cDNA library is prepared as follows:

HCV particles are isolated from the sera of Korean patients with hepatitis C by precipitation thereof with ultracentrifuge; the HCV RNA is extracted from the HCV particles; double stranded cDNAs are synthesized from the HCV RNA with a random primer or oligo d(T) primer and reverse transcriptase; the cDNA fragments are cloned, either after propagation by employing PCR or directly to UNI-ZAPXR vector (Stratagene Co. 11099 N. Torrey, Pines Road., Calif., U.S.A), after attachment of Eco RI adaptor thereto, and the vector is packaged into virus particles to prepare cDNA library (Saiki, P. K. et al., Science, 230, 1350(1985)).

Generally, hepatitis virus particles can be isolated from the serum or the liver of-patients or champanzees contracted with hapatitis. In the present invention, HCV particles are isolated from the sera of hepatitis C patients; and the total RNA of HCV is extracted from the HCV particles precipitated by ultracentrifuge followed by phenol extraction and ethanol precipitation.

Thereafter, said HCV total RNA is used as a template for the preparation of cDNA in the reaction employing a Zap-cDNA synthesis kit (Cat. No. 200400, Stratagene Co., 11099 N. Torrey Pines Rd., La Jolla, Calif. 92037, USA).

Said cDNA is synthesized by the reaction of reverse transcriptase, using the total RNA and random primer RANPSHCV or oligo d(T) primer (SEQ ID NO: 2), wherein primer RANPSHCV (SEQ ID NO: 1) (5'-TTT TTCATGAT-TGGTGGTGGAACTGGACCGTCTCGAG NNNNNN-3'; N refers to A, G, T or C) and oligo d(T) primer (5'-GAGAGAGAGAGAGAGAGAGAACTAGTCTCG AG(T)$_{18}$-3') comprise 6 random nucleotides (primer RANPSHCV) or 18 T(oligo d(T) primer) in each 3'-terminal region, and a recognition site of restriction endonuclease Xho I.

For the purpose of introducing a recognition site of Eco RI (5'-GAATTC-3') into the synthesized cDNA for the convenience of cloning, an Eco RI adaptor (SEQ ID NO: 3) (5'-CCCCCCGAATTCGGCACGAG-3') (3'-GGGGGGCTTAAGCCGTGCTC-5') is attached to the synthesized cDNA fragments. And, thereafter, the cDNA fragments are propagated by PCR with primer PSHCV (SEQ ID NO: 4) (5'-TTTTCATGATTGGTGGTGGA-3') and Eco RI primer (the upper stand of the Eco RI adaptor); the cDNA fragments are digested partially with restriction endonucleases Eco RI and Xho I; the digested cDNA is ligated with UNI-ZAPXR vector, a variant of λ gt 11, digested with Eco RI and Xho I; and, the resulting DNA is packaged in vitro into particles of λ phage with Gigapack II Gold Packaging Kit (Cat. No. 200214, Stratagene Co., USA) followed by amplification by infecting the particles into *E. coli* cells to prepare cDNA library.

The cDNA library is plated on *E. coli* cells to form phage plaques, which are, then, screened by an immunological method as described by Huynh (DNA cloning: A Practical Approach, Vol. 1, pp. 49–78, IRL Press, UK (1985)) to select the phage clones reactive with the antibody in the serum of hepatitis C patients, which are supposed to be able to produce polypeptides derived from KHCV cDNA.

On the other hand, the UNI-ZAPXR vector can be excised in *E. coli* to produce a phagemid pBluescript containing KHCV cDNA fragment (Short et al., Nucl. Acid. Res., 16, 7583–7600(1988)) which is easier to treat as a normal plasmid; and, further, pBluescript can be obtained optionally as either single-stranded or double-stranded form since it has f1 replication origin as well as Col E1 origin.

Double-stranded pBluescript DNA isolated from *E. coli* infected with positive plaque is digested with restriction endonucleases Eco RI and Xho I to confirm the existence and the length of the KHCV cDNA fragment inserted between the Eco RI and the Xho I recognition sites by gel electrophoresis; and the nucleotide sequence of the cDNA fragment is determined by using Sanger's method (Proc. Natl. Acad. Sci. U.S.A., 74, 5463(1977)).

Thereafter, new oligonucleotide probes are synthesized on the basis of the determined nucleotide sequence of the clone cDNA to screen the cDNA library for the purpose of obtaining the remaining region of a full KHCV cDNA; and, subsequently, the new cDNA clones so obtained are again used to screen to further obtain KHCV cDNA clones. Also, a portion of KHCV cDNA may be obtained by PCR, using the primers synthesized on the basis of the predetermined nucleotide sequence of KHCV cDNA.

The overlapping cDNA fragments may be connected to determine the full sequence of KHCV cDNA; and an open reading frame is deduced therefrom.

A KHCV cDNA which has the full cDNA sequence so obtained is designated as KHCV-LBC1, which was deposited with American Type Culture Collection (ATCC) on May 14, 1991, with an accession number of ATCC 75008 under the terms of the Budapest Treaty on the International Recognition of the Deposit of Microorganisms for the Purpose of Patent Procedure.

Figure 1:
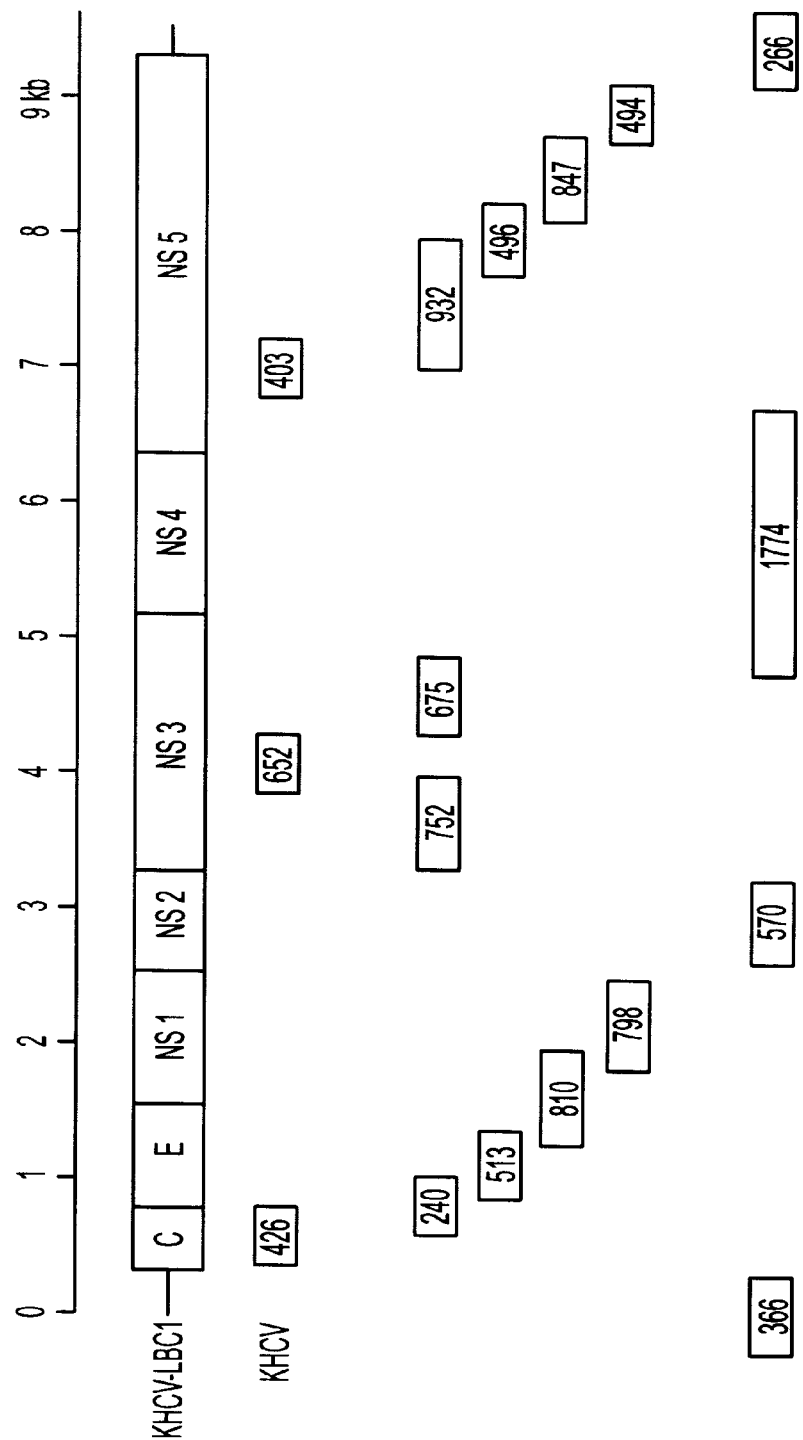
FIG. 1 shows the relative positions of various KHCV cDNA clones on KHCV-LBC 1.

The full nucleotide sequence of KHCV-LBC1 and the amino acid sequence encoded therein are described in FIGS. 2-1 to 2-11; and, the position of each cDNA clone on KHCV-LBC1 sequence is disclosed in FIGS. 1 and 3. KHCV-LBC1 has a long open reading frame consisting of 9030 nucleotides covering from the 343rd nucleotide (A) to the 9372 nd nucleotide (G), counting from 5'-end.

The identification number of a given amino acid is assigned, hereinafter depending on the position of the amino acid in the polypeptide encoded in the above 9030 nucleotides in the direction from the 5'- to the 3'-end.

In the 5'-terminal region of KHCV-LBC1 prepared in accordance with the present invention, 13 more nucleotides than the Japanes type HCV (Kato, N. et al., Proc. Natl. Acad. Sci. U.S.A. 87, 95224(1990)) are found to exist. As described in FIG. 6, in comparison with the American type HCV. There is, 1 more nucleotide discovered; and 3 nucleotides among the 22 nucleotides constructing a hairpin structure of the 5'-terminal region are determined to be different. The 5'-terminal region generally plays an important role in expressing a viral gene and regulation thereof; and, a hairpin structure consisting of 22 nucleotides is supposed to be a recognition site for replicase and core protein; and, therefore, even a minute structural difference in the region may entail a significant and material difference in its role or specificity.

Similarly, the full nucleotide sequence of KHCV-LBC1 and the amino acid sequence encoded therein are compared with those of the American type HCV and the Japanese type HCV, with the result that: in case of the American type, the nucleotide sequence of KHCV-LBC1 is homologous up to the level of about 78.3% and the amino acid sequence encoded therein exhibits about 84.2% homology; and, is case of the Japanese type, the nucleotide sequence has a 90.9% homology, and the amino sequence has a 93% homology (see FIGS. 4 to 6). The above results clearly show that KHCV-LBC1 is a cDNA of a new type of HCV which is distinctly different from the already identified HCVs.

Preparation of Partial cDNA Fragments of KHCV Variants

KHCV RNA is extracted from said KHCV isolated from the sera of hepatitis C patients, respectively; and cDNA of each KHCV RNA is synthesized by PCR to obtain cDNA fragments corresponding to the NS2 region or NS5 region. The length of each cDNA fragment so obtained is about 340 bp of NS2 and 320 bp NS5, respectively.

The cDNA fragments are inserted into M13mp18 and M13mp19 (New England Biolabs, 32 Tozer Road Beverly, Mass. 01915-5599, U.S.A) to determine their nucleotide sequences (see FIGS. 7 to 25). Their nucleotide sequences of the NS2 region have 91 to 94% homology (see FIGS. 27 and 28); and the NS5 region exhibits 96 to 99% homology (FIG. 29) while the amino acid sequences encoded in the NS2 and the NS5 regions have a homology of 90 to 94% and 93 to 99%, respectively (see FIG. 26).

Moreover, it is also discovered that, depending on the amino acids with the respective numbers of 842, 849 and 853 which are encoded in the NS2 region, KHCVs can be divided into two subtypes: i.e., KHCV-L1 and KHCV-L2. The cDNAs of KHCV included in KHCV-L1 encode phenylalanine, leucine and threonine as the amino acids with their respective identification numbers of 842, 849 and 853; while the cDNAs included in KHCV-L2 encode leucine, phenylalanine and alanine, respectively. As a subtype KHCV-L1, there are included: KHCV-LBC1, KHCV-LBC20, KHCV-LBC23, KHCV-LBC26 and KHCV-LBC32; while KHCV-L2 subtype includes: KHCV-LBC2, KHCV-LBC3, KHCV-LBC21, KHCV-LBC25, KHCV-LBC27, KHCV-LBC28, KHCV-LBC29, KHCV-LBC30 and KHCV-LBC31.

It should be noted that the above characteristics cannot be found in the case of the American type HCV wherein the amino acids are cysteine, phenylalamine and valine. However, the Japanese type has the same characteristics as KHCV-L2, i.e., the amino acids in the above positions are leucine, phenylalanine and alanine, respectively.

The M13 phage group (M13mp18-NS2L1) which contains M13mp18 phage comprising each of the cDNAs included in KHCV-L1, except KHCV-LBC1, i.e., KHCV-LBC20, KHCV-LBC23, KHCV-LBC26 and KHCV-LBC32 was deposited with American Type Culture Collection on Mar. 13, 1992 with the accession number of ATCC 75211, and, the M13 phage group (M13mp18-NS2L2) which contains M13 mp phage comprising each of the cDNAs included in KHCV-L2, i.e., KHCV-LBC2, KHCV-LBC3, KHCV-LBC21, KHCV-LBC25, KHCV-LBC27, KHCV-LBC28, KHCV-LBC29, KHCV-LBC30 and KHCV-LBC31 was deposited with ATCC on the same day with the accession number of ATCC 75212.

The cDNAs of this invention may be chemically synthesized in addition to the methods given in Examples hereof, using the nucleotide sequence information provided in FIGS. 2-1 to 2-16 and FIGS. 7 to 25. Such chemical synthesis can be carried out using a known method such as the phosphoamidite solid support method of Matteucci et al. (J. Am. Chem. Soc., 103, 3185(1981)).

Further, because of the degeneracy of the genetic code, it will be understood that there are many potential nucleotide sequences that could code for the amino acid sequence shown in FIGS. 2-1 to 2-16 and FIGS. 7 to 25.

Construction of an Expression Vector and Production of Protein Thereby

Various expression systems may be used to prepare an expression vector containing a KHCV cDNA fragment in accordance with the present invention, including a vector capable of directing production of a fused protein with other polypeptide than the one derived from KHCV.

For instance, such a vector system may be constructed by employing a ubiquitin expression system. In yeast, ubiquitin has been known to be excised by ubiquitinase on the exact site very next to Arg-Gly-Gly (Ozkaynak et al., Nature, 312, 663–666(1987)). Bachmair reported in Science, 234, 178–186(1986) that a foreign protein fused with ubiquitin can also be excised on the site next to Arg-Gly-Gly of ubiquitin.

Accordingly, a desired KHCV protein can be obtained by expressing a fused polynucleotide of a KHCV cDNA fragment and ubiquitin gene in yeast since the fused protein is then excised to remove ubiquitin by ubiquitinase of a yeast cell, and, as a result, the KHCV protein remains alone.

Further, if the fused polynucleotide comprising a KHCV cDNA fragment and a ubiquitin gene is expressed in *E. coli*, the fused protein containing ubiquitin would be obtained. The ubiquitin, however, can be excised in vitro by ubiquitinase; and KHCV protein free from ubiquitinase can be obtained. The fused protein per se, of course, can be used for the purpose of the invention; and so can the KHCV protein per se as long as it retains the necessary characteristic of KHCV protein, e.g., anti-genicity of KHCV.

The above expression system may be effectively employed where the desired protein is unstable and can be digested easily by protease in a host cell since the ubiquitin can protect the desired protein from the protease attack or stabilize it.

An expression vector utilizing the ubiquitin system may be prepared by insertion of a KHCV cDNA fragment into an expression vector which comprises a ubiquitin gene.

On the other hand, a fused expression vector utilizing maltose binding protein (MBP) system may be used as an expression vector of this invention. In this system, KHCV cDNA fragment is connected after mal E1 gene encoding MBP; and, the fused protein of MBP and KHCV protein is produced thereby (Guam et al., Gene, 67, 21–30(1987); Maina et al., Gene, 74, 369–373(1988); Amann et al., Gene, 40, 183–190(1985); Duplay et al., J. Biol. Chem., 259, 10606–10613(1984)).

The above MBP expression system is convenient for the reason that the fused protein containing MBP may be easily purified by utilizing the affinity of MBP to maltose; and that MBP has an excisable site by protease factor Xa in C-terminal region, which enables KHCV protein to be freed from MBP.

For the purpose of obtaining a desired KHCV protein, a compatible host cell is transformed with an expression vector containing a KHCV cDNA fragment; and the transformed cell is cultured under a condition that allows the expression.

A KHCV cDNA fragment to be expressed may be prepared by employing a restriction endonuclease or a nuclease with a larger fragment or KHCV-LBC1; and by carrying out PCR with primers and KHCV-LBC1 or the fragments thereof as a template. The length and nucleotide sequence of each primer can be determined according to the position and length of the KHCV cDNA fragment to be expressed; and the primer may be completely or partially complementary to any strand of double-staranded KHCV cDNA.

Once prepared and isolated, the KHCV cDNA fragment of this invention is inserted into an appropriate expression vehicle which contains the elements necessary for transcription and translation of the inserted gene sequences. Useful cloning vehicles may consist of segments of other non-KHCV polynucleotide including synthetic DNA sequences such as various known bacterial plasmids, phage DNA, combinations of plasmids which have been modified to employ phage DNA or other expression control sequences, or yeast plasmids.

Selection of an appropriate host organism is affected by a number of factors as known in the art. These factors include, for example, compatibility with the chosen vector, toxicity of the proteins encoded by the recombinant plasmid, ease of recovery of the desired protein, protein characteristics, biosafety and costs. A blance of these factors must be considered, and it must be understood that not all hosts will be equally effective for expression of a particular recombinant DNA molecule.

Suitable host organisms which can be used in this invention include, but are not limited to, plant, mammalian, insect cells or yeast cells and bacteria such as *Escherichia coli*.

The polypeptides dervied from KHCV cDNA include all the core proteins, non-structural proteins and envelope proteins and a portion thereof, which could be used for preparing diagnostic agents or vaccines in the form of a mixture thereof or alone. The polypeptides produced in a host cell may be isolated and purified by a combined use of conventional methods, e.g., cell disruption, centrifugation, dialysis, salting-out, chromatography, gel filtration, electrophoresis and electroelution.

The polypeptides of this invention can also be isolated from KHCV particles, or can be chemically synthesized by a suitable method such as exclusive solid phase synthesis, partial solid phase method, fragment condensation or classical solution synthesis. Solid phase synthesis as described by Merrifield (J. Am. Chem. Soc., 85, 2149(1963)) is preferred.

On the other hand, amino acid substitutions in proteins which do not substantially alter biological and immunological activities have been known to occur and have been described, e.g., by Neurath et al., in "The Proteins", Academic Press, New York (1979), in particular in FIG. 6 appearing on page 14 thereof. Most frequently observed amino acid substitutions are Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, Asp/Gly, and vice versa.

Such functionally equivalent amino acid substitutions of the exemplary embodiments of this invention are within the scope of the invention as long as the resulting proteins retain one or more antigenic determinants of KHCV.

In this specification, standard single-letter or three-letter abbreviations are used to represent nucleotides and amino acids. The meanings of these abbreviations can be found in standard biochemistry textbooks, such as Lehninger, Principles of Biochemistry, Worth Publishers Inc., New York, pp. 96, 798(1984).

Diagnostic Method of Hepatitis C Using KHCV Antigen Polypeptides for the Detection of KHCV Antibodies The present invention also relates to a diagnostic method using a diagnostic agent containing KHCV polypeptides with one or more KHCV epitopes. The diagnostic method using KHCV polypeptide(s) is a specific and accurate for detecting KHCV antibodies in the serum of hepatitis C patients than any of the existing methods.

The novel diagnostic method comprises the following steps:

First, a diagnostic agent containing one or more KHCV polypeptides is added to a solid support, e.g., well of microtiter plate to make said KHCV antigen adsorb onto the surface of the well;

Second, a putative sample diluted with a diluent is added to the antigen-coated well where the antigen-antibody complex would be formed if there were anti-KHCV antibodies in the serum;

Third, enzyme, e.g., HRP (horseradish peroxidase) conjugated anti-human IgG is added to the well to allow the anti-human IgG-HRP to bind the antibodies of the complex formed in the second step; and Finally, substrates for the enzyme, e.g., O-phenylene diamine dihydrochloric acid (OPD) and hydrogen peroxide for peroxidase are added to the well to develop a color reaction. When the putative serum contains anti-KHCV antibodies, color appears as a result of the reaction of the enzyme with the substrates. The color reaction is stopped by addition of diluted sulfuric acid.

The degree of color intensity can be measured with a microwell reader; and the existence of anti-HCV antibodies can be determined on the basis of the result. The solid support for the diagnositc method may be of polystrene bead or nitrocellulose strip.

Further, the present invention provides a hepatitis C diagnostic kit which comprises the necessary agents to carry out the above procedure, essentially consisting of a diagnostic agent containing KHCV polypeptide(s) which carries one or more KHCV epitopes.

Preparation of Antibodies

The present invention provides antibodies directed against polypeptide(s) derived from KHCV cDNA. Briefly, appropriate animals are selected and the desired immunization protocol are followed. After an appropriate period of time, the spleens of such animals are excised and individual spleen cells are fused, typically, with myeloma cells under appropriate selection conditions. Thereafter, the cells are clonally separated and the supernatant of each clone is tested for its production of an appropriate antibody specific for the desired region of the antigen.

An animal, e.g., a mouse, may be immunized by employing a conventional method such as the following:

A substantially purified antigen is injected into the mouse intramuscularly, intraperitoneally, intradermally or intravenously, more specifically, serveral times with intervals of 14 to 21 days in a total amount of 100 to 200 μg per mouse. A conventional adjuvant such as Freund's complete adjuvant or incomplete adjuvant may be used together, if necessary. Three days after a final injection, spleen cells of the mouse are removed for fusion with mouse myeloma cells whose survival rate is over 95% and which is in log phase.

The fusion of the cells may be carried out by employing a known method in the art, e.g., as described by Lovborg in *Monoclonal antibodies: Production & Maintenance*, William Heinemann, Medical Books Ltd. (1982) The fused cells so obtained are diluted serially by employing a known method as described, e.g., in *Current Protocols in Immunology*, Wiley Interscience (1991), to detect a clone which produces the desired antibodies.

A desired clone may be screened by using a conventional method such as enzyme immuno assay, plaque method, spot method, Ouchterlony method and radioimmunoassay as described in *Hybridoma Methods & Monoclonal Antibodies*, Research and Development Press, pp 30–53(1982).

The desired monoclonal antibodies may be easily obtained by one skilled in the art, using the cloned antibody-producing cell line; and, further purified by employing a conventional method such as affinity chromatography.

The antibodies are useful for the purification of KHCV antigens and for the development of an improved diagnostic method to detect KHCV antigens in putative samples.

Preparation of Diagnostic Oligonucleotide Probe and Kit

On the basis of the determined nucleotide sequence of KHCV cDNAs shown in FIGS. 2-1 to 2-11 and FIGS. 7 to 25, at least 8 nucleotides complementary to any of the KHCV cDNA strands may be prepared by excision or synthetically. The oligonucleotides may be used as probes for hybridization after labelling, e.g., with radioactive labels, or as primers for PCR with KHCV cDNAs as a template for the detection of KHCV in serum sample.

The oligonucleotides may be either completely or partially complementary to a KHCV cDNA strand, depending on the circumstances.

The oligonucleotides should contain at least 8 nucleotides, preferably 10 to 12 nucleotides, and, more preferably, about 20 nucleotides.

Preparation of Vaccines and Administration Thereof

Inactivated or attenuated KHCV prepared by employing a known method in the art as well as one or more of the polypeptides encoded in KHCV cDNA fragments of this invention may be formulated, along with a physiologically acceptable carrier, into vaccines. Suitable carriers include, e.g., 0.01 to 0.1M phosphate buffer of neutral pH or physiological saline solution.

Enhanced immunity against HCV can be produced by adding an adjuvant or immunopotentiator to the vaccine, or presenting the polypeptides in a larger form, either as a cross-linked complex or conjugated to a carrier form.

Suitable adjuvants for the vaccination may include, but are not limited to, Adjuvant 65 (containing peanut oil, mannide monooleate and aluminum monostearate); mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl)propanediamine, methoxyhexadecyclglycerol and pluronic polyols; polyanions such as pyran, dextran sulfate, poly IC, polyacrylic acid and carbopol; peptides such as muramyl dipeptide, dimethylglycine and tuftsin; and oil emulsions. The proteins of the present invention may also be administered following their incorporation into liposomes or other microcarriers.

The immunogenicity of the proteins of the invention, especially their smaller fragments, can be enhanced by cross-linking or by coupling to an immunogenic carrier molecule (i.e., a macromolecule having the property of independently eliciting an immunological response in a host animal, to which the proteins and protein fragments of the invention can be covalently linked). Cross-linking or conjugation to a carrier molecule may be required because small protein fragments sometimes act as haptens (molecules which are capable of specifically binding to an antibody but incapable of eliciting antibody production, i.e., which are not immunogenic). Conjugation of such fragments to an immunogenic carrier molecule renders the fragments immunogenic through what is commonly known as the "carrier effect".

Suitable carrier molecules include, e.g., proteins and natural or synthetic polymeric compounds such as polypeptides, polysaccharides, lipopolysaccharides, etc. One of the useful carriers is a glycoside called Quil A, disclosed by Morein et al. (Nature, 308, 457(1984)). Protein carrier molecules are especially preferred, including, but not limited to, mammalian serum proteins such as keyhole limpet hemocyanin, human or bovine gammaglobulin, human, bovine or rabbit serum albumin, or methylated or other derivatives of such proteins. Other usable protein carriers will be apparent to those skilled in the art.

Covalent coupling to a carrier molecule can be carried out by using various methods well known in the art, the exact choice of which may be dictated by, e.g., the nature of the carrier molecule used. When the immunogenic carrier molecule is a protein, the proteins or fragments of the invention may be coupled to such carrier protein by water soluble carbodiimides such as dicyclohexylcarbodiimide, or glutaraldehyde.

Coupling agents such as these can also be used to cross-link the proteins and their fragments to themselves so as to obviate the use of a separate carrier molecule. Such cross-linking among the proteins or their fragment aggregates can also increase immunogenicity.

Incorporation into liposomes or other microcarriers may provide the effect of releasing the vaccines over a prolonged period of time.

The vaccine may be administered in a single dose schedule, or preferably in a multiple dose schedule. An effective dose of the polypeptides present in the vaccine formulas may range from about 5 to about 200 $\mu$g depending on the body weight of the subject to be immunized, the capacity of the subject's immune system to produce antibodies, and the degree of immunity desired. Initial vaccinations are preferably followed by booster vaccinations given from one to several months later. Multiple boosters may be administered.

Standard routes of administration can be used such as subcutaneous, intradermal, intramuscular or intravenous administration.

The following examples are intended to specifically exemplify the present invention without limiting the scope of the invention; and the experimental methods used in Examples are practiced in accordance with Reference Examples given hereinbelow unless otherwise stated.

Unless otherwise specified, percentages given below for solids in solid mixtures, liquids in liquids and solids in liquids are on a wt/wt, vol/vol and wt/vol basis, respectively.

REFERENCE EXAMPLE 1

Digestion of DNA with Restriction Endonuclease

Restrction enzymes and reaction buffers were purchased from NEB (New England Biolabs, Jolla, Mass., U.S.A.).

The reaction was generally carried out in a sterilized eppendorf tube with a reaction volume ranging from 50 to 100 $\mu$l, at a temperature of 37° C. for 1 to 2 hours. Thereafter, the reaction mixture was heat-treated at 65° C. for 15 minutes (or extracted with phenol and precipitated with ethanol in the case of a heat-resistant endonuclease) to inactivate the restriction endonuclease.

10×reaction buffer for the reaction of a restriction endonuclease has the following composition:

10×NEB reaction buffer 1: 100 mM bis Tris propane-HCl, 100 mM $MgCl_2$, 10 mM dithiothreitol (DTT), pH 7.0

10×NEB reaction buffer 2: 100 mM Tris-HCl, 100 mM $MgCl_2$, 500 mM NaCl, 10 mM DTT, pH 7.0

10×NEB reaction buffer 3: 100 mM Tris-HCl, 100 mM $MgCl_2$, 1000 mM NaCl, 10 mM DTT, pH 7.0

10×NEB reaction buffer 4: 200 mM Tris-acetate, 100 mM magnesium acetate, 500 mM potassium acetate, 10 mM DTT, pH 7.0

REFERENCE EXAMPLE 2

Phenol Extraction and Ethanol Precipitation

After the completion of the enzyme reaction, the reaction mixture was extracted with phenol for the purpose of inactivating the enzyme or recovering the DNA in the reaction mixture, wherein phenol preequilibrated with a buffer containing 10 mM Tris-HCl (pH 8.0) and 1 mM EDTA was used. Phenol extraction was carried out by mixing equal volumes of the sample and the phenol with vigorous shaking; centrifuging the mixture at 15,000 rpm for 5 minutes; and transferring the aqueous layer into a new tube. The above procedure was repeated two or three times.

The aqueous layer was, then, extracted with an equal volume of chloroform (chloroform:isoamyl alcohol=24:1) and the aqueous layer was separated again; 0.1 volume of 3M sodium acetate and 2.5 volume of ethanol were added thereto; and, the mixture was centrifuged at 15,000 rpm and 4° C. for 20 minutes after having left it at −70° C. for 30 minutes or at −20° C. for 12 hours, to recover the nucleic acid.

REFERENCE EXAMPLE 3

Ligation Reaction

Ligation reaction of DNA was carried out by employing $T_4$ DNA ligase and 10×ligation reaction buffer (0.5M Tris-HCl, 0.1M $MgCl_2$, 0.2M DTT, 10 mM ATP, 0.5 mg/ml bovine serum albumin (BSA)) purchased from NEB. The reaction volume was generally 20 $\mu$l, and 10 units of $T_4$ ligase was used for the ligation of cohesive ends of DNA while 100 units was used for the ligation of blunt ended DNAs.

The reaction was carried out at 16° C. for 5 hours or at 4° C. for over 14 hours; and, after the reaction was completed, the reaction mixture was heated at 65° C. for 15 minutes to inactivate $T_4$ DNA ligase.

REFERENCE EXAMPLE 4

Transformation of E. coli

E. coli strains used for the following examples include E. coli HB101(ATCC 33694), E. coli W3110(ATCC 27325), E. coli JM101(ATCC 33876) and E. coli JM105(ATCC 47016). Transformation of E. coli was carried out by employing a method known in the art, e.g., as described by Maniatis et al., in Molecular Cloning: A Laboratory Manual, Cold Spring Harbor Press, N.Y. (1982), or by Cohen in Proc. Natl. Acad. Sci. U.S.A., 69, 2110(1972).

REFERENCE EXAMPLE 5

Transformation of Yeast

Yeast was transformed using a method described by Beggs in Nature, 275, 104(1978) or described by Hinnen et al., in Proc. Natl. Acad. Sci. U.S.A., 75, 1929(1978).

REFERENCE EXAMPLE 6

Synthesis of Oligonucleotides

Oligonucleotides were synthesized by employing a DNA synthesizer (Applied Biosystems Inc., 380B, U.S.A.) of automatic solid phase phosphoamidite chemistry.

The synthesized oligonucleotides were purified by using denaturing polyacrylamide gel (2M urea, 12% acrylamide and bis (29:1), 50 mM Tris, 50 mM broic acid, 1 mM EDTA) electrophoresis and SEP-PAK (Waters Inc., U.S.A) column chromatography; and the amount was determined by measuring O.D. at 260 nm.

REFERENCE EXAMPLE 7

Polymerase Chain Reaction (PCR)

To a mixture of 10 to 100 ng of a template DNA, 10 $\mu$l of 10×Taq polymerase reaction buffer (10 mM Tris-HCl, 500 mM KCl, 15 mM MgCl$_2$, 0.1% (w/v) gelatin, pH 8.3), 10 μl of a mixture of dNTP's (each of dGTP, dATP, dTTP and dCTP is 2 mM), 2 μg of each primer (generally, 2 primers were used for a reaction, and in the case that 3 primers were used, the primer located in the middle was used in an amount of 0.02 μg), and 0.5 μl of Ampli Taq DNA polymerase (Perkin Elmer Cetus, U.S.A.) was added distilled water in an amount to make a total volume of 100 μl; and 50 μl of mineral oil was added thereto to protect the reaction mixture from evaporation.

The PCR was carried out by using a thermal cycler (Perkin Elmer Cetus, U.S.A.); and the thermal cycle was programmed to repeat 25 times or more, the cycle of: 95° C. for 1 minute→55° C. for 1 minute→72° C. for 2 minutes, finally, the reaction was carried out at 72° C. for 10 minutes.

After the reaction was completed, the mixture was extracted with phenol and the PCR products were recovered by precipitation with ethanol; and, the precipitate was dissolved in 20 μl of TE buffer solution (10 mM Tris-HCl, 1 mM EDTA, pH 7.5).

EXAMPLE 1

Preparation of KHCV cDNA KHCV-LBC1

(1-A): Isolation of HCV from Serum of Korean Hepatitis C Patients and Extraction of the Viral Genomic RNA Therefrom 50 ml of serum from Korean patients with chronic hepatitis diagnosed as non-A, non-B hepatitis (ALT<60IU: The serum was supplied from the Korea University Hospital and the Catholic University Hospital in Korea) was ultracentrifuged to preciptate the HCV particles by the method proposed by Bradley, D. W. et al. in Gastroenterology, 88, 773(1985). 50 ml of serum was 6-fold diluted with TENB buffer solution (0.05M Tris, pH 8.0, 0.001M EDTA (ethylene diaminetetraacetic acid), 0.1M NaCl) and ultracentrifuged at 28,000 rpm, room temperature for 6 hours using Beckman Rotor SW28 (Beckman Inc., Model L8-80M).

Extraction of the viral genomic RNA from precipitated viral particles was carried out by using the method proposed by Cholozynski, P. and Sacchi, N. in Anal. Biochem., 162, pp 156–159 (1987). The precipitated viral particles were suspended in 8 ml of RNA extraction solution (4M guanidine thiocyanate, 24 mM Na-citrate, pH 7.0, 0.5% sarcosyl, 0.1M 2-mercaptoethanol). 0.8 ml of 2M sodium acetate (pH 4.0), 8 ml of phenol (BRL Inc., U.S.A.; saturated with distilled water) and 1.6 ml of chloroform-isoamyl alcohol (49:1, v/v) were added thereto and the resulting mixture was then centrifuged at 12,000×g, 4° C. for 15 minutes. The supernatant was poured into a new test tube; and a same volume of isopropanol and glycogen (2 μg/ml supernatant) as carrier was added thereto. The mixture was kept in a freezer at −20° C. for 1 hour and then centrifuged at 12,000×g, 4° C. for 20 minutes to obtain RNA precipitate. The precipitate was suspended in 75% ethanol, centrifuged in the same manner as above, and then dried for 10 minutes in a vaccum. The viral RNA precipitate was dissolved in 400 μl of TE buffer solution (10 mM Tris, pH 7.5, 1 mM EDTA) and used in the next step. The viral RNA solution for later use may be kept at −70° C.

(1-B): Preparation of KHCV cDNA Library (1-B-1): Preparation of KHCV cDNA

For preparation of cDNA, Zap-cDNA Synthesis Kit (Stratagene Inc., USA) was used. The hepatitic C viral RNA prepared in Example (1-A) was used as a template for reverse transcriptase, and oligo-d(T) primer (SEQ ID NO: 2) having the nucleotide sequence of 5'-GAGAGAGAGAGAGAGAGAGAACTAGTCTCGAG (T)$_{18}$-3' and a random primer having the nucleotide sequence of 5'-TTTTTCATGATTGGTGGTGGAACTGG ACCGTCTCGAGNNNNNN-3' wherein Ns may be the same or different and each is A,T,C or G (hereinafter to be referred as "RANPSHCV" (SEQ ID NO: 1)) synthesized using a DNA synthesizer (Applied Biosystems Inc., U.S.A., Model 380 B) were used.

A first strand of cDNA was prepared as follows. 18 μl of hepatitis viral RNA solution prepared in Example (1-A) was mixed with 2 μl of 0.1M CH$_3$HgOH, and the mixture was stood for 10 minutes at a room temperature to unfold a secondary structure of RNA. 2 μl of 1M β-mercaptoethanol was added thereto and the mixture was kept for 5 minutes at room temperature. To the treated RNA solution were added 5 μl of reverse transcriptase reaction buffer solution (500 mM Tris-HCl, pH 8.3, 750 mM KCl, 30 mM MgCl$_2$, 10 mM dithiothreitol (DTT)), 2.5 μl of 10 mM each of dATP, dGTP, dTTP and 5-methyl-dCTP, 2 μl of oligo-d(T) primer (1.4 μg/μl) or 2 μl of RANPSHCV (1.0 μg/μl), 15 μl of distilled water treated with diethylpyrocarbonate (DEPC) and 1.0 μl of RNase inhibitor (1 unit/μl, Promega Inc., USA), in this order; the mixture was stood for 10 minutes at room temperature to the primers to the template; and then 2.5 μl of MMLV reverse transcriptase (18 units/μl, Superscript RNase H⁻ reverse transcriptase, BRL Inc., Cat. No. 8853SA) was added thereto. The reaction mixture was incubated for 1 hour at 37° C. to synthesize the first strand of cDNA.

A second strand of cDNA was prepared as follows: To 45 μl of the first strand solution so obtained were added 40 μl of 10×second strand buffer solution (188 mM Tris-HCl, pH 6.9, 906 mM KCl, 46 mM MgCl$_2$, 1.5 mM β-NAD (nicotinamide adenine dinucleotide), 100 mM (NH$_4$)$_2$SO$_4$), 6.0 μl of 10 mM dNTP's mixture (10 mM each of DATP, dCTP, dTTP and dGTP) and 298 μl of distilled water in order, and 1.0 μl of RNase H (4 units/μl) and 10.0 μl of DNA polymerase I (11 units/μl) were then dropped along the wall of the test tube. After instantly mixing it, the reaction mixture was then incubated for 2.5 hours at 16° C.

The reaction solution was subjected to extraction with a same volume of phenol-chloroform (1:1(v/v), phenol being already saturated with 0.5M Tris-HCl (pH 7.5) and 0.1% (v/v) β-mercaptoethanol), 3 times. The upper aqueous phase was taken and mixed with 0.1 volume of 3M sodium acetate and 2-fold volume of 100% ethanol. The mixture was stood at −20° C. overnight and centrifuged at 12,000×g, 4° C. for 20 minutes to obtain the cDNA precipitate.

(1-B-2): Preparation of cDNA Library

In order to make the double stranded cDNA prepared in Example (1-B-1) into a blunt ended one, the cDNA precipitate was dissolved in 43.5 μl of distilled water. 39 μl of the cDNA solution was taken and then mixed with 5.0 μl of T4 DNA polymerase reaction solution (670 mM Tris-HCl, pH 8.8, 166 mM (NH$_4$)$_2$SO$_4$, 67 mM MgCl$_2$, 100 mM β-mercaptoethanol, 67 μM EDTA), 2.5 μl of 2.5 mM dNTP's mixture and 3.5 μl of T4 DNA polymerase (2.9 units/μl). The reaction mixture was stood for 30 minutes at 37° C. and the resulting product was extracted with phenol-chloroform and precipitated with ethanol in the same manner as in Example (1-B-1).

In order to introduce a recognition site for restriction enzyme Eco RI at 5'-end, the blunt-ended double stranded cDNA prepared above was treated as follows: To the blunt-ended cDNA were added 7.0 μl of Eco RI adaptor (Stratagene Inc., Zap-cDNA Synthesis Kit Cat. No. 200400, Calif., U.S.A.), 1.0 μl of 10×ligation buffer solution, 1.0 μl of T4 DNA ligase (1000 units/μl) and 1.0 μl of 10 mM ATP, and was stood overnight at 4° C. The resulting mixture was then heated to 70° C. for 10 minutes to inactivate the ligase.

The cDNA so obtained may be directly subjected to a cloning. In the present example, however, said cDNA was amplified and then used in the cloning step.

For the amplification of cDNA, its PCR was carried out as follows: To the cDNA solution prepared above were added 10 μl of 10×PCR buffer solution (200 mM Tris-HCl, pH 8.3, 15 mM MgCl$_2$, 250 mM KCl, 0.5% Tween 20, 1 mg/ml gelatin), 10 μl of 2 mM dNTP's mixture, 5 μl of primer, PSHCV (SEQ ID NO: 4) having the nucleotide sequence of 5'-TTTTTCATGATTGGTGGTGGA-3' and 5 μl of upper strand (5'-CCCCCCGAATTCGGCACGAG-3') of the Eco RI adaptor (SEQ ID NO: 3), 1 μl (2.5 units) of Taq DNA polymerase (Perkin Elmer-Cetus Inc., 761 Main Avenue, Norwalk, Conn. 06859-0010, U.S.A.) and 69 μl of distilled water; and the PCR was then carried out using a thermal cycler (Perkin Elmer-Cetus Inc., USA) which was programmed to repeat 25 times the cycle of: 95° C. for 30 seconds→55° C. for 30 seconds→72° C. for 2 minutes. After completing the reaction, the residual primers and dNTPs were removed using Centricon 100 (Amicon Inc., Cat. No. 4200, P.O. Box 91954, Chicago, Ill. 60693, U.S.A.). The product so obtained was extracted with phenol-chloroform and precipitated with ethanol in the same manner as above, and then dissolved in 16 μl of TE buffer solution.

To the resulting solution were added 2 μl of 10×buffer solution (0.5M NaCl, 0.5M Tris-HCl, 50 mM MgCl$_2$, 5 mM DTT, pH 7.9) and 1 μl of each of Eco RI and Xho I (New England Biolabs Inc., 30 Tozer Rd., Berverly, Mass., U.S.A.), and the reaction mixture was then stood for 10 minutes at 37° C. to digest the cDNA partially. The cDNA fragments were extracted with phenol-chloroform and precipitated with ethanol in the same manner as above, and then dissolved in 10 μl of TE buffer solution.

The cDNA fragment so obtained was cloned into vector UNI-ZAPXR as follows. To 10 μl of Eco RI-Xho I digested cDNA fragments solution obtained above were added 2.0 μl of 10×ligation buffer solution, 2.0 μl of 10 mM ATP, 4 μl of of vector UNI-Z APXR solution (1 μg/μl) already treated with Eco RI/Xho I and 2.0 μl of T4 DNA ligase (4 Weiss units/μl); and the reaction mixture was then incubated for 10 hours at 16° C.

(1-B-3): In Vitro Packaging of the Vector Containing cDNA into Phase and Amplification of the cDNA Library In order to package the ligated DNA prepared in Example (1-B-2) into phage, 10 μl of the final solution obtained in Example (1-B-2) was added to Gigapack II Gold Packaging Extract (Stratagene Inc., U.S.A.) and the reaction mixture was stood for 2 hours at room temperature.

To the resulting mixture were added 500 μl of phage diluting solution (5.8 g of NaCl, 2.0 g of MgSO$_4$.7H$_2$O, 50 ml of 1M Tris-HCl, pH 7.5, 5 ml of 2% gelatin per liter) and 20 μl of chloroform (see Kretz et al., Nucl. Acid. Res., 17, 5409(1989)).

The infection and amplification were carried out as follows. PLK-F' (Stratagene Inc., Zap-cDNA Synthesis Kit Cat. No. 200400), *E. coli* merA⁻, merB⁻ strain, was cultured in LB medium (10 g of Bacto-trypton, 5 g of yeast extracts, 10 g of NaCl per liter) until O.D.$_{600}$ (Optical Density at 600 nm) reached 0.5. The cultured cells were precipitated and dissolved in 10 mM MgSO$_4$, adjusting their O.D.$_{600}$ to 1.0. 600 μl of the solution was mixed with 200 μl of packaging mixture; the reaction mixture was then stood for 15 minutes at 37° C. to allow the phages to infect into *E. coli*. To the resulting *E. coli* was added 6.5 ml of 0.7% NZY agar (7 g of NZ amines, 5 g of NaCl, 2 g of MgSO$_4$.7H$_2$O, 5 g of yeast extracts, 7 g of bactoagar per liter) melted and kept to 48° C.; and the mixture was applied on a 150 mm-diameter NZY agar plate (7 g of NZ amines, 5 g of NaCl, 2 g of MgSO$_4$7H$_2$O, 5 g of yeast extracts, 16 g bacto-agar per liter) and then incubated for 5 to 8 hours at 37° C. to generate the phage plaques.

10 ml of phage diluting solution was poured onto the plate; the plate was shaken mildly for 15 hours at 4° C. to dissolve the phages; and the resulting mixture was centrifuged at 4,000×g to precipitate *E. coli* cells, which were then removed off. To the HCV cDNA library solution so obtained was added 0.3% volume of chloroform; and the titer of the cDNA library was determined to be about 10$^{10}$ to 10$^{13}$ PFU (plaque forming units)/ml. 100% DMSO (dimethyl sulfoxide) was added thereto be make a concentration of 7% (v/v); and the cDNA library was kept at −70° C.

(1-C): Screening of the cDNA Library by Immunoassay and Determination of cDNA Sequence.

The cDNA library was screened by the immunoscreening method disclosed by Huynh, T. V. et al., *DNA Cloning Techniques: A Practical Approach* (D. M. Glover, ed.), pp 49–78, IRL Press, Oxford (1985), using the HCV antibody purified from the supernatant after ultracentrifuging the 6-fold diluted serum prepared in Example (1-A) by protein G affinity column chomatography (Genex Inc., U.S.A.).

The cDNA library solution prepared in Example (1-B-3) was diluted to be 50,000 PFU per 150 mm-diameter of plate; the diluted cDNA library solution was mixed with 600 μl of *E. coli* XL-1 blue (Stratagene Inc., U.S.A., Zap-cDNA Synthesis Kit Cat. No. 200400) culture (O.D.$_{600}$=0.5) prepared by the same method as in Example (1-B-2) and 6.5 ml of 0.7% NYZ agar was added thereto. Each mixture was applied on a 40 NZY agar plate and cultured for 12 hours at 37° C. to produce 2×10$^6$ phage plaques.

Thereafter, plaque lift membrane of nylon filters (Bio-Rad Inc., Cat. No. 162-163, USA) of 137 mm diameter were impregnated with 10 mM IPTG (isopropyl-β-D-thiogalactopyranoside) solution and then blot-dried on Whatman 3MM filter. Each filter was placed above the agar in a plate; and incubated for 3.5 hours at 37° C. Each of the filters blotted with the phage plaques was then washed with 15 ml of washing solution (10 mM Tris-HCl, pH 8.0, 150 mM NaCl, 0.05% Tween 20). To the filters was added 15 ml of blocking solution (1% bovine serum albumin, 20 mM Tris-HCl, pH 7.5, 150 mM NaCl); and incubated with gentle shaking for 1 hour at room temperature. Each of the filters was then washed 5 times by mild shaking with 15 ml of TBST buffer solution (20 mM Tris-HCl, pH 7.5, 150 mM NaCl, 0.05% (v/v) Tween-20) for 5 minutes at room temperature. The filters were put in 15 ml of the solution prepared by diluting the purified HCV antibody (final protein concentration: 8.2 mg/ml) 1:200 with TBS buffer solution (20 mM Tris-HCl, pH 7.5, 150 mM NaCl) containing 1% (w/v) FBS (fetal bovine serum) with mild shaking for 1 hour at room temperature; and then washed 5 times with mild shaking in TBST buffer solution for 5 minutes at room temperature, respectively. Each of the filters was put in 15 ml of solution prepared by diluting biotinylated-goat anti-human IgG and avidin conjugated-alkaline phosphatase (Pierce Inc., USA. Cat. Nos. 31770C, 21321C) 1:2000 with TBS buffer solution containing 1% (w/v) FBS, with mild shaking for 1 hour at room temperature; and then washed 5 times with gentle shaking in 15 ml of TBST buffer solution for 5 minutes at room temperature. Each of the filters was then blot-dried on Whatman 3MM filter.

For the coloring reaction, each of the filters was reacted in 15 ml of coloring solution (100 mM Tris-HCl, pH 9.5, 100 mM NaCl, 5 mM $MgCl_2$, 5 mg nitro blue-tetrazolium, 2.5 mg 5-bromo-4-chloro-3-indolyl phosphate) in a dark room at room temperature for 30 minutes. The purple-colored, positive phage plaques were confirmed with eyes, which were expected to express the cDNA encoding a recombinant HCV antigen. Each of the filters was washed with TBS buffer solution once; and coloring stopping solution (20 mM Tris-HCl, pH 2.9, 1mM EDTA) was added thereto to stop the coloring process. Each of the filters was dried at room temperature and then recorded on polaroid film.

Positive plaques were isolated; and incubated in 1 ml of phage diluting solution (10 mM Tris-HCl, pH 7.5, 10 mM $MgCl_2$) for 1 to 2 hours at room temperature. The above immunoscreening assay was repeated to obtain the clones as a single phage plaque.

Each of the phage plaques confirmed as haboring the recombinant HCV gene was put into a sterilized microfuge tube containing 500 µl of 5M buffer solution (5.8 g of NaCl, 2.0 g of $MgSO_4$, 50 µl of 1M Tris-HCl, pH 7.5, 5 ml of 2% gelatin per liter); 20 µl of chloroform was added thereto; and then the contents of the tube was cultured with shaking for 1 to 2 hours at room temperature. 200 µl (>1×10$^5$ phage particles) of the solution so obtained, 1 µl of helper phage R408 (>1×10$^6$ PFU/ml, Stratagene Inc., U.S.A.) and 20 µl of E. coli XL-1 cell supension (O.D.$_{600}$=1.0) were mixed, and then the mixture was incubated at 37° C. for 15 minutes. To the resulting culture was added 5 ml of 2×YT medium (10 g of NaCl, 10 g of yeast extract, 16 g of Bacto-tryptone per liter), which was then cultured with shaking for 3 hours at 37° C. and then heated to 70° C. for 20 minutes. The resulting culure was diluted 1:100; and 200 µl of the diluted culture was mixed with 200 µl of E. coli XL1-Blue cell (O.D.$_{600}$=1.0). After incubating at 37° C. for 1 hour, 100 µl of the resulting culture was applied on LB plates containing ampicillin (50 µg/ml); and incubated at 37° C. for 10 hours to obtain pBluescript phagemid colonies haboring double stranded cDNA.

In order to prepare single stranded DNA, pBluescript colonies obtained above were incubated in a LB agar medium containing antibiotic tetracycline (12.5 µg/ml) and screened to obtain the positive colonies again; and the positive single colonies as obtained were incubated in tetracycline$^+$ LB broth medium (2 to 3 ml) over-night. The culture was then incubated in 0.3 ml of super liquid medium (35 g Bacto-tryptone, 20 g yeast extract, 5 g NaCl, adjusted to pH 7.5 with NaOH) and cultured with shaking at 37° C. The culture was infected with helper phage R408 and the culturing was carried out for 8 hours until O.D.$_{600}$ reached 0.3.

In effectuating the infection, the ratio of phage:cell largely depends on the type of cDNA harbored in pBluescript, and may be 20:1, 10:1, 1:1 or 1:10. The single stranded DNAs were extracted from the supernatant of the culture obtained above.

The isolation and purification of double stranded phagemid and single stranded phagemid was carried out by the method proposed by Sambrook, J. et al. in *Molecular Cloning*, 1, 2.73–2.81, Cold Spring Harbor, N.Y. (1989).

The length of the cDNA fragment contained in each clone was determined by digesting the double stranded phagemid with the restriction endonucleases Eco RI and Xho I; and 3 clones having cDNA fragments with different length were obtained.

The nucleotide sequences of the 3 recombinant cDNAs were determined using the purified single stranded recombinant pBluescript phagemid or the double stranded pBluescript phagemid as a template and using M13-20 mer, primer T7, primer KS, primer SK or primer T3 (Stratagene Inc., USA) in accordance with Sanger's method (Proc. Natl. Acad. Sci. U.S.A., 74, 5405(1977)), in which the resulting cDNA fragments were named KHCV 426, KHCV 652 and KHCV 403, respectively (see FIGS. 1 to 3).

(1-D): Screening of Recombinant Phages Harboring KHCV cDNA Using Oligonucleotide Probe and Determination of Nucleic Acid Sequence (1-D-1): Isolation of cDNA Clones Overlapping with KHCV 652

In order to screen those recombinant phages harboring HCV cDNA which had not been screened by the above immunoscreening method, plaque hybridization was carried out by using the method described by Benton, W. D. et al., Science, 196, 180(1977); Connor, B. J. et al., Proc. Natl. Acad. Sci. U.S.A., 80, 278(1983); and Jacob, K. et al., Nature, 313, 805(1985), using as probes oligonucleotides P652a (SEQ ID NO: 5) (5'-TTCATACCCGTTGAGTCTATGGAAACTACT-3') and P652b (SEQ ID NO: 6) (5'-GCCATTCCAAGAAGAAGTGTGACGAACTCG-3') whose nucleotide sequences were selected from the nucleotide sequence of the cDNA KHCV 652 determined in Example (1-C).

The cDNA library solution prepared in Example (1-B) in an amount containing 50,000PFU was taken and then mixed with 600 µl of E. coli XL1-blue (diluted for O.D.$_{600}$ to be 0.5) prepared in Example (1-B-3) and mixed with 0.7% NZY agar. The mixture was poured onto a 150 mm NZY plate and incubated at 37° C. for 12 hours. From the total 30 plates, 1.5×10$^6$ phage plaques were obtained.

Thereafter, 137 mm-diameter-Nylon filters were carfully put on the plates, respectively, to blot the plaques to the filters. The nylon filters were then removed and dried in air.

Each of the dried filters was placed on Whatman 3MM paper saturated with 0.2M NaOH/1.5M NaCl for 1 to 2 minutes; and on Whatman 3MM paper saturated with 0.4M Tris-HCl, pH 7.6 and 2×SSC (SSC: 17.53 g of NaCl, 8.82 g of sodium citrate, pH 7.0 per liter) for 1 to 2 minutes; and then dried in a vacuum oven at 80° C. for 2 hours.

After the drying, filters were washed with 500 ml of 3×SSC/0.1% SDS solution at room temperature 3 to 4 times; and washed with the same solution at 65° C. for 2 hours. Each of the filters was prehybridized in 500 ml of prehybridization solution (6×SSC, 5×Denhardt solution (0.2 g of Ficoll, 0.2 g of polyvinylpyrrolidone, 0.2 g of BSA per liter), 0.05% sodium pyrophosphate, 100 µg/ml of boiled herring sperm DNA, 0.5% SDS) for 1 hour at 37° C. The filters were moved into hydridization solution (6×SSC, Denhardt solution, 100 µg/ml yeast tRNA, 0.05% sodium pyrophosphate); and 30 ng of each of P652a and P652b labeled with $^{32}$P was added thereto. The hybridization reaction was carried out for 24 hours at 48° C.

The probes used above were labeled as follows. To a mixture of 32 ng of probe, 7.5 µl of 10×T4 kination buffer solution (0.5M Tris-HCl, pH 7.5, 0.1M $MgCl_2$, 50 mM DTT, 0.5 mg/ml BSA), 100 µCi (γ-$^{32}$P)ATP and 50 units of T4 nucleotide kinase was added distilled water in a total volume of 75 µl. The kination reaction was carried out for 30 minutes at 37° C.

After completing the hybridization, the filters were washed 5 times with 6×SSC/0.05% sodium pyrophoshate solution for 10 minutes at room temperature; and once with the same solution for 30 minutes at 60° C. The washing was further carried out while raising the temperature by 2° C. over 15 minutes until the filter was confirmed to be completely washed by checking with a Geiger counter (Ludlum Model 13). The washed filters were exposed to X-ray film (Kadak X-Omat AR) for 24 to 48 hours at −70° C.

The plaques confirmed as positive were screened off in the same manner as described above to obtain the plaques as a single phage plaque.

From the positive plaques so obtained, the double stranded phagemid and the single stranded phagemid were prepared and the nucleotide sequence was determined by the same method used in Example (1-C).

The cDNA clones overlapping with KHCV652 were named as KHCV 752 and KHCV675, respectively; and their length, position, nucleotide sequence and the amino acid sequence encoded therein are shown in FIGS. 1 to 3.

(1-D-2): Isolation of cDNA Overlapping with KHCV 426

Oligonucleotides P426a (SEQ ID NO: 7) (5'-ACGAGACCTCCCGGGGCACTCGCAAGCACC-3') and P426b (SEQ ID NO: 8) (5'-CGTAATTTGGGTAAGGTCATCGACACCCTC-3'), which were modeled on the basis of the nucleotide sequence of KHCV 426 cDNA obtained in Example (1-C), were synthesied. Using the oligonucleotides P426a and P426b as probes, plaque hybridization was carried out in the same manner as in Example (1-D-1). The cDNA clone overlapping with KHCV426 was detected by the same method as described in Example (1-C); and designated as KHCV 240, whose length, position and nucleotide sequence and amino acid sequence encoded therein are shown in FIGS. 1 to 3.

(1-D-3): Isolation of cDNA Overlapping with KHCV 240

Oligonucleotide P240b (SEQ ID NO: 10) (5'-GTCCGGGTGCTGGAGGACGGCGTGAACTA-3'), which was modeled on the basis of the nucleotide sequence of KHCV 240 determined in Example (1-D-2), was synthesized. Using the oligonucleotide P240b as a probe, the cDNA library prepared in Example (1-B) was screened in the same manner as in Example (1-D-1). The cDNA clone so obtained containing about 110 nucleotides overlapping with KHCV 240 was designated as KHCV 513; and its nucleotide sequence was determined by Sanger's method. The length, position and nucleotide sequence of KHCV 513 and the amino acid sequence encoded therein are shown in FIGS. 1 to 3.

(1-D-4): Isolation of cDNA Overlapping with KHCV 513

Oligonucleotide P513b (SEQ ID NO: 10) (5'-CGCATGGCCTGGGATATGATGATGAACTGG-3'), which was modeled on the basis of the nucleotide sequence of KHCV 513 determined in Example (1-D-3), was synthesized. Using the oligonucleotides P513b as a probe, the cDNA library prepared in Example (1-B) was screened in the same manner as in Example (1-D-1). The 810 bp of cDNA clone which comprises about 130 bp of nucleotides overlapping with KHCV 513 was named as KHCV 810; and its nucleotide sequence was determined by Sanger's method. The length, position and nucleotide sequence of KHCV 810 and the amino acid sequence encoded therein are shown in FIGS. 1 to 3.

(1-D-5): Isolation of cDNA Overlapping with KHCV 810

Oligonucleotide P810b (SEQ ID NO: 11) (5'-AAATGAGACGGACGTGCTGCTCCTTAAC-3'), which was modeled on the basis of the nucleotide sequence of KHCV 810 determined in Example (1-D-4), was synthesized. Using the oligonucleotides P810b as a probe, the library prepared in Example (1-B) was screened in the same manner as in Example (1-D-1). The cDNA clone so obtained which comprises about 65 bp of nucleotides overlapping with KHCV 810 was named KHCV 798; and its nucleotide sequence was determined by Sanger's method. The length, position and nucleotide sequence of KHCV 798 and the amino acid sequence encoded in KHCV 798 are shown in FIGS. 1 to 3.

(1-D-6): Isolation of cDNA Overlapping with KHCV 403

Oligonucleotides P403A (SEQ ID NO: 12) (5'-GTGAAGAATTCGGGGGCCGGAACCTGGCAT-3') and P403B (SEQ ID NO: 13) (5'-GCTGACCTCATTGAGGCCAACCTCTTGT-3'), which were modeled on the basis of the nucleotide sequence of KHCV 403 determined in Example (1-D-5), were synthesized. Using the oligonucleotides P403A and P403B as probes, the library prepared in Example (1-B) was screened in the same manner as in Example (1-D-1). The cDNA clone so obtained which comprises about 160 bp of nucleotides overlapping with KHCV 403 was named KHCV 932; and its nucleotide sequence was determined by Sanger's method. The length, position and nucleotide sequence of KHCV 932 and the amino acid sequence encoded in KHCV 932 are shown in FIGS. 1 to 3.

(1-D-7): Isolation of cDNA Overlapping with KHCV 932

Oligonucleotide P932b (SEQ ID NO: 14) (5'-CCGGGACGTGCTTAAGGAGATGAAGGCGAA-3'), which was modeled on the basis of the nucleotide sequence of KHCV 932 determined in Example (1-D-6), was synthesized. Using the oligonucleotide P932b as a probe, the cDNA library prepared in Example (1-B) was screened in the same manner as in Example (1-D-1). The cDNA clone so obtained which comprises about 185 bp of nucleotides overlapping with KHCV 932 was named KHCV 496; and its nucleotide sequence was determined by Sanger's method. The length, position and nucleotide sequence of KHCV 496 and the amino acid sequence encoded in KHCV 496 are shown in FIGS. 1 to 3.

(1-D-8): Isolation of cDNA Overlapping with KHCV 496

Oligonucleotide P496b (SEQ ID NO: 15) (5'-CGTGTATGCGAGAAGATGGCCCTTTATGAC-3'), which was modeled on the basis of the nucleotide sequence of KHCV 496 determined in Example (1-D-7), was synthesized. Using the oligonucleotide P496b as a probe, the library prepared in Example (1-B) was screened in the same manner as in Example (1-D-1). The cDNA clone of 847 bp which comprises about 160 bp of nucleotides overlapping with KHCV 496 was named KHCV 847; and its nucleotide sequence was determined by Sanger's method. The length, position and nucleotide sequence of KHCV 847 and the amino acid sequence encoded in KHCV 847 are shown in FIGS. 1 to 3.

(1-D-9): Isolation of cDNA Overlapping to KHCV 847

Oligonucleotide P847b (SEQ ID NO: 16) (5'-TGCGTGGGAGACAGCTAGACACACTCCAG-3'), which was modeled on the basis of the nucleotide sequence on 3'-end side of KHCV 847 determined in Example (1-D-8), was synthesized. Using the oligonucleotide P847b as a probe, the cDNA library prepared in Example (1-B) was screened in the same manner as in Example (1-D-1). The cDNA clone of 494 bp so obtained which comprises about 94 bp of nucleotides overlapping with KHCV 847 was named KHCV 494; and its nucleotide sequence was determined by Sanger's method. The length, position and nucleotide sequence of KHCV 494 and the amino acid sequence encoded in KHCV 494 are shown in FIGS. 1 to 3.

(1-E): Preparation of cDNA by PCR (1-E-1): Preparation of the KHCV cDNA Between KHCV 798 and KHCV 752

In order to clone the HCV cDNA between the 3'-end of KHCV 798 and the 5'-end of KHCV 752, primers P798b (SEQ ID NO: 17) (5'-CTGGTTCCCGGAGCGGCATAC-3') modeled on the basis of the nucleotide sequence on the 3'-end side of KHCV 798 and P752a (SEQ ID NO: 18) (5'-CCAGGTGATGACTTTGGTCTCCAT-3') modeled on the basis of the nucleotide sequence on the 5'-end side of KHCV 752 were synthesized. Using the primers P798b and P752a and the cDNA library prepared in of Example (1-B-1) using the primer of RANPSHCV, the polymerase chain reaction was carried out as in Reference Example 7. After completing the reaction, some of the resulting mixture was subjected to 5% polyacrylamide gel electrophoresis (PAGE) to confirm the amplification of the cDNA. To the remaining mixture was added 10 units of Klenow fragment, a DNA polymerase; and the reaction mixture was incubated for 30 minutes at 37° C. to make both ends to be blunt. The reaction mixture was subjected to PAGE and the DNA was electrically eluted to isolate the pure DNA. The purified DNA fragment was cloned into phage M13mp18 and its nucleotide sequence was determined. The DNA so obtained was named KHCV 570; and its nucleotide sequence and the amino acid sequence encoded therein are shown in FIGS. 1 to 3.

KHCV 240 prepared in Example (1-D-2), KHCV 513 prepared in Example (1-D-3), KHCV 810 prepared in Example (1-D-4), KHCV 798 prepared in Example (1-D-5) and KHCV 570 prepared above overlapped in part each other; and thus they were connected into a long open reading frame, which was named KHCV 2661.

(1-E-2): Preparation of KHCV cDNA Between KHCV 403 and KHCV 675

In order to clone a HCV cDNA fragment lying between KHCV 403 prepared in Example (1-C) and KHCV 675 prepared in Example (1-D-1), primers P675b (SEQ ID NO: 19) (5'-TCGATTCTTCGGTCCTGTGTGAGTGT-3') and P675b$_2$ (SEQ ID NO: 20) (5'-AAAAAGAATTCGGATCCATGACGCGGGTTGTGCGTGGTAC-3') modeled on the basis of the nucleotide sequence on the 3'-end side of KHCV 675 and P403a$_2$ (SEQ ID NO: 21) (5'-CCCCCTCAGAGTCGACTCACTTCACGTTGTCAGTGGTCAT-3') modeled on the basis of the nucleotide sequence on the 5'-end side of KHCV 403 were synthesized. Using the primers P675b, P675b$_2$ and P403a$_2$ prepared above and P403a prepared in Example (1-D-6), PCR was carried out as follows.

To a mixture of 0.2 $\mu$g of P674b, 0.2 $\mu$g of P403a, 2 $\mu$l of cDNA prepared in Example (1-B-1) using the random primer RANPSHCV, 10 $\mu$l of 10×PCR buffer solution, 10 $\mu$l of 2 mM dNTP's mixture, and 2.5 units of Taq polymerase was added distilled water to adjust the total volume to be 100 $\mu$l. The mixture was subjected to a first PCR by repeating 10 times the cycle of: 95° C. for 2 minutes→55° C. for 2 minutes→72° C. for 3 minutes. After adding 2 $\mu$g of P675b$_2$ and 2 $\mu$g of P403a$_2$ to the resulting mixture, the second PCR was carried out by repeating 20 times the above thermal cycle.

After completing the reaction, the amplification of the cDNA was confirmed; and the sequence of the cDNA was determined in the same manner as in Example (1-E-1). The cDNA so obtained was named KHCV 1774, and its nucleotide sequence and the amino acid sequence encoded therein are shown in FIGS. 1 to 3.

(1-E-3): Cloning of 3'-end Region of KHCV cDNA and Determination of Nucleotide Sequence Thereof In order to clone cDNA corresponding to the 3'-end region of HCV genome, PCR using the primers RANPSHCV and DA17PSHCV (SEQ ID NO: 22) (5'-TGGTGGTGGAACTGGACCGTA$_1$-3') was carried out as follows.

Primer PSHCVSL (SEQ ID NO: 23), 5'-AAAAGTCGACTGGTGGTGGAACTGGACCGT-3', contains 21 fixed nucleotides of primer RANPSHCV or DA17PSHCV of Example (1-B-1) and Sal I recognition site (5'-GTCGAC-3'); while primer KHCVR60 (SEQ ID NO: 24), 5'-GTGTCCGCGCTAAGCTACTGTCC-3', contains those nucleotides designed from the nucleotide sequence of the 3'-end region of KHCV 494 of Example (1-D-9). Using primers PSHCV and KHCVR60, a first PCR was carried out in the same manner as in Reference Example 7.

In a second PCR, primer KHCVR61 (SEQ ID NO: 25) (5'-TGTGGCAAGTACCTCTTCAACTGG-3') was synthesized. KHCVR61 consists of a sequence complementary to the nucleotide sequence of the 3'-end region of KHCV 494, and closer to the 3'-end than KHCVR60.

10 $\mu$l of KHCVR61 was added to the mixture resulted from the first PCR, and the second PCR was then carried out by the same method as in Reference Example 7.

After completing the reaction, amplification of cDNA was confirmed and its nucleotide sequence was determined in the same manner as in Example (1-E-1). The cDNA so obtained, having 266 nucleotides, was named KHCV 266. The position and nucleotide sequence of KHCV 266 and the amino acid sequence encoded therein are shown in FIGS. 1 to 3. In the nucleotide sequence of KHCV 266, two terminator codons were found, although poly(A)$^+$ tail was not found.

(1-E-4): Cloning of 5'-end Region of KHCV cDNA and Determination of Nucleotide Sequence Using primer KHCVL69 (SEQ ID NO: 26) (5'-GTCCTGTGGGCGGCGGTTGGTGTTACG-3') modeled on the basis of the 5'-end side nucleotides of KHCV 426 prepared in Example (1-C), a single stranded cDNA was prepared in the same manner as in Example (1-B-1). 50 $\mu$l of the mixture resulted from the above was diluted with 1 ml of TE buffer solution (10 mM Tris-HCl, pH 7.5, 1 mm EDTA). The diluted mixture was concentrated to 10 $\mu$l by using Centricon 100 (Amicon Inc., U.S.A., #4200) so as to remove the residual primers and dNTPs.

In order to make a poly d(T) tailed cDNA or poly d(G) tailed cDNA, to 10 $\mu$l of the cDNA solution so obtained were added 4 $\mu$l of 5×tailing buffer solution (0.5M potassium cacodylate, pH 7.2, 10 mM CoCl$_2$, 1 mM DTT), 4 $\mu$l of 1 mM dTTP (or 4 $\mu$l of 1 mM dGTP) and 10 units of terminal deoxynucleotide transferase (BRL Inc., U.S.A., #80085B); and distilled water was added to adjust the total volume to be 50 $\mu$l. The reaction mixture was stood for 30 munutes at 37° C. and then heated to 65° C. for 5 minutes.

The poly d(T)$^+$ tailed cDNA (or the poly d(G) tailed cDNA) so obtained was amplified by PCR using primers KHCVL70 (SEQ ID NO: 27) (5'-TTGAGGTTTAGGATTCGTGCTCAT-3') (or dC12R1R0 (SEQ ID NO: 28); 5'AAGGATCCGTCGACATCGATAATACGACTCACTATAGGGA(C)$_{12}$-3'), dT17R1R0 (SEQ ID NO: 29) (5'-AAGGATCCGTCGACATCGATAATACGAC TCACTATAGGGA(T)$_{17}$-3'), R0 (SEQ ID NO: 30) (5'-AAGGATCCGTCGACATC-3') and R1 (SEQ ID NO: 31) (5'-GACATCGATAATACGACTCAC-3') designed from the nucleotide sequence of KHCV 426 prepared in Example (1-C).

To 2 $\mu$l of cDNA solution were added 5 $\mu$l of 10×Taq polymerase buffer solution (100 mM Tris-HCl, pH 8.3, 500 mM KCl, 15 mM MgCl$_2$, 0.1% gelatin), 5 $\mu$l of 1.5 mM dNTPs mixture, 2.0 $\mu$g of KHCVL69 and 2.0 $\mu$g of dT17R1R0; and distilled water was added to adjust the total volume to be 50 $\mu$l. The mixture was heated to 95° C. for 7 minutes and then cooled to 75° C. 2.5 units of Taq DNA polymerase was added thereto; and 30 $\mu$l of mineral oil was then added to prevent evaporation thereof. The reaction mixture was cooled to 45° C. for 2 minutes to allow the primers to complementarily bind the single stranded cDNA, and then reacted at 72° C. for 22 minutes. A first PCR was carried out by repeating 30 times the cycle of: 95° C. for 45 seconds→4 50° C. for 25 seconds→72° C. for 2 minutes; and finally at 72° C. for 15 minutes.

2 μg of primer R0 (or R1) and 2 μg of KHCVL70 were added to 10 μl of the mixture resulted from the above; and a second PCR was carried out by repeating 30 times the same cycle as above. After completing the reaction, amplification of the cDNA, having 380 bp, was confirmed and its nucleotide sequence was determined in the same manner as in Example (1-E-1). The cDNA clone so obtained was named KHCV 366, and the position and nucleotide sequence of KHCV 366 and the amino acid sequence encoded therein are shown in FIGS. 1 to 3.

The KHCV cDNA clones obtained in Example 1 connected to a full length KHCV cDNA having 9372 nucleotides; and the full length cDNA was named KHCV-LBC1, which was deposited with ATCC on May 14, 1991 with the accession No. of 75008.

EXAMPLE 2

Preparation of HCV Subtype cDNA (2-A): Extraction of RNA

To 100 μl of each serum collected from 13 Korean patients with hepatitis C (Samples #2, #3, #20, #21, #23, #25, #26, #27, #28, #29, #30, #31 and #32) was added 300 μl of RNAzol B (Cinna/Biotecx, P.O. Box 1421, Friendwood, Tex., U.S.A.) to disrupt the cells; and the KHCV RNAs were then extracted in the same manner as in Example (1-A). The KHCV RNAs extracted from these 13 samples were named LBC2, LBC3, LBC20, LBC21, LBC23, LBC25, LBC26, LBC27, LBC28, LBC29, LBC30, LBC31 and LBC32, respectively.

(2-B): Preparation of cDNA

Using the HCV RNAs prepared in Example (2-A) as templates and random primers (5'-NNNNNN-3', wherein Ns may be the same or different and may be G, A, T or C with the same proportion) as primers for reverse transcriptase, the HCV cDNAs were prepared in the same manner as in Example (1-B-1). The cDNAs so obtained were named KHCV-LBC2 cDNA, KHCV-LBC3 cDNA, KHCV-LBC20 cDNA, KHCV-LBC21 cDNA, KHCV-LBC23 cDNA, KHCV-LBC25 cDNA, KHCV-LBC26 cDNA, KHCV-LBC27 cDNA, KHCV-LBC28 cDNA, KHCV-LBC29 cDNA, KHCV-LBC30 cDNA, KHCV-LBC31 cDNA and KHCV-LBC32 cDNA, respectively.

(2-C): Amplification of KHCV cDNA by PCR (2-C-1): Design of Primers

The primers for the amplification of the NS2 and the NS5 regions of HCV cDNAs were designed from the regions relatively commonly present in the nucleotide sequences of the Japanese type reported by Kato et al., Proc. Natl. Acad. Sci. USA, 87, 9524–9528 (1990) and Takamizawa et al., J. Virol., 65, 1105–1113(1991); of the American type reported by Choo et al., Sicence, 244, 359–363 (1989); and of the KHCV-LBC1 prepared in Example 1. The positions of the nucleotide sequences prepared above were numbered on the basis of the nucleotdies sequence of KHCV-LBC1.

Primers for Amplification of NS2 Region of HCV cDNA NS2S1 (SEQ ID NO: 32) (5'-CGGGAGATGGCCGCATCGTG-3') corresponded to the strand of the fragment from the 2776th to the 2795th nucleotides in KHCV-LBC1; and NS2N1 (SEQ ID NO: 33) (5'-ACCTGCTAGTGCGGCCAGCTTCAT-3') corresponded to the complementary strand of the fragment from the 3180th to the 3157th nucleotides of KHCV-LBC1, which were used in carrying out a first PCR for the amplification of the NS2 region of HCV cDNA. NS2S2 (SEQ ID NO: 34) (5'-TTTTGGATCCGCGGTTTTTGTAGGTCTGGT-3') corresponded to the strand of the fragment from the 2803rd to the 2822 nd nucleotides in KHCV-LBC1, which had a BamH I recognition site for the convenience of cloning; and NS2N2 (SEQ ID NO: 35) (5'-AAAGTCGACATGAAGACCATTTGGAC-3') corresponded to the complementary strand of the fragment from the 3159th to the 3142 nd nucleotides in KHCV-LBC1, which had a Sal I recongnition site at its 5'-end for the convenience of cloning. NS2S2 and NSS2N2 were used in carrying out a second PCR.

Primers for Amplifiction of NS5 Region of HCV cDNA NS5S1 (SEQ ID NO: 36) (5'-ATGGGGATCCATATGACACCCGCTG(T/C)TTTGA-3', wherein T/C means Thymines and Cytosines mixed in the ratio of 1:1), the nucleotide sequence from the 10th nucleotide (as counted from the 5'-end of NS5S1) to the 3'-end corresponded to the nucleotide sequence of the fragment from the 8252 nd to the 8273rd nucleotides in KHCV-LBC1. In NS5N1 (SEQ ID NO: 37) (5'-CCCCGTCGACCTAGTCATAGCCTCCGTGAA-3'), the nucleotide sequence from the 9th nucleotide to the 3'-end corresponded to the complementary strand of the fragment from the 8635th to the 8614th nucleotides in KHCV-LBC1. Primer NS5N1 was used in carrying out a first PCR for the amplification of the NS5 region.

In NS5S2 (SEQ ID NO: 38) (5'-TTTGAGGATCCACGGTCACTGAGAA(T/C)GACAT-3', wherein T/C has the same meaning as above), the nucleotide sequence from the 12th nucleotide to the 3'-end corresponded to the strand of the fragment from the 8278th to the 8297th nucleotides in KHCV-LBC1, and NS5S2 had a BamH I recognision site at its 5'-end. Primer NS5S2 was used in corrying out a second PCR.

The above primers were synthesized using DNA synthesizer (Applied Biosystems Inc., Model 380 B, USA) employing automized solid phase phosphoamidite chemistry. The synthesized primers were isolated by electrophoresis using denaturation polyacrylamide gel (2M urea, 12% acrylamide and bis acryamide (29:1, w/w) in 50 mM Tris, 50 mM boric acid, 1 mM EDTA-Na$_2$), and purified through C18 column chromatography (SEPAK; Waters Inc., USA) using a mixture of acetonitrile-water (50:50, v/v) as an eluent. The concentration of each primer was determined by an O.D. value at 260 nm.

(2-C-2): PCR for Amplification of NS2 Region of KHCV cDNA

A first PCR was carried out as follows. To 5 μl of each of KHCV-LBC2 cDNA, KHCV-LBC3 cDNA, KHCV-LBC20 cDNA, KHCV-LBC21 cDNA, KHCV-LBC23 cDNA, KHCV-LBC25 cDNA, KHCV-LBC26 cDNA, KHCV-LBC27 cDNA, KHCV-LBC28 cDNA, KHCV-LBC29 cDNA, KHCV-LBC30 cDNA, KHCV-LBC31 cDNA and KHCV-LBC32 cDNA prepared in Example (2-B) were added 10 μl of 10×Taq polymerase buffer solution (10 mM Tris-HCl, pH 8.3, 500 mM HCl, 15 mM MgCl$_2$, 0.1% (w/v) gelatin), 10 μl of 2 mM dNTP's mixture, 0.2 μg of NS2S1, 0.2 μg of NS2N1 and 0.5 μl of AmpliTaq DNA polymerase (Perkin Elmer-Cetus, USA); and distilled water was added to adjust the total volume to be 100 μl. To each of such solution, 50 μl of mineral oil was added to prevent evaporation thereof. The first PCR was carried out by repeating 40 times the thermal cycle of: 95° C. for 2 minutes→55° C. for 2 minutes→72° C. for 3 minutes. The second PCR was carried out using 1 ml of first PCR products and 2 μg of NS2S2/NS2N2 primer set by repeating 25 times.

Each of the resulting mixtures was mixed with a same volume of phenol/chloroform and then centrifuged to removed the residual enzymes. To each of the supernatants were added 0.1 volume of 3M sodium acetate and a 2.5-fold volume of absolute ethanol; and the resulting mixture was then centrifuged to yield 340 bp of double stranded DNA.

The DNA fragments from the 13 different templates were named NS2-LBC2, NS2-LBC3, NS2-LBC20, NS2-LBC 21, NS2-LBC 23, NS2-LBC25, NS2-LBC26, NS2-LBC27, NS2-LBC28, NS2-LBC29, NS2-LBC30, NS2-LBC31 and NS2-LBC32, respectively.

(2-C-3): PCR for Amplification of NS5 Region of HCV cDNA

Primers NS5S1 and NS5N1 were used to carry out a first PCR and Primers NS5S2 and NS5N1 were used to carry out a second PCR in the same manner as in Example (2-C-2) to obtain 320 bp of DNA segments.

The resultant DNA fragments amplified from KHCV-LBC20 cDNA, KHCV-LBC21 cDNA, KHCV-LBC23 cDNA, KHCV-LBC25 cDNA, KHCV-LBC26 cDNA, KHCV-LBC27 cDNA, KHCV-LBC28 cDNA, KHCV-LBC29 cDNA, KHCV-LBC30 cDNA, KHCV-LBC31 cDNA and KHCV-LBC32 cDNA were named NS5-LBC20, NS5-LBC 21, NS5-LBC 23, NS5-LBC25, NS5-LBC27, NS5-LBC28, NS5-LBC29, NS5-LBC30, NS5-LBC31 and NS5-LBC32, respectively.

Each of the fragments was digested with Sal I and BamH I; the digested fragment was cloned into M13mp19; and its nucleotide sequence was determined by using Sanger's method. Each of the nucleotide sequences is shown in FIGS. 7 to 26, respectively.

EXAMPLE 3

Preparation of Vector for the Expression of KHCV cDNA Fragments in Yeast (3-A): Amplification of KHCV cDNA Fragments (3-A-1): Preparation of Fragments K384, K510, K573, K897, K403 and K590

<Step 1>

In order to connect a ubiquitin gene to each of the KHCV cDNA fragments cloned in Examples (1-C), (1-D) and (1-E) (hereinafter, the gene made by connecting the ubiquitin gene to the KHCV cDNA fragments will be referred to as "UB-KHCV") and to clone the UB-KHCV into an expression vector for yeasts, the primers disclosed below were synthesized.

Primer PCOREUBI (SEQ ID NO: 39) (5'-CTTGGTGTTGAGACTCCGCGGTGGTATGAGCACG AATCCTAAACC-3') contains 25 nucleotides on the 5'-end region overlapping with the 3'-end region of the ubiquitin gene; and the other nucleotides correspond to the region from the 343rd to the 360th nucleotides of KHCV-LBC1.

Primer PSALCORE14 (SEQ ID NO: 40) (5'-GGGGTCGACTATTAGCATGTGAGGGTGTGGATGAC-3') contains a stop codon to stop translation just after the 726th nucleotide and a recognition site of Sal I.

Primer PSALCORE17 (SEQ ID NO: 41) (5'-GGGGTCGACTATTAGGGCAGATTCCCTGTTGCATA-3') contains a stop codon to stop translation just after the 852 nd nucleotide and a recognition site of Sal I.

Primer PSALCORE22 (SEQ ID NO: 42) (5'-GGGGTCGACTATTAAGCGGAACTGGGGATGG TCAA-3') contains a stop codon to stop translation just after the 915th nucleotide and a recognition site of Sal I.

Primer PK403UBI (SEQ ID NO: 43) (5'-CTTGGTGTTGAGACTCCGGTGGTACGGGCATGA CCACTGACAA-3') contains 25 nucleotides on the 5'-end region which are the same as those of PCOREBUI; and the other nucleotides are designed to initiate translation from the 6649th nucleotide of KHCV-LBC1.

Primer PK573UBI (SEQ ID NO: 44) (5'-CTTGGTGTTGAGACTCCGCGGTGGTACATGGAC AGGCGCCCTGA-3') contains 25 nucleotides on the 5'-end region which are the same as those of PCOREUBI; and the other nucleotides are designed to initiate translation from the 7612th nucleotide of KHCV-LBC1.

Primer PK403SAL (SEQ ID NO: 45) (5'-GACTGGTCGACTATTACTCTTGCCGCCACAAGAG GTT-3') is designed to stop translation just after the 7050th nucleotide of KHCV-LBC1; and has a recognition site of Sal I and two stop codons (TAATAG).

Primer PK897UBI (SEQ ID NO: 46) (5'-CTTGGTGTTGAGACTCCGCGGTGGTGCGGTGGA ATTCATACCCG-3') contains 25 nucleotides on the 5'-end region which are the same as those of PCOREUBI and the other nucleotides are designed to initiate translation from the 3916th nucleotide of KHCV-LBC1.

Primer PK897SAL (SEQ ID NO: 47) (5'-GACTGGTCGACTATTAACACGTATTACAGTCGAT CAC-3') is designed to stop translation just after the 4713th nucleotide of KHCV-LBC1; and has a recognition site of Sal I and two stop codons (TAATAG).

Primer PK573SAL (SEQ ID NO: 48) (5'-GACTGGTCGACTATTAGTACTGGAATCCGTATGA GGAG-3') is designed to stop translation just after the 8184th nucleotide of KHCV-LBC1; and has a recognition site of Sal I and two stop codons (TAATAG) on the 3'-end site.

Primer P426B (SEQ ID NO: 49) (5'-GGGTGGGCAGGATGGCTCCTG-3') consists of the region from the 616th to the 636th nucleotides of KHCV-LBC1.

Primer P240B (SEQ ID NO: 50) (5'-CCTGTTGCATAGTTCACGCCGT-3') consists of the region from the 842 nd to the 821st nucleotides of KHCV-LBC1.

Primer P652B (SEQ ID NO: 51) (5'-GTCATTCCAAGAAGAAATGTGACGAGCTCGCTG CAAAG-3') consists of the region from the 4523rd to the 4560th nucleotides of KHCV-LBC1.

Primer P403B (SEQ ID NO: 52) (5'-GCTGACCTCATTGAGGCCAACCTCTTGT-3') consists of the region from the 7012th to the 7039th nucleotides of KHCV-LBC1.

<Step 2>

A single cDNA fragment was prepared from 3 clones, i.e., KHCV426, KHCV240 and KHCV 513 overlapping with each other, as follows. To a mixture of 2.0 μg of PCOREUBI, 0.02 μg of P426B, 2 μg of P240B and 50 ng of KHCV-LBC1 DNA were added 10 μl of 10X Taq polymerase buffer solution, 10 μl of 10 nM dNTP's mixture and 2.5 units of Taq polymerase; and distilled water was added thereto to adjust the total volume to be 100 μl. A first PCR was then carried out by repeating 25 times the thermal cycle as in Reference Example 7. The resulting mixture was subjected to 5% polyacrylamide gel electrophoresis to isolate 500 bp of the PCR product (hereinafter, referred as "PCR product A"). Thereafter, using 50 ng of PCR product A and 50 ng of KHCV-LBC1 DNA as templates, and 2 μg of PCOREUBI and 2 μg of PSALCORE22 as primers, a second PCR was carried out under the same condition as in the above first PCR. The resulting mixture was subjected to 5% polyacrylamide gel electorphoresis to isolate 580 bp of the final product (hereinafter, referred to as "PCR product B"), which was then dissolved in 50 μl of TE buffer solution.

<Step 3>

In order to carry out further PCRs using the PCR product B obtained in Step 2 as a template, 3 different test tubes, i.e., Tube A containing 2 μg of PCOREUBI and 2 μg of PSALCORE14, Tube B containing 2 μg of PCOREUBI and 2 μg of PSALCORE17, and Tube C containing 2 μg of PCOREUBI and 2 μg of PSALCORE22, in addition to 50 ng of the PCR product B added to each of the tubes, were prepared.

On the other hand, for PCRs using KHCV-LBC1 DNA as a template, other 3 different test tubes, i.e., Tube D containing 2 μg of PK897SAL, 0.02 μg of P652B and 2 μg of PK897UBI, Tube E containing 2 μg of PK403SAL and 2 μg of PK403UBI; and Tube F containing 2 μg of PK573SAL and 0.022 μg of P403Bb and 2 μg of PK573UBI, in addition to 50 ng of KHCV-LBC1 added to each of the tubes, were also prepared.

Thereafer, to each of Tubes A to F were added 10 μl of 10×Taq polymerase buffer solution, 10 μl of 10 mM dNTP's mixture and 25 units of Taq polymerase; and distilled water was added thereto to adjust the total volume to be 100 μl. The PCRs were carried out under the same condition as in Step 2.

<Step 4>

The PCR products obtained in Step 3 were subjected to 5% polyacrylamide gel electrophoresis. As a result, it was confirmed that 384 bp DNA fragment was produced in Tube A, 510 bp of DNA in Tube B, 573 bp of DNA in Tube C, 798 bp of DNA in Tube D, 402 bp of DNA in Tube E, and 573 bp of DNA in Tube F were amplified. The DNA fragments were purified by the same polyacrylamide gel electrophoresis as above; and named fragment K384, fragment K510, fragment K573, fragment K897, fragment K403 and fragment K590, respectively.

(3-A-2): Preparation of cDNA Fragment Encoding KHCV Envelope Protein

<Step 1>

In order to connect the synthesized ubiquitin gene to each of E 2N gene and E 2C gene, which corresponds to the region from the 1510th to the 2010th nucleotides and the region from the 2011th to the 2529th nucleotides of KHCV-LBC1, respectively, and to clone each into an expression vector of yeasts, the following primers were synthesized.

Primer PE2NUBI (SEQ ID NO: 52) (5'-CTTGGTGTTGAGACTCCGCGGTGGTGGGGCGCA AGGTCGGGCCGCT-3') contains 25 nucleotides on the 5'-end region overlapping with the 3'-end region of ubiquitin gene; and the other nucleotides correspond to the region from the 1510th to the 1530th nucleotides of KHCV-LBC1.

Primer PE2NSAL (SEQ ID NO: 53) (5'-GACTGGACTATTAATTCATCCAGGTAGAACCGA ACCA-3') contains a stop codon to stop translation just after the 2010th nucleotide of KHCV-LBC1; and a recognition site of Sal I.

Primer PE2CUBI (SEQ ID NO: 54) (5'-CTTGGTGTTGAGACTCCGCGGTGGTGGCACTG GGTTCACCAAGACA-3') contains 25 nucleotides on the 5'-region overlapping with the 25 nucleotides on the 3'-end region of ubiquitin gene; and the other nucleotides correspond to the region from the 2011th to the 2031th nucleotides of KHCV-LBC1.

Primer PE2CSAL (SEQ ID NO: 55) (5'-GACTGGACTATTACGCGTCCGCCAGAAGAAGG AAGAG-3') contains a stop codon to stop translation after the 2529th nucleotide of KHCV-LBC1; and a recognition site of Sal I.

<Step 2>

Tube A was provided with 2 μg of each of PE2NUBI and PE2NSAL, and Tube B was provided with 2 μg of each of PE2CUBI and PE2CSAL. To each of Tubes A and B were added 50 μg of KHCV-LBC1, 10 μl of 10×polymerase buffer solution, 10 μl of 10 mM dNTP's mixture and 2.5 units of Taq polymerase; and distilled water was added thereto to adjust the total volume to be 100 ml. The PCRs were carried out by repeating 25 times the same thermal cycle as in Reference Example 7.

<Step 3>

The PCR products obtained in Step 2 were subjected to 5% polyacrylamide gel electrophoresis. As a result, it was confirmed that 501 bp of DNA in Tube A and 519 bp of DNA in Tube B were amplified, respectively. The DNAs were purified by the same polyacrylamide gel electrophoresis as above and named segment E2N and segment E2C, respectively.

(3-B): Preparation of Expression Vector for Yeast (3-B-1): Preparation of pYLBC-A/G-UB-CORE14, PYLBC-A/G-UB-CORE17, pYLBC-A/G-UB-CORE22, pYLBC-A/G-UB-KHCV897, PYLBC-A/G-UB-KHCV403 and PYLBC-A/G-UB-KHCV573

2 μg of plasmid pYLBC-A/G-UB-HGH(ATCC74071) was completely digested with Pst I and Sal I in NEB buffer solution 3, while 2 μg of the same plasmid was completely digested with Pst I and Sac II in NEB buffer solution 4 referred to in Reference Example 1. The resulting mixtures were subjected to 0.7% agarose gel electrophoresis to isolate 9.8 kb fragment and 3.4 kb fragment, which were named fragments PL2 and PT2, respectively.

Among the fragments of K384, K510, K573, K987, K403 and K590 prepared in Example (3-A-1), fragments K897, K403 and K590 were completely digested with Sal I and Sac II in NEB buffer solution 3; fragments K384, K510 and K573 were completely digested with Sal I in NEB buffer solution 3, respectively. The products were extracted with phenol/chloroform and precipitated with ethanol; and dissolved in 20 μl of TE buffer solution. Fragments K384, K510 and K573 were further partially digested with Sac II in NBE buffer solution 4 for 10 minutes; and the products were extracted with phenol/chloroform and precipitated with ethanol; and dissolved in 20 μl of TE buffer solution.

The above fragments were used in the ligation as follows. Ligation Tube A was provided with 100 ng of fragment K384; Ligation Tube B was provided with 100 ng of fragment K510; Ligation Tube C was provided with 100 ng of fragment K573; Ligation Tube D was provided with 100 ng of fragment K897; Ligation Tube E was provided with 100 ng of fragment K403; and Ligation Tube F was provided with 100 ng of fragment K573. To each of the tubes were added 100 ng of fragment PL2, 100 ng of fragment PT2, 2 μl of 10×ligation buffer solution and 10 units of T4 DNA ligase; and distilled water was added to adjust the total volume to be 20 μl. The ligation was carried out for 12 hours at 16° C.

E. coli HB101(ATCC 33694) was transformed with each of the ligated vectors respectively.

The vector containing K384 was isolated and named PYLBC-A/G-UB-CORE14; the vector containing K510 was isolated and named pYLBC-A/G-UB-CORE17; the vector containing K573 was isolated and named pYLBC-A/G-UB-CORE22; the vector containing K897 was isolated and named pYLBC-A/G-UB-KHCV897; the vector containing K403 was isolated and named pYLBC-A/G-UB-KHCV403; and the vector containing K590 was isolated and named pYLBC-A/G-UB-KHCV573 (see FIGS. 30).

(3-B-2): Preparation of pYLBC-A/G-UB-E2N and pYLBC-A/G-UB-E2C

2 μg of plasmid pYLBC-A/G-UB-HGH(ATCC 74071) was completely digested with Pst I and Sal I in NEB buffer solution 3, and 2 μg of the same plasmid was completely digested with Pst I and Sac II in NEB buffer solution 4. The resulting mixtures were subjected to 0.7% agarose gel electrophoresis to isolate 9.8 kb and 3.4 kb fragments, which were named fragment PL2 and fragment PT2, respectively.

Each of fragments E2N and E2C prepared in Example (3-A-2) was completely digested with Sac II in NEB buffer solution 4 and further partially digested with Sal I in NEB buffer solution 3. Each of the products was extracted with phenol/chloroform and precipitated with ethanol; and dissolved in 20 μl of TE buffer solution. The fragments were named fragment E2N-T2/L and fragment E2C-T2/L, respectively.

Ligation Tube G was provided with 100 ng of E2N-T2/L and Ligation Tube F was provided with 100 ng of E2C-T2/L. To each of the tubes were added 10 ng of PL2, 10 ng of PT2, 2 μl of 10×ligation buffer solution and 10 units of T4 DNA ligase; and distilled water was added to adjust the total volume to be 20 μl. The reaction was carried out for 12 hours at 16° C. E. coli HB101(ATCC 33694) was transformed with each of the ligated vectors. The vector containing fragment E2N-T2/L was named pYLBC-A/G-UB-E2N; and the vector containing fragment E2C-T2/L was named pYLBC-A/G-UB-E2C (see FIG. 30).

(3-C): Transformation of Yeast and Production of Protein

Yeasts were transformed with the expression vectors prepared in Example (3-B-2) by the same method as in Reference Example 5. Of the transformed yeasts, Saccharomyces cerevisiae DC 04 transformed with pYLBC-A/G-UB-KHCV403 (S. cerevisiae pYLBC-A/G-UB-KHCV 403) was deposited with accession number of ATCC 74079 on Jun. 27, 1991; and Saccharomyces cerevisiae DC 04 transformed with pYLBC-A/G-UB-CORE14 (S. cerevisiae DC 04-UB-CORE 14) was deposited with the accession number of ATCC 74081 on Jul. 1, 1991; and Saccharomyces cerevisiae DC 04 transformed with pYLBC-A/G-UB-E2C (S. cerevisiae DC 04-UB-E2C) was deposited with the accession number of ATCC 74117 on Dec. 11, 1991, to American Type Culture Collection under the terms of Butapest Treaty on the International Recognition of the Deposit of Microorganisms for the Purpose of Patent Procedure.

Among the transformed yeasts, Saccharomyces cerevisiae DC 04-UB-KHCV403 was cultured in 3 ml of leucine-deficient medium (6.7 g of yeast nitrogen base without amino acids (Difco Inc., U.S.A.), 2.5 g of amino acids mixture without leucine per liter, and 5% glucose) at 30° C. overnight. The culture was transferred into 100 ml of YEPD medium (2% peptone, 1% yeast extracts, 2% glucose) and cultured at 30° C. overnight to produce the KHCV protein. The resulting culture had the O.D. value, at 650 nm, of about 25. The other transformed yeasts were cultured in the same manner as above to produce the KHCV proteins.

Each of the cultures was harvested the amount corresponding to the O.D.$_{650}$ value of 10; and centrifuged. Each of the precipitates was suspended in 400 μl of buffer solution (10 mM Tris-HCl, pH 7.5, 1 mM EDTA, 2 mM PMSF (phenylmethylsulfonyl fluoride), 8M urea); and then vigorously shaken with a same volume of glass beads (diameter 0.4 mm) to destroy the cell walls. The yeast extracts so obtained were subjected to 15% sodiumdodecyl sulfate (SDS)-polyacrylamide gel electrophoresis (SDS-PAGE) by employing Laemmli's method (Laemmli et al., Nature, 277, 680(1970)); and the gel was stained with Coomassie brilliant blue R250 to confirm the production of KHCV proteins (see FIG. 31-A).

The proteins separated on the gel were blotted onto a nitro cellulose filter. The filter was put in PBS (10 mM phosphate, pH 7.0, 0.15M NaCl) containing 0.2% Tween 20; and shaken for 2 hours at room temperature to block the non-specific binding of IgG to the proteins. The filter was put in IgG solution prepared by diluting IgG (8.2 mg/ml) affinity purified from Korean HCV patients with 200-fold volume of PBS containing 0.5% gelatin and 0.05% Tween 20; and mildly shaken for 1 hour at room temperature to react the protein and IgG. The filter was then washed with PBS containing 0.2% Tween 20 for 5 minutes, 4 times. The filter was put in an anti-human IgG solution prepared by diluting Anti-Human IgG-HRP labeled with horseradish peroxidase (Bio-Rad Lab., U.S.A., goat anti-human IgG-HRP) with 200-fold volume of PBS containing 0.5% gelatin and 0.05% Tween 20, and shaken for 1 hour at room temperature. The filter was washed with PBS containing 0.2% Tween 20 for 5 minutes, 4 times; and with 50 mM Tris buffer solution (pH 7.0), 2 times.

To the filter were added 50 mM Tris buffer solution containing 400 μg/ml 4-chloro-1-naphthol and 0.03% hydrogen peroxide to develop a color reaction. The results from the above western blotting are shown in FIG. 31-B. In FIG. 31-B, lane 2 shows the result of the extracts of the yeast transformed with pYLBC-A/G-UB-CORE 14; lane 3 shows the result of the extracts of the yeast transformed with pYLBC-A/G-UB-KHCV 897; lane 5 shows the result of the extracts of the yeast transformed with pYLBC-A/G-UB-KHCV 403; lane 6 shows the result of the extracts of the yeast transformed with pYLBC-A/G-UB-KHCV 573; lanes 1 and 4 show the results of the extracts of yeasts having no KHCV expression vector; and lane M represents the standard protein molecular size markers (unit: kilodalton).

FIG. 32 shows the SPS-PAGE and western blotting results to confirm the productions of E2N and E2C proteins. In FIG. 32, lane 1 shows the extracts of yeast transformed with a plasmid without KHCV gene; lane 2 shows the extracts of the yeast transformed with pYLBC-A/G-UB-E2N; lanes 3 to 5 show the extracts of the yeast transformed with pYLBC-A/G-UB-E2N; and lane 6 shows the standard molecular size markers, i.e., 200, 97, 72, 43, 29, 18 and 14 kilodaltons from the top of the gel.

EXAMPLE 4

Preparation of the Vector Expressing KHCV cDNA Fragments in E. coli (4-A): Preparation of Expression Vector Containing trp Promoter (4-A-1): Preparation of KHCV cDNA Fragments The fragments K384, K510, K573, K879, E2N and E2C prepared in Example (3-A-1) and (3-A-2) were used.

Envelope 1(E1) fragment, which is located from the 916th to 1509th nucleotides of KHCV-LBC1, was prepared by PCR in the same manner as in Example (3-A-1), using the following primers:

Primer PEIUBI (SEQ ID NO: 56) (5'-CTTGGTGTTGAGACTCCGCGGTGGTTATGAAGT GGGCAACGCGTCC-3') contains 25 nucleotides on the 5'-end region overlapping with ubiquitin gene; region of the 916th to the 936th nucleotides of KHCV-LBC1.

Primer PEISAL (SEQ ID NO: 57) (5'-GACT GGACTATTACCCTGTCACGTGGGTGGTGGTTCC-3') contains a codon to terminate translation after the 1509th nucleotide of KHCV-LBC1; and a recognition site of Sal I.

(4-A-2): Preparation of Ubiquitin Gene

<Step 1>

3 different oligonucleotides as disclosed below were designed from information on the ubiquitin gene reported by Ozkaynak, et al., EMBO. J. 6, 1429–1439(1987) and synthesized using a DNA synthesizer as follows:

UBI1 (SEQ ID NO: 58): 5'-CCCCATATGCAAATTTTCGTCAAAACTCTAACAGGGAAGACTATAACCCTAGAGGTTGAATCTTCCGACACTATTGACAACGTCAA-3'

UBI2 (SEQ ID NO: 59): 5'-TAGTTGCTTACCAGCAAAAATCAATCTCTGCTGATCCGGAGGGATACCTTCTTTATCTTTGAATTTTACTTTTGACGTTGTCAATAGTCTC-3'

UBI3 (SEQ ID NO: 60): 5'-ACCACCGCGG AGTCTCAACACCAAGTGAAGAGTAGATTCCT TTTG-GATGTTGTAGTCAGACAAGGTTCTACC ATGTTCTAGTTGCTTACCAGCAAAAA-3'

UBI1 was designed to have a recognition site of Nde I (5'-CATATG-3') at the 5'-end and about 20 nucleotides overlapping with UBI2; and UBI3 is designed to have a recognition site of Sac II (5'-CCGCGG-3') without any change in the amino acid sequence encoded therein (see FIG. 33).

<Step 2>

To the mixture of 2 μg of UBI1, 0.02 μg of UBI2 and 2 μg of UBI3 were added 10 μl of 10×PCR buffer solution, 10 μl of 2 mM dNTP's mixture and 0.5 μl of Taq polymerase; and distilled water was added thereto to adjust the total volume to be 100 μl. The PCR was carried out in the same manner as in Reference Example 7. The resulting mixture was subjected to 5% polyacrylamide gel electrophoresis to isolate 240 bp of DNA, which was named fragment Ub; and the isolated fragment was dissolved in 20 μl of TE buffer solution.

(4-A-3): Ligation of Ubiquitin Gene to KHCV cDNA

Each of the fragments prepared in Example (4-A-1) was ligated to fragment Ub by PCR as follows.

As primers for the PCR, the primers prepared in Step 1 of Example (3-A-1) and Step 1 of Example (4-A-2) were used.

7 different test tubes were prepared as follows:

Tube A was provided with 50 ng of fragment K384, 50 ng of fragment Ub, 2 μg of primer UBIL and 2 μg of primer PSALCORE14; Tube B was provided with 50 ng of fragment K510, 50 ng of fragment Ub, 2 μg of primer UBI1 and 2 μg of primer PSALCORE17; Tube C was provided with 50 ng of fragment K573, 50 ng of fragment Ub, 2 μg of primer UBI1 and 2 μg of primer PSALCORE22; Tube D was provided with 50 ng of fragment K897, 50 ng of fragment Ub, 2 μg of primer UBI1 and 2 μg of primer PKHCV897SAL; Tube E was provided with 50 ng of fragment E2N, 50 ng of fragment Ub, 2 μg of primer UBI1 and 2 μg of primer PE2NSAL; Tube F was provided with 50 ng of fragment E2C, 50 ng of fragment Ub, 2 μg of primer UBI1 and 2 μg of primer PE2CSAL; and Tube G was provided with 50 ng of fragment E1, 50 ng of fragment Ub, 2 μg of primer UBI1, and 2 μg of primer PE1SAL.

To each of the tubes were added 10 μl of 10×polymerase reaction buffer solution, 10 μl of 2 mM dNTP's mixture and 0.5 μl of Taq polymerase; and distilled water was added thereto to adjust the total volume to be 100 μl. PCRs were carried out under the same condition as in Reference Example 7. Each of the PCR products was digested with NdeI and Sal I in NEB buffer solution 3; and the fragments obtained in Tubes A to G were named fragments UBCORE14, UBCORE17, UBCORE22, UBKHCV897, UBE2N, UBE2C and UBE1, respectively.

(4-A-4): Preparation of the Expression Vector

<Step 1>

2 μg of ptrp 332-HGH (see Korean Patent Publication No. 91-457, KFCC-10667) was completely digested with Pst I and Sal I; and 2 μg of the plasmid was completely digested with Pst I and Nde I in NEB buffer solution 4. The products were separated on 0.7% agarose gel from which 1.5 Kb and 0.8 Kb fragments were isolated; and named fragments PB and PS, respectively.

<Step 2>

Using the fragments prepared in the above Step 1 and Example (4-A-3), ligation was carried out as follows:

Ligation Tube A was provided with 100 ng of UBCORE14; Ligation Tube B was provided with 100 ng of UBCORE17; Ligation Tube C was provided with 100 ng of UBCORE22; Ligation Tube D was provided with 100 ng of UBKHCV897; Ligation Tube E was provided with 100 ng of UBE2N; Ligation Tube F was provided with 100 ng of UBE2C; and Ligation Tube G was provided with 100 ng of UBE1. To each of the tubes were added 100 ng of PB, 100 ng of PS, 2 μl of 10×ligation buffer solution and 10 units of T4 DNA ligase; and distilled water was added thereto to adjust the total volume to be 20 μl. The reaction was carried out for 12 hours at 16° C. Each of the ligated vectors was isolated; and E. coli HBL101(ATCC 33694) was transformed with each of the vectors. The vector containing fragment UBCORE14 was isolated and named ptrpH-UB-CORE14; the vector containing fragment UBCORE17 was isolated and named ptrpH-UB-CORE17; the vector containing fragment UBCORE22 was isolated and named ptrpH-UB-CORE22; the vector containing fragment UBKHCV 897 was isolated and named ptrpH-UB-KHCV897; the vector containing fragment UBE2N was isolated and named ptrpH-UB-E2N; the vector containing fragment UBE2C was isolated and named ptrpH-UB-E2C; and the vector containing fragment UBE1 was isolated and named ptrpH-UB-E1 (see FIG. 34).

(4-B): Preparation of Vectors pMAL-KHCV Containing tac Promoter (4-B-1): Amplification of KHCV cDNA Fragments <Step 1>

In order to express the KHCV cDNA fragments to the MBP-fused proteins in E. coli by employing tac promoter, the primers discribed below were synthesized using a DNA synthesizer.

Primer PK426R (SEQ ID NO: 61): 5'-CTCCGAATTCGGTGCTTGCGAGTGCCCC-3'

Primer PK426X (SEQ ID NO: 62): 5'-CACG CTCGAGGCATGTGAGGGTGTCGATGAC-3'

Primer PSALCORE17 (SEQ ID NO: 41): 5'-GGG GTCGACTATTAGGGCAGATTCCCTGTTGC-3'

Primer P426B (SEQ ID NO: 49): 5'-GGGT GGGCAGGATGGCTCCTG-3'

Primer PK513R (SEQ ID NO: 63): 5'-CTCCGAATT CGGCACGAGGCTGGAGGACGGCGTGAACT-3'

Primer PK513X (SEQ ID NO: 64): 5'-CAC GCTCGAGAGGCGACCAGTTCATCATCAT-3'

Primer PK80R (SEQ ID NO: 65): 5'-CTCCGAATTC GGCACGAGGGTTTCCCAGCTGTTCACCTT-3'

Primer PK810X (SEQ ID NO: 66): 5'-CACGCT CGAGATTCAGCCATGTACAACCGAACC-3'

Primer PK798R (SEQ ID NO: 67): 5'-CTCCGA ATTCGGCACGAGGGACGTGCTGCTCCTTAAC-3'

Primer PK798X (SEQ ID NO: 68): 5'-CACGCTC GAGCAGAAGCAGCGGCCATACGCC-3'

Primer PK754R (SEQ ID NO: 69): 5'-AAAAAGAATT CGGCACGAGGCTGCGAGATTGGGCTCACA CG-3'

Primer PK754X (SEQ ID NO: 70): 5'-AAAAACTC GAGCCGCATAGTAGTTTCCATAGACTCAAC GGGTATGAATT-3'

Primer PK652R (SEQ ID NO: 71): 5'-AAAAAGA ATTCGGCACGAGGTTCATACCCGTTGAGTC TATGGAA-3'

Primer PK652X (SEQ ID NO: 72): 5'-ATTATT GTC-GACTATCTATCTACTCGAGTCACAGCT TTGCAGCGAGCTCGT-3'

Primer PK403R (SEQ ID NO: 73): 5'-AAAAAGAATTCACGGGCATGACCACTGAC-3'

Primer PK403X (SEQ ID NO: 74): 5'-ATTATTCTCG AGTATCACTCTTGCCGCCACAAGAG-3'

Primer PK271R (SEQ ID NO: 75): 5'-AAAAAGAATTCACTAGCCTTACAGGCCGG-3'

Primer PK271X (SEQ ID NO: 76): 5'-CACGCTCGAGTCACGTGACCAGGTAAAGGTC-3'

Primer PK495R (SEQ ID NO: 77): 5'-CCCCCGAATTCGGCACGAGCGCTGCGGAGGAAAGCAAGTT-3'

Primer PK495X (SEQ ID NO: 78): 5'-AAAAACTCGAGGACCACGTCATAAAGGGCCA-3'

Primer PK494R (SEQ ID NO: 79): 5'-AAAAGAATTCGGCACGAGCGATGCATCTGGTAAAAGGGT-3'

Primer PK494X (SEQ ID NO: 80): 5'-AAAACTCGAGATTGGAGTGAGTTTGAGCTT-3'

<Step 2>

11 different test tubes were prepared, which were provided with the primers as follows:

Tube A: Primer PK426R 2 μg, Primer PK426X 2 μg
Tube B: Primer PK426R 2 μg, Primer PK426B 20 ng, PSALCORE17 20 μg
Tube C: Primer PK513R 2 μg, Primer PK513X 2 μg
Tube D: Primer PK810R 2 μg, Primer PK810X 2 μg
Tube E: Primer PK798R 2 μg, Primer PK798X 2 μg
Tube F: Primer PK754R 2 μg, Primer PK754X 2 μg
Tube G: Primer PK652R 2 μg, Primer PK652X 2 μg
Tube H: Primer PK403R 2 μg, Primer PK403X 2 μg
Tube I: Primer PK271R 2 μg, Primer PK271X 2 μg
Tube J: Primer PK495R 2 μg, Primer PK495X 2 μg
Tube K: Primer PK494R 2 μg, Primer PK494X 2 μg To each of the tubes were added 10 ng of KHCV-LBC1 (ATCC 75008), 10 μl of 10×polymerase buffer solution, 10 μl of 10 mM dNTP's mixture and 0.5 μl (2 units) of Taq polymerase; and distilled water was added thereto to adjust the total volume to be 100 μl.

Each of the reaction mixtures was added 50 μl of mineral oil to prevent evaporation; and PCRs were carried out in the same manner as in Reference Example 7.

(4-B-2): Preparation of Expression Vector

2 μg of pMAL-CR1 (New England Biolabs Inc., Cat. No. 800, 11099 North Torrey Pines Road, La Jolla, Calif., U.S.A.) was completely digested with Eco RI and Sal I in NEB buffer solution 3. The product was exracted with phenol/chloroform and precipitated with ethanol. The precipitate was dissolved in 40 μl of TE buffer solution.

The PCR products prepared in Step 2 of Example (4-B-1) were digested with Eco RI and Xho I as follows:

1 μl of each of the PCR products in Tubes A and C to F, H and J to M was completely digested with Eco RI and Xho I; 3 μg of each of the PCR products in Tubes G and I was completely digested with Xho I and then partially digested with Eco RI; and 1 μl of the PCR product in tube C was completely digested with Eco RI and Sal I. Eco RI-Xho I and Eco RI-Sal I fragments so obtained were isolated and dissolved in 20 μl of TE buffer solution in the same manner as in Reference Example 1, respectively.

To 5 μl of each of the above cDNA fragments digested with Eco RI-Xho I and Eco RI and Sal I were added 2 μl of 10×ligation buffer solution, 1 μl (50 ng) of pMal-CR1 treated with Eco RI and Sal I above and 10 units of T4 DNA ligase; and distilled water was added thereto to adjust the total volume to be 20 μl. The reaction was carried out for 12 hours at 16° C.

Each of the ligated vectors was isolated; and *E. coli* HB101(ATCC 33694) was transformed with each of the recombinant vectors. The vectors in Tubes A to K were named pMAL-KHCV426, pMAL-KHCV555, pMAL-KHCV513, pMAL-KHCV810, pMAL-KHCV798, pMAL-KHCV754, pMAL-KHCV652, pMAL-KHCV403, pMAL-KHCV271, pMAL-KHCV495 and pMAL-KHCV494, respectively.

The vector used for the above recombinant vector, pMAL-CR1, is described in FIG. 35.

(4-C): Expression of KHCV cDNA Fragments in *E. coli*

(4-C-1): Expression of KHCV cDNA Fragments by Vector Containing trp Promoter

<Step 1>

*E. coli* W3110(ATCC 38335) was transformed with each of the plasmids prepared in Example (4-A). Of them, *E. coli* W3110 transformed with ptrpH-UB-KHCV897 (*E. coli* W3110 ptrpH-UB-KHCV 897) was deposited with the accession number of ATCC 69640 on Jun. 27, 1991*; E. coli* W3110 transformed with ptrpH-UB-CORE17 (*E. coli* W3110 ptrpH-UB-CORE 17) was deposited with the accession number of ATCC 68641 on Jun. 27, 1991*; E. coli* W3110 transformed with ptrpH-UB-CORE14 (*E. coli* W3110 ptrpH-UB-CORE 14) was deposited with the accession number of ATCC 68642 on Jul. 1, 1991*; E. coli* W3110 transformed with ptrpH-UB-E1 (*E. coli* W3110 ptrpH-UB-E 1) was deposited with the accession number of ATCC 68878 on Dec. 11, 1991; and *E. coli* W3110 transformed with ptrpH-UB-E2N (*E. coli* W3110 ptrpH-UB-E2N) was deposited with the accession number of ATCC 68966 on Apr. 22, 1992, to American Type Cultue Collection under the terms of Budapest Treaty on the International Recognition of the Deposit of Microorganisms for the Purpose of Patent Procedure.

*E. coli* transformed with ptrpH-UB-CORE14 was cultured with shaking in liquid LB medium (1% Bactotryptone, 0.5% yeast extracts, 1% NaCl) containing 50 μg/ml ampicillin at 37° C. for 12 hours. 5 ml of the culture was transferred into 1 l of M9 medium (40 mM $K_2HPO_4$, 22 mM $KH_2PO_4$, 8.5 mM NaCl, 18.7 mM $NH_4Cl$, 1% glucose, 0.1 mM $MgSO_4$, 0.1 mM $CaCl_2$, 0.4% casamino acid, 10 μl/ml Vit. $B_1$, 40 μg/ml ampicillin); and cultured with shaking for 3 to 4 hours at 37° C. When its O.D. value at 650 nm reached 0.5, indolacrylic acid (IAA) was added to the culture to adjust the final concentration to be 1.4 mM. After 5 hours, the resulting culture was centrifuged at 3000 rpm for 25 minutes to collect the *E. coli* cell precipitate.

The other recombinant *E. coli* cells were cultured in the same manner as above to produce the KHCV proteins.

<Step 2>

Each of the cells was suspended in the buffer solution and then subjected to 15% SDS-PAGE by employing Laemmli's method (Nature 227, 680(1970)) to confirm the expression of the ubiquitin-KHCV protein. The results are shown in FIGS. 36 to 38.

In FIG. 36, lane M represents the standard molecular size marker, i.e., 72, 43, 29 and 18 kilodaltons from the top; lane 1 shows the products of *E. coli* having plasmid without KHCV gene; lane 2 shows the products of *E. coli* transformed with ptrpH-UB-CORE14 wherein 23 kd protein was produced; lane 3 shows the products of *E. coli* transformed with ptrpH-UB-CORE17 wherein 27 kd protein was produced; lane 4 shows the products of *E. coli* transformed with ptrpH-UB-CORE22 wherein 29 kd protein was produced; lane 5 shows the products of *E. coli* transformed with ptrpH-UB-KHCV897 wherein 40 kd protein was produced; and lane 6 shows the purified KHCV UB 897, protein.

In FIG. 37, lane 1 shows the products of *E. coli* having plamid without KHCV gene; lanes 2 to 5 show the products of *E. coli* transformed with ptrpH-UB-E1 harvested after 2,4,6 and 12 hours from the addition time of IAA, respectively; and lane 6 represents the standard molecular size markers, i.e., 72, 43, 29, 18 and 14 kilodaltons from the top.

Figure 38:
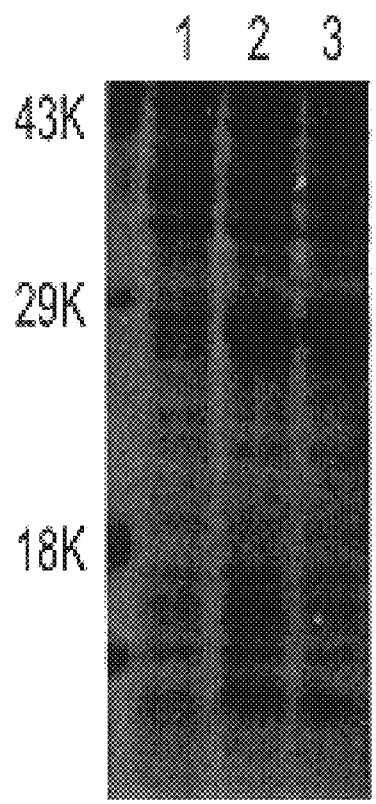

In FIG. 38, lane 1 shows the products of *E. coli* having plasmid without KHCV gene; lane 2 shows the products of *E. coli* transformed with ptrpH-UB-E2C; and lane 3 shows the products of *E. coli* transformed with ptrpH-UB-E2N.

Figure 39:
Figure 40:
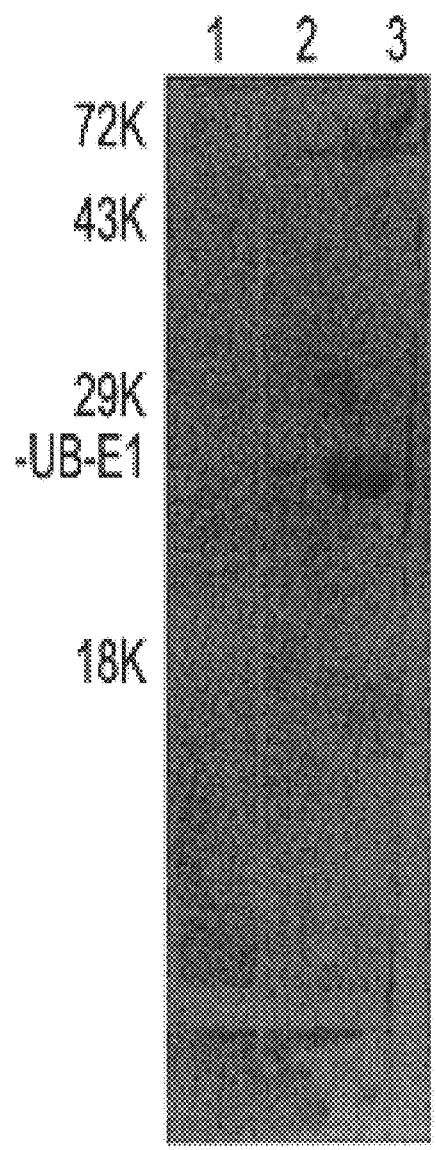
Figure 41:
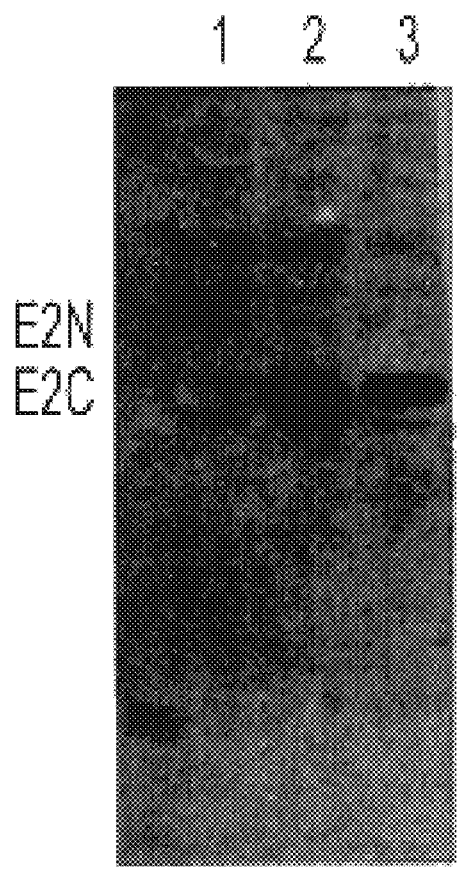

Western blotting was carried out in the same manner as in Example (3-C) to confirm that the proteins produced in recombinant *E. coli* are specifically bound to KHCV antibody. The results are shown in FIGS. 39 to 41.

(4-C-2): Expression of KHCV cDNA by Vector Containing tac Promoter

<Step 1>

*E. coli* D1210(ATCC 27325) was transformed with each of the plasmids prepared in Example (4-B) in the same manner as in Reference Example 4. Among them, *E. coli* D1210 transformed with pMAL-KHCV555 (*E. coli* D1210 pMAL-KHCV555) was deposited with the accession number of 68639 on Jun. 27, 1991 at American Type Cultrue Collection under the terms of Buadpest Treaty on the International Recognition of the Deposit of Microorganisms for the Purpose of Patent Procedure.

The transformed *E. coli* was cultured in liquid LB medium containing 50 µl/ml ampicillin with shaking for 12 hours, and 5 ml of the culture was transferred into 1 l of M9 medium (6 g of $Na_2HPO_4$, 3 g of $KH_2PO_4$, 0.5 g of NaCl, 1 g of $NH_4Cl$, 2 µl of 1M $MgSO_4$, 100 µl of 20% glucose, 0.1 ml of $CaCl_2$ per liter) and cultured with shaking for 3 to 4 hours at 37° C. When its O.D. value at 650 nm reached 0.5, IPTG was added to the culutre to adjust its concentration to be 0.2 mM. After 5 hours, the resulting culture was centrifuged at 3000 rpm for 25 minutes to collect the *E. coli* cell precipitate.

<Step 2>

Figure 42:
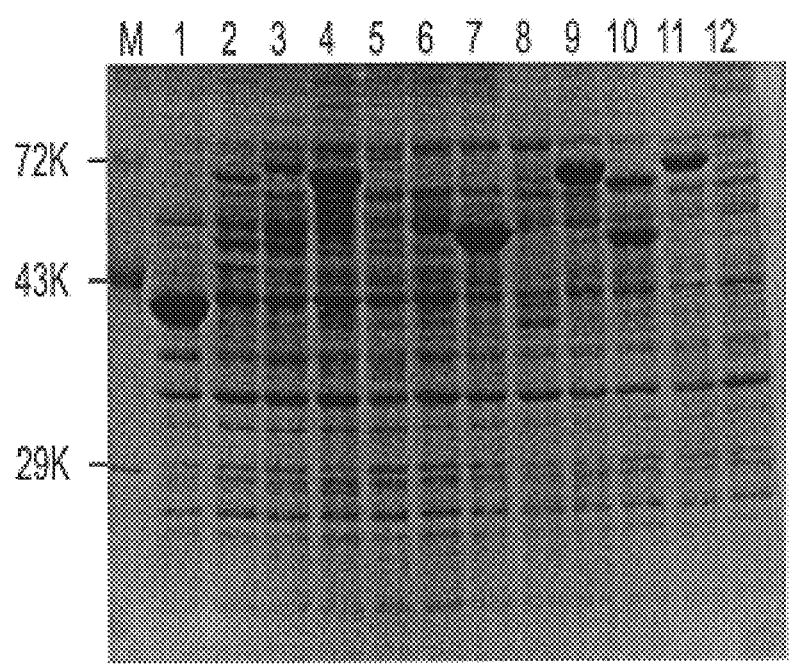

The cell precipitate was suspended in a buffer solution and then subjected to 15% SDS-PAGE by employing Laemmli's method (Nature 227, 680(1970)) to confirm the expression of KHCV proteins. The results are shown in FIG. 42. In FIG. 42, lane M represents the standard molecular size marker; lane 1 shows the products of *E. coli* transformed with pMAL-CR1, wherein 40 kd protein was produced; lane 2 shows the products of *E. coli* transformed with pMAL-KHCV 426, wherein 65 kd protein (MBP-KHCV 426 protein) was produced; lane 3 shows the products of *E. coli* transformed with pMAL-KHCV 555, wherein 70 kd protein (MBP-KHCV555 protein) was produced; lane 4 shows the products of *E. coli* transformed with pMAL-KHCV513, wherein 65 kd protein (MBP-KHCV513 protein) was produced; lane 5 shows the products of *E. coli* transformed with pMAL-KHCV810, wherein 75 kd protein (MBP-KHCV810 protein) was produced; lane 6 shows the products of *E. coli* transformed with pMAL-KHCV798, wherein 72 kd protein (MBP-KHCV798 protein) was produced; lane 7 shows the products of *E. coli* transformed with pMAL-KHCV27, wherein 50 kd protein (MBP-KHCV271 protein) was produced; lane 8 shows the products of *E. coli* transformed with pMAL-KHCV754, wherein 72 kd protein (MBP-KHCV754 protein) was produced; lane 9 shows the products of *E. coli* transformed with pMAL-KHCV652, wherein 70 kd protein (MBP-KHCV652 protein) was produced; lane 10 shows the products of *E. coli* transformed with pMAL-KHCV403, wherein 65 kd protein (MBP-KHCV403 protein) was produced; lane 11 shows the products of *E. coli* transformed with pMAL-KHCV495, wherein 70 kd protein (MBP-KHCV495 protein) was produced; lane 12 shows the products of *E. coli* transformed with pMAL-KHCV494, wherein 70 kd protein (MBP-KHCV494 protein) was produced.

Figure 43:
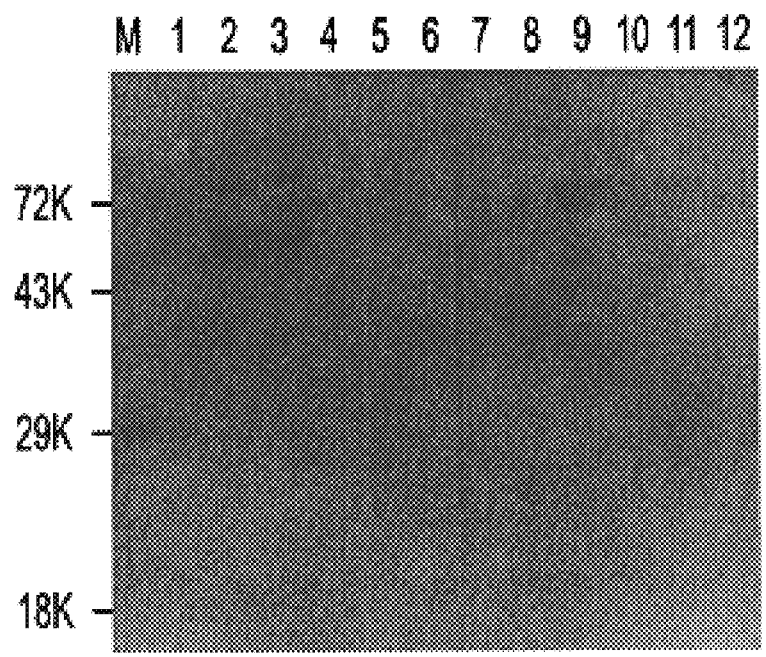
Figure 44:
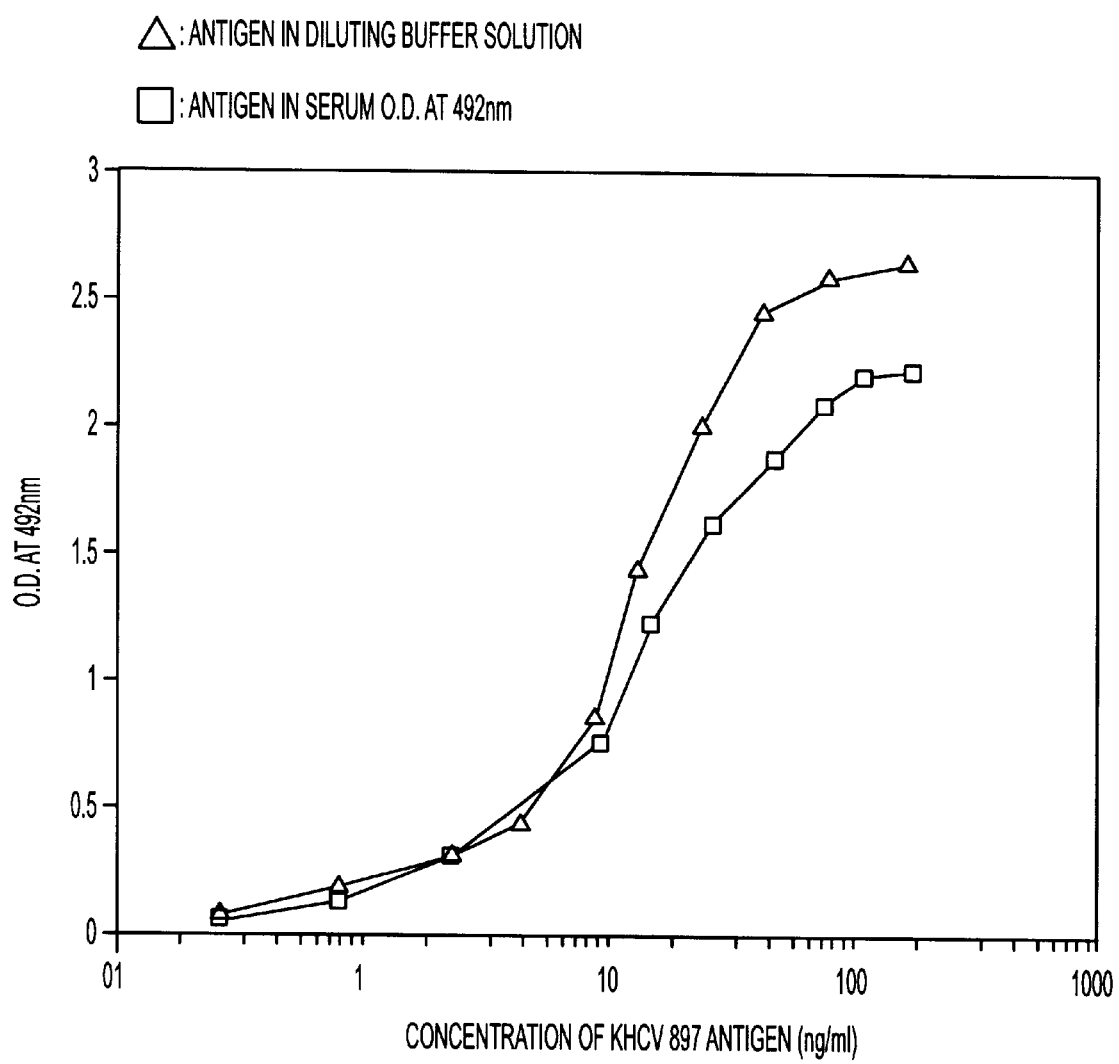
Figure 45:
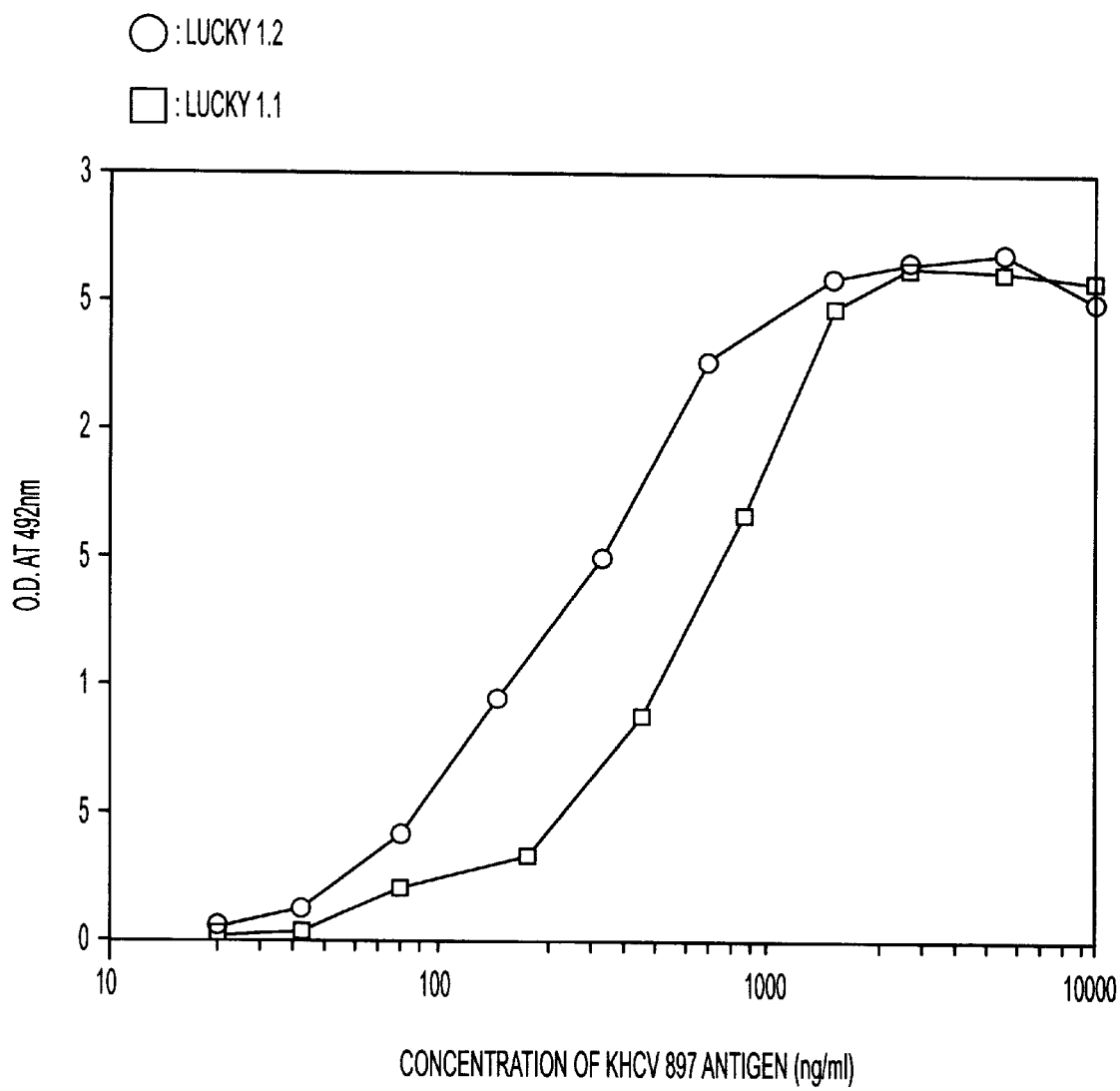

Western blotting was carried out in the same manner as in Example (3-C) to confirm that the above proteins are specifically bound to KHCV antibody. The results are shown in FIG. 43.

(4-C-3): Digestion of MBP from Fused Protein

Each of the MBP-fused proteins was dialysed to Factor Xa buffer solution (20 mM Tris-HCl, pH 8.0, 100 mM NaCl, 2 mM $CaCl_2$, 1 mM azide) for 24 hours. 0.2 µg of each of the dialysed proteins (1 mg/ml) was then mixed with 0.2 µg of Factor Xa (New England Biolabs Inc., Cat. #800-10L); and the reaction mixtures were stood for 24 hours at room temperature.

Each of the resulting mixtures was heated to 100° C. for 5 minutes; and the products were subjected to SDS-PAGE in the same manner as in Example (1-C) to confirm that the MBPs were removed from their fused proteins. The MBP-removed proteins were named KHCV 426 protein, KHCV 555 protein, KHCV 513 protein, KHCV 810 protein, KHCV 798 protein, KHCV 271 protein, KHCV 754 protein, KHCV 652 protein, KHCV 403 protein, KHCV 495 protein and KHCV 494 protein, respectively.

As described above, various lengths and sequences of KHCV cDNAs for the preparation of expression vectors could be prepared by PCR method using various combinations of the primers; and, therefore, it is apparent that other similar KHCV cDNA fragments can be readily synthesized by one skilled in the art, on the basis of the above disclosures. It is also apparent that other KHCV antigen proteins can be readily synthesized by one skilled in the art on the basis of the above disclosures since such KHCV antigen proteins are dependent on the KHCV cDNA. Further, it is apperant that, for the preparation of KHCV cDNAs and KHCV antigen proteins, not only the enzymes, linkers and the other materials used in Examples but also their equivalents can be employed.

EXAMPLE 5

Purification of KHCV Protein Expressed in Yeast Cell (5-A): Purification of KHCV 403 Protein Step 1: Culture of Recombinant Yeast Cell

*Saccharomyces cerevisiae* DCO4-UB-KHCV403 transformed with a vector (pYLBC-A/G-UB-KHCV403) containing KHCV 403 cDNA fragment and ubiquitin gene was cultured in 10 ml of a leucine-deficient medium (0.67% yeast nitrogen base without amino acid, 5% glucose and 0.25% of mixture of amino acids without leucine) at 30° C. for 12 hours; then, the culture was transferred into 100 ml of YEPD medium containing 5% glucose (2% peptone, 1% yeast extract, 5% glucose) and cultured with shaking at a temperature of 30° C. for about 6 hours; and the culture was transferred to 1 l of YEPD medium containing 5% glucose and cultured at 30° C. for 6 hours, to obtain a seed culture for fermentation.

10 l of YEPD medium containing 2% glucose was charged to 14 l fermentor (Bench Top Fermentor: NBS Company, U.S.A.); and the seed culture was inoculated thereto and cultured with shaking at a speed of 250 rpm and at 30° C. for about 48 hours. The culture was centrifuged at a speed of 2500 rpm for 20 minutes with a centrifuge (Beckman J-6B, Rotor JS 4.2) to obtain the recombinant yeast cell paste.

Step 2: Disruption of Yeast Cells

The recombinant yeast cell obtained in Step 1 was suspended in 500 ml of buffer (50 mM Tris, pH 8.5, 5 mM EDTA, 10 mM β-mercaptoethanol, 1 mM phenylmethylsulfonylfluoride, 1 µg/ml pepstatin A); and glass beads having a diameter of 0.4 mm were added in an amount equivalent to 50% (v/v) of the total volume. The resultants were homogenized at 4° C. for 5 minutes with a homogenizer (Bead Beater, Biospec Product, U.S.A.) to disrupt the cell membrane. The disrupted cells were filtered using a filter (Whatman, 3MM, U.S.A.) to remove the glass beads and obtain the yeast homogenate.

Step 3: Identification of Specific Antigen Protein

A small amount of the yeast homogenate obtained in Step 2 was subjected to electrophoresis on 15% SDS-polyacrylamide gel. The result showed that ubiquitins were excised in the cell and proteins expressed from KHCV 403 cDNA (hereinafter referred to as KHCV 403 protein) were produced with a molecular weight of about 17,000 dalton.

The proteins separated on the gel were blotted onto a nitrocellulose filter; and then the filter was placed into phosphate buffered saline (PBS: 10 mM phosphate, 0.15M NaCl, pH 7.0) containing 0.5% Tween-20 in a tray and mildly stirred at a room temperature for 2 hours to block non-specific binding of immunoglobulin G. Subsequently, immunoglobulin G (8.2 mg/ml) which was affinity purified from the serum of a patient with Korean hepatitis C was diluted in a ratio of 1/200 (v/v) with PBS containing 0.5% gelatin and 0.05% Tween 20; 10 ml of the diluted IgG was added to the filter; the tray was shaken mildly at a room temperature for 1 hour; and the filter was washed four times for 5 minutes each with PBS containing 0.05% Tween-20. An anti-human immunoglobulin G labelled with horseradish peroxidase (Bio Rad Lab, Goat Anti-Human IgG-HRP) was diluted with PBS containing 0.5% gelatin and 0.05% Tween-20 in a ratio of 1/200 (V/V) and added to the filter. The filter was reacted with mild shaking at a room temperature for 1 hour. The filter was washed four times for 5 minutes each with PBS containing 0.05% Tween-20 and then twice with 50 mM Tris buffer (pH 7.0). To the filter was added 50 mM Tris buffer (pH 7.0) containing 400 μg/ml 4-chloro-1-naphtol and 0.03% hydrogen peroxide to develop a color reaction. The result showed that KHCV 403 protein of an entire yeast homogenate alone was immunologically reacted with the serum of the patient with hepatitis C to exhibit a visible band; and, therefore, said KHCV 403 protein alone is an immunoreactive protein which can bind to antibodies against KHCV.

Step 4: Removal of Dissolved Protein

The yeast homogenate obtained in Step 2 was centrifuged at 11,000 rpm with a centrifuge (Beckmn J2-21, Rotor JA 14) to remove the supernatant and obtain the insoluble precipitate containing KHCV 403 protein.

Step 5: Dissolution and Fractionation of the Precipitate with Urea

The precipitate obtained in Step 4 was dissolved in 750 ml of a buffer (50 mM Tris, pH 8.5, 5 mM EDTA, 10 mM β-mercaptoethanol, 1 mM phenylmethylsulfonylfluoride, 1 μg/ml pepstatin A) containing 8M urea. The solution was centrifuged to remove undissolved precipitates and collect the supernatant. The supernatant was dialyzed with a buffer (10 mM Tris, pH 9.0, 2 mM EDTA, 5 mM β-mercaptoethanol) containing 2M urea and centrifuged to remove the precipitates and obtain the supernatant containing KHCV 403 protein.

Step 6: First DEAE Ion Exchange Chromatography

The supernatant obtained in Step 5 was passed over DEAE-Sepharose column (Pharmacia, FF, 5 cm×15 cm, U.S.A.) equilibrated with a buffer (10 mM Tris, pH 9.0, 2 mM EDTA, 5 mM β-mercaptoethanol) containing 2M urea. The bound proteins were eluted by adding 750 ml of a buffer (10 mM Tris, pH 9.0, 2 mM EDTA, 5 mM β-mercaptoethanol) containing 0.2M sodium chloride.

Step 7: Second DEAE Ion Exchange Chromatography

The protein fractions which contained KHCV 403 protein were collected and dialyzed with a buffer (10 mM Tris, pH 9.0, 2 mM EDTA, 5 mM β-mercaptoethanol) to remove urea and then passed over DEAE-Sepharose column equilibrated with said buffer. A buffer (10 mM Tris, pH 9.0, 2 mM EDTA, 4 mM β-mercaptoethanol) containing 0.1M sodium chloride was added to separate out the eluted protein; and 500 ml of the buffer having a concentration gradient of 0.1M to 0.2M sodium chloride was added to fractionate the column-bound proteins. The fractions were subjected to SDS-PAGE to collect the fractions containing highly purified KHCV 403 protein.

Step 8: FPLC-phenyl Chromatography

The fractions obtained in Step 7 were dialyzed with a buffer (50 mM Tris, pH 7.4, 2 mM EDTA, 5 mM β-mercaptoethanol) containing 1.5M sodium chloride and passed over FPLC-phenyl superose column (Pharmacia, HR 10/10, 1 cm×8 cm, U.S.A.) equilibrated with said buffer; and 160 ml of the buffer containing a concentration gradient of 1.5 to 0M sodium chloride was added to fractionate the proteins. The fractions were subjected to SDS-PAGE to identify the purity. The fractions containing highly purified KHCV 403 proteins were separately pooled to obtain KHCV 403 proteins having a purity of more than 95%.

(5-B): Purification of KHCV CORE 14 Protein

Step 1: Culture of Recombinant Yeast Cells

*Saccharomyces cerevisiae* DCO4-UB-CORE 14 transformed with a vector (pYLBC-A/G-UB-CORE 14) containing a cDNA fragment encoding KHCV CORE 14 protein and ubiquitin gene was cultured in a leucine deficient medium containing 5% glucose in accordance with the process of Step 1 of Example (5-A); 20 ml of the culture was transferred to 100 ml of YEPD medium containing 4% glucose and cultured with shaking at 30° C. for 6 hours; and transferred to 1 l of YEPD medium containing 2% glucose and cultured at 30° C. for 24 to 48 hours. The culture was centrifuged to collect cell precipitates.

Step 2: Disruption of Yeast Cells

The recombinant yeast cell precipitates obtained in Step 1 were suspended in 30 ml of a buffer (50 mM Tris, pH 7.5, 5 mM EDTA, 10 mM β-mercaptoethanol, 1 mM phenylmethylsulfonylfluoride, 1 μg/ml pepstatin); and glass beads having a diameter of 0.4 mm were added in an amount equivalent to 50% of the total volume. The resultants were homogenized for 5 minutes at 4° C. with a homogenizer (Bead Beater, Biospec Product, U.S.A.) 3 times to disrupt the cell membrane and obtain the yeast homogenate.

Step 3: Identification of Specific Antigen Protein

A small amount of the yeast homogenate obtained in Step 2 was subjected to electrophoresis on 15% SDS-polyacrylamide gel and stained with coomassie brilliant blue. The result showed that the ubiquitin was excised from the KHCV protein and the protein expressed in KHCV cDNA (hereinafter referred to as KHCV CORE 14 protein) was produced with a molecular weight of about 16,000 dalton.

Western blotting was carried out in accordance with Step 3 of Example (5-A). The result indicated that KHCV CORE 14 protein alone was immunologically reactive with the serum of the patient with hepatitis C to exhibit a visible band.

Step 4: Removal of Soluble Proteins and Washing of Insoluble Precipitate

The yeast homogenate obtained in Step 2 was centrifuged at 11,000 rpm with a centrifuge (Beckman J2-21, Rotor JA-14) to remove dissolved proteins and obtain insoluble precipitate containing KHCV CORE 14 protein. The precipitate was suspended in 0.5 l of PBS containing 1% Triton X-100, 1 mM EDTA and 10 mM β-mercaptoethanol with stirring for 10 minutes and centrifuged. The precipitate was washed once with 10 mM phosphate solution (pH 6.5).

Step 5: Dissolution of the Precipitate with 8M Urea

The insoluble precipitate obtained in Step 4 was suspended in 10 mM sodium phosphate solution (pH 6.5) containing 8M urea, 1 mM EDTA and 10 mM β-mercaptoethanol; and stirred for 12 hours at 4° C. to dissolve KHCV CORE 14 protein. The solution was centrifuged for 20 minutes at 15,000 rpm with a centrifuge (Beckman J2-21, Rotor JA20) to obtain the supernatant.

Step 6: CM-ion Exchange Resin Chromatography

The solution containing KHCV CORE14 protein obtained in Step 5 was passed at a flow rate of 1 ml/min. over a column (2.5 cm×10 cm) having 25 ml of CM (carboxymethyl)-Sepharose resin (Pharmacia, Sweden) equiribrated with a buffer (pH6.5) containing 6M urea, 1 mM EDTA, 10 mM β-mercaptoethanol and 10 mM phosphate. The materials remaining in the column in free form were thoroughly washed with said equilibrating buffer solution. The proteins adsorbed in the column were eluted at a flow rate of 3 ml/min. with 500 ml of said equilibrating buffer solution with a concentration gradient of 0 to 0.5M sodium chloride. The eluate was subjected to SDS polyacrylamide gel electrophoresis, which indicated that KHCV CORE14 protein was eluted at about 0.3M sodium chloride. Fractions containing KHCV CORE 14 protein were collected for use in the next step.

Step 7: S-200 Gel Permeation Chromatography

The fractions collected in Step 6 were passed over YM5 ultrafiltration membrane (Amicon, U.S.A.) to concentrate to 10 ml. The concentrate was passed over S-200 Sephacryl column (Pharmacia, Sweden, 2.5 cm×100 cm) equilibrated with PBS solution containing 6M urea, 1 mM EDTA and 10 mM β-mercaptoethanol at a flow rate of 0.5 ml/min. to separate them according to the in molecular weight. The collected protein fractions were subjected to 15% SDS-polyacrylamide gel electrophoresis. Fractions containing highly purified KHCV CORE14 protein were collected and dialyzed with PBS buffer at 4° C. to remove urea and obtain 4 mg of highly purified KHCV CORE14 protein.

It should be understood that the proteins encoded in other KHCV cDNA fragments expressed in yeast may also be purified by other processes similar to one described above.

EXAMPLE 6

Purification of KHCV Protein Expressed in *E. coli*

(6-A): Purification of KHCV UB 897 Protein

Step 1: Culture of Recombinant *E. coli*

*E. coli* W3110 ptrpH-KHCV 897(ATCC 68640) transformed with a vector (ptrpH-UB-KHCV 897) comprising KHCV 897 cDNA fragment with ubiquitin gene was cultured with shaking for 12 hours in LB medium (10 g of Bactotriptone, 5 g of yeast extract, 10 g of NaCl per liter) containing 50 μg/ml of ampicillin. 5 ml of the culture was transferred to 1 l of M9 medium (40 mM $K_2HPO_4$, 22 mM $KH_2PO_4$, 8.5 mM NaCl, 18.7 mM $NH_4Cl$, 1% glucose, 0.1 mM $MgSO_4$, 0.1 mM $CaCl_2$, 0.4% casamino acid, 10 μg/ml of Vit. $B_1$) containing 40 μg/ml of ampicillin and cultured with shaking for about 3 to 4 hours at 37° C. Indoleacrylic acid (IAA) was added so as to make the final concentration of 0.14 mM and produce KHCV UB 897 protein when O.D. value of the culture at 650 nm reached 0.5. After about 5 hours from the addition of IAA, the cell culture was centrifuged at 2,500 rpm for 20 minutes with a centrifuge (Beckman J-6B, Rotor JS 4.2) to obtain *E.coli* cell precipitate. The precipitate was washed once with phosphate buffered saline (10 mM phosphate, pH 7.0, 0.15M sodium chloride).

Step 2: Disruption of Cells 3 g of *E. coli* cell precipitate obtained in Step 1 was suspended in 40 ml of a buffer (50 mM Tris, pH 8.5, 5 mM EDTA, 2 mM β-mercaptoethanol, 1 mM phenylmethylsulfonylfluoride, 1 μg/ml pepstatin A). 0.3 ml of 50 mg/ml lysozyme solution was added to the suspension, left at 37° C. for 1 hour and subjected to ultrasonication on ice for 5 minutes and at an output of 70% with an ultrasonicator (HEAT SYSTEMS-ULTRASONICS INC., W225, U.S.A.) to disrupt the cell and obtain a homogenate of *E. coli* cell.

Step 3: Identification of Specific Antigen Protein

A small amount of the homogenate of *E. coli* cell obtained in step 2 was subjected to 12% SDS-PAGE. The result indicated that the KHCV protein expressed by said vector (hereinafter referred to as KHCV UB 897 protein) have a molecular weight of 39,000 dalton.

Thereafter, proteins separated on gel were transferred onto a nitrocellulose filter and subjected to Western-blotting in the same manner as Step 3 of Example (5-A). The result showed that only KHCV UB 897 protein was immunologically reacted with the serum of the patient with hepatitis C to exhibit a visible band. In the light of the result, it can be seen that said expressed KHCV UB 897 protein is an immunoreactive protein which can bind to antibodies against HCV.

Step 4: Removal of Soluble Protein

The cell homogenate obtained in Step 2 was centrifuged at 11,000 rpm for 25 minutes with a centrifuge (Beckman J2-21, Rotor JA 14) to remove dissolved proteins and obtain insoluble precipitate.

Step 5: Washing of Insoluble Precipitate with Triton X-100 and Tris Buffer

The precipitate obtained in Step 4 was suspended in 50 ml of a buffer (50 mM Tris, pH 8.5, 5 mM EDTA, 2 mM β-mercaptoethanol) containing 1% Triton X-100. The suspension was stirred at a room temperature for 30 minutes and centrifuged at 11,000 rpm for 25 minutes with a centrifuge (Beckman J2-21, Rotor JA 14) to remove the supernatant and obtain insoluble precipitate. Subsequently, the precipitate was suspended in 50 ml of a buffer (50 mM Tris, pH 8.5, 5 mM EDTA, 2 mM β-mercaptoethanol). The suspension was stirred and recentrifuged to remove the supernatant and obtain insoluble precipitate.

KHCV UB 897 protein having a purity of at least 60% was obtained through the above simple washing procedure only.

Step 6: Dissolution of Insoluble Precipitate with 8M Urea

The insoluble precipitate containing KHCV UB 897 protein obtained in Step 5 was suspended in 50 ml of a buffer containing 8M urea (20 mM phosphate, pH 6.0, 2 mM EDTA, 2 mM β-mercaptoethanol). The suspension was stirred at a room temperature for 1 hour and centrifuged to remove insoluble precipitate and obtain the supernatant.

Step 7: S-Sepharose Ion Exchange Chromatography

The supernatant obtained in Step 6 was passed over S-Sepharose column (Pharmacia, FF, 2.5 cm×7 cm, U.S.A.) equilibrated with a buffer (20 mM phosphate, pH 6.0, 2 mM EDTA, 2 mM β-mercaptoethanol) containing 4M urea and was eluted with 600 ml of the buffer having a concentration gradient of 0 to 0.2M sodium chloride. Protein fractions were subjected to SDS-PAGE to collect the fractions comprising highly purified KHCV UB 897 protein.

Step 8: Removal of Urea and FPLC-Mono Q Ion Exchange Chromatography

The protein fractions comprising KHCV UB 897 protein collected in Step 7 were dialyzed against a buffer (10 mM Tris, pH 8.5, 2 mM EDTA, 2 mM β-mercaptoethanol) to remove urea, loaded over FPLC-Mono Q ion exchange resin column (Pharmacia, HR 5/5) equilibrated with said buffer and eluted with 40 ml of the buffer having a concentration gradient of 0 to 0.4M sodium chloride. The fractions comprising high purified KHCV UB 897 protein were collected to obtain KHCV UB 897 protein having a purity of at least 90%.

(6-B): Purification of KHCV UB CORE 17 Protein

Step 1: Culture of Recombinant *E. coli*

*E. coli* W3110 ptrpH-UB-CORE 17(ATCC 68641) transformed with a vactor (ptrpH-UB-CORE 17) containing a cDNA of hepatitis C virus and ubiquitin gene was cultured in LB medium containing 50 μg/ml ampicillin, 100 μg/ml tryptophan at 37° C. for 12 hours; 50 ml of the culture was transfered to 1 l M9 medium and cultured at 37° C. for 6 to 8 hours; and collected a cell precipitate as described in step 1 of Example (6-A).

Step 2: Disruption of Cell 3 g of *E. coli* cell precipitate obtained in Step 1 was suspended in 20 ml of a buffer (50 mM Tris, pH 7.5, 5 mM EDTA, 10 mM β-mercaptoethanol, 1 mM phenylmethylsulfonyl fluoride, 1 μg/ml pepstatin) at 4° C. 3 mg of lysozyme was added to the suspension and stirred for 5 minutes. The resultant was subjected to ultrasonic treatment for 20 minutes in an ice bath with an ultrasonicator (Heat Systemas-Ultrasonics, Inc., W225, U.S.A.) to disrupt the cells and obtain a cell homogenate.

Step 3: Identification of Specific Antigen Protein

Said *E. coli* cell homogenate obtained in Step 2 was subjected to electrophoresis on 15% SDS-polyacrylamide gel and stained with coomassie brilliant blue. The result indicated that the protein having a molecular weight of about 27,000 dalton (hereinafter referred to as KHCV UB CORE 17 protein) was produced.

Subsequently, proteins separated on gel were transferred onto a nitrocellulose filter, which was subjected to western-blotting in accordance with the same process as in Step 3 of Example (5-A). The result showed that only KHCV UB-CORE 17 protein in the whole *E. coli* cell homogenate was immunologically reacted with the serum of the patient with hepatitis C to exhibit-a visible band.

Step 4: Treatment with Urea

The cell homogenate obtained in Step 2 was centrifuged at 12,000 rpm for 20 minutes with a centrifuge (Beckman J2-21, Rotor JA2) to remove insoluble materials and obtain the supernatant. To the supernatant was added 9M urea solution to a final concentration of 6M and stirred at 4° C. for 12 hours.

Step 5: Treatment with Acid

To the solution obtained in Step 4 was added 1M sodium acetate (pH 4.5) to a concentration of 10 mM; and 1M acetic acid to pH 5.0. The mixture was stirred for 1 hour and centrifuged at 11,000 rpm with a centrifuge (Beckman J2-21, Rotor JA 14) to remove the precipitate and obtain the supernatant.

Step 6: Mono-S Chromatography

The supernatant obtained in Step 5 was purified by passing it over FPLC Mono-S column (HR 5/5, Pharmacia, Sweden). UB-CORE 17 protein solution was loaded over the column equilibrated with buffer A (pH 5.0) containing 8M urea, 1 mM EDTA, 1 mM β-mercaptoethanol and 10 mM acetic acid, which was then washed with said buffer A. Thereafter, buffer B containing 8M urea, 1 mM EDTA, 1 mM β-mercaptoethanol, 10 mM acetic acid and 1M sodium chloride was added gradually to an amount of 17.5% for first 5 minutes, 35% for next 55 minutes and 100% for final 10 minutes at a flow rate of 0.8 ml/min to elute the protein. KHCV UB-CORE 17 protein was eluted when the amount of buffer B reached 25%, i.e., when the concentration of sodium chloride was 0.25M.

Step 7: S-200 Gel Permeation Chromatography

The protein solution obtained in Step 6 was passed over S-200 Sephacryl column (Pharmacia, Sweden, 2.5 cm×100 cm) equilibrated with PBS solution containing 6M urea, 1 mM EDTA and 1 mM β-mercaptoethanol at a flow rate of 0.5 ml/min. to separate it according to the molecular weight. Protein fractions were collected and subjected to SDS-polyacrylamide gel electrophoresis to collect the fractions comprising KHCV UB-CORE 17 protein. The fractions were dialyzed against PBS solution at 4° C. to obtain 4 mg of KHCV UB-CORE 17 protein having a purity of at least 90%.

(6-C): Puriciication of UB-E1 Protein

Step 1: Culture of Recombinant Bacterial Cell

*E. coli* W3110 ptrpH-UB-E1(ATCC 68878), which is capable of producing a fused protein of KHCV E1 protein and ubiquitin (UB), was cultured and collected in accordance with the same process as in Step 1 of Example (6-A).

Step 2: Disruption of Cell

The bacteria cell precipitate obtained in Step 1 was suspended in 50 ml of a buffer 1 (20 mM Tris, pH 7.5, 1 mM EDTA, 2 mM β-mercaptoethanol, 1 mM phenylmethylsulfonyl fluoride, 1 μg/ml pepstatin A). A lysozyme solution was added to the suspension to a final concentration of 0.2 mg/ml, cultured at 37° C. for 30 minutes and subjected to ultrasonic treatment on ice at an output of 70% and for 5 minutes with an ultrasonicator to disrupt the cells and obtain the homogenate.

Step 3: Identification of Expression of Specific Antigen

The homgenate obtained in Step 2 was subjected to electrophoresis on 15% SDS-polyacrylamide gel, which indicated that proteins having a molecular weight of about 27,000 dalton (hereinafter referred to as UB-E1 protein) were expressed with the vector.

The proteins separated on gel were blotted onto Immobilon P filter (MILLIPORE, Cat. No. IPUH 00010, pore size 0.45 μm) and subjected to western-blotting in the same manner as in Step 3 of Example (5-A).

The result showed that only UB-E1 protein in the entire cell homogenate was immunologically reacted with the serum of the patient with hepatitis C to produce a visible band.

Step 4: Removal of Soluble Protein

The cell homogenate obtained in Step 2 was centrifuged at 11,000 rpm for 25 minutes with a centrifuge (Beckman J2-21, Rotor JA14) to remove soluble proteins and obtain insoluble precipitate.

Step 5: Washing of Insoluble Precipitate

The precipitate obtained in Step 4 was suspended in 30 ml of a buffer 1 (20 mM Tris, pH 7.5, 1 mM EDTA, 2 mM β-mercaptoethanol) containing 1% Triton X-100. The suspension was stirred at a room temperature for 30 minutes and centrifuged at 11,000 rpm for 25 minutes with a centrifuge (Beckman J2-21, Rotor JA 14) to remove proteins soluble in 1% Triton X-100 and obtain precipitated proteins. The precipitate was suspended in 30 ml of buffer 1 with stirring and recentrifuged to obtain insoluble proteins.

UB-E1 protein having a purity of at least 60% was obtained by the above simple washing procedure.

Step 6: Dissolution and Fractionation of Insoluble Precipitate

The insoluble precipitate comprising UB-E1 proteins obtained in Step 5 was suspended in 50 ml of buffer 2 containing 8M guanidine HCl (50 mM Tris, pH 9.0, 1 mM EDTA, 2 mM β-mercaptoethanol). The suspension was stirred at a room temperature for 30 minutes and centrifuged at 11,000 rpm for 25 minutes with centrifuge to remove the insoluble precipitate and obtain the supernatant. The supernatant was diluted with buffer 2 to have the final concentration of 0.5M guanidine HCl; and centrifuged to remove the supernatant and obtain a precipitate containing the UB-E1 protein.

Step 7: Dissolution of Insoluble Precipitate

The insoluble precipitate comprising UB-E1 protein obtained in Step 6 was suspended in 20 ml of buffer 3 (50 ml sodium carbonate, pH 9.5, 1 mM EDTA, 2 mM β-mercaptoethanol) containing 8M urea. The suspension was stirred at a room temperature for 1 hour to remove the insoluble precipitate and obtain the supernatant by centrifugation at 11,000 rpm for 25 minutes (Beackman J2-21, Rotor JA14).

Step 8: Q-Sepharose Ion Exchange Chromatography

The supernatant obtained in Step 7 was passed over Q-Sepharose column (Pharmacia, FF, 1.2 cm×7 cm) equilibrated with said buffer 3; and 100 ml of the buffer having a concentration gradient of 0 to 0.4M sodium chloride was added to elute the bound proteins. The protein fraction was subjected to electrophoresis on 15% SDS-polyacrylamide gel to collect a fraction comprising UB-E1 protein and obtain UB-E1 protein having a purity of at least 90%.

(6-D): Purification of KHCV UB-CORE 14 Protein

Step 1: Culture of Recombinant *E. coli*

*E. coli* W3110 ptrpH-UB-CORE 14(ATCC 68642) transformed with a vector (ptrpH-UB-CORE 14) containing cDNA fragment of KHCV and ubiquitin gene was cultured in LB medium containing 50 μg/ml ampicillin and 100 μg/ml tryptophan at 37° C. for 12 hours; 50 n of the culture was transferred to 1 l M9 medium and cultured at 37° C. for 6 to 8 hours; and collected cell paste in accordance with the same process as in Step 1 of Example (6-A).

Step 2: Disruption of Cells 4 g of *E. coli* cells obtained in Step 1 was suspended in 20 ml of a buffer (50 mM Tris, pH 7.5, 5 mM EDTA, 10 mM β-mercaptoethanol, 1 mM phenylmethylsulfonylfluoride, 1 μg/ml pepstatin) at 4° C. 4 mg of lysozyme was added to the suspension, stirred for 5 minutes and subjected to ultrasonic treatment in ice-bath for 20 minutes with an ultrasonicator to disrupt the cells.

Step 3: Identifiction of Specific Antigen Protein

A small amount of the homogenate obtained in Step 2 was subjected to electrophoresis on 15% SDS-polyacrylamide gel as described in the previous section and stained with Coomassie brilliant blue. The result was indicated that the proteins about 23,000 dalton (hereinafter referred to as KHCV UB-CORE 14 protein) was expressed.

Subsequently, the proteins separated in the above SDS-PAGE were blotted onto a nitrocellulose filter. The filter was subjected to western-blotting in accordance with the same process as in Step 3 of Example (5-A). The result showed that the KHCV UB-CORE 14 protein in the entire *E. coli* homogenate was immunologically reacted with the serum of a hepatitis C patient to exhibit a visible band.

Step 4: Treatment with Urea

The homogenate obtained in Step 2 was centrifuged at 12,000 rpm for 20 minutes with a centrifuge (Beckman J2-21, Rotor JA 20) to remove the insoluble material and obtain the supernatant. 9M urea was added to the supernatant to the final concentration of 8M and stirred for 12 hours at room temperature.

Step 5: Treatment with Acid

To the solution obtained in Step 4 was added 1M sodium acetate (pH 4.5) to be the final concentration of 10 mM, followed by an addition of 1M acetic acid to be pH=5.0 with stirring for 1 hour at room temperature. The solution was centrifuged at 11,000 rpm with a centrifuge (Beckman J2-21, Rotor JA 14) to remove the precipitate and obtain the supernatant.

Step 6: CM-ion Exchange Chromatography

The solution containing KHCV UB-CORE 14 protein obtained in Step 5 was passed at a flow rate of 1 ml/min. over a column (2.5 cm×10 cm) having 25 ml of CM-Sepharose resin (Pharmacia, Sweden) equilibrated with a buffer (pH 5.0) containing 8M urea, 1 mM EDTA, 10 mM β-mercaptoethanol and 10 mM acetate. Materials remaining in the column in free form were thoroughly washed with said equilibrating buffer solution. Proteins bound to in the column were eluted at a flow rate of 3 ml/min. with 500 ml of said equilibrating buffer solution having a concentration gradient of 0 to 0.5M sodium chloride. The eluate was subjected to SDS-polyacryl amide gel electrophoresis, which indicated that KHCV UB-CORE 14 protein was eluted at about 0.3M. The fractions containing KHCV UB-CORE 14 were collected for use in the next step.

Step 7: S-200 Gel Permeation Chromatography

The fractions collected in Step 6 were passed over YM5 ultrafiltration membrane (Amicon, U.S.A.) to concentrate to a volume of 10 nm. The concentrate was passed over S-200 Sephacryl column (2.5 cm×100 cm, Pharmacia, Sweden) equilibrated with PBS solution containing 6M urea, 1 mM EDTA and 1 mM β-mercaptoethanol at a flow rate of 0.5 ml/min to separate proteins according to their molecular weight. The protein fractions were subjected to SDS-polyacrylamide gel electrophoresis. Fractions comprising KHCV UB-CORE 14 protein were collected.

Step 8: Mono-S Chromatography

The solution of KHCV UB-CORE 14 protein obtained in Step 7 was further purified by passing it over FPLC Mono-S column (HR 5/5, Pharmacia, Sweden). The KHCV UB-CORE 14 protein solution was diluted with the same volums of buffer A, passed over the column equilibrated with buffer A (pH 7) containing 6M urea, 1 mM EDTA, 1 mM β-mercaptoethanol and 10 mM phosphate, which was then washed with said buffer A. Thereafter, buffer B containing 6M urea, 1 mM EDTA, 1 mM β-mercaptoethanol, 10 mM phosphate and 0.5M sodium chloride was added gradually to an amount of 35% for first 5 minutes, 70% for next 55 minutes and 100% for final 10 minutes at a flow rate of 0.8 ml/min to elute the bound proteins. The KHCV UB-CORE 14 protein was eluted when the amount of buffer B reached 60%, i.e., when the concentration of sodium chloride became 0.25M.

The fraction was dialyzed against PBS solution at 4° C. to obtain 4 mg of KHCV UB-CORE 14 protein having a purity of at least 90%.

(6-E): Purification of UB-E2N Protein

Step 1: Culture of Recombinant Bacterial Cell

*E. coli* W3110 ptrpH-UB-E2N(ATCC 68966) which is capable of producing a fused protein of KHCV E2N protein and ubiquitin was cultured with shaking for 12 hours in LB medium containing 50 μg/ml ampicillin. 10 ml of the culture was transferred to 1 l of M9 medium containing 2% casamino acid and 10 μg/ml of tryptopan; and cultured with shaking at 37° C. for about 3 hours. To the culture was added indoleacrylic acid (IAA) to be the final concentration of 50 μg/ml when its O.D. at 650 nm was 0.2 to induce the production of recombinant UB-E2N protein. After about 5 hours from the addition of IAA, the culture was centrifuged at 3,500 rpm for 25 minutes with a centrifuge (Beckman J-6B, Rotor JS4.2) to collect the cell precipitate. The precipitate was washed once with PBS.

Step 2: Identification of the Specific Antigen

The homogenate was subjected to electrophoresis on 15% SDS-polyacrylamide gel. The result indicated that UB-E2N protein was expressed in a molecular weight of about 28,000 dalton.

Subsequently, proteins separated on the gel were blotted onto a Immobilone P filter (Millipore, Cat. No. IPUH 00010, pore size 0.45 μm). The filter was placed into PBS (10 mM phosphate, pH 7.0, 0.15M sodium chloride) containing 0.5% Tween 20 and shaken at a room temperature for 2 hours to block a non-specific binding of immunoglobulin G. 10 ml of the serum of a hepatitis C patient as described previously diluted with PBS containing 0.5% gelatin and 0.05% Tween in a ratio of 1:20 was added thereto. The resultant was reacted with mild shaking at a room temperature for 1 hour and washed with four times for 5 minutes each with PBS containing 0.05% Tween 20. Anti-human immunoglobulin G labelled with an alkaline phosphatase (Boehringer Manheim, Cat. No. 605 415, Anti-Human IgG-ALP) was diluted with PBS containing 0.5% gelatin and 0.05% Tween 20 in a ratio of 1:1000 and 10 ml of the diluted solution was added to the filter. The resultant was reacted with shaking at room temperature for 1 hour and washed four times with PBS containing 0.05% Tween 20 and two times with 100 mM Tris buffer (pH 9.5, 5 mM magnesium chloride, 100 mM sodium chloride) for 5 minutes each.

To the filter was added 100 mM Tris buffer containing 125 μg/ml of nitro blue tetrazorium (Pierce, NBT) and 25 μg/ml of bromo chloro indole phosphate (Pierce, BCIP) to develop a color reaction. As a result, the UB-E2N protein in the entire cell homogenate was immunologically reacted with the serum of a hepatitis C patient to produce a visible band.

Step 3: Disruption of Cells and Removal of Soluble Protein

About 3 g of the cell precipitate obtained in Step 1 was suspended in 50 ml of buffer 1 (20 CM Tris, pH 7.5, 1 mM EDTA, 2 mM β-mercaptoethanol, 1 mM phenylmethylsulfonyl fluoride, 1 μg/ml pepstatin A); and lysozyme solution was added to the final concentration of 0.2 mg/ml, reacted at 37° C. for 30 minutes and subjected to ultrasonic treatment in ice at an output of 70% for 5 minutes with an ultrasonicator to disrupt the cells and obtain the lysate. The homogenate was centrifuged at 11,000 rpm for 25 minutes with a centrifuge (Beckman J2-21, Rotor JA 14) to remove soluble proteins and obtain the insoluble precipitate.

Step 4: Washing of Insoluble Precipitate with Triton X-100 and Tris Buffer

The precipitate obtained in Step 3 was suspended in 30 ml of buffer 1 (20 mM Tris, pH 7.5, 1 mM EDTA, 2 mM β-mercaptoethanol) containing 1% Triton X-100. The suspension was stirred at a room temperature for 30 minutes and centrifuged at 11,000 rpm for 25 minutes with a centrifuge (Backman J2-21, Rotor JA14) to remove a soluble proteins and obtain the precipitated protein. The precipitate was suspended in 30 ml of buffer 1. The suspension was stirred and recentrifuged to obtain insoluble proteins.

The UB-E2N protein having a purity of at least 70% was obtained through the above simple washing procedure.

Step 5: Dissolution of Insoluble Precipitate with 8M Urea

The insoluble precipitate comprising UB-E2N protein obtained in Step 4 was suspended in 40 ml of buffer 2 (50 mM Tris, pH 9.0, 1 mM EDTA, 2 mM β-mercaptoethanol) containing 8M urea. The suspension was stirred at room temperature for 1 hour and centrifuged to remove the insoluble precipitate and obtain the supernatant.

Step 6: S-200 Gel Permeation Chromatography 40 ml of 8M urea solution comprising UB-E2N obtained in Step 5 was concentrated to a volume of 5 ml with YM10 ultrafiltration membrane (Amicon), passed at a flow rate of 40 ml/hour over S-200 resin column (2.5 cm×90 cm, Pharmacia, U.S.A.) equilibrated with buffer 2 containing 4M urea, and collected fractions with 2 ml/tube. The fractions were subjected to electrophoresis on SDS polyacrylamide gel to pool the fractions comprising UB-E2N protein.

Step 7: Q-Sepharose Ion Exchange Chromatography

The solution comprising UB-E2N protein obtained in Step 6 was passed over Q-Sepharose column (FF, 1.2 cm×7 cm, Pharmacia, U.S.A.) equilibrated with buffer 2 containing 4M urea; and 150 ml of the buffer having a concentration gradient of 0 to 1.0M sodium chloride was added to elute bound proteins. The fractions were subjected to electrophoresis on SDS-polyacrylamide gel to collect fractions of the UB-E2N having a purity of at least 80%.

Step 8: Removal of Urea and FPLC-phenyl Chromatography 4M urea solution comprising UB-E2N protein obtained in Step 7 was concentrated to a volume of 8 ml with YM 10 ultrafiltration membrane (Amicon) and dialyzed against buffer 3 (20 mM Tris, pH 9.0, 1 mM EDTA, 2 mM β-mercaptoethanol, 0.2M sodium chloride) using a dialysis membrane (Spectrum Medical Industries, Inc., M.W. cut off 6,000–8,000) to remove the urea. To the solution was added sodium chloride to a final concentration of 1M. The resultant was passed over FPLC-phenyl Sepharose column (Pharmacia, HR 5/5, 0.5 cm×5 cm); and 40 ml of the buffer having a concentration gradient of 1.0M to 0 M sodium chloride was added to elute bound proteins. The fractions were subjected to electrophoresis on SDS-polyacrylamide gel to pool the fractions comprising UB-E2N protein having a purity of at least 90%.

(6-F): Purification of UB-E2C Protein

Step 1: Culture of Recombinant Cells

*E. coli* W3110 which is capable of producing a fused protein of KHCV E2C protein and ubiquitin was cultured with shaking for 12 hours in LB containing 50 μg/ml of ampicillin. 20 ml of the culture was transferred to 1 l of M9 medium containing 2% casamino acid and 10 μg/ml of tryptopan cultured with shaking at a temperature of 37° C. for about 2 hours. To the culture was added indoleacrylic acid (IAA) to a final concentration of 50 μg/ml when the O.D. at 650 nm was 0.3 to induce the production of recombinant UB-E2C protein. After about 3 hours from the addition of IAA, the culture was centrifuged at 3,500 rpm for 25 minutes with a centrifuge (Beckman J6, Rotor HS4) to collect the cell precipitate. The precipitate was washed once with PBS.

Step 2: Identification of Specific Antigen

The precipitate was subjected to electrephoresis on 15% SDS polyacrylamide gel. The result indicated that the UB-E2C protein was expressed in a molecular weight of about 25,000 dalton.

Subsequently, proteins separated on gel were blotted onto Immobilone P Filter (MILLIPORE, cat. #. IPUH 00010, pore size 0.45 μm). The filter was placed into PBS containing 0.5% Tween 20 and shaken at room temperature for 2 hours to block a non-speific binding of immunolobulin G. 10 ml of the serum from a hepatitis C patient diluted with PBS containing 0.5% gelatin and 0.05% Tween in a ratio of 1:20 was added thereto. The resultant was mildly shaken at room temperature for 1 hour and washed with four times for 5 minutes each with PBS containing 0.05% Tween 20. Anti-human immunoglobulin G labelled with horseradish peroxidase (Bio-Rad Lab. Anti-Human IgG-HRP) was diluted with PBS containing 0.5% gelatin and 0.05% Tween 20 in a ratio of 1:500 and 10 ml of the diluted solution was added to the filter. The resultant was reacted with shaking at room temperature for 1 hour and washed four times with PBS containing 0.05% Tween 20 and two times with 50 mM Tris buffer (pH 7.0) for 5 minutes each.

To the filter was added 50 mM Tris buffer containing 400 µg/ml 4-chloro-1-naphtol and 0.03% hydrogen peroxide to develop color reaction. As a result, the UB-E2C protein in the entire cell homogenate was immunologically reacted with the serum of a hepatitis C patient to exhibit a visible band.

Step 3: Disruption of Cells and Removal of Soluble Protein

About 1 g of the cell precipitate obtained in Step 1 was suspended in 50 ml of a lysis buffer (20 mM Tris, pH 7.5, 1 mM EDTA, 2 mM β-mercaptoethanol, 1 mM phenylm-ethylsulfonyl fluoride and 1 µg/ml pepstatin A); and lysozyme solution was added to a final concentration of 0.5 mg/ml, incubated at 37° C. for 30 minutes and subjected to ultrasonic treatment in ice at an output of 70% for about 5 minutes with an ultrasonicator to disrupt cells and obtain a homogenate. The homogenate was centrifuged at 11,000 rpm for 25 minutes with a centrifuge (Beckman J2-21, Rotor JA 14) to remove soluble proteins and obtain an insoluble precipitate.

Step 4: Washing of Insoluble Precipitate with Triton X-100 and Tris Buffer

The precipitate obtained in Step 3 was suspended in 20 ml of buffer 1 (20 mM Tris, pH 7.5, 1 mM EDTA, 2 mM β-mercaptoethanol) containing 1% Triton X-100. The suspension was stirred at room temperature for 30 minutes and centrifuged at 11,000 rpm for 25 minutes with a centrifuge (Beckman J2-21, Rotor JA14) to remove soluble proteins and obtain precipitated proteins. The precipitate was suspended in 30 ml of buffer 1. The suspension was stirred and recentrifuged to obtain insoluble proteins.

Step 5: Dissolution of Insoluble Precipitate with 8M Urea

The insoluble precipitate comprising UB-E2C protein obtained in Step 4 was suspended in 20 ml of buffer 2 (50 mM carbonate, pH 9.5, 1 mM EDTA, 2 mM β-mercaptoethanol) containing 8M urea. The suspension was stirred at a room temperature for 1 hour and centrifuged to remove the insoluble precipitate and obtain the supernatant.

Step 6: FPLC-Mono Q Ion Exchange Chromatography

The supernatant obtained in Step 5 was passed over FPLC-Mono Q column (Pharmacia, HR 5/5, 0.5 cm×5 cm, U.S.A.) equilibrated with buffer 2 containing 0.1M sodium chloride; and then 40 ml, of the buffer having a concentration gradient of 0.1 to 0.4M sodium chloride was added to elute bound proteins. The fractions were subjected to electrophoresis on SDS-polyacrylamide gel to pool the fractions having a purity of at least 80%.

Step 7: Removal of Urea and FPLC-phenyl Chromatography 8M urea solution comprising UB-E2C protein obtained in Step 6 was concentrated to a volume of 14 ml with YM 10 ultrafiltration membrane and dialyzed against buffer 3 (20 mM Tris, pH 9.0, 1 mM EDTA, 2 mM β-mercaptoethanol, 0.2M sodium chloride) using a dialysis membrane (Spectrum Medical Industries, Inc., M.W. cut off 6,000–8,000) to remove the urea. To the solution was added sodium chloride to a final concentration of 1M. The resultant was passed over FPLC-phenyl Sepharose column (Pharmacia, HR 5/5, 0.5 cm×5 cm); and 40 ml of the buffer having a concentration gradient of 1M to 0 M sodium chloride was added to elute the bound proteins. The fractions were subjected to electrophoresis on SDS-polyacrylamide gel to pool the fractions comprising UB-E2C protein having a purity of at least 90%.

EXAMPLE 7

Detection of Anti-KHCV Antibodies to KHCV Recombinant Proteins (7-A): Reactivity of Mixed Positive and Negative Serum Sample vs. Concentration of Antigen Each of KHCV 403, KHCV 897 and KHCV UB-CORE 14 protein was diluted serially in two folds with 50 mM sodium borate buffer (pH 9.0) from a concentration of 0.25 µg/ml, 2.0 µg/ml and 2.0 µg/ml, respectively. The diluted protein solutions were added to the wells of a microtiter plate (Dynatech, Immulon type 1 microtiter plate) in an amount of 200 µl/well and incubated at 37° C. for 2 hours wherein the plate was covered with a para-film to minimize evaporation of the solution.

The plate coated for 2 hours was washed once with PBS containing 0.05% (v/v) Tween-20 (pH 7.4, hereinafter referred to as the washing solution). PBS containing 0.1% gelatin (v/v) was added to the wells in an amount of 210 µl/well; and was incubated at 37° C. for 2 hours. The wells were washed twice with 300 µl of said washing solution; and 190 µl of PBS containing 0.25% gelatin, 1 mM EDTA, 1.0% (v/v) Triton X-100 and 0.02% Thimerosal; and 10 µl of a positive serum sample of a HCV patient or a negative serum sample was added to every well and mixed for several seconds; and incubated at 37° C. for 1 hour. The positive serum sample of a HCV patient and the negative sample used were tested by a diagnostic kit for hepatitis C using C-100 antigen which is manufactured by Ortho Diagnostic Systems, Raritan, N.J., 88869, U.S.A, respectively, prior to use. The serum samples were supplied by Severance Hospital attached to Yonsei University located in Korea.

The wells which were reacted at 37° C. for 1 hour were washed five times with 300 µl of the washing solution; and anti-human IgG γ-chain immunoglobulin labelled with horseradish peroxidase (HRP) (Bio-Rad Company, Richmond, Calif. 94804, U.S.A, 0.1 mg protein/ml) was diluted in 5000 folds with PBS containing 10% fetal bovine serum, 1% Ficoll (Sigma, v/v), 0.02% Thimerosal and 0.05% Tween-20; and the diluted solution was added to the wells in an amount of 200 µl/well. The resultant was incubated at 37° C. for 1 hour and washed 5 times with said washing solution. Thereafter, 200 µl of O-phenylene diamine dihychloric acid (OPD, Sigma, 10 mg/ml) which was dissolved in 50 mM citrate buffer and was adjusted to pH 5.5 by adding phosphate was added to each well and incubated at room temperature for 30 minutes in the dark. To the resultant was added 50 µl of 4N sulfuric acid per each well to stop the color development; and O.D. of each well was determined at the wavelength of 492 nm with Dynatech Microtiter Plate Reader (see FIG. 19).

(7-B): Preparation of Diagnostic Kit

The antigens of purified KHCV UB-CORE 14, KHCV 897 and KHCV 403 protein were used to prepare a diagnostic kit. The antigens may be diluted to an optimum concentration with 10 mM sodium carbonate buffer (pH 9.5)

or 50 mM sodium borate buffer (pH 9.0); added to the wells of Immulon type 1 microtiter plate comprising 96 wells (Dynatech) in an amount of 150 to 200 µl/well; and incubated at a temperature of 4° C. for 12 to 18 hours to allow the antigen to adsorb to the walls of plate.

The optimum concentrations of each antigens are 0.18 to 0.75 µg/ml for KHCV UB-CORE 14 protein, 0.06 to 0.3 µg/ml for KHCV 897 protein and 0.12 to 0.5 µg/ml for KHCV 403 protein. 0.3 µg/ml of each antigen was used in this example.

The content of each after coating well was removed with an aspirator. The plate was washed with PBS (PBS, pH 7.4) containing 0.05% (v/v) Tween-20 and blocked with PBS (210 µg/well) (pH 7.4) containing 0.1% (w/v) gelatin for 2 hours at 37° C. and washed with said washing solution 3 times. The moisture remained in the wells was removed with an absorption apparatus.

190 µl of a buffer (10 mM Tris, pH 7.5, 150 mM NaCl, 0.2% Triton X-100, 0.1 mM EDTA, 0.02% Thimerosal) containing 1% (v/v) bovine serum and 10 µl of sample to be tested were added to each well and incubated at 37° C. for 1 hour to induce a binding reaction of HCV antibody in a sample with antigen adsorbed in the wells. The plate was washed five times with PBS (pH 7.4) containing 0.05% (v/v) Tween 20; and 200 µl of an anti-human IgG-HRP (Goat anti-human IgG-HRP, Bio-Rad Lab., U.S.A.) which was diluted with a buffer (10 mM Tris, pH 7.5, 150 mM NaCl, 0.02% Thimerosal, 1% Ficoll) containing 10% (v/v) bovine serum albumin was added thereto and incubated at 37° C. for 1 hour followed by washing with PBS (pH7.4) containing 0.05% (v/v) Tween 20. 200 µl of OPD solution was added to develop a color reaction at room temperature for 30 minutes. Thereafter, 50 µl of 4N sulfuric acid per well was added to stop the reaction and then the O.D. was determined at a wavelength of 492 nm. The cut-off value which is a standard value for determination of positivity or negativity was settled as 0.4 plus average absorbance (O.D.) of the negative sample.

The results for each KHCV protein and mixed antigen in accordance with the above are represented in Table 1. The comparative HCV diagnostic reagent was commercially available from Ortho Diagnostic Systems and used in accordance with the manufacturer's instruction.

TABLE 1

Reactivity of KHCV proteins to the antibodies against KHCV determined by Enzyme Immunoassay

| Sample No. | Antigen KHCV 897 protein | Antigen KHCV UB-CORE 14 protein | Antigen KHCV 403 protein | Mixed Antigen (of three proteins) | Ortho HCV Diagnostic Kit |
|---|---|---|---|---|---|
| 1 | ++ | +++ | − | ++++ | − |
| 2 | ++++ | ++++ | ++ | ++++ | + |
| 3 | + | − | − | ++ | − |
| 4 | + | + | − | ++ | − |
| 5 | ++++ | ++++ | ++++ | ++++ | + |
| 6 | ++ | − | − | +++ | − |
| 7 | ++++ | +++ | − | ++++ | + |
| 8 | − | ++ | − | +++ | − |
| 9 | − | − | +++ | ++++ | − |
| 10 | − | +++ | − | ++++ | − |
| 11 | ++ | + | − | +++ | − |

TABLE 1-continued

Reactivity of KHCV proteins to the antibodies against KHCV determined by Enzyme Immunoassay

| Sample No. | Antigen KHCV 897 protein | Antigen KHCV UB-CORE 14 protein | Antigen KHCV 403 protein | Mixed Antigen (of three proteins) | Ortho HCV Diagnostic Kit |
|---|---|---|---|---|---|
| 12 | ++++ | +++ | +++ | ++++ | + |
| 13 | ++ | − | − | ++ | − |

Note:
1) ++++: Cut off value + 1.5 ≦ absorbance(O.D.)
+++: Cut off value + 1.0 ≦ absorbance < Cut off value + 1.5
++: Cut off value + 0.5 ≦ absorbance < Cut off value + 1.0
+: Cut off value ≦ absorbance < Cut off value + 0.5
−: absorbance < Cut off value
2) Cut off value was 0.32 for KHCV 897 protein, 0.27 for KHCV UB-CORE 14 protein, 0.35 for KHCV 403 protein, 0.483 for mixed antigens and 0.453 for Ortho diagnostic kit, respectively.
3) Ortho HCV diagnostic kit was commerically available from Ortho Diagnostic Systems, U.S.A.

(7-C): Accuracy of Diagnosis

To demonstrate the accuracy of the result of the present diagnosis, 17 serum samples which had been diagnosed as positive by using the diagnostic kit for hepatitis C manufactured and sold by Ortho Diagnostic Systems were diagnosed again with the diagnostic kit of the present invention; and also with the immunoblotting kit (Chiron RIBA HCV Test System, 2 nd Generation, manufactured by Ortho Diagnostic Systems, U.S.A., Product Code 933491) which is recommended as a confirmation assay and comprises 4 antigens except one SOD control antigen (see Van der Poel, C. L. et al., Lancet, 337, 317–319 (1991)). These results are summarized in Table 2, which show that the diagnostic method of the present invention has a lower false positive than Ortho's diagnostic kit for hepatitis C.

TABLE 2

Comparison of Diagnosis with Ortho's 2nd Generation Immunoblotting Kit and the Present Diagnostic Kit

| Sample No. | Antigens of Ortho 2nd Generation Immunoblotting Kit | | | | | Judgment* | Present Diagnostic Kit** (7-B) |
|---|---|---|---|---|---|---|---|
| | 5-1-1 | C100-3 | C33c | C22-3 | SOD | | |
| 1** | +/− | +/− | − | − | − | − | − |
| 2 | ++++ | ++++ | ++++ | ++++ | − | + | ++++ |
| 3 | + | +/− | ++++ | ++++ | − | + | ++++ |
| 4 | + | ++++ | ++++ | +/− | − | + | ++++ |
| 5 | − | − | − | − | − | − | − |
| 6 | − | − | − | − | − | − | − |
| 7 | − | +/− | − | − | − | − | − |
| 8 | − | − | − | − | − | − | − |
| 9 | − | +/− | − | − | − | − | − |
| 10 | − | − | − | − | − | − | − |
| Positive Control | ++ | ++++ | ++++ | ++ | − | + | ++++ |
| Negative Control | − | − | − | − | − | − | − |

*If a sample found to have more than one +, i.e. , show a positive reaction in at least two antigens except the SOD control antigen, then it was judged to be positive.
**Mixed antigen obtained from Example(7-B) was used as the reagent.

EXAMPLE 8

Determination of Presence of Hepatitis C Virus with Polymerase Chain Reaction Using Probe (8-A): Extraction of RNA of Hepatitis C Virus To 100 μl of a serum to be tested were added 100 μl of TNE solution (100 mM Tris-HCl, pH 8.0, 0.2 mM EDTA, 0.2M NaCl), 300 μl of RNAzol solution (TM Cinna Scientific, Inc., Tex. 77546, U.S.A) and 300 μl of chloroform which was mixed with shaking thoroughly. The resultant was centrifuged at 15,000 rpm and at a temperature of 4° C. for 5 minutes with Eppendorf microfuge to form a precipitate. The supernatant was collected and extracted with 300 μl of phenol and 300 μl of chloroform. The extract was precipitated and the precipitate was dissolved in 10 μl of TE buffer (10 mM Tris HCl, pH 8.0, 0.1 mM EDTA) and stored at a temperature of −70° C.

(8-B): Determination of Presence of Hepatitis C Virus with Polymerase Chain Reaction RNA extracted in the above was mixed with 4 μl of distilled water and 1 μl of 0.1M CH$_3$HgOH and left at a room temperature for 10 minutes. 0.5 μl of 1M β-mercaptoethanol, 10 μl of RNasin, 5 μl of 5×RT buffer (BRL, Gaithersburg, Md., 20877, U.S.A), 1.25 μl of dNTP (10 mM dGTP, dTTP, dCTP and dATP), 1 μg of random primer, 1.25 μl (18 unit/μl) of Superscript H$^-$Reverse Transcriptase (BRL, U.S.A.) were added thereto; and then, distilled water was added to a total volume of 25 μl and reacted at a temperature of 42° C. for 1 hour. After the reaction, the resultant was heated at a temperature of 65° C. for 15 minutes to inactivate enzymes and used for polymerase chain reaction.

A first polymerase chain reaction was carried out as follows. 0.5 μl of Amplitaq DNA polymerase (Perkin Elmer Cetus, U.S.A.) was mixed with 10 μl of 10×Taq polymerase buffer (10 mM Tris-HCl, pH 8.3, 500 mM KCl, 155 mM MgCl$_2$, 0.1% (w/v) gelatin), 10 μl of a mixture of 1.25 mM dNTPs, 2 μg of primer A (SEQ ID NO: 125)of 5'-CATAGTGGTCTGCGGAACCG-3', 2 μg of primer B (SEQ ID NO: 126) of 5'-TTGAGGTTTAGGATTCGTGC-3' and 75 μl of distilled water. 50 μl of mineral oil was added thereto to prevent evaporation of the solution; and, the first PCR was carried out by repeating 40 times the thermal cycle of: 95° C. for 2 minutes, 55° C. for 2 minutes and 72° C. for 3 minutes.

A second PCR was carried out by repeating twenty times under the same condition as the first PCR after mixing 1 μl of the product of the first PCR with 1 μl of primer C (SEQ ID NO: 127) of 5'-TACACCGGAATTGCCAGGAC-3' and 1 μl of primer D (SEQ ID NO: 128) of 5'-TCATGGTGCACGGTCTACGAG-3'.

About 5 μl the second of PCR product was subjected to 7% polyacrylamide gel electrophoresis to determine the presence of hepatitis C virus wherein the positive sample exhibited a DNA band of 182 bp.

EXAMPLE 9

Preparation of Specific Antibody Against Hepatitis C Antigen of KHCV Protein (9-A): Immunization KHCV 897 protein dissolved in saline was mixed with an equivalent amount of Freund's complete adjuvant; and 0.2 ml of a mixture containing 50 μg of the protein was injected intraperitoneally to about 10 week old Balb/c mouse. 30 μg of the protein mixed with Freund's incomplete adjuvant was injected at intervals of 2 to 3 weeks. After 2 weeks of the second injection, small amount of blood was drawn from the tail of the mouse and subjected to an enzyme immunoassay to determine the antibody titer. 50 to 100 μg of the protein 0.5 ml of saline was further injected when the titer reached to 10,000. Antibody titer was operationally defined as that dilution of serum that resulted in 0.2 absorbance units background in ELISA procedure. After 3 to 4 days, spleen cells of the mouse were used for the preparation of a cell producing monoclonal antibody.

(9-B): Cell Fusion

Immunized spleen cells were fused with P3×63-Ag8.653 (ATCC CRL 1580) which was a myeloma cell of mouse. 5×10$^7$ spleen cells of immunized mouse was mixed with 2×10$^7$ P3×63-Ag8.653 and centrifuged at 300×g for 10 minutes. The cell precipitate was washed with IMDM medium (Gibco, U.S.A.) and centrifuged. The supernatant was discarded and 1 ml of 50% PEG (Kodak, molecular weight of 1450 dalton) solution was added dropwise over one minute to the cell precipitate with stirring. The resultant was centrifuged at 200×g for two minutes; and 5 ml of IMDM medium was added slowly over three minutes, followed by the addition of 5 ml of IMDM medium containing 10% fetal bovine serum over five minutes with stirring.

IMDM medium containing 10% fetal bovine serum was added thereto to a total volume of 50 ml and centrifuged for 10 minutes.

The supernatant was discarded; and IMDM-HAT medium prepared by adding 10% fetal bovine serum, 100 μM hypoxanthine, 0.4 μM amino-pterin and 16 μM thymidine to IMDM medium was added thereto to dilute the cell concentration to be 5×10$^5$ cells of P3×63-Ag 8.653 per ml. The resultant was added to a plate (96 wells) for tissue culture in an amount of 0.1 ml/well. 0.1 ml IMDM-HAT medium containing 1×10$^5$ cells/ml of intraperitoneal macrophage was added to the wells and cultured 1 day prior to the fusion. The myeloma cell and unfused spleen cell cannot grow in HAT medium.

Accordingly, the cells grown in the medium were considered to be the fused cells. An assay of antibody activity was carried out with the supernatant which was sampled when the hybridoma was grown to a level of 10 to 50%.

(9-C): Screening of Titer of Monoclonal Antibody

Titration of monoclonal antibodies produced in Step (9-B) was carried out in accordance with the following enzyme immunoassay.

Step 1

KHCV 897 protein was dissolved in 50 mM sodium borate buffer (pH 9.0) to a concentration of 2 μl/ml. 100 μl of the solution was added to each well of Immulon type I plate (Dynatech) and incubated at a temperature of 37° C. for 2 hours.

Step 2

The wells were washed once with PBS (pH 7.4) containing 0.05% Tween-20 (v/v) (hereinafter referred to as the washing solution); and 200 μl of PBS containing 0.1% gelatin (w/v) was added thereto to block the adsorption sites of the proteins which remained in the well at a temperature of 37° C. for 1 hour.

Step 3

The wells of Step 2 were washed twice with the washing solution; and 50 μl of PBS containing 0.25% gelatin (w/v), 1.0 mM EDTA, 1% Triton X-100 (v/v) and 0.02% Thimerosal was added thereto. 50 μl of the supernatant wherein the fused cells had been grown was added to each well and incubated at a temperature of 37° C. for 1 hour.

Step 4

The wells treated in Step 3 were washed five times with the washing solution. Anti-mouse IgG-HRP (Boehringer Manheim, Cat. No. 605-250) labelled with horseradish peroxidase (HRP) was diluted with PBS containing 10% (v/v) fetal bovine serum, 1% (v/v) Ficoll, 0.02% (v/v) Thimerosal and 0.05% (v/v) Tween-20 in a ratio of 1:5000; and the diluted solution was added to the wells in an amount of 100 µl/well and incubated at a temperature of 37° C. for 1 hour. After the reaction, the plate was washed five times with the washing liquid.

Step 5

100 µl of 50 mM citrate/phosphate buffer (pH 5.5) containing 10 mg/5 ml of O.P.D. (Sigma Chemical Co.) was added to each well and reacted at a room temperature in the dark for 30 minutes; and 50 µl of 2N sulfuric acid was added thereto to stop the reaction. The absorbance was determined at a wavelength of 492 nm. Hybridoma which exhibited the desired antibody activity was transferred to and grown in a 6 well plate or 24 well plate wherein, if necessary, the peritoneal macrophages of mouse may be used as a feeder layer to provide a growth factor necessary for the growth of the fused cell.

(9-D): Production of Antibody 4 cell lines, i.e., Lucky 1.1, 1.2, 1.3 and 1.4 which produced the desired monoclonal antibodies were obtained.

The antibodies of the present invention were available from either the supernatant in which clones were cultured by the conventional method or the ascite fluid containing the clones grown in peritoneum of a Balb/c mouse.

$2.5 \times 10^6$ fused cells were injected intraperitoneally to a Balb/c mouse which had been pretreated with 0.5 ml of Pristane (Sigma) 7 to 14 days before. After 1 to 2 weeks, seroperitoneum liquid was obtained; and antibodies were isolated therefrom in accordance with a conventional method.

(9-E): Detection of Characteristics of Monoclonal Antibody

The characteristics of antibodies prepared from each clone obtained in Example (9-D) were evaluated as follows.

Step 1: Antibody's Subclass

The subclass of the mouse antibodies was determined by using the Hybridoma sub-Isotyping Kit (Calbiochem, U.S.A.). The results are shown in Table 3.

Step 2: Enzyme Immunoassay

200 µl of KHCV 897 protein dissolved in 50 mM sodium borate buffer in a concentration of 2 µl/ml was added to each well of microtiter plate (Dynatech Immunolon type 1) and incubated at a temperature of 37° C. for 2 hours. The plate was washed with PBS containing 0.05% Tween-20 (v/v). The antibodies obtained from each clone were purified by a conventional method, adjusted to a concentration of 1 mg/ml and diluted serially in two folds with PBS containing 0.25% gelatin (v/v), 1.0% Triton X-100, 0.02% Thimerosal and 1 mM EDTA. 210 µl of PBS containing 0.1% gelatin was added to each well and incubated at a temperature of 37° C. for 1 hour. The plate was washed with the washing solution.

200 µl of anti-mouse IgG (Boehringer Manheim, Cat. No. 605-250) labelled with horseradish peroxidase which was dissolved in PBS containing 10% FBS (v/v), 1% Ficoll (v/v) and 0.05% (v/v) Tween-20 was added to each well and incubated at a temperature of 37° C. for 1 hour. The development reaction was carried out in the same manner as in Example (9-C). The EIA efficiency of each antibody was determined as a reciprocal number of the dilution fold when the O.D. value at 495 nm was more than 1.0. The results are given in Table 3.

Step 3: Determination of Molecular Weight

Each clone was cultured in a plate or peritoneum of a mouse. The supernatant or ascite fluid obtained therefrom was subjected to protein-G Sepharose column affinity chromatography (Pharmacia) to isolate IgG which was then subjected to SDS-PAGE to determine the molecular weight of the heavy chain and the light chain in the mouse antibody obtained above. The results are represented in Table 3.

Step 4: Determination of Epitope

The variants in which a portion of KHCV 897 cDNA was differently excised were constructed to encode the following proteins; and the reactivity of the proteins to each monoclonal antibody was examined.

(1) KHCV 897 protein: A protein comprised of amino acids 1192 to 1457 of the amino acid sequence encoded in KHCV-LBC1

(2) KHCV 290 protein: A protein comprised of amino acids 1192 to 1289 of the amino acid sequence encoded in KHCV-LBC1

(3) KHCV 430 protein: A protein comprised of amino acids 1192 to 1335 of the amino acid sequence encoded in KHCV-LBC1

(4) KHCV 570 protein: A protein comprised of amino acids 1192 to 1382 of the amino acid sequence encoded in KHCV-LBC1

(5) KHCV 652 protein: A protein comprised of amino acids 1192 to 1407 of the amino acid sequence encoded in KHCV-LBC1

(6) KHCV 150 protein: A protein comprised of amino acids 1408 to 1457 of the amino acid sequence encoded in KHCV-LBC1

(7) KHCV 257 protein: A protein comprised of amino acids 1371 to 1457 of the amino acid sequence encoded in KHCV-LBC1

(8) KHCV 518 protein: A protein comprised of amino acids 1285 to 1457 of the amino acid sequence encoded in KHCV-LBC1

A sample for SDS-PAGE was prepared by adding a buffer (Laemmli, U. K., Nature 277, 680(1970)) to E. coli cell which expressed each KHCV cDNA fragment and was boiled at a temperature of 100° C. for 5 minutes. The reactivity of the prepared sample to antibody was examined by an immuno blotting method (Towbin, H., J. Immunol. Methods 72, 313–340(1984)). The results are given in Tables 3 and 4.

It can be seen from the result that antibodies obtained from Lucky 1.1 have a recognition site for amino acids 1192 to 1289 of the amino acid sequence of hepatitis C; and Lucky 1.2, 1.3 and 1.4 have a recognition site for amino acids 1371 to 1407. Two monoclonal antibodies whose epitopes are different from each other may be used to prepare a kit by which the antigens in a serum sample can be using detected by using Sandwich Enzyme Immunoassay and the like.

TABLE 3

Characteristics of Monoclonal Antibodies of the Present Invention

| Monoclonal Antibody | Antibody Subclass | Molecular Weight | EIA Efficiency | Binding Site (Amino Acid Sequence) |
|---|---|---|---|---|
| Lucky 1.1 | IgG1 | 162,000 | × 51,200 | 1192–1289 |
| Lucky 1.2 | IgG1 | 159,700 | × 102,400 | 1371–1407 |
| Lucky 1.3 | IgG1 | 180,800 | × 51,200 | 1371–1407 |
| Lucky 1.4 | IgG1 | 177,700 | × 400 | 1371–1407 |

TABLE 4

Immuno Reactivity of Excised Mutant with Antibodies

| Antibody Antigen | Lucky 1.1 | Lucky 1.2 | Lucky 1.3 | Lucky 1.4 |
|---|---|---|---|---|
| KHCV 897 | + | + | + | + |
| KHCV 290 | + | − | − | − |
| KHCV 430 | + | − | − | − |
| KHCV 570 | + | − | − | − |
| KHCV 652 | + | − | − | − |
| KHCV 150 | − | − | − | − |
| KHCV 257 | − | + | + | + |
| KHCV 518 | − | + | + | + |
| Negative Control | − | − | − | − |
| Recognition Site of Amino Acid sequence | 1192–1289 | 1371–1407 | 1371–1407 | 1371–1407 |

The cell lines of Lucky 1.1 and Lucky 1.2 were deposited on Dec. 18, 1991 under the terms of the Budapest Treaty with the American Type Culture Collection (ATCC) and were assigned Accession Nos. 10949 and 10950, respectively.

EXAMPLE 10

Diagnostic Agent Comprising an Antibody against KHCV Antigen

Step 1: Labelling of Onoclonal Antibody of Lucky 1.1 with Horseradish Peroxidase As a first step, said Lucky 1.1 cell line was labelled with horseradish peroxidase by using the known periodate method (Nakane et a!., J. Histochemcytochem., 22, 1084 (1974)) as follows.

0.3 ml of 0.1M sodium periodate in a 10 mM sodium phosphate buffer (ph 7.0) was added to 1.2 ml of distilled water in which 5 mg of peroxidase was dissolved; and the mixture was reacted at a room temperature for 20 minutes. The resultant was dialyzed against 1 mM sodium acetate buffer for 16 hours. 1.5 ml of peroxidase solution was mixed with 1 ml of antibody to be labelled which had been previously prepared by dissolving it in 20 mM sodium carbonate (pH 9.5) in a concentration of 10 mg/ml; and the mixture was reacted at a room temperature for 2 hours. Schiff base which was unreacted was reduced off by addition of 100 µl of 4 mg/ml sodium monohydride in distilled water. The resultant was subjected to dialysis against PBS (pH 7.4) overnight, and then passed over Sephacryl S 300 chromatography column to remove monoclonal antibodies which were not labelled.

Step 2: Adsorption of Monoclonal Antibody of Lucky 1.2 to Microtiter Plate

200 µl of 5 µg/ml Lucky 1.2 diluted with PBS was added to each well to allow its adsorption onto the wall of the well at a 37° C. for 2 hours.

Step 3: Blocking of Non-specific Binding

The microtiter prepared in Step 2 was washed once with PBS containing 0.05% Tween-20 and 0.02% Thimerosal (hereinafter referred to as the washing solution). 200 µl of PBS containing 0.1% gelatin was added to each well to coat the protein adsorption site over 1 hour; and the plate was washed twice with the washing solution.

Step 4: Diagnosis of Presence of Antigen

200 µl of KHCV 897 antigen which was diluted serially in two folds from 200 ng/ml with PBS containing 0.25% (w/v) gelatin, 1.0% (v/v) Triton X-100, 1 mM EDTA and 0.02% Timerosal was added to each well. For comparison, KHCV protein was added to a normal blood sample to a concentration of 400 ng/ml; the normal blood sample containing the KHCV antigen was diluted serially in two folds; and 100 µl of the diluted blood was mixed with 100 µl of said buffer and added to each well. This was intended to show that the presence of an antigen of hepatitis C in blood can be detected by Sandwich Enzyme Immunoassay by using the antibodies obtained. The normal blood wherein KHCV 897 antigen was not added was used as a negative control. The plate was incubated at a temperature of 37° C. for 1 hour and washed five times with the washing solution.

Step 5: Screening of Antigen with Lucky 1.1 Labelled with Peroxidase

200 µl of Lucky 1.1 which was diluted to a concentration of 5 µg/ml with PBS containing 10% (v/v) fetal bovine serum, 1% Ficoll, 0.05% Tween-20 and 0.02% Thimerosal was added to each well, which was incubated at a temperature of 37° C. for 1 hour.

Step 6: Color Development Reaction

The plate treated in Step 5 was washed five times with the washing solution; and 200 µl of O.P.D. developing reagent which was prepared by adding O-phenylenediamine (Sigma) to 50 mM citrate/phosphate buffer (pH 5.5) to a concentration of 2 mg/ml was added to each well and left at a room temperature in the dark for 30 minutes to develop a color reaction. 50 µl of 4N sulfuric acid was added to stop the reaction. Absorbance thereof was determined at a wavelength of 492 nm. The results are presented in FIG. 43.

EXAMPLE 11

Screening of Antigen in Serum of a Hepatitis C Patient with Sandwich Enzyme Immunoassay 100 µl of a serum to be analyzed which was mixed with 100 µl of the buffer used in Step 4 of Example 10 was added to each well of the microtiter prepared by the same process as in Example 10 to which monoclonal antibody was already adsorbed; and the antigen in the serum was screened by the same process as in Example 10. The results are given in Table 5.

220 samples of 231 samples (220/231) exhibited the absorbance value (O.D.) at 492 nm of less than 0.15; other 11 samples exhibited the values ranging from 0.15 to 0.8, which were judged to be positive. In accordance with Halbert's method (Halbert, S. P. et al., Clin, Chim. Acta 127, 69(1983)), the cut-off value was settled to be an absorbance of 0.15.

Antibodies against KHCV for 15 samples including the 11 positive samples were screened in accordance with the same process as in Example 7. The results are shown in Table 6. The results may be suggest that the sandwich ELISA for KHCV 897 antigen detection is valuable and can use for early detection of KHCV infection. Along with EIA for antibody detection, the ELISA for antigen detection should be used for HCV patient care and protection.

TABLE 5

Absorbance of Samples Determined by Sandwich Enzyme Immunoassay

| Absortance | Number of Samples | Percentage[1] |
|---|---|---|
| >= 0.5 | 1 | 0.43 |
| 0.3–0.5 | 3 | 1.30 |
| 0.2–0.3 | 4 | 1.73 |
| 0.15–0.2 | 3 | 1.30 |

TABLE 5-continued

Absorbance of Samples Determined by Sandwich Enzyme Immunoassay

| Absortance | Number of Samples | Percentage[1] |
|---|---|---|
| <0.15 | 220 | 95.24 |
| Total | 231 | 100.00 |

Note: [1] Percentage (%) = (The number of tested samples) / (The number of total samples)

TABLE 6

Detection of Hepatitis C Antibody and Antigen

| Sample | Antibody of Hepatitis C | Antigen of Hepatitis C |
|---|---|---|
| 1 | − | + |
| 2 | − | + |
| 3 | − | − |
| 4 | − | + |
| 5 | − | + |
| 6 | − | + |
| 7 | − | − |
| 8 | + | − |
| 9 | − | + |
| 10 | − | + |
| 11 | − | + |
| 12 | − | + |
| 13 | − | + |
| 14 | + | + |
| 15 | − | − |

Note: 1) The cut-off value was set to be an absorbance value of 0.15 for antigen diagnosis and 0.33 for antibody diagnosis.

Accordingly, KHCV proteins of the present invention, especially using the mixed antigen containing 3 proteins, is more reactive to the antibodies against KHCV than the commercially available HCV diagnostic kit as shown in Table 1; the diagnostic kit of the present invention produces more accurate test results than the commercial kit; and is more convenient and economical than the confirmation assay kit as shown in Table 2.

While the invention has been described in connection with certain specific embodiments, it should be recognized that various modifications and changes as may be apparent to those skilled in the art to which the invention pertains may be made and also fall within the scope of the invention as defined by the claims that follow.

```
                           SEQUENCE LISTING (1) GENERAL INFORMATION:

(iii) NUMBER OF SEQUENCES: 128

(2) INFORMATION FOR SEQ ID NO: 1:

(i) SEQUENCE CHARACTERISTICS:
          (A) LENGTH: 43 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: primer RANPSHCV (xi) SEQUENCE DESCRIPTION: SEQ ID NO: 1

TTTTTCATGA TTGGTGGTGG AACTGGACCG TCTCGAGNNN NNN                        43

(2) INFORMATION FOR SEQ ID NO: 2

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: DNA (ix) FEATURE:
          (D) OTHER INFORMATION: oligo d(T) primer (xi) SEQUENCE DESCRIPTION: SEQ ID NO: 2
```

GAGAGAGAGA GAGAGAGAGA ACTAGTCTCG AGTTTTTTTT TTTTTTTTTT                50

(2) INFORMATION FOR SEQ ID NO: 3

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (ix) FEATURE:
        (D) OTHER INFORMATION: Eco RI Adaptor, used as Eco RI primer (xi) SEQUENCE DESCRIPTION: SEQ ID NO: 3

CCCCCCGAAT TCGGCACGAG                                                 20

(2) INFORMATION FOR SEQ ID NO: 4

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PSHCV (xi) SEQUENCE DESCRIPTION: SEQ ID NO: 4

TTCATGAT TGGTGGTGGA                                                   20

(2) INFORMATION FOR SEQ ID NO: 5

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P652a (xi) SEQUENCE DESCRIPTION: SEQ ID NO: 5

CATACCCG TTGAGTCTAT GGAAACTACT                                        30

(2) INFORMATION FOR SEQ ID NO: 6

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P652b (xi) SEQUENCE DESCRIPTION: SEQ ID NO: 6

CATTCCAA GAAGAAGTGT GACGAACTCG                                        30

(2) INFORMATION FOR SEQ ID NO: 7

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P426a (xi) SEQUENCE DESCRIPTION: SEQ ID NO: 7

GAGACCTC CCGGGGCACT CGCAAGCACC                                                  30

(2) INFORMATION FOR SEQ ID NO: 8

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P426b (xi) SEQUENCE DESCRIPTION: SEQ ID NO: 8

TAATTTGG GTAAGGTCAT CGACACCCTC                                                  30

(2) INFORMATION FOR SEQ ID NO: 9

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P240b (xi) SEQUENCE DESCRIPTION: SEQ ID NO: 9

GTCCGGGTGC TGGAGGACGG CGTGAACTA                                                 29

(2) INFORMATION FOR SEQ ID NO: 10

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P513b (xi) SEQUENCE DESCRIPTION: SEQ ID NO: 10

CGCATGGCCT GGGATATGAT GATGAACTGG                                                30

(2) INFORMATION FOR SEQ ID NO: 11

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
              (D) OTHER INFORMATION: probe oligonucleotide P810b (xi) SEQUENCE DESCRIPTION: SEQ ID NO: 11

AAATGAGACG GACGTGCTGC TCCTTAAC                                                 28

(2) INFORMATION FOR SEQ ID NO: 12

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: probe oligonucleotide P403A (xi) SEQUENCE DESCRIPTION: SEQ ID NO: 12

GTGAAGAATT CGGGGCCGG AACCTGGCAT                                                30

(2) INFORMATION FOR SEQ ID NO: 13

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: probe oligonucleotide P403B (xi) SEQUENCE DESCRIPTION: SEQ ID NO: 13

GCTGACCTCA TTGAGGCCAA CCTCTTGT                                                 28

(2) INFORMATION FOR SEQ ID NO: 14

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: probe oligonucleotide P932b (xi) SEQUENCE DESCRIPTION: SEQ ID NO: 14

CCGGGACGTG CTTAAGGAGA TGAAGGCGAA                                               30

(2) INFORMATION FOR SEQ ID NO: 15

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (ix) FEATURE:
              (D) OTHER INFORMATION: probe oligonucleotide P496b (xi) SEQUENCE DESCRIPTION: SEQ ID NO: 15

CGTGTATGCG AGAAGATGGC CCTTTATGAC                                               30

(2) INFORMATION FOR SEQ ID NO: 16

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P847b (xi) SEQUENCE DESCRIPTION: SEQ ID NO: 16

TGCGTGGGAG ACAGCTAGAC ACACTCCAG                              29

(2) INFORMATION FOR SEQ ID NO: 17

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P798b (xi) SEQUENCE DESCRIPTION: SEQ ID NO: 17

CTGGTTCCCG GAGCGGCATA C                                        21

(2) INFORMATION FOR SEQ ID NO: 18

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P752a (xi) SEQUENCE DESCRIPTION: SEQ ID NO: 18

CCAGGTGATG ACTTTGGTCT CCAT                                  24

(2) INFORMATION FOR SEQ ID NO: 19

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P675b (xi) SEQUENCE DESCRIPTION: SEQ ID NO: 19

TCGATTCTTC GGTCCTGTGT GAGTGT                              26

(2) INFORMATION FOR SEQ ID NO: 20

(i) SEQUENCE CHARACTERISTICS:
        (A) LENGTH: 39 base pairs
        (B) TYPE: nucleic acid
        (C) STRANDEDNESS: single (D) TOPOLOGY: linear (ii) MOLECULE TYPE: DNA (ix) FEATURE:
        (D) OTHER INFORMATION: probe oligonucleotide P652b(2)

(xi) SEQUENCE DESCRIPTION: SEQ ID NO: 20

AAAAAGAATT CGGATCCATG ACGCGGTTGT GCGTGGTAC                    39

(2) INFORMATION FOR SEQ ID NO: 21

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: probe oligonucleotide P403a(2)

(xi) SEQUENCE DESCRIPTION: SEQ ID NO: 21

CCCCCTCAGA GTCGACTCAC TTCACGTTGT CAGTGGTCAT                   40

(2) INFORMATION FOR SEQ ID NO: 22

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer DA17PSHCV (xi) SEQUENCE DESCRIPTION: SEQ ID NO: 22

TGGTGGTGGA ACTGGACCGT A                                       21

(2) INFORMATION FOR SEQ ID NO: 23

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PSHCVSL (xi) SEQUENCE DESCRIPTION: SEQ ID NO: 23

AAAAGTCGAC TGGTGGTGGA ACTGGACCGT                              30

(2) INFORMATION FOR SEQ ID NO: 24

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer KHCVR60

(xi) SEQUENCE DESCRIPTION: SEQ ID NO: 24

GTGTCCGCGC TAAGCTACTG TCC                                              23

(2) INFORMATION FOR SEQ ID NO: 25

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer KHCVR61

(xi) SEQUENCE DESCRIPTION: SEQ ID NO: 25

TGTGGCAAGTA CCTCTTCAA CTGG                                             24

(2) INFORMATION FOR SEQ ID NO: 26

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer KHCVL69

(xi) SEQUENCE DESCRIPTION: SEQ ID NO: 26

GTCCTGTGGG CGGCGGTTGG TGTTACG                                          27

(2) INFORMATION FOR SEQ ID NO: 27

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer KHCVL70

(xi) SEQUENCE DESCRIPTION: SEQ ID NO: 27

TTGAGGTTTA GGATTCGTGC TCAT                                             24

(2) INFORMATION FOR SEQ ID NO: 28

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer dC12R1RO (xi) SEQUENCE DESCRIPTION: SEQ ID NO: 28

AGGATCCGT CGACATCGAT AATACGACTC ACTATAGGGA CCCCCCCCCC CC               52

(2) INFORMATION FOR SEQ ID NO: 29

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer dT17R1RO (xi) SEQUENCE DESCRIPTION: SEQ ID NO: 29

ATCCGT CGACATCGAT AATACGACTC ACTATAGGGA TTTTTTTTTT TTTTTTT                57

(2) INFORMATION FOR SEQ ID NO: 30

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer RO (xi) SEQUENCE DESCRIPTION: SEQ ID NO: 30

AAGGATCCGT CGACATC                                                        17

(2) INFORMATION FOR SEQ ID NO: 31

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer R1

(xi) SEQUENCE DESCRIPTION: SEQ ID NO: 31

GACATCGATA ATACGACTCA C                                                   21

(2) INFORMATION FOR SEQ ID NO: 32

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer NS2S1, corresponds to the strand
                of the fragment comprising from the 2776th
                to the 2795th nucleotides in KHCV-LBC1

(xi) SEQUENCE DESCRIPTION: SEQ ID NO: 32

CGGGAGATGG CCGCATCGTG                                                     20

(2) INFORMATION FOR SEQ ID NO: 33

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
    (D) OTHER INFORMATION: primer NS2N1, corresponds to the complementary strand of the fragment comprising from the 3180th to the 3157th nucleotides in KHCV-LBC1

(xi) SEQUENCE DESCRIPTION: SEQ ID NO: 33

```
ACCTGCTAGT GCGGCCAGCT TCAT                                              24
```

(2) INFORMATION FOR SEQ ID NO: 34

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: primer NS2S2, includes the strand of the fragment from the 2803rd to the 2822nd nucleotides in KHCV-LBC1

(xi) SEQUENCE DESCRIPTION: SEQ ID NO: 34

```
TTTTGGATCC GCGGTTTTTG TAGGTCTGGT                                        30
```

(2) INFORMATION FOR SEQ ID NO: 35

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: primer NS2N2, includes the complementary strand of the fragment from the 3159th to the 3142th nucleotides in KHCV-LBC1

(xi) SEQUENCE DESCRIPTION: SEQ ID NO: 35

```
AAAGTCGACA TGAAGACCAT TTGGAC                                            26
```

(2) INFORMATION FOR SEQ ID NO: 36

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: primer NS5S1, the nucleotide sequence from the 10th nucleotide to the 3'-end corresponded to the nucleotide sequence of the fragment from the 8252nd to the 8173rd nucleotides in KHCV-LBC1

(xi) SEQUENCE DESCRIPTION: SEQ ID NO: 36

```
ATGGGGATCC ATATGACACC CGCTGYTTTG A                                      31
```

(2) INFORMATION FOR SEQ ID NO: 37

(i) SEQUENCE CHARACTERISTICS:
        (A) LENGTH: 30 base pairs
        (B) TYPE: nucleic acid

```
            (C) STRANDEDNESS: single
            (D) TOPOLOGY: linear (ii) MOLECULE TYPE: DNA (ix) FEATURE:
            (D) OTHER INFORMATION: primer NS5N1, the nucleotide sequence
                from the 9th nucleotide to the 3'-end corresponded to the
                complementary strand of the fragment from the 8635th to
                the 8614th nucleotides in KHCV-LBC1

(xi) SEQUENCE DESCRIPTION: SEQ ID NO: 37

CCCCGTCGAC CTAGTCATAG CCTCCGTGAA                                        30

(2) INFORMATION FOR SEQ ID NO: 38

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer NS5S2, the nucleotide sequence
                from the 12th nucleotide to the 3'-end corresponded to the
                strand of the fragment from the 8278th to the 8297th
                nucleotides in KHCV-LBC1

(xi) SEQUENCE DESCRIPTION: SEQ ID NO: 38

TTTGAGGATC CACGGTCACT GAGAAYGACA T                                      31

(2) INFORMATION FOR SEQ ID NO: 39

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer PCOREUBI, include the strand of
                the fragment from the 343rd to the 360th nucleotides in
                KHCV-LBC1

(xi) SEQUENCE DESCRIPTION: SEQ ID NO: 39

CTTGGTGTTG AGACTCCGCG GTGGTATGAG CACGAATCCT AAACC                       45

(2) INFORMATION FOR SEQ ID NO: 40

(i) SEQUENCE CHARACTERISTICS:
            (A) LENGTH: 35 base pairs
            (B) TYPE: nucleic acid
            (C) STRANDEDNESS: single
            (D) TOPOLOGY: primer PSALCORE14, contains a stop codon to stop
                translation just after the 726th nucleotide of KHCV-LBC1

(ii) MOLECULE TYPE: DNA (ix) FEATURE:

(xi) SEQUENCE DESCRIPTION: SEQ ID NO: 40

GGGGTCGACT ATTAGCATGT GAGGGTGTCG ATGAC                                  35

(2) INFORMATION FOR SEQ ID NO: 41

(i) SEQUENCE CHARACTERISTICS:
            (A) LENGTH: 32 base pairs
```

(B) TYPE: nucleic acid
                (C) STRANDEDNESS: single
                (D) TOPOLOGY: primer PSALCORE17, contains a stop codon to stop
                    translation just after the 852nd nucleotide of KHCV-LBC1

(ii) MOLECULE TYPE: DNA (ix) FEATURE:

(xi) SEQUENCE DESCRIPTION: SEQ ID NO: 41

GGGGTCGACT ATTAGGGCAG ATTCCCTGTT GC                                         32

(2) INFORMATION FOR SEQ ID NO: 42

(i) SEQUENCE CHARACTERISTICS:
                (A) LENGTH: 35 base pairs
                (B) TYPE: nucleic acid
                (C) STRANDEDNESS: single
                (D) TOPOLOGY: primer PSALCORE22, contains a stop codon to stop
                    translation just after the 915th nucleotide of KHCV-LBC1

(ii) MOLECULE TYPE: DNA (ix) FEATURE:

(xi) SEQUENCE DESCRIPTION: SEQ ID NO: 42

GGGGTCGACT ATTAAGCGGA ACTGGGGATG GTCAA                                      35

(2) INFORMATION FOR SEQ ID NO: 43

(i) SEQUENCE CHARACTERISTICS:
                (A) LENGTH: 43 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: primer PK403UBI, designed to initiate
                    translation from the 6649th nucleotide of KHCV-LBC1

(xi) SEQUENCE DESCRIPTION: SEQ ID NO: 43

CTTGGTGTTG AGACTCCGGT GGTACGGGCA TGACCACTGA CAA                             43

(2) INFORMATION FOR SEQ ID NO: 44

(i) SEQUENCE CHARACTERISTICS:
                (A) LENGTH: 44 base pairs
                (B) TYPE: nucleic acid
                (C) STRANDEDNESS: single
                (D) TOPOLOGY: linear (ii) MOLECULE TYPE: DNA (ix) FEATURE:
                (D) OTHER INFORMATION: primer PK573UBI, designed to initiate
                    translation from the 7612th nucleotide of KHCV-LBC1

(xi) SEQUENCE DESCRIPTION: SEQ ID NO: 44

CTTGGTGTTG AGACTCCGCG GTGGTACATG GACAGGCGCC CTGA                            44

(2) INFORMATION FOR SEQ ID NO: 45

(i) SEQUENCE CHARACTERISTICS:
                (A) LENGTH: 37 base pairs
                (B) TYPE: nucleic acid
                (C) STRANDEDNESS: single
                (D) TOPOLOGY: primer PK403SAL, designed to stop translation
                    just after the 7050th nucleotide of KHCV-LBC1

(ii) MOLECULE TYPE: DNA (ix) FEATURE:

(xi) SEQUENCE DESCRIPTION: SEQ ID NO: 45

GACTGGTCGA CTATTACTCT TGCCGCCACA AGAGGTT                                            37

(2) INFORMATION FOR SEQ ID NO: 46

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK897UBI, designed to initiate
            translation from the 3916th nucleotide of KHCV-LBC1

(xi) SEQUENCE DESCRIPTION: SEQ ID NO: 46

CTTGGTGTTG AGACTCCGCG GTGGTGCGGT GGAATTCATA CCCG                                    44

(2) INFORMATION FOR SEQ ID NO: 47

(i) SEQUENCE CHARACTERISTICS:
        (A) LENGTH: 37 base pairs
        (B) TYPE: nucleic acid
        (C) STRANDEDNESS: single
        (D) TOPOLOGY: primer PK897SAL, designed to stop translation
            just after the 4713th nucleotide of KHCV-LBC1

(ii) MOLECULE TYPE: DNA (ix) FEATURE:

(xi) SEQUENCE DESCRIPTION: SEQ ID NO: 47

GACTGGTCGA CTATTAACAC GTATTACAGT CGATCAC                                            37

(2) INFORMATION FOR SEQ ID NO: 48

(i) SEQUENCE CHARACTERISTICS:
        (A) LENGTH: 38 base pairs
        (B) TYPE: nucleic acid
        (C) STRANDEDNESS: single
        (D) TOPOLOGY: primer PK573SAL, designed to stop translation
            just after the 8184th nucleotide of KHCV-LBC1

(ii) MOLECULE TYPE: DNA (ix) FEATURE:

(xi) SEQUENCE DESCRIPTION: SEQ ID NO: 48

GACTGGTCGA CTATTAGTAC TGGAATCCGT ATGAGGAG                                           38

(2) INFORMATION FOR SEQ ID NO: 49

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer P426B, consists of the region
            from the 616th to the 636th nucleotides of KHCV-LBC1

(xi) SEQUENCE DESCRIPTION: SEQ ID NO: 49

```
GGGTGGGCAG GATGGCTCCT G                                                      21

(2) INFORMATION FOR SEQ ID NO: 50

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer P240B, consists of the region
            from the 842nd to the 821st nucleotides of KHCV-LBC1

(xi) SEQUENCE DESCRIPTION: SEQ ID NO: 50

CCTGTTGCAT AGTTCACGCC GT                                                     22

(2) INFORMATION FOR SEQ ID NO: 51

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer P652B, consists of the region
            from the 4523rd to the 4560th nucleotides of KHCV-LBC1

(xi) SEQUENCE DESCRIPTION: SEQ ID NO: 51

GTCATTCCAA GAAGAAATGT GACGAGCTCG CTGCAAAG                                    38

(2) INFORMATION FOR SEQ ID NO: 52

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PE2NUBI, contains 25 nucleotides
            on the 5'-end region overlapping with the 3'-end region of
            ubiquitin gene and the other nucleotides correspond to the
            region from the 1510th to the 1530th nucleotides of
            KHCV-LBC1

(xi) SEQUENCE DESCRIPTION: SEQ ID NO: 52

CTTGGTGTTG AGACTCCGCG GTGGTGGGGC GCAAGGTCGG GCCGCT                           46

(2) INFORMATION FOR SEQ ID NO: 53

(i) SEQUENCE CHARACTERISTICS:
        (A) LENGTH: 37 base pairs
        (B) TYPE: nucleic acid
        (C) STRANDEDNESS: single
        (D) TOPOLOGY: primer PE2NSAL, designed to stop translation
            just after the 2010th nucleotide of KHCV-LBC1

(ii) MOLECULE TYPE: DNA (ix) FEATURE:

(xi) SEQUENCE DESCRIPTION: SEQ ID NO: 53
```

```
GACTGGACTA TTAATTCATC CAGGTACAAC CGAACCA                              37
```

(2) INFORMATION FOR SEQ ID NO: 54

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PE2CUBI, contains 25 nucleotides on the 5'-end region overlapping with the 3'-end region of ubiquitin gene and the other nucleotides correspond to the region from the 2011th to the 2031st nucleotides of KHCV-LBC1

(xi) SEQUENCE DESCRIPTION: SEQ ID NO: 54

```
CTTGGTGTTG AGACTCCGCG GTGGTGGCAC TGGGTTCACC AAGACA                    46
```

(2) INFORMATION FOR SEQ ID NO: 55

(i) SEQUENCE CHARACTERISTICS:
        (A) LENGTH: 37 base pairs
        (B) TYPE: nucleic acid
        (C) STRANDEDNESS: single
        (D) TOPOLOGY: primer PE2CSAL, designed to stop translation just after the 2529th nucleotide of KHCV-LBC1

(ii) MOLECULE TYPE: DNA (ix) FEATURE:

(xi) SEQUENCE DESCRIPTION: SEQ ID NO: 55

```
GACTGGACTA TTACGCGTCC GCCAGAAGAA GGAAGAG                              37
```

(2) INFORMATION FOR SEQ ID NO: 56

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PE1UBI, contains 25 nucleotides on the 5'-end region overlapping with ubiquitin gene and the other nucleotides correspond to the region from the 916th to the 936th nucleotides of KHCV-LBC1

(xi) SEQUENCE DESCRIPTION: SEQ ID NO: 56

```
CTTGGTGTTG AGACTCCGCG GTGGTTATGA AGTGGGCAAC GCGTCC                    46
```

(2) INFORMATION FOR SEQ ID NO: 57

(i) SEQUENCE CHARACTERISTICS:
        (A) LENGTH: 37 base pairs
        (B) TYPE: nucleic acid
        (C) STRANDEDNESS: single
        (D) TOPOLOGY: primer PE1SAL, designed to stop translation just after the 1509th nucleotide of KHCV-LBC1

(ii) MOLECULE TYPE: DNA (ix) FEATURE:

(xi) SEQUENCE DESCRIPTION: SEQ ID NO: 57

```
GACTGGACTA TTACCCTGTC ACGTGGGTGG TGGTTCC                                37
```

(2) INFORMATION FOR SEQ ID NO: 58

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide UBI1

(xi) SEQUENCE DESCRIPTION: SEQ ID NO: 58

```
CCCCATATGC AAATTTTCGT CAAAACTCTA ACAGGGAAGA CTATAACCCT AGAGGTTGAA        60

TCTTCCGACA CTATTGACAA CGTCAA                                            86
```

(2) INFORMATION FOR SEQ ID NO: 59

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide UBI2

(xi) SEQUENCE DESCRIPTION: SEQ ID NO: 59

```
TAGTTGCTTA CCAGCAAAAA TCAATCTCTG CTGATCCGGA GGGATACCTT CTTTATCTTT        60

GAATTTTACT TTTGACGTTG TCAATAGTCT C                                      91
```

(2) INFORMATION FOR SEQ ID NO: 60

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: oligonucleotide UBI3

(xi) SEQUENCE DESCRIPTION: SEQ ID NO: 60

```
ACCACCGCGG AGTCTCAACA CCAAGTGAAG AGTAGATTCC TTTTGGATGT TGTAGTCAGA        60

CAAGGTTCTA CCATCTTCTA GTTGCTTACC AGCAAAAA                               98
```

(2) INFORMATION FOR SEQ ID NO: 61

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK426R (xi) SEQUENCE DESCRIPTION: SEQ ID NO: 61

```
CTCCGAATTC GGTGCTTGCG AGTGCCCC                                          28
```

(2) INFORMATION FOR SEQ ID NO: 62

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK426X (xi) SEQUENCE DESCRIPTION: SEQ ID NO: 62

CACGCTCGAG GCATGTGAGG GTGTCGATGA C        31

(2) INFORMATION FOR SEQ ID NO: 63

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK513R (xi) SEQUENCE DESCRIPTION: SEQ ID NO: 63

CTCCGAATTC GGCACGAGGC TGGAGGACGG CGTGAACT        38

(2) INFORMATION FOR SEQ ID NO: 64

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK513X (xi) SEQUENCE DESCRIPTION: SEQ ID NO: 64

CACGCTCGAG AGGCGACCAG TTCATCATCA T        31

(2) INFORMATION FOR SEQ ID NO: 65

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK810R (xi) SEQUENCE DESCRIPTION: SEQ ID NO: 65

CTCCGAATTC GGCACGAGGG TTTCCCAGCT GTTCACCTT        39

(2) INFORMATION FOR SEQ ID NO: 66

(i) SEQUENCE CHARACTERISTICS:
        (A) LENGTH: 33 base pairs
        (B) TYPE: nucleic acid

```
        (C) STRANDEDNESS: single
        (D) TOPOLOGY: linear (ii) MOLECULE TYPE: DNA (ix) FEATURE:
        (D) OTHER INFORMATION: primer PK810X (xi) SEQUENCE DESCRIPTION: SEQ ID NO: 66

CACGCTCGAG ATTCATCCAG GTACAACGGA ACC                               33

(2) INFORMATION FOR SEQ ID NO: 67

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK798R (xi) SEQUENCE DESCRIPTION: SEQ ID NO: 67

CTCCGAATTC GGCACGAGGG ACGTGCTGCT CCTTAAC                            37

(2) INFORMATION FOR SEQ ID NO: 68

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK798X (xi) SEQUENCE DESCRIPTION: SEQ ID NO: 68

CACGCTCGAG CAGAAGCAGC GGCCATACGC C                                 31

(2) INFORMATION FOR SEQ ID NO: 69

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK754R (xi) SEQUENCE DESCRIPTION: SEQ ID NO: 69

AAAAAGAATT CGGCACGAGG CTGCGAGATT GGGCTCACAC G                       41

(2) INFORMATION FOR SEQ ID NO: 70

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer PK754X
```

(xi) SEQUENCE DESCRIPTION: SEQ ID NO: 70

AAAAACTCGA GCCGCATAGT AGTTTCCATA GACTCAACGG GTATGAATT              49

(2) INFORMATION FOR SEQ ID NO: 71

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer PK652R (xi) SEQUENCE DESCRIPTION: SEQ ID NO: 71

AAAAAGAATT CGGCACGAGG TTCATACCCG TTGAGTCTAT GGAA                   44

(2) INFORMATION FOR SEQ ID NO: 72

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer PK652X (xi) SEQUENCE DESCRIPTION: SEQ ID NO: 72

ATTATTGTCG ACTATCTATC TACTCGAGTC ACAGCTTTGC AGCGAGCTCG T           51

(2) INFORMATION FOR SEQ ID NO: 73

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer PK403R (xi) SEQUENCE DESCRIPTION: SEQ ID NO: 73

AAAAAGAATT CACGGGCATG ACCACTGAC                                    29

(2) INFORMATION FOR SEQ ID NO: 74

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (ix) FEATURE:
            (D) OTHER INFORMATION: primer PK403X (xi) SEQUENCE DESCRIPTION: SEQ ID NO: 74

ATTATTCTCG AGTATCACTC TTGCCGCCAC AAGAG                             35

(2) INFORMATION FOR SEQ ID NO: 75

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: primer PK271R (xi) SEQUENCE DESCRIPTION: SEQ ID NO: 75

AAAAAGAATT CACTAGCCTT ACAGGCCGG                                          29

(2) INFORMATION FOR SEQ ID NO: 76

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: primer PK271X (xi) SEQUENCE DESCRIPTION: SEQ ID NO: 76

CACGCTCGAG TCACGTGACC AGGTAAAGGT C                                       31

(2) INFORMATION FOR SEQ ID NO: 77

(i) SEQUENCE CHARACTERISTICS:
           (A) LENGTH: 40 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: primer PK495R (xi) SEQUENCE DESCRIPTION: SEQ ID NO: 77

CCCCCGAATT CGGCACGAGC GCTGCGGAGG AAAGCAAGTT                              40

(2) INFORMATION FOR SEQ ID NO: 78

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (ix) FEATURE:
           (D) OTHER INFORMATION: primer PK495X (xi) SEQUENCE DESCRIPTION: SEQ ID NO: 78

AAAAACTCGA GGACCACGTC ATAAAGGGCC A                                       31

(2) INFORMATION FOR SEQ ID NO: 79

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: DNA (ix) FEATURE:
             (D) OTHER INFORMATION: primer PK494R (xi) SEQUENCE DESCRIPTION: SEQ ID NO: 79

AAAAGAATTC GGCACGAGCG ATGCATCTGG TAAAAGGGT                                    39

(2) INFORMATION FOR SEQ ID NO: 80

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: primer PK494X (xi) SEQUENCE DESCRIPTION: SEQ ID NO: 80

AAAACTCGAG ATTGGAGTGA GTTTGAGCTT                                              30

(2) INFORMATION FOR SEQ ID NO: 81

(i) SEQUENCE CHARACTERISTICS:
             (A) LENGTH: 105 amino acids
             (B) TYPE: amino acid
             (D) TOPOLOGY: linear (ii) MOLECULE TYPE: protein (xi) SEQUENCE DESCRIPTION: SEQ ID NO: 81

Leu Leu Thr Leu Ser Pro His Tyr Lys Val Phe Leu Ala Arg Phe
 1               5                  10                  15

Ile Trp Trp Leu Gln Tyr Leu Ile Thr Arg Thr Glu Ala His Leu
                20                  25                  30

Gln Val Trp Val Pro Pro Leu Asn Val Arg Gly Gly Arg Asp Ala
                35                  40                  45

Val Ile Leu Leu Thr Cys Ala Val Tyr Pro Glu Leu Ile Phe Asp
                50                  55                  60

Ile Thr Lys Leu Leu Leu Ala Thr Leu Gly Pro Leu Met Val Leu
                65                  70                  75

Gln Ala Gly Leu Ile Arg Val Pro Tyr Phe Val Arg Ser Gly Leu
                80                  85                  90

Ile Arg Ala Cys Met Leu Val Arg Lys Val Ala Gly Gly His Tyr
                95                  100                 105

(2) INFORMATION FOR SEQ ID NO: 82

(i) SEQUENCE CHARACTERISTICS:
             (A) LENGTH: 106 amino acids
             (B) TYPE: amino acid
             (D) TOPOLOGY: linear (ii) MOLECULE TYPE: protein (xi) SEQUENCE DESCRIPTION: SEQ ID NO: 82

Leu Leu Thr Leu Ser Pro His Tyr Lys Val Phe Leu Ala Arg Phe
 1               5                  10                  15

Ile Trp Trp Leu Gln Tyr Leu Ile Thr Arg Thr Glu Ala His Leu
                20                  25                  30

Gln Val Trp Val Pro Pro Leu Asn Val Arg Gly Gly Arg Asp Ala

```
                    35                  40                  45
Ile Ile Leu Leu Ala Cys Ala Val His Pro Glu Leu Ile Phe Asp
                50                  55                  60

Ile Thr Lys Leu Leu Leu Ala Ile Leu Gly Pro Leu Met Val Leu
                65                  70                  75

Gln Ala Ser Ile Ile Arg Val Pro Tyr Ser Val Arg Ala Gln Gly
                80                  85                  90

Leu Ile Arg Ala Cys Met Leu Val Arg Lys Ala Ala Gly Gly His
                95                 100                 105

Tyr
```

(2) INFORMATION FOR SEQ ID NO: 83

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 83

```
Leu Leu Thr Leu Ser Pro His Tyr Lys Val Phe Leu Ala Arg Phe
 1               5                  10                  15

Ile Trp Trp Leu Gln Tyr Leu Ile Thr Arg Thr Glu Ala His Leu
                20                  25                  30

Gln Val Trp Val Pro Pro Leu Asn Val Arg Gly Gly Arg Asp Ala
                35                  40                  45

Ile Ile Leu Leu Thr Cys Val Val His Pro Glu Leu Ile Phe Asp
                50                  55                  60

Ile Thr Lys Leu Leu Leu Ala Ile Leu Gly Pro Leu Met Val Leu
                65                  70                  75

Gln Ala Ser Ile Ile Arg Val Pro Tyr Phe Val Arg Ala Gln Gly
                80                  85                  90

Leu Ile Arg Ala Cys Met Leu Val Arg Lys Val Ala Gly Gly His
                95                 100                 105

Tyr
```

(2) INFORMATION FOR SEQ ID NO: 84

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 84

```
Leu Leu Thr Leu Ser Pro His Tyr Lys Val Phe Leu Ala Arg Phe
 1               5                  10                  15

Val Trp Trp Leu Gln Tyr Leu Ile Thr Arg Thr Glu Ala His Leu
                20                  25                  30

Gln Val Trp Val Pro Pro Leu Asn Val Arg Gly Gly Arg Asp Ala
                35                  40                  45

Ile Thr Leu Leu Thr Cys Val Val His Pro Glu Leu Ile Phe Asp
                50                  55                  60

Ile Thr Lys Tyr Leu Leu Ala Ile Phe Gly Pro Leu Met Val Leu
                65                  70                  75

Gln Ala Gly Ile Thr Arg Val Pro Tyr Phe Val Arg Ala Gln Gly
```

```
                    80              85              90
Leu Ile Arg Ala Cys Met Leu Val Arg Lys Val Ala Gly Gly His
                    95              100             105
Tyr (2) INFORMATION FOR SEQ ID NO: 85

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO: 85

Leu Phe Thr Leu Ser Pro His Tyr Lys Val Phe Leu Ala Arg Leu
 1               5                  10                  15

Ile Trp Trp Leu Gln Tyr Phe Ile Thr Arg Ala Glu Ala His Leu
                20                  25                  30

Gln Val Trp Ile Pro Pro Leu Asn Val Arg Gly Gly Arg Asp Ala
                35                  40                  45

Ile Ile Leu Leu Thr Cys Ala Val His Ser Glu Leu Ile Phe Asp
                50                  55                  60

Ile Thr Lys Ile Leu Leu Ala Ile Leu Gly Pro Leu Met Val Leu
                65                  70                  75

Gln Ala Gly Leu Thr Arg Val Pro Tyr Phe Val Ser Ala Gln Gly
                80                  85                  90

Leu Ile (2) INFORMATION FOR SEQ ID NO: 86

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 86

Leu Leu Thr Leu Ser Pro Tyr Tyr Lys Val Phe Leu Ala Arg Leu
 1               5                  10                  15

Ile Trp Trp Leu Gln Tyr Phe Ile Thr Arg Ala Glu Ala His Leu
                20                  25                  30

Gln Val Trp Ile Pro Pro Leu Asn Val Arg Gly Gly Arg Asp Ala
                35                  40                  45

Ile Ile Leu Leu Ala Cys Ala Val His Pro Glu Pro Ile Phe Asp
                50                  55                  60

Ile Thr Lys Tyr Leu Leu Ala Ile Phe Gly Pro Leu Met Val Leu
                65                  70                  75

Gln Ala Gly Ile Thr Arg Val Pro Tyr Phe Trp Arg Ala Gln Gly
                80                  85                  90

Leu Ile Arg Ala Cys Met Leu Ala Arg Lys Val Ala Gly Gly His
                95                  100                 105

Tyr (2) INFORMATION FOR SEQ ID NO: 87

(i) SEQUENCE CHARACTERISTICS:
        (A) LENGTH: 106 amino acids
```

(B) TYPE: amino acid
            (D) TOPOLOGY: linear (ii) MOLECULE TYPE: protein (xi) SEQUENCE DESCRIPTION: SEQ ID NO: 87

```
Leu Leu Thr Leu Ser Pro His Tyr Lys Val Phe Leu Ala Arg Leu
 1               5                  10                  15

Met Trp Trp Leu Gln Tyr Phe Leu Thr Arg Ala Glu Ala His Leu
                20                  25                  30

Gln Val Trp Val Pro Ser Leu Asn Val Arg Gly Gly Arg Asp Ala
                35                  40                  45

Ile Ile Leu Leu Thr Cys Ala Val Tyr Pro Glu Leu Ile Phe Asp
                50                  55                  60

Ile Thr Lys Leu Leu Leu Ala Thr Leu Gly Pro Leu Met Val Leu
                65                  70                  75

Gln ala Gly Leu Thr Arg Val Pro Tyr Phe Val Arg Ala Gln Gly
                80                  85                  90

Leu Ile Arg Ala Cys Met Leu Val Arg Lys Val Val Gly Gly His
                95                 100                 105

Tyr
```

(2) INFORMATION FOR SEQ ID NO: 88

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 88

```
Leu Leu Thr Leu Ser Pro Tyr Tyr Lys Val Leu Leu Ala Arg Leu
 1               5                  10                  15

Ile Trp Trp Leu Gln Tyr Phe Ile Thr Arg Ala Glu Ala His Leu
                20                  25                  30

Gln Val Trp Ala Pro Pro Leu Asn Val Arg Gly Gly Arg Asp Ala
                35                  40                  45

Ile Ile Leu Leu Met Cys Val Val His Pro Glu Leu Ile Phe Asp
                50                  55                  60

Ile Thr Lys Ile Leu Leu Ala Val Leu Gly Pro Leu Thr Val Leu
                65                  70                  75

Gln Ala Gly Ile Thr Arg Val Pro Tyr Phe Val Arg Ala Gln Trp
                80                  85                  90

Leu Ile Arg Ala Cys Met Leu Val Arg Asn Ile Ala Gly Gly His
                95                 100                 105

Tyr
```

(2) INFORMATION FOR SEQ ID NO: 89

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 89

```
Leu Leu Thr Leu Ser Pro His Tyr Lys Val Phe Leu Ala Ser Leu
 1               5                  10                  15
```

```
Met Trp Trp Leu Gln Tyr Phe Leu Thr Arg Ala Glu Ala His Leu
             20                  25                  30

Gln Val Trp Val Pro Ser Leu Asn Val Arg Gly Gly Arg Asp Ala
             35                  40                  45

Ile Ile Leu Leu Thr Cys Ala Val Tyr Pro Glu Leu Ile Leu Asp
             50                  55                  60

Ile Thr Lys Leu Leu Leu Ala Ile Leu Gly Pro Leu Met Val Leu
             65                  70                  75

Gln Ala Ser Ile Ile Arg Val Pro Tyr Phe Val Arg Ala Gln Gly
             80                  85                  90

Leu Ile Arg Ala Cys Met Leu Val Arg Lys Ala Ala Gly Gly His
             95                 100                 105

Tyr (2) INFORMATION FOR SEQ ID NO: 90

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 90

Leu Leu Thr Leu Ser Pro His Tyr Lys Val Phe Leu Ala Arg Leu
 1               5                  10                  15

Thr Trp Trp Leu Gln Tyr Phe Leu Thr Arg Ala Glu Ala His Leu
             20                  25                  30

Gln Val Trp Val Pro Ser Leu Asn Val Arg Gly Gly Arg Asp Ala
             35                  40                  45

Ile Ile Leu Leu Thr Cys Ala Val Tyr Pro Glu Leu Ile Phe Asp
             50                  55                  60

Ile Thr Lys Leu Leu Leu Ala Thr Leu Gly Pro Leu Met Val Leu
             65                  70                  75

Gln Ala Gly Leu Thr Arg Val Pro Tyr Phe Val Arg Ala Gln Gly
             80                  85                  90

Leu Ile Arg Ala Cys Met Leu Val Arg Lys Val Ala Gly Gly His
             95                 100                 105

Tyr (2) INFORMATION FOR SEQ ID NO: 91

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 91

Leu Leu Thr Leu Ser Pro Tyr Tyr Lys Val Phe Leu Ala Arg Leu
 1               5                  10                  15

Ile Trp Trp Leu Gln Tyr Phe Ile Thr Arg Ala Glu Ala His Leu
             20                  25                  30

Gln Val Trp Val Pro Pro Leu Asn Val Arg Gly Gly Arg Asp Ala
             35                  40                  45

Ile Ile Leu Leu Thr Cys Ala Val Tyr Pro Glu Leu Ile Phe Asp
             50                  55                  60
```

```
Ile Thr Lys Leu Leu Leu Ala Ile Leu Gly Pro Leu Met Val Leu
             65                  70                  75

Gln Ala Ser Ile Ile Arg Val Pro Tyr Phe Val Arg Ala Gln Gly
             80                  85                  90

Leu Ile Arg Ala Cys Met Leu Val Arg Lys Ala Ala Gly Val Asn
             95                 100                 105

Tyr
```

(2) INFORMATION FOR SEQ ID NO: 92

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 92

```
Leu Phe Thr Leu Ser Pro His Cys Lys Val Phe Leu Ala Arg Leu
 1               5                  10                  15

Ile Trp Trp Leu Gln Tyr Phe Ile Thr Arg Ala Glu Ala His Leu
             20                  25                  30

Gln Val Trp Ile Pro Pro Leu Asn Val Arg Gly Gly Arg Asp Ala
             35                  40                  45

Ile Ile Leu Leu Ala Cys Ala Val His Pro Glu Leu Ile Phe Asp
             50                  55                  60

Ile Thr Lys Leu Leu Leu Ala Ile Leu Gly Pro Leu Met Val Leu
             65                  70                  75

Gln Ala Ser Ile Ile Arg Val Pro Tyr Leu Tyr Arg Ala Gln Gly
             80                  85                  90

Leu Ile Arg Ala Cys Met Leu Val Arg Lys Ala Ala Gly Gly His
             95                 100                 105

Tyr
```

(2) INFORMATION FOR SEQ ID NO: 93

(i) SEQUENCE CHARACTERISTICS:
        (A) LENGTH: 106 amino acids
        (B) TYPE: amino acid
       (D) TOPOLOGY: linear (ii) MOLECULE TYPE: protein (xi) SEQUENCE DESCRIPTION: SEQ ID NO: 93

```
Leu Phe Asn Leu Ser Pro His Tyr Lys Val Phe Leu Ala Arg Leu
 1               5                  10                  15

Ile Trp Trp Leu Gln Tyr Phe Ile Thr Arg Ala Glu Ala His Leu
             20                  25                  30

Gln Val Trp Ile Pro Pro Leu Asn Val Gln Gly Gly Arg Asp Ala
             35                  40                  45

Ile Ile Leu Leu Ala Cys Ala Val His Pro Glu Leu Ile Phe Asp
             50                  55                  60

Ile Thr Lys Leu Leu Leu Ala Ile Leu Gly Pro Leu Met Val Leu
             65                  70                  75

Gln Ala Ser Ile Ile Arg Val Pro Tyr Phe Val Arg Ala Gln Gly
             80                  85                  90

Leu Ile Arg Ala Cys Met Leu Val Arg Lys Ala Ala Gly Gly His
             95                 100                 105
```

Tyr (2) INFORMATION FOR SEQ ID NO: 94

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO: 94

```
Ala Val Glu Phe Ile Pro Val Glu Ser Met Glu Thr Thr Met Arg
 1               5                  10                  15

Ser Pro Val Phe Thr Asp Asn Pro Ser Pro Ala Val Pro Gln
                20                  25                  30

Thr Phe Gln Val Ala His Leu His Ala Pro Thr Gly Ser Gly Lys
                35                  40                  45

Ser Thr Arg Val Pro Ala Ala Tyr Ala Ala Gln Gly Tyr Lys Val
                50                  55                  60

Leu Val Leu Asn Pro Ser Val Ala Ala Thr Leu Gly Phe Gly Ala
                65                  70                  75

Tyr Met Ser Lys Ala His Gly Ile Asp Pro Asn Leu Arg Thr Gly
                80                  85                  90

Val Arg Thr Ile Thr Thr Gly Ala
                95
```

(2) INFORMATION FOR SEQ ID NO: 95

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO: 95

```
Gly Glu Ile Pro Phe Tyr Gly Lys Ala Ile Pro Ile Glu Ala Ile
 1               5                  10                  15

Lys Gly Gly Arg His Leu Ile Phe Cys His Ser Lys Lys Lys Cys
                20                  25                  30

Asp Glu Leu Ala Ala Lys Leu
                35
```

(2) INFORMATION FOR SEQ ID NO: 96

(i) SEQUENCE CHARACTERISTICS:
        (A) LENGTH: 9472 base pairs
        (B) TYPE: nucleic acid
        (C) STRANDEDNESS: double
        (D) TOPOLOGY: linear (ii) MOLECULE TYPE: DNA (ix) FEATURE:
        (D) OTHER INFORMATION: KHCV-LBC1, Fig. 2

(xi) SEQUENCE DESCRIPTION: SEQ ID NO: 96

```
TGCCAGCCCC CGATTGGGGG CGACACTCCA CCATAGATCA CTCCCCTGTG AGGAACTACT    60
GTCTTCACGC AGAAAGCGTC TAGCCATGGC GTTAGTATGA GTGTCGTGCA GCCTCCAGGA   120
CCCCCCCTCC CGGGAGAGCC ATAGTGGTCT GCGGAACCGG TGAGTACACC GGAATTGCCA   180
```

-continued

```
GGACGACCGG GTCCTTTCTT GGATCAACCC GCTCAATGCC TGGAGATTTG GGCGTGCCCC      240

CGCGAGACTG CTAGCCGAGT AGTGTTGGGT CGCGAAAGGC CTTGTGGTAC TGCCTGATAG      300

GGTGCTTGCG AGTGCCCCGG GAGGTCTCGT AGACCGTGCA CC ATG AGC ACG AAT         354
                                              Met Ser Thr Asn
                                               1
```

| | | | | | | | | | | | | | | | | |
|---|---|---|---|---|---|---|---|---|---|---|---|---|---|---|---|---|
| CCT | AAA | CCT | CAA | AGA | AAA | ACC | AAA | CGT | AAC | ACC | AAC | CGC | CGC | CCA | CAG | 402 |
| Pro | Lys | Pro | Gln | Arg | Lys | Thr | Lys | Arg | Asn | Thr | Asn | Arg | Arg | Pro | Gln | |
| 5 | | | | 10 | | | | 15 | | | | | | 20 | | |
| GAT | ATT | AAG | TTC | CCG | GGC | GGT | GGT | CAG | ATC | GTT | GGA | GGA | GTT | TAC | TTG | 450 |
| Asp | Ile | Lys | Phe | Pro | Gly | Gly | Gly | Gln | Ile | Val | Gly | Gly | Val | Tyr | Leu | |
| | | | 25 | | | | | 30 | | | | | 35 | | | |
| TTG | CCG | CGC | AGG | GGC | CCC | AGG | TTG | GGT | GTG | CGC | GCG | ACT | AGG | AAG | ACT | 498 |
| Leu | Pro | Arg | Arg | Gly | Pro | Arg | Leu | Gly | Val | Arg | Ala | Thr | Arg | Lys | Thr | |
| | | | 40 | | | | | 45 | | | | | 50 | | | |
| TCC | GAG | CGG | TCG | CAA | CCT | CGT | GGA | AGG | CGA | CAG | CCT | ATC | CCC | AAG | GCT | 546 |
| Ser | Glu | Arg | Ser | Gln | Pro | Arg | Gly | Arg | Arg | Gln | Pro | Ile | Pro | Lys | Ala | |
| | | | | 55 | | | | | 60 | | | | 65 | | | |
| CGC | CGG | CCC | GAG | GGC | AGG | GCC | TGG | GCT | CAG | CCC | GGG | TAC | CCT | TGG | CCC | 594 |
| Arg | Arg | Pro | Glu | Gly | Arg | Ala | Trp | Ala | Gln | Pro | Gly | Tyr | Pro | Trp | Pro | |
| | 70 | | | | | 75 | | | | | 80 | | | | | |
| CTC | TAT | GGC | AAT | GAG | GGC | TTG | GGG | TGG | GCA | GGA | TGG | CTC | CTG | TCA | CCC | 642 |
| Leu | Tyr | Gly | Asn | Glu | Gly | Leu | Gly | Trp | Ala | Gly | Trp | Leu | Leu | Ser | Pro | |
| 85 | | | | | 90 | | | | | 95 | | | | | 100 | |
| CGC | GGC | TCC | CGG | CCT | AGT | TGG | GGC | CCC | ACG | GAC | CCC | CGG | CGT | AAG | TCG | 690 |
| Arg | Gly | Ser | Arg | Pro | Ser | Trp | Gly | Pro | Thr | Asp | Pro | Arg | Arg | Lys | Ser | |
| | | | | 105 | | | | | 110 | | | | | 115 | | |
| CGT | AAT | TTG | GGT | AAG | GTC | ATC | GAC | ACC | CTC | ACA | TGC | GGC | TTC | GCC | GAC | 738 |
| Arg | Asn | Leu | Gly | Lys | Val | Ile | Asp | Thr | Leu | Thr | Cys | Gly | Phe | Ala | Asp | |
| | | | 120 | | | | | 125 | | | | | 130 | | | |
| CTC | ATG | GGG | TAC | ATT | CCG | CTC | GTC | GGC | GCC | CCC | CTA | GGG | GGC | GTT | GCC | 786 |
| Leu | Met | Gly | Tyr | Ile | Pro | Leu | Val | Gly | Ala | Pro | Leu | Gly | Gly | Val | Ala | |
| | | | 135 | | | | | 140 | | | | | 145 | | | |
| AGG | GCC | CTG | GCA | CAT | GGT | GTC | CGG | GTG | CTG | GAG | GAC | GGC | GTG | AAC | TAT | 834 |
| Arg | Ala | Leu | Ala | His | Gly | Val | Arg | Val | Leu | Glu | Asp | Gly | Val | Asn | Tyr | |
| | 150 | | | | | 155 | | | | | 160 | | | | | |
| GCA | ACA | GGG | AAT | CTG | CCC | GGT | TGC | TCT | TTC | TCT | ATC | TTC | CTC | TTG | GCT | 882 |
| Ala | Thr | Gly | Asn | Leu | Pro | Gly | Cys | Ser | Phe | Ser | Ile | Phe | Leu | Leu | Ala | |
| 165 | | | | | 170 | | | | | 175 | | | | | 180 | |
| CTG | CTG | TCT | TGT | TTG | ACC | ACC | CCA | GTT | TCC | GCT | TAT | GAA | GTG | CGT | AAC | 930 |
| Leu | Leu | Ser | Cys | Leu | Thr | Thr | Pro | Val | Ser | Ala | Tyr | Glu | Val | Arg | Asn | |
| | | | | 185 | | | | | 190 | | | | | 195 | | |
| GCG | TCC | GGG | ATG | TAC | CAT | GTC | ACG | AAC | GAC | TGC | TCC | AAC | TCA | AGC | ATT | 978 |
| Ala | Ser | Gly | Met | Tyr | His | Val | Thr | Asn | Asp | Cys | Ser | Asn | Ser | Ser | Ile | |
| | | | 200 | | | | | 205 | | | | | 210 | | | |
| GTG | TAT | GAG | GCA | GCG | GAC | ATG | ATC | ATG | CAC | ACT | CCC | GGG | TGC | GTG | CCC | 1026 |
| Val | Tyr | Glu | Ala | Ala | Asp | Met | Ile | Met | His | Thr | Pro | Gly | Cys | Val | Pro | |
| | | 215 | | | | | 220 | | | | | 225 | | | | |
| TGC | GTT | CGG | GAG | GAC | AAC | TCC | TCC | CGT | TGC | TGG | GTG | GCA | CTT | ACT | CCC | 1074 |
| Cys | Val | Arg | Glu | Asp | Asn | Ser | Ser | Arg | Cys | Trp | Val | Ala | Leu | Thr | Pro | |
| | 230 | | | | | 235 | | | | | 240 | | | | | |
| ACG | CTC | GCG | GCC | AGG | AAT | GCC | AGC | GTC | CCC | ACT | ACG | ACA | TTG | CGA | CGC | 1122 |
| Thr | Leu | Ala | Ala | Arg | Asn | Ala | Ser | Val | Pro | Thr | Thr | Thr | Leu | Arg | Arg | |
| 245 | | | | | 250 | | | | | 255 | | | | | 260 | |
| CAT | GTC | GAC | TTG | CTC | GTT | GGG | GTA | GCT | GCT | TTC | TGT | TCC | GCT | ATG | TAC | 1170 |
| His | Val | Asp | Leu | Leu | Val | Gly | Val | Ala | Ala | Phe | Cys | Ser | Ala | Met | Tyr | |
| | | | | 265 | | | | | 270 | | | | | 275 | | |
| GTG | GGG | GAC | CTC | TGC | GGA | TCT | GTT | TTC | CTT | GTT | TCC | CAG | CTG | TTC | ACC | 1218 |
| Val | Gly | Asp | Leu | Cys | Gly | Ser | Val | Phe | Leu | Val | Ser | Gln | Leu | Phe | Thr | |
| | | | 280 | | | | | 285 | | | | | 290 | | | |

```
TTT TCG CCT CGC CGG CAT GAG ACG GTA CAG GAC TGC AAC TGC TCA ATC      1266
Phe Ser Pro Arg Arg His Glu Thr Val Gln Asp Cys Asn Cys Ser Ile
        295                 300                 305

TAT CCC GGC CGC GTA TCA GGT CAC CGC ATG GCC TGG GAT ATG ATG ATG      1314
Tyr Pro Gly Arg Val Ser Gly His Arg Met Ala Trp Asp Met Met Met
    310                 315                 320

AAC TGG TCG CCT ACA ACA GCC CTA GTG GTA TCG CAG CTA CTC CGG ATC      1362
Asn Trp Ser Pro Thr Thr Ala Leu Val Val Ser Gln Leu Leu Arg Ile
325                 330                 335                 340

CCA CAA GCT GTC GTG GAC ATG GTG ACA GGG TCC CAC TGG GGA ATC CTG      1410
Pro Gln Ala Val Val Asp Met Val Thr Gly Ser His Trp Gly Ile Leu
                345                 350                 355

GCG GGC CTT GCC TAC TAT TCC ATG GTG GGG AAC TGG GCT AAG GTC TTA      1458
Ala Gly Leu Ala Tyr Tyr Ser Met Val Gly Asn Trp Ala Lys Val Leu
            360                 365                 370

ATT GCG ATG CTA CTC TTT GCC GGC GTT GAC GGA ACC ACC CAC GTG ACA      1506
Ile Ala Met Leu Leu Phe Ala Gly Val Asp Gly Thr Thr His Val Thr
        375                 380                 385

GGG GGG GCG CAA GGT CGG GCC GCT AGC TCG CTA ACG TCC CTC TTT AGC      1554
Gly Gly Ala Gln Gly Arg Ala Ala Ser Ser Leu Thr Ser Leu Phe Ser
    390                 395                 400

CCT GGG CCG GTT CAG CAC CTC CAG CTC ATA AAC ACC AAC GGC AGC TGG      1602
Pro Gly Pro Val Gln His Leu Gln Leu Ile Asn Thr Asn Gly Ser Trp
405                 410                 415                 420

CAT ATC AAC AGG ACC GCC CTG AGC TGC AAT GAC TCC CTC AAC ACT GGG      1650
His Ile Asn Arg Thr Ala Leu Ser Cys Asn Asp Ser Leu Asn Thr Gly
                425                 430                 435

TTT GTT GCC GCG CTG TTC TAC AAA TAC AGG TTC AAC GCG TCC GGG TGC      1698
Phe Val Ala Ala Leu Phe Tyr Lys Tyr Arg Phe Asn Ala Ser Gly Cys
            440                 445                 450

CCG GAG CGC TTG GCC ACG TGC CGC CCC ATT GAT ACA TTC GCG CAG GGG      1746
Pro Glu Arg Leu Ala Thr Cys Arg Pro Ile Asp Thr Phe Ala Gln Gly
        455                 460                 465

TGG GGT CCC ATC ACT TAC ACT GAG CCT CAT GAT TTG GAT CAG AGG CCC      1794
Trp Gly Pro Ile Thr Tyr Thr Glu Pro His Asp Leu Asp Gln Arg Pro
    470                 475                 480

TAT TGC TGG CAC TAC GCG CCT CAA CCG TGT GGT ATT GTG CCC ACG TTG      1842
Tyr Cys Trp His Tyr Ala Pro Gln Pro Cys Gly Ile Val Pro Thr Leu
485                 490                 495                 500

CAG GTG TGT GGC CCA GTA TAC TGC TTC ACC CCG AGT CCT GTT GCG GTG      1890
Gln Val Cys Gly Pro Val Tyr Cys Phe Thr Pro Ser Pro Val Ala Val
                505                 510                 515

GGG ACT ACC GAT CGT TTC GGT GCC CCT ACA TAC AGA TGG GGG GCA AAT      1938
Gly Thr Thr Asp Arg Phe Gly Ala Pro Thr Tyr Arg Trp Gly Ala Asn
            520                 525                 530

GAG ACG GAC GTG CTG CTC CTT AAC AAC GCC GGG CCG CCG CAA GGC AAC      1986
Glu Thr Asp Val Leu Leu Leu Asn Asn Ala Gly Pro Pro Gln Gly Asn
        535                 540                 545

TGG TTC GGC TGT ACA TGG ATG AAT GGC ACT GGG TTC ACC AAG ACA TGT      2034
Trp Phe Gly Cys Thr Trp Met Asn Gly Thr Gly Phe Thr Lys Thr Cys
    550                 555                 560

GGG GGC CCC CCG TGT AAC ATC GGG GGG GTC GGC AAC AAT ACC TTG ACC      2082
Gly Gly Pro Pro Cys Asn Ile Gly Gly Val Gly Asn Asn Thr Leu Thr
565                 570                 575                 580

TGC CCC ACG GAC TGC TTC CGA AAG CAC CCC GGG GCC ACT TAC ACC AAA      2130
Cys Pro Thr Asp Cys Phe Arg Lys His Pro Gly Ala Thr Tyr Thr Lys
                585                 590                 595

TGC GGT TCG GGG CCT TGG TTA ACA CCC AGG TGC TTA GTC GAC TAC CCG      2178
Cys Gly Ser Gly Pro Trp Leu Thr Pro Arg Cys Leu Val Asp Tyr Pro
```

```
                        600                  605                   610
TAC AGG CTC TGG CAT TAC CCC TGC ACT GTC AAC TTT ACC ATC TTT AAG         2226
Tyr Arg Leu Trp His Tyr Pro Cys Thr Val Asn Phe Thr Ile Phe Lys
                615                  620                  625

GTT AGG ATG TAC GTG GGG GGC GCG GAG CAC AGG CTC GAC GCC GCA TGC         2274
Val Arg Met Tyr Val Gly Gly Ala Glu His Arg Leu Asp Ala Ala Cys
            630                  635                  640

AAC TGG ACT CGG GGA GAG CGT TGT GAC CTG GAG GAC AGG GAT AGG TCA         2322
Asn Trp Thr Arg Gly Glu Arg Cys Asp Leu Glu Asp Arg Asp Arg Ser
645                 650                  655                  660

GAG CTT AGC CCG CTG CTG CTG TCT ACA ACA GAG TGG CAG GTA CTG CCC         2370
Glu Leu Ser Pro Leu Leu Leu Ser Thr Thr Glu Trp Gln Val Leu Pro
                665                  670                  675

TGT TCC TTC ACA ACC CTA CCG GCT CTG TCC ACT GGT TTG ATT CAT CTC         2418
Cys Ser Phe Thr Thr Leu Pro Ala Leu Ser Thr Gly Leu Ile His Leu
            680                  685                  690

CAT CAG AAC ATC GTG GAC ATA CAA TAC CTG TAC GGT ATA GGG TCG GCG         2466
His Gln Asn Ile Val Asp Ile Gln Tyr Leu Tyr Gly Ile Gly Ser Ala
        695                  700                  705

GTT GTC TCC TTT GCG ATC AAA TGG GAG TAT ATT GTG CTG CTC TTC CTT         2514
Val Val Ser Phe Ala Ile Lys Trp Glu Tyr Ile Val Leu Leu Phe Leu
    710                  715                  720

CTT CTG GCG GAC GCG CGC GTC TGC GCT TGC TTG TGG ATG ATG CTG CTG         2562
Leu Leu Ala Asp Ala Arg Val Cys Ala Cys Leu Trp Met Met Leu Leu
725                  730                  735                  740

GTA GCG CAA GCC GAG GCC GCC TTA GAG AAC CTG GTG GTC CTC AAT GCA         2610
Val Ala Gln Ala Glu Ala Ala Leu Glu Asn Leu Val Val Leu Asn Ala
                745                  750                  755

GCG TCC GTG GCC GGA GCG CAT GGC ATT CTT TCC TTC ATT GTG TTC TTC         2658
Ala Ser Val Ala Gly Ala His Gly Ile Leu Ser Phe Ile Val Phe Phe
            760                  765                  770

TGT GCT GCC TGG TAC ATC AAG GGC AGG CTG GTT CCC GGA GCG GCA TAC         2706
Cys Ala Ala Trp Tyr Ile Lys Gly Arg Leu Val Pro Gly Ala Ala Tyr
        775                  780                  785

GCC CTC TAT GGC GTA TGG CCG CTG CTT CTG CTT CTG CTG GCG TTA CCA         2754
Ala Leu Tyr Gly Val Trp Pro Leu Leu Leu Leu Leu Leu Ala Leu Pro
    790                  795                  800

CCA CGG GCG TAC GCC ATG GAC CGG GAG ATG GCC GCA TCG TGC GGA GGC         2802
Pro Arg Ala Tyr Ala Met Asp Arg Glu Met Ala Ala Ser Cys Gly Gly
805                  810                  815                  820

GCG GTT TTT GTA GGT CTG GTA CTC TTG ACC TTG TCA CCA CAC TAT AAA         2850
Ala Val Phe Val Gly Leu Val Leu Leu Thr Leu Ser Pro His Tyr Lys
                825                  830                  835

GTG TTC CTT GCC AGG TTC ATA TGG TGG CTA CAA TAT CTC ATC ACC AGA         2898
Val Phe Leu Ala Arg Phe Ile Trp Trp Leu Gln Tyr Leu Ile Thr Arg
            840                  845                  850

ACC GAA GCG CAT CTG CAA GTG TGG GTC CCC CCT CTC AAC GTT CGG GGG         2946
Thr Glu Ala His Leu Gln Val Trp Val Pro Pro Leu Asn Val Arg Gly
        855                  860                  865

GGT CGC GAT GCC ATC ATC CTC CTC ACA TGC GTG GTC CAC CCA GAG CTA         2994
Gly Arg Asp Ala Ile Ile Leu Leu Thr Cys Val Val His Pro Glu Leu
    870                  875                  880

ATC TTT GAC ATC ACA AAA TAT TTG CTC GCC ATA TTC GGC CCG CTC ATG         3042
Ile Phe Asp Ile Thr Lys Tyr Leu Leu Ala Ile Phe Gly Pro Leu Met
885                  890                  895                  900

GTG CTC CAG GCC GGC ATA ACT AGA GTG CCG TAC TTC GTG CGC GCA CAA         3090
Val Leu Gln Ala Gly Ile Thr Arg Val Pro Tyr Phe Val Arg Ala Gln
                905                  910                  915

GGG CTC ATT CGT GCA TGC ATG TTG GCG CGG AAA GTC GTG GGG GGT CAT         3138
```

```
Gly Leu Ile Arg Ala Cys Met Leu Ala Arg Lys Val Val Gly Gly His
            920                 925                 930

TAC GTC CAA ATG GTC TTC ATG AAG CTG GCC GCA CTA GCA GGT ACG TAC            3186
Tyr Val Gln Met Val Phe Met Lys Leu Ala Ala Leu Ala Gly Thr Tyr
            935                 940                 945

GTT TAT GAC CAT CTT ACT CCA CTG CGA GAT TGG GCT CAC ACG GGC TTA            3234
Val Tyr Asp His Leu Thr Pro Leu Arg Asp Trp Ala His Thr Gly Leu
950                 955                 960

CGA GAC CTT GCA GTG GCA GTA GAG CCC GTT GTC TTC TCT GAC ATG GAG            3282
Arg Asp Leu Ala Val Ala Val Glu Pro Val Val Phe Ser Asp Met Glu
965                 970                 975                 980

ACC AAA GTC ATC ACC TGG GGG GCA GAC ACC GCG GCG TGC GGG GAC ATC            3330
Thr Lys Val Ile Thr Trp Gly Ala Asp Thr Ala Ala Cys Gly Asp Ile
            985                 990                 995

ATC TTG GCC TGC CCT GCT TCC GCC CGA AGG GGG AAG GAG ATA CTT CTG            3378
Ile Leu Ala Cys Pro Ala Ser Ala Arg Arg Gly Lys Glu Ile Leu Leu
            1000                1005                1010

GGA CCG GCC GAT AGT CTT GAA GGA CAG GGG TGG CGA CTC CTT GCG CCC            3426
Gly Pro Ala Asp Ser Leu Glu Gly Gln Gly Trp Arg Leu Leu Ala Pro
            1015                1020                1025

ATC ACG GCC TAC TCC CAA CAA ACG CGA GGC CTG CTT GGT TGC ATC ATC            3474
Ile Thr Ala Tyr Ser Gln Gln Thr Arg Gly Leu Leu Gly Cys Ile Ile
            1030                1035                1040

ACT AGC CTT ACA GGC CGG GAC AAG AAC CAG GTT GAG GGG GAG GTT CAA            3522
Thr Ser Leu Thr Gly Arg Asp Lys Asn Gln Val Glu Gly Glu Val Gln
1045                1050                1055                1060

GTG GTT TCC ACC GCA ACA CAA TCT TTC CTG GCG ACC TGC ATC AAT GGC            3570
Val Val Ser Thr Ala Thr Gln Ser Phe Leu Ala Thr Cys Ile Asn Gly
            1065                1070                1075

GTG TGT TGG ACT GTC TTC CAC GGC GCC GGC TCA AAG ACC CTA GCC GGC            3618
Val Cys Trp Thr Val Phe His Gly Ala Gly Ser Lys Thr Leu Ala Gly
            1080                1085                1090

CCA AAG GGT CCA ATC ACC CAA ATG TAC ACC AAT GTA GAC CAG GAC CTT            3666
Pro Lys Gly Pro Ile Thr Gln Met Tyr Thr Asn Val Asp Gln Asp Leu
            1095                1100                1105

GTT GGC TGG CCG GCA CCT CCT GGG GCG CGT TCC CTG ACA CCA TGC ACT            3714
Val Gly Trp Pro Ala Pro Pro Gly Ala Arg Ser Leu Thr Pro Cys Thr
            1110                1115                1120

TGC GGC TCC TCG GAC CTT TAC CTG GTC ACG AGA CAT GCT GAT GTC ATT            3762
Cys Gly Ser Ser Asp Leu Tyr Leu Val Thr Arg His Ala Asp Val Ile
1125                1130                1135                1140

CCG GTG CGC CGG CGG GGT GAC GGT AGG GGG AGC CTA CTC CCC CCC AGG            3810
Pro Val Arg Arg Arg Gly Asp Gly Arg Gly Ser Leu Leu Pro Pro Arg
            1145                1150                1155

CCT GTC TCC TAC TTG AAG GGC TCC TCG GGT GGT CCA CTG CTC TGC CCT            3858
Pro Val Ser Tyr Leu Lys Gly Ser Ser Gly Gly Pro Leu Leu Cys Pro
            1160                1165                1170

TCG GGG CAC GCT GTC GGC ATA CTT CCG GCT GCT GTA TGC ACC CGG GGG            3906
Ser Gly His Ala Val Gly Ile Leu Pro Ala Ala Val Cys Thr Arg Gly
            1175                1180                1185

GTT GCC ATG GCG GTG GAA TTC ATA CCC GTT GAG TCT ATG GAA ACT ACT            3954
Val Ala Met Ala Val Glu Phe Ile Pro Val Glu Ser Met Glu Thr Thr
            1190                1195                1200

ATG CGG TCT CCG GTC TTC ACG GAC AAT CCG TCT CCC CCG GCT GTA CCG            4002
Met Arg Ser Pro Val Phe Thr Asp Asn Pro Ser Pro Pro Ala Val Pro
1205                1210                1215                1220

CAG ACA TTC CAA GTG GCC CAC TTA CAC GCT CCC ACC GGC AGC GGC AAG            4050
Gln Thr Phe Gln Val Ala His Leu His Ala Pro Thr Gly Ser Gly Lys
            1225                1230                1235
```

```
AGC ACT AGG GTG CCG GCT GCA TAT GCA GCC CAA GGG TAC AAG GTG CTC    4098
Ser Thr Arg Val Pro Ala Ala Tyr Ala Ala Gln Gly Tyr Lys Val Leu
        1240            1245            1250

GTC CTA AAT CCG TCC GTC GCC GCC ACC TTG GGT TTT GGG GCG TAT ATG    4146
Val Leu Asn Pro Ser Val Ala Ala Thr Leu Gly Phe Gly Ala Tyr Met
        1255            1260            1265

TCC AAG GCA CAT GGT ATC GAC CCC AAC CTT AGA ACT GGG GTA AGG ACC    4194
Ser Lys Ala His Gly Ile Asp Pro Asn Leu Arg Thr Gly Val Arg Thr
        1270            1275            1280

ATC ACC ACA GGT GCC CCT ATC ACA TAC TCC ACC TAT GGC AAG TTC CTT    4242
Ile Thr Thr Gly Ala Pro Ile Thr Tyr Ser Thr Tyr Gly Lys Phe Leu
1285            1290            1295            1300

GCC GAC GGT GGC GGC TCC GGG GGC GCC TAT GAC ATC ATA ATG TGT GAT    4290
Ala Asp Gly Gly Gly Ser Gly Gly Ala Tyr Asp Ile Ile Met Cys Asp
                1305            1310            1315

GAG TGC CAC TCA ACT GAC TCG ACT ACC ATT TAT GGC ATC GGC ACA GTC    4338
Glu Cys His Ser Thr Asp Ser Thr Thr Ile Tyr Gly Ile Gly Thr Val
            1320            1325            1330

CTG GAC CAA GCG GAG ACG GCT GGA GCG CGG CTC GTG GTG CTC TCC ACC    4386
Leu Asp Gln Ala Glu Thr Ala Gly Ala Arg Leu Val Val Leu Ser Thr
            1335            1340            1345

GCT ACG CCT CCG GGA TCG GTC ACC GTG CCA CAC CTC AAT ATC GAG GAG    4434
Ala Thr Pro Pro Gly Ser Val Thr Val Pro His Leu Asn Ile Glu Glu
        1350            1355            1360

GTG GCC CTG TCT AAT ACT GGA GAG ATC CCC TTC TAC GGC AAA GCC ATT    4482
Val Ala Leu Ser Asn Thr Gly Glu Ile Pro Phe Tyr Gly Lys Ala Ile
1365            1370            1375            1380

CCC ATC GAG GCT ATC AAG GGG GGA AGG CAT CTC ATT TTC TGC CAT TCC    4530
Pro Ile Glu Ala Ile Lys Gly Gly Arg His Leu Ile Phe Cys His Ser
                1385            1390            1395

AAG AAG AAG TGT GAC GAA CTC GCC GCA AAG CTG TCA GGC CTC GGA CTC    4578
Lys Lys Lys Cys Asp Glu Leu Ala Ala Lys Leu Ser Gly Leu Gly Leu
            1400            1405            1410

AAT GCC GTA GCG TAT TAC CGG GGT CTT GAC GTG TCC GTC ATA CCG ACC    4626
Asn Ala Val Ala Tyr Tyr Arg Gly Leu Asp Val Ser Val Ile Pro Thr
            1415            1420            1425

AGC GGA GAC GTT GTT GTC GTG GCG ACG GAC GCT CTA ATG ACG GGC TTT    4674
Ser Gly Asp Val Val Val Val Ala Thr Asp Ala Leu Met Thr Gly Phe
        1430            1435            1440

ACC GGC GAC TTT GAC TCA GTG ATC GAC TGT AAT ACG TGT GTC ACC CAG    4722
Thr Gly Asp Phe Asp Ser Val Ile Asp Cys Asn Thr Cys Val Thr Gln
1445            1450            1455            1460

ACA GTC GAT TTC AGC TTG GAC CCC ACC TTC ACC ATT GAG ACG ACG ACC    4770
Thr Val Asp Phe Ser Leu Asp Pro Thr Phe Thr Ile Glu Thr Thr Thr
                1465            1470            1475

GTG CCC CAA GAC GCA GTG TCG CGC TCG CAG AGG CGA GGC AGG ACT GGT    4818
Val Pro Gln Asp Ala Val Ser Arg Ser Gln Arg Arg Gly Arg Thr Gly
            1480            1485            1490

AGG GGC AGG GCT GGC ATA TAC AGG TTT GTG ACT CCA GGA GAA CGG CCC    4866
Arg Gly Arg Ala Gly Ile Tyr Arg Phe Val Thr Pro Gly Glu Arg Pro
        1495            1500            1505

TCG GGC ATG TTC GAT TCT TCG GTC CTG TGT GAG TGT TAT GAC GCG GGT    4914
Ser Gly Met Phe Asp Ser Ser Val Leu Cys Glu Cys Tyr Asp Ala Gly
        1510            1515            1520

TGT GCG TGG TAC GAA CTC ACG CCC GCT GAG ACC TCG GTT AGG TTG CGG    4962
Cys Ala Trp Tyr Glu Leu Thr Pro Ala Glu Thr Ser Val Arg Leu Arg
1525            1530            1535            1540

GCG TAC CTA AAC ACA CCA GGG TTG CCC GTC TGC CAG GAC CAT CTG GAG    5010
Ala Tyr Leu Asn Thr Pro Gly Leu Pro Val Cys Gln Asp His Leu Glu
        1545            1550            1555
```

```
TTC TCG GAG GGT GTC TTC ACA GGC CTC ACC CAC ATA GAT GCC CAC TTC    5058
Phe Ser Glu Gly Val Phe Thr Gly Leu Thr His Ile Asp Ala His Phe
            1560                1565                1570

TTA TCC CAG ACT AAA CAG GCA GGA GAG AAC TTC CCC TAC TTG GTA GCA    5106
Leu Ser Gln Thr Lys Gln Ala Gly Glu Asn Phe Pro Tyr Leu Val Ala
            1575                1580                1585

TAC CAG GCT ACA GTG TGC GCC AGG GCT CAA GCC CCA CCT CCA TCG TGG    5154
Tyr Gln Ala Thr Val Cys Ala Arg Ala Gln Ala Pro Pro Pro Ser Trp
            1590                1595                1600

GAT GAA ATG TGG AGG TGT CTC ATA CGG CTG AAA CCT ACG CTG CAC GGG    5202
Asp Glu Met Trp Arg Cys Leu Ile Arg Leu Lys Pro Thr Leu His Gly
1605                1610                1615                1620

CCA ACA CCC CTG CTG TAT AGG TTA GGA GCC GTC CAA AAT GAG GTC ACC    5250
Pro Thr Pro Leu Leu Tyr Arg Leu Gly Ala Val Gln Asn Glu Val Thr
                1625                1630                1635

CTC ACA CAC CCC ATA ACC AAA TTC ATC ATG ACA TGT ATG TCG GCT GAC    5298
Leu Thr His Pro Ile Thr Lys Phe Ile Met Thr Cys Met Ser Ala Asp
            1640                1645                1650

CTG GAG GTC GTC ACC AGC ACC TGG GTG CTG GTA GGC GGA GTC CTC GCA    5346
Leu Glu Val Val Thr Ser Thr Trp Val Leu Val Gly Gly Val Leu Ala
            1655                1660                1665

GCT CTG GCC GCG TAC TGC CTG ACA ACA GGC AGC GTG GTC ATT GTG GGC    5394
Ala Leu Ala Ala Tyr Cys Leu Thr Thr Gly Ser Val Val Ile Val Gly
            1670                1675                1680

AGG ATC ATC CTG TCC GGG AAG CCG GCT ATC ATC CCC GAT AGG GAA GTT    5442
Arg Ile Ile Leu Ser Gly Lys Pro Ala Ile Ile Pro Asp Arg Glu Val
1685                1690                1695                1700

CTC TAC CAG GAG TTC GAC GAG ATG GAG GAG TGT GCC TCA CAC CTC CCT    5490
Leu Tyr Gln Glu Phe Asp Glu Met Glu Glu Cys Ala Ser His Leu Pro
                1705                1710                1715

TAC TTC GAA CAG GGA ATG CAG CTC GCC GAG CAA TTC AAA CAG AAG GCG    5538
Tyr Phe Glu Gln Gly Met Gln Leu Ala Glu Gln Phe Lys Gln Lys Ala
            1720                1725                1730

CTC GGG TTG CTG CAA ACA GCC ACC AAG CAG GCG GAG GCT GCT GCT CCC    5586
Leu Gly Leu Leu Gln Thr Ala Thr Lys Gln Ala Glu Ala Ala Ala Pro
            1735                1740                1745

GTG GTG GAG TCC AAG TGG CGA GCC CTT GAG ACC TTC TGG GCG AAG CAC    5634
Val Val Glu Ser Lys Trp Arg Ala Leu Glu Thr Phe Trp Ala Lys His
            1750                1755                1760

ATG TGG AAC TTC ATT AGT GGG ATA CAG TAC TTG GCA GGC TTG TCC ACT    5682
Met Trp Asn Phe Ile Ser Gly Ile Gln Tyr Leu Ala Gly Leu Ser Thr
1765                1770                1775                1780

CTG CCT GGG AAC CCC GCA ATA CGA TCA CCG ATG GCA TTC ACA GCC TCC    5730
Leu Pro Gly Asn Pro Ala Ile Arg Ser Pro Met Ala Phe Thr Ala Ser
                1785                1790                1795

ATC ACC AGC CCG CTC ACC ACC CAG CAT ACC CTC TTG TTT AAC ATC TTG    5778
Ile Thr Ser Pro Leu Thr Thr Gln His Thr Leu Leu Phe Asn Ile Leu
            1800                1805                1810

GGG GGA TGG GTG GCT GCC CAA CTC GCC CCC CCC AGC GCT GCC TCA GCT    5826
Gly Gly Trp Val Ala Ala Gln Leu Ala Pro Pro Ser Ala Ala Ser Ala
            1815                1820                1825

TTC GTG GGC GCC GGC ATC GCT GGA GCC GCT GTT GGC ACG ATA GGC CTT    5874
Phe Val Gly Ala Gly Ile Ala Gly Ala Ala Val Gly Thr Ile Gly Leu
            1830                1835                1840

GGG AAG GTG CTT GTG GAC ATT CTG GCA GGT TAT GGA GCA GGG GTG GCG    5922
Gly Lys Val Leu Val Asp Ile Leu Ala Gly Tyr Gly Ala Gly Val Ala
1845                1850                1855                1860

GGC GCA CTT GTG GCC TTT AAG ATC ATG AGC GGC GAG ATG CCT TCA GCC    5970
Gly Ala Leu Val Ala Phe Lys Ile Met Ser Gly Glu Met Pro Ser Ala
```

```
                1865              1870              1875
GAG GAC ATG GTC AAC TTA CTC CCT GCC ATC CTT TCT CCC GGT GCC CTG    6018
Glu Asp Met Val Asn Leu Leu Pro Ala Ile Leu Ser Pro Gly Ala Leu
            1880              1885              1890

GTC GTC GGG ATT GTG TGT GCA GCA ATA CTG CGT CGG CAT GTG GGC CCA    6066
Val Val Gly Ile Val Cys Ala Ala Ile Leu Arg Arg His Val Gly Pro
            1895              1900              1905

GGG GAA GGG GCT GTG CAG TGG ATG AAC CGG CTG ATA GCG TTC GCC TCG    6114
Gly Glu Gly Ala Val Gln Trp Met Asn Arg Leu Ile Ala Phe Ala Ser
            1910              1915              1920

CGG GGT AAC CAC GTC TCC CCC AGG CAC TAT GTG CCA GAG AGC GAG CCT    6162
Arg Gly Asn His Val Ser Pro Arg His Tyr Val Pro Glu Ser Glu Pro
1925              1930              1935              1940

GCA GCG CGT GTT ACC CAG ATC CTT TCC AGC CTC ACC ATC ACT CAG CTG    6210
Ala Ala Arg Val Thr Gln Ile Leu Ser Ser Leu Thr Ile Thr Gln Leu
            1945              1950              1955

TTG AAG AGA CTC CAC CAG TGG ATT AAT GAG GAC TGC TCT ACG CCA TGC    6258
Leu Lys Arg Leu His Gln Trp Ile Asn Glu Asp Cys Ser Thr Pro Cys
            1960              1965              1970

TCC AGC TCG TGG CTA AGG GAG ATT TGG GAC TGG ATC TGC ACG GTG TTG    6306
Ser Ser Ser Trp Leu Arg Glu Ile Trp Asp Trp Ile Cys Thr Val Leu
            1975              1980              1985

ACT GAC TTC AAG ACC TGG CTC CAG TCC AAG CTC CTG CCG CGA TTA CCG    6354
Thr Asp Phe Lys Thr Trp Leu Gln Ser Lys Leu Leu Pro Arg Leu Pro
            1990              1995              2000

GGA GTC CCT TTT TTC TCA TGC CAA CGC GGG TAT AAG GGA GTC TGG CGG    6402
Gly Val Pro Phe Phe Ser Cys Gln Arg Gly Tyr Lys Gly Val Trp Arg
2005              2010              2015              2020

GGG GAC GGC ATC ATG CAC ACC ACC TGC CCA TGC GGA GCA CAG ATC ACC    6450
Gly Asp Gly Ile Met His Thr Thr Cys Pro Cys Gly Ala Gln Ile Thr
            2025              2030              2035

GGA CAC GTC AAA AAC GGT TCC ATG AGG ATC GTT GGG CCT AAA ACC TGC    6498
Gly His Val Lys Asn Gly Ser Met Arg Ile Val Gly Pro Lys Thr Cys
            2040              2045              2050

AGC AAC ACG TGG TAC GGG ACA TTC CCC ATC AAC GCG TAC ACC ACG GGC    6546
Ser Asn Thr Trp Tyr Gly Thr Phe Pro Ile Asn Ala Tyr Thr Thr Gly
            2055              2060              2065

CCC TGC ACA CCC TCC CCG GCG CCA AAC TAT TCC AAG GCA TTG TGG AGA    6594
Pro Cys Thr Pro Ser Pro Ala Pro Asn Tyr Ser Lys Ala Leu Trp Arg
            2070              2075              2080

GTG GCC GCT GAG GAG TAC GTG GAG GTC ACG CGG GTG GGA GAT TTT CAC    6642
Val Ala Ala Glu Glu Tyr Val Glu Val Thr Arg Val Gly Asp Phe His
2085              2090              2095              2100

TAC GTG ACG GGC ATG ACC ACT GAC AAC GTG AAG TGT CCA TGC CAG GTT    6690
Tyr Val Thr Gly Met Thr Thr Asp Asn Val Lys Cys Pro Cys Gln Val
            2105              2110              2115

CCG GCC CCC GAA TTC TTC ACG GAG GTG GAT GGA GTG CGG TTG CAC AGG    6738
Pro Ala Pro Glu Phe Phe Thr Glu Val Asp Gly Val Arg Leu His Arg
            2120              2125              2130

TAC GCT CCG GCG TGC AGA CCT CTC CTA CGG GAG GAG GTC GTA TTC CAG    6786
Tyr Ala Pro Ala Cys Arg Pro Leu Leu Arg Glu Glu Val Val Phe Gln
            2135              2140              2145

GTC GGG CTC CAC CAG TAC CTG GTC GGG TCA CAG CTC CCA TGC GAG CCC    6834
Val Gly Leu His Gln Tyr Leu Val Gly Ser Gln Leu Pro Cys Glu Pro
            2150              2155              2160

GAA CCG GAT GTA GCA GTG CTC ACT TCC ATG CTC ACT GAC CCC TCC CAC    6882
Glu Pro Asp Val Ala Val Leu Thr Ser Met Leu Thr Asp Pro Ser His
2165              2170              2175              2180

ATT ACA GCA GAG ACG GCT AAG CGT AGG CTG GCC AGG GGG TCT CCC CCC    6930
```

```
                                                                -continued

Ile Thr Ala Glu Thr Ala Lys Arg Arg Leu Ala Arg Gly Ser Pro Pro
                2185                2190                2195

TCC TTG GCC AGC TCT TCA GCT AGC CAG TTG TCT GCG CCT TCC TTG AAG      6978
Ser Leu Ala Ser Ser Ser Ala Ser Gln Leu Ser Ala Pro Ser Leu Lys
                2200                2205                2210

GCG ACA TGC ACT ACC CAT CAT GAC TCC CCG GAC GCT GAC CTC ATT GAG      7026
Ala Thr Cys Thr Thr His His Asp Ser Pro Asp Ala Asp Leu Ile Glu
                2215                2220                2225

GCC AAC CTC TTG TGG CGG CAA GAG ATG GGC GGG AAC ATC ACC CGC GTG      7074
Ala Asn Leu Leu Trp Arg Gln Glu Met Gly Gly Asn Ile Thr Arg Val
                2230                2235                2240

GAG TCA GAG AAT AAG GTG GTA ATC CTG GAC TCT TTC GAC CCG CTC CGA      7122
Glu Ser Glu Asn Lys Val Val Ile Leu Asp Ser Phe Asp Pro Leu Arg
2245                2250                2255                2260

GCG GAG GAT GAT GAG GGG GAA ATA TCC GTT CCG GCG GAG ATC CTG CGG      7170
Ala Glu Asp Asp Glu Gly Glu Ile Ser Val Pro Ala Glu Ile Leu Arg
                2265                2270                2275

AAA TCC AGG AAA TTC CCC CCA GCG CTG CCC ATA TGG GCG CCG CCG GAT      7218
Lys Ser Arg Lys Phe Pro Pro Ala Leu Pro Ile Trp Ala Pro Pro Asp
                2280                2285                2290

TAC AAC CCT CCG CTG CTA GAG TCC TGG AAG GAC CCG GAC TAC GTT CCT      7266
Tyr Asn Pro Pro Leu Leu Glu Ser Trp Lys Asp Pro Asp Tyr Val Pro
                2295                2300                2305

CCG GTG GTA CAC GGG TGC CCG TTG CCG CCC ACC AAG GCC CCT CCA ATA      7314
Pro Val Val His Gly Cys Pro Leu Pro Pro Thr Lys Ala Pro Pro Ile
                2310                2315                2320

CCA CCT CCA CGG AGG AAG AGG ACG GTT GTC CTG ACA GAA TCC ACC GTG      7362
Pro Pro Pro Arg Arg Lys Arg Thr Val Val Leu Thr Glu Ser Thr Val
2325                2330                2335                2340

TCT TCT GCC TTG GCG GAG CTC GCT ACT AAG ACC TTC GGC AGC TCC GGA      7410
Ser Ser Ala Leu Ala Glu Leu Ala Thr Lys Thr Phe Gly Ser Ser Gly
                2345                2350                2355

TCG TCG GCC ATC GAC AGC GGT ACG GCG ACC GCC CCT CCT GAC CAA GCC      7458
Ser Ser Ala Ile Asp Ser Gly Thr Ala Thr Ala Pro Pro Asp Gln Ala
                2360                2365                2370

TCC GGT GAC GGC GAC AGA GAG TCC GAC GTT GAG TCG TTC TCC TCC ATG      7506
Ser Gly Asp Gly Asp Arg Glu Ser Asp Val Glu Ser Phe Ser Ser Met
                2375                2380                2385

CCC CCC CTT GAG GGA GAG CCG GGG GAC CCC GAT CTC AGC GAC GGA TCT      7554
Pro Pro Leu Glu Gly Glu Pro Gly Asp Pro Asp Leu Ser Asp Gly Ser
                2390                2395                2400

TGG TCC ACC GTG AGC GAG GAG GCT AGT GAG GAC GTC GTC TGC TGT TCG      7602
Trp Ser Thr Val Ser Glu Glu Ala Ser Glu Asp Val Val Cys Cys Ser
2405                2410                2415                2420

ATG TCC TAC ACA TGG ACA GGC GCC CTG ATC ACG CCA TGC GCT GCG GAG      7650
Met Ser Tyr Thr Trp Thr Gly Ala Leu Ile Thr Pro Cys Ala Ala Glu
                2425                2430                2435

GAA AGC AAG TTG CCC ATC AAC CCG TTG AGC AAT TCT TTG CTA CGT CAC      7698
Glu Ser Lys Leu Pro Ile Asn Pro Leu Ser Asn Ser Leu Leu Arg His
                2440                2445                2450

CAC AAC ATG GTC TAT GCT ACA ACA TCC CGC AGC GCA GGC CTG CGG CAG      7746
His Asn Met Val Tyr Ala Thr Thr Ser Arg Ser Ala Gly Leu Arg Gln
                2455                2460                2465

AAG AAG GTC ACC TTT GAC AGA CTG CAA GTC CTG GAC GAC CAC TAC CGG      7794
Lys Lys Val Thr Phe Asp Arg Leu Gln Val Leu Asp Asp His Tyr Arg
                2470                2475                2480

GAC GTG CTT AAG GAG ATG AAG GCG AAG GCG TCC ACA GTT AAG GCT AAA      7842
Asp Val Leu Lys Glu Met Lys Ala Lys Ala Ser Thr Val Lys Ala Lys
2485                2490                2495                2500
```

```
CTT CTA TCT GTA GAA GAA GCC TGC AAA CTG ACG CCC CCA CAT TCG GCC      7890
Leu Leu Ser Val Glu Glu Ala Cys Lys Leu Thr Pro Pro His Ser Ala
            2505                2510                2515

AAA TCC AAA TTT GGC TAC GGG GCG AAG GAC GTC CGG AGC CTA TCC AGC      7938
Lys Ser Lys Phe Gly Tyr Gly Ala Lys Asp Val Arg Ser Leu Ser Ser
            2520                2525                2530

AGG GCC GTT ACC CAC ATC CGC TCC GTG TGG AAG GAC CTG CTG GAA GAC      7986
Arg Ala Val Thr His Ile Arg Ser Val Trp Lys Asp Leu Leu Glu Asp
            2535                2540                2545

ACT GAA ACA CCA ATT AGC ACT ACC ATC ATG GCA AAA AAT GAG GTT TTC      8034
Thr Glu Thr Pro Ile Ser Thr Thr Ile Met Ala Lys Asn Glu Val Phe
            2550                2555                2560

TGT GTC CAA CCA GAG AAG GGA GGC CGC AAG CCA GCT CGC CTT ATC GTG      8082
Cys Val Gln Pro Glu Lys Gly Gly Arg Lys Pro Ala Arg Leu Ile Val
2565            2570                2575                2580

TTC CCA GAT CTG GGA GTT CGT GTA TGC GAG AAG ATG GCC CTT TAT GAC      8130
Phe Pro Asp Leu Gly Val Arg Val Cys Glu Lys Met Ala Leu Tyr Asp
            2585                2590                2595

GTG GTC TCC ACC CTT CCT CAG GCC GTG ATG GGC TCC TCA TAC GGA TTC      8178
Val Val Ser Thr Leu Pro Gln Ala Val Met Gly Ser Ser Tyr Gly Phe
            2600                2605                2610

CAG TAC TCT CCT AAG CAG CGG GTC GAG TTC CTG GTG AAT ACC TGG AAA      8226
Gln Tyr Ser Pro Lys Gln Arg Val Glu Phe Leu Val Asn Thr Trp Lys
            2615                2620                2625

TCA AAG AAA TGC CCC ATG GGC TTC TCA TAT GAC ACC CGC TGT TTT GAC      8274
Ser Lys Lys Cys Pro Met Gly Phe Ser Tyr Asp Thr Arg Cys Phe Asp
            2630                2635                2640

TCA ACG GTC ACT GAG AAT GAC ATC CGT GTT GAG GAG TCA ATT TAC CAA      8322
Ser Thr Val Thr Glu Asn Asp Ile Arg Val Glu Glu Ser Ile Tyr Gln
2645            2650                2655                2660

TGT TGT GAC TTG GCC CCC GAA GCC AAA CTG GCC ATA AAG TCG CTC ACA      8370
Cys Cys Asp Leu Ala Pro Glu Ala Lys Leu Ala Ile Lys Ser Leu Thr
            2665                2670                2675

GAG CGG CTC TAT ATC GGG GGT CCC CTG ACT AAT TCA AAA GGG CAG AAC      8418
Glu Arg Leu Tyr Ile Gly Gly Pro Leu Thr Asn Ser Lys Gly Gln Asn
            2680                2685                2690

TGC GGT TAC CGC CGG TGC CGC GCG AGC GGC GTG CTG ACG ACT AGC TGC      8466
Cys Gly Tyr Arg Arg Cys Arg Ala Ser Gly Val Leu Thr Thr Ser Cys
            2695                2700                2705

GGT AAT ACC CTC ACA TGT TAC CTG AAA GCC ACT GCG GCC TGT CGA GCT      8514
Gly Asn Thr Leu Thr Cys Tyr Leu Lys Ala Thr Ala Ala Cys Arg Ala
            2710                2715                2720

GCG AAG CTC CGG GAC TGC ACG ATG CTC GTG AAC GGA GAC GAC CTT GTC      8562
Ala Lys Leu Arg Asp Cys Thr Met Leu Val Asn Gly Asp Asp Leu Val
2725            2730                2735                2740

GTT ATC TGT GAA AGC GCG GGA ACC CAA GAG GAT GCG GCG AGC CTA CGA      8610
Val Ile Cys Glu Ser Ala Gly Thr Gln Glu Asp Ala Ala Ser Leu Arg
            2745                2750                2755

GTC TTC ACG GAG GCT ATG ACT AGG TAC TCT GCC CCC CCT GGG GAC CCG      8658
Val Phe Thr Glu Ala Met Thr Arg Tyr Ser Ala Pro Pro Gly Asp Pro
            2760                2765                2770

CCT CAA CCG GAA TAC GAC TTG GAG TTG ATA ACA TCA TGT TCC TCC AAT      8706
Pro Gln Pro Glu Tyr Asp Leu Glu Leu Ile Thr Ser Cys Ser Ser Asn
            2775                2780                2785

GTG TCG GTC GCA CAC GAT GCA TCT GGT AAA AGG GTG TAC TAC CTC ACC      8754
Val Ser Val Ala His Asp Ala Ser Gly Lys Arg Val Tyr Tyr Leu Thr
            2790                2795                2800

CGT GAC CCT ACC ACC CCC CTT GCA CGG GCT GCG TGG GAG ACA GCT AGA      8802
Arg Asp Pro Thr Thr Pro Leu Ala Arg Ala Ala Trp Glu Thr Ala Arg
2805            2810                2815                2820
```

```
CAC ACT CCA GTC AAC TCC TGG CTA GGC AAC ATC ATC ATG TAT GCG CCC      8850
His Thr Pro Val Asn Ser Trp Leu Gly Asn Ile Ile Met Tyr Ala Pro
             2825                2830                2835

ACC TTA TGG GCA AGG ATG ATT CTG ATG ACT CAT TTC TTC TCC ATC CTT      8898
Thr Leu Trp Ala Arg Met Ile Leu Met Thr His Phe Phe Ser Ile Leu
             2840                2845                2850

CTA GCT CAG GAG CAA CTT GAA AAA ACC CTA GAT TGT CAG ATC TAC GGG      8946
Leu Ala Gln Glu Gln Leu Glu Lys Thr Leu Asp Cys Gln Ile Tyr Gly
             2855                2860                2865

GCC TGT TAC TCC ATT GAA CCA CTT GAT CTA CCT CAG ATC ATT GAG CGA      8994
Ala Cys Tyr Ser Ile Glu Pro Leu Asp Leu Pro Gln Ile Ile Glu Arg
             2870                2875                2880

CTC CAT GGT CTT AGC GCA TTT TCA CTC CAT AGT TAC TCT CCA GGC GAG      9042
Leu His Gly Leu Ser Ala Phe Ser Leu His Ser Tyr Ser Pro Gly Glu
2885                2890                2895                2900

ATC AAT AGG GTG GCT TCA TGC CTC AGA AAA CTT GGG GTA CCA CCC TTG      9090
Ile Asn Arg Val Ala Ser Cys Leu Arg Lys Leu Gly Val Pro Pro Leu
             2905                2910                2915

CGA GCC TGG AGA CAT CGG GCC AGA AGT GTC CGC GCT AAG CTA CTG TCC      9138
Arg Ala Trp Arg His Arg Ala Arg Ser Val Arg Ala Lys Leu Leu Ser
             2920                2925                2930

CAG GGG GGG AGG GCC GCC ACT TGT GGC AAG TAC CTC TTC AAC TGG GCG      9186
Gln Gly Gly Arg Ala Ala Thr Cys Gly Lys Tyr Leu Phe Asn Trp Ala
             2935                2940                2945

GTG AGG ACC AAG CTC AAA CTC ACT CCA ATC CCA GCC GCG TCC CGG TTG      9234
Val Arg Thr Lys Leu Lys Leu Thr Pro Ile Pro Ala Ala Ser Arg Leu
             2950                2955                2960

GAC TTG TCC GGC TGG TTC GTT GCT GGT TAC AGC GGG GGA GAC ATA TAT      9282
Asp Leu Ser Gly Trp Phe Val Ala Gly Tyr Ser Gly Gly Asp Ile Tyr
2965                2970                2975                2980

CAC AGC CTG TCT CGT GCC CGA CCC CGC TGG TTC ATG TTG TGC CTA CTC      9330
His Ser Leu Ser Arg Ala Arg Pro Arg Trp Phe Met Leu Cys Leu Leu
             2985                2990                2995

CTA CTT TCC GTG GGG GTA GGC ATC TAC CTG CTC CCC AAC CGA TGAATGG      9380
Leu Leu Ser Val Gly Val Gly Ile Tyr Leu Leu Pro Asn Arg
             3000                3005                3010

GAGCTAAACA CTCCAGGCCA ATAGGCCGTT TCTCTTTTTT TTTTTTTTTT TTTTTTTTTT    9440

TTTTTTTTTT TTTTTTTTTT TTTTTTTTTT TT                                  9472

(2) INFORMATION FOR SEQ ID NO: 97

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC2, Fig. 7

(xi) SEQUENCE DESCRIPTION: SEQ ID NO: 97

CTC TTT ACC CTG TCA CCA CAC TAC AAA GTG TTC CTC GCT AGG CTC ATA       48
Leu Phe Thr Leu Ser Pro His Tyr Lys Val Phe Leu Ala Arg Leu Ile
 1           5                10                  15

TGG TGG TTA CAG TAT TTT ATC ACC AGG GCC GAA GCG CAC CTG CAA GTG       96
Trp Trp Leu Gln Tyr Phe Ile Thr Arg Ala Glu Ala His Leu Gln Val
             20                25                  30

TGG ATC CCC CCC CTC AAC GTT CGG GGG GGC CGC GAT GCC ATC ATC CTC      144
Trp Ile Pro Pro Leu Asn Val Arg Gly Gly Arg Asp Ala Ile Ile Leu
```

```
                35                   40                   45
CTC ACG TGT GCG GTC CAC TCA GAG CTG ATT TTT GAC ATC ACC AAG ATC        192
Leu Thr Cys Ala Val His Ser Glu Leu Ile Phe Asp Ile Thr Lys Ile
     50                   55                   60

TTG CTC GCC ATA CTT GGT CCG CTC ATG GTA CTC CAG GCT GGC CTA ACC        240
Leu Leu Ala Ile Leu Gly Pro Leu Met Val Leu Gln Ala Gly Leu Thr
 65                   70                   75                   80

AGA GTG CCG TAC TTT GTC AGC GCT CAA GGG CTC ATC C                      277
Arg Val Pro Tyr Phe Val Ser Ala Gln Gly Leu Ile
                     85                   90
```

(2) INFORMATION FOR SEQ ID NO: 98

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: KHCV366

(xi) SEQUENCE DESCRIPTION: SEQ ID NO: 98

```
GGCCAGCCCC CGATTGGGGG CGACACTCCA CCATAGATCA CTCCCCTGTG AGGAACTACT       60

GTCTTCACGC AGAAAGCGTC TAGCCATGGC GTTAGTATGA GTGTCGTGCA GCCTCCAGGA      120

CCCCCCCTCC CGGGAGAGCC ATAGTGGTCT GCGGAACCGG TGAGTACACC GGAATTGCCA      180

GGACGACCGG GTCCTTTCTT GGATCAACCC GCTCAATGCC TGGAGATTTG GCGTGCCCC       240

CGCGAGACTG CTAGCCGAGT AGTGTTGGGT CGCGAAAGGC CTTGTGGTAC TGCCTGATAG      300

GGTGCTTGCG AGTGCCCCGG GAGGTCTCGT AGACCGTGCA CC ATG AGC ACG AAT        354
                                              Met Ser Thr Asn
                                               1

CCT AAA                                                                360
Pro Lys
 5
```

(2) INFORMATION FOR SEQ ID NO: 99

(i) SEQUENCE CHARACTERISTICS:
        (A) LENGTH: 359 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: HCPT-CHIRON, Fig 6

(xi) SEQUENCE DESCRIPTION: SEQ ID NO: 99

```
GCCAGCCCCC TGATGGGGGC GACACTCCAC CATGAATCAC TCCCCTGTGA GGAACTACTG       60

TCTTCACGCA GAAAGCGTCT AGCCATGGCG TTAGTATGAG TGTCGTGCAG CCTCCAGGAC      120

CCCCCCTCCC GGGAGAGCCA TAGTGGTCTG CGGAACCGGT GAGTACACCG GAATTGCCAG      180

GACGACCGGG TCCTTTCTTG GATCAACCCG CTCAATGCCT GGAGATTTGG GCGTGCCCCC      240

GCAAGACTGC TAGCCGAGTA GTGTTGGGTC GCGAAAGGCC TTGTGGTACT GCCTGATAGG      300

GTGCTTGCGA GTGCCCCGGG AGGTCTCGTA GACCGTGCAC C ATG AGC ACG AAT CCT     356
                                             Met Ser Thr Asn Pro
                                              1                 5

AAA                                                                    359
```

Lys (2) INFORMATION FOR SEQ ID NO: 100

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: JHCV-NCI, Fig 6

(xi) SEQUENCE DESCRIPTION: SEQ ID NO: 100

```
TTGGGGGCGA CACTCCACCA TAGATCACTC CCCTGTGAGG AACTACTGTC TTCACGCAGA      60

AAGCGTCTAG CCATGGCGTT AGTATGAGTG TTGTGCAGCC TCCAGGACCC CCCCTCCCGG     120

GAGAGCCATA GTGGTCTGCG AACCGGTGA  GTACACCGGA ATTGCCAGGA CGACCGGGTC     180

CTTTCTTGGA TCAACGCGCT CAATGCCTGG AGATTTGGGC GTGCCCCCGC GAGACTGCTA     240

GCCGAGTAGT GTTGGGTCGC GAAAGGCCTT GTGGTACTGC CTGATAGGGT GCTTGCGAGT     300

GCCCCGGGAG GTCTCGTAGA CCGTGCATC  ATG AGC ACA AAT CCT AAA              347
                                 Met Ser Thr Asn Pro Lys
                                  1               5
```

(2) INFORMATION FOR SEQ ID NO: 101

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC3, Fig.8

(xi) SEQUENCE DESCRIPTION: SEQ ID NO: 101

```
CTC TTG ACC TTG TCA CCA TAC TAT AAA GTG TTC CTC GCT AGG CTC ATA        48
Leu Leu Thr Leu Ser Pro Tyr Tyr Lys Val Phe Leu Ala Arg Leu Ile
 1               5                  10                  15

TGG TGG TTG CAA TAT TTT ATC ACC AGA GCC GAG GCG CAC TTG CAA GTG        96
Trp Trp Leu Gln Tyr Phe Ile Thr Arg Ala Glu Ala His Leu Gln Val
                 20                  25                  30

TGG ATC CCC CCT CTC AAC GTC CGG GGA GGC CGT GAT GCA ATC ATC CTC       144
Trp Ile Pro Pro Leu Asn Val Arg Gly Gly Arg Asp Ala Ile Ile Leu
         35                  40                  45

CTG GCG TGT GCG GTC CAC CCA GAG CCG ATC TTT GAC ATC ACA AAA TAT       192
Leu Ala Cys Ala Val His Pro Glu Pro Ile Phe Asp Ile Thr Lys Tyr
 50                  55                  60

TTG CTC GCC ATA TTC GGC CCG CTC ATG GTG CTC CAG GCC GGC ATA ACT       240
Leu Leu Ala Ile Phe Gly Pro Leu Met Val Leu Gln Ala Gly Ile Thr
 65                  70                  75                  80

AGA GTG CCG TAC TTC TGG CGC GCA CAA GGG CTC ATT CGT GCA TGC ATG       288
Arg Val Pro Tyr Phe Trp Arg Ala Gln Gly Leu Ile Arg Ala Cys Met
                 85                  90                  95

TTG GCG CGG AAA GTC GCT GGG GGT CAT TAC                               318
Leu Ala Arg Lys Val Ala Gly Gly His Tyr
                100                 105
```

(2) INFORMATION FOR SEQ ID NO: 102

```
    (i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC20, Fig. 9

(xi) SEQUENCE DESCRIPTION: SEQ ID NO: 102

CTC TTG ACC TTG TCA CCA CAC TAT AAA GTG TTC CTT GCC AGG TTC ATA      48
Leu Leu Thr Leu Ser Pro His Tyr Lys Val Phe Leu Ala Arg Phe Ile
1               5                   10                  15

TGG TGG CTA CAA TAT CTC ATC ACC AGA ACC GAA GCG CAT CTG CAA GTG      96
Trp Trp Leu Gln Tyr Leu Ile Thr Arg Thr Glu Ala His Leu Gln Val
                20                  25                  30

TGG GTC CCC CCT CTC AAC GTT CGA GGA GGC CGT GAT GCC GTC ATC CTC     144
Trp Val Pro Pro Leu Asn Val Arg Gly Gly Arg Asp Ala Val Ile Leu
            35                  40                  45

CTC ACG TGC GCA GTC TAC CCA GAG CTA ATC TTT GAC ATC ACC AAA CTC     192
Leu Thr Cys Ala Val Tyr Pro Glu Leu Ile Phe Asp Ile Thr Lys Leu
        50                  55                  60

CTG CTT GCC ACA CTC GGT CCG CTC ATG GTG CTC CAG GCT GGC TTA ATT     240
Leu Leu Ala Thr Leu Gly Pro Leu Met Val Leu Gln Ala Gly Leu Ile
65                  70                  75                  80

AGA GTG CCG TAC TTC GTA CGC TCA GGG CTC ATT CGT GCA TGC ATG TTG     288
Arg Val Pro Tyr Phe Val Arg Ser Gly Leu Ile Arg Ala Cys Met Leu
                85                  90                  95

GTG CGG AAA GTT GCT GGG GGT CAT TAT                                 315
Val Arg Lys Val Ala Gly Gly His Tyr
            100                 105

(2) INFORMATION FOR SEQ ID NO: 103

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC21, Fig. 10

(xi) SEQUENCE DESCRIPTION: SEQ ID NO: 103

CTC TTG ACC CTG TCA CCA CAC TAT AAA GTG TTC CTC GCT AGG CTC ATG      48
Leu Leu Thr Leu Ser Pro His Tyr Lys Val Phe Leu Ala Arg Leu Met
1               5                   10                  15

TGG TGG TTA CAA TAC TTC CTC ACC AGA GCC GAA GCG CAC TTG CAA GTG      96
Trp Trp Leu Gln Tyr Phe Leu Thr Arg Ala Glu Ala His Leu Gln Val
                20                  25                  30

TGG GTC CCC TCT CTC AAC GTT CGA GGA GGC CGC GAT GCC ATC ATC CTC     144
Trp Val Pro Ser Leu Asn Val Arg Gly Gly Arg Asp Ala Ile Ile Leu
            35                  40                  45

CTC ACG TGC GCA GTC TAC CCA GAG CTA ATC TTT GAC ATC ACC AAA CTC     192
Leu Thr Cys Ala Val Tyr Pro Glu Leu Ile Phe Asp Ile Thr Lys Leu
        50                  55                  60

TTG CTT GCC ACA CTC GGC CCG CTC ATG GTG CTC CAG GCT GGC TTA ACT     240
Leu Leu Ala Thr Leu Gly Pro Leu Met Val Leu Gln Ala Gly Leu Thr
65                  70                  75                  80

AGA GTG CCG TAC TTT GTG CGC GCC CAG GGG CTC ATT CGT GCG TGC ATG     288
Arg Val Pro Tyr Phe Val Arg Ala Gln Gly Leu Ile Arg Ala Cys Met
```

```
                    85                  90                  95
TTG GTG CGG AAA GTT GTG GGG GGC CAT TAT                              318
Leu Val Arg Lys Val Val Gly Gly His Tyr
            100                 105
```

(2) INFORMATION FOR SEQ ID NO: 104

(i) SEQUENCE CHARACTERISTICS:
       (A) LENGTH: 318 base pairs
       (B) TYPE: nucleic acid
       (C) STRANDEDNESS: single
       (D) TOPOLOGY: linear (ii) MOLECULE TYPE: DNA (ix) FEATURE:
        (D) OTHER INFORMATION: NS2-LBC23, Fig. 11

(xi) SEQUENCE DESCRIPTION: SEQ ID NO: 104

```
CTC TTG ACC TTG TCA CCA CAC TAT AAA GTG TTC CTT GCC AGG TTC ATA      48
Leu Leu Thr Leu Ser Pro His Tyr Lys Val Phe Leu Ala Arg Phe Ile
1               5                   10                  15

TGG TGG CTA CAA TAT CTC ATC ACC AGA ACC GAA GCG CAT CTG CAA GTG      96
Trp Trp Leu Gln Tyr Leu Ile Thr Arg Thr Glu Ala His Leu Gln Val
            20                  25                  30

TGG GTC CCC CCT CTC AAC GTT CGG GGG GGT CGC GAT GCC ATC ATC CTC     144
Trp Val Pro Pro Leu Asn Val Arg Gly Gly Arg Asp Ala Ile Ile Leu
        35                  40                  45

CTC GCG TGT GCG GTC CAC CCA GAG CTG ATC TTT GAC ATC ACC AAA CTC     192
Leu Ala Cys Ala Val His Pro Glu Leu Ile Phe Asp Ile Thr Lys Leu
    50                  55                  60

TTG CTC GCC ATA CTC GGT CCG CTC ATG GTG CTC CAG GCT AGC ATA ATT     240
Leu Leu Ala Ile Leu Gly Pro Leu Met Val Leu Gln Ala Ser Ile Ile
65                  70                  75                  80

CGA GTG CCG TAC TCC GTG CGC GCT CAA GGC CTC ATT CGT GCA TGC ATG     288
Arg Val Pro Tyr Ser Val Arg Ala Gln Gly Leu Ile Arg Ala Cys Met
                85                  90                  95

TTG GTG CGG AAA GCC GCC GGG GGT CAT TAT                              318
Leu Val Arg Lys Ala Ala Gly Gly His Tyr
            100                 105
```

(2) INFORMATION FOR SEQ ID NO: 105

(i) SEQUENCE CHARACTERISTICS:
       (A) LENGTH: 318 base pairs
       (B) TYPE: nucleic acid
       (C) STRANDEDNESS: single
       (D) TOPOLOGY: linear (ii) MOLECULE TYPE: DNA (ix) FEATURE:
        (D) OTHER INFORMATION: NS2-LBC25, Fig. 12

(xi) SEQUENCE DESCRIPTION: SEQ ID NO: 105

```
CTC TTG ACC TTG TCA CCA TAC TAT AAG GTG CTC CTC GCT AGG CTC ATA      48
Leu Leu Thr Leu Ser Pro Tyr Tyr Lys Val Leu Leu Ala Arg Leu Ile
1               5                   10                  15

TGG TGG TTG CAA TAT TTT ATC ACC AGA GCC GAG GCG CAC TTG CAA GTG      96
Trp Trp Leu Gln Tyr Phe Ile Thr Arg Ala Glu Ala His Leu Gln Val
            20                  25                  30

TGG GCT CCC CCC CTT AAC GTT CGG GGG GGC CGC GAT GCC ATC ATC CTC     144
Trp Ala Pro Pro Leu Asn Val Arg Gly Gly Arg Asp Ala Ile Ile Leu
        35                  40                  45

CTC ATG TGT GTA GTT CAC CCG GAG CTA ATC TTT GAC ATC ACA AAA ATC     192
```

-continued

```
Leu Met Cys Val Val His Pro Glu Leu Ile Phe Asp Ile Thr Lys Ile
         50                  55                  60

CTG CTC GCC GTG CTC GGT CCG CTC ACG GTG CTC CAG GCT GGC ATA ACC      240
Leu Leu Ala Val Leu Gly Pro Leu Thr Val Leu Gln Ala Gly Ile Thr
 65                  70                  75                  80

CGA GTG CCG TAC TTT GTG CGC GCT CAA TGG CTC ATT CGT GCG TGC ATG      288
Arg Val Pro Tyr Phe Val Arg Ala Gln Trp Leu Ile Arg Ala Cys Met
                 85                  90                  95

TTG GTG CGG AAC ATC GCT GGG GGT CAT TAT                              318
Leu Val Arg Asn Ile Ala Gly Gly His Tyr
                100                 105
```

(2) INFORMATION FOR SEQ ID NO: 106

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC26, Fig. 13

(xi) SEQUENCE DESCRIPTION: SEQ ID NO: 106

```
CTC TTG ACC TTG TCA CCA CAC TAT AAA GTG TTC CTT GCC AGG TTC ATA       48
Leu Leu Thr Leu Ser Pro His Tyr Lys Val Phe Leu Ala Arg Phe Ile
 1                   5                  10                  15

TGG TGG CTA CAA TAT CTC ATC ACC AGA ACC GAA GCG CAT CTG CAA GTG       96
Trp Trp Leu Gln Tyr Leu Ile Thr Arg Thr Glu Ala His Leu Gln Val
                 20                  25                  30

TGG GTC CCC CCT CTC AAC GTT CGG GGG GGT CGC GAT GCC ATC ATC CTC      144
Trp Val Pro Pro Leu Asn Val Arg Gly Gly Arg Asp Ala Ile Ile Leu
                 35                  40                  45

CTC ACA TGC GTG GTC CAC CCA GAG CTA ATC TTT GAC ATC ACC AAA CTC      192
Leu Thr Cys Val Val His Pro Glu Leu Ile Phe Asp Ile Thr Lys Leu
 50                  55                  60

TTG CTC GCC ATA CTC GGT CCG CTC ATG GTG CTC CAG GCT AGC ATA ATT      240
Leu Leu Ala Ile Leu Gly Pro Leu Met Val Leu Gln Ala Ser Ile Ile
 65                  70                  75                  80

CGA GTG CCG TAC TTT GTG CGC GCT CAA GGC CTC ATT CGT GCA TGT ATG      288
Arg Val Pro Tyr Phe Val Arg Ala Gln Gly Leu Ile Arg Ala Cys Met
                 85                  90                  95

TTG GTG CGG AAA GTT GCT GGG GGT CAT TAT                              318
Leu Val Arg Lys Val Ala Gly Gly His Tyr
                100                 105
```

(2) INFORMATION FOR SEQ ID NO: 107

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC27, Fig. 14

(xi) SEQUENCE DESCRIPTION: SEQ ID NO: 107

```
CTC TTG ACT CTG TCG CCA CAC TAT AAA GTG TTC CTC GCT AGC CTC ATG       48
Leu Leu Thr Leu Ser Pro His Tyr Lys Val Phe Leu Ala Ser Leu Met
 1                   5                  10                  15
```

-continued

```
TGG TGG TTA CAA TAC TTC CTC ACC AGA GCC GAA GCG CAC TTG CAA GTG      96
Trp Trp Leu Gln Tyr Phe Leu Thr Arg Ala Glu Ala His Leu Gln Val
        20                  25                  30

TGG GTC CCC TCT CTC AAC GTT CGA GGA GGC CGC GAT GCC ATC ATC CTC     144
Trp Val Pro Ser Leu Asn Val Arg Gly Gly Arg Asp Ala Ile Ile Leu
            35                  40                  45

CTC ACG TGC GCA GTC TAC CCA GAG CTA ATC TTA GAC ATC ACC AAA CTC     192
Leu Thr Cys Ala Val Tyr Pro Glu Leu Ile Leu Asp Ile Thr Lys Leu
    50                  55                  60

TTG CTC GCC ATA CTC GGT CCG CTC ATG GTG CTC CAG GCT AGC ATA ATT     240
Leu Leu Ala Ile Leu Gly Pro Leu Met Val Leu Gln Ala Ser Ile Ile
65                  70                  75                  80

CGA GTG CCG TAC TTC GTA CGC GCT CAA GGC CTC ATT CGT GCA TGC ATG     288
Arg Val Pro Tyr Phe Val Arg Ala Gln Gly Leu Ile Arg Ala Cys Met
                85                  90                  95

TTG GTG CGG AAA GCC GCC GGG GGT CAT TAT                             318
Leu Val Arg Lys Ala Ala Gly Gly His Tyr
            100                 105
```

(2) INFORMATION FOR SEQ ID NO: 108

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC28, Fig. 15

(xi) SEQUENCE DESCRIPTION: SEQ ID NO: 108

```
CTC TTG ACC CTG TCA CCG CAC TAT AAA GTG TTC CTC GCT AGG CTC ACG      48
Leu Leu Thr Leu Ser Pro His Tyr Lys Val Phe Leu Ala Arg Leu Thr
1               5                   10                  15

TGG TGG TTA CAA TAC TTC CTC ACC AGA GCC GAA GCG CAC TTG CAA GTG      96
Trp Trp Leu Gln Tyr Phe Leu Thr Arg Ala Glu Ala His Leu Gln Val
        20                  25                  30

TGG GTC CCC TCT CTC AAC GTT CGA GGA GGC CGC GAT GCC ATC ATC CTC     144
Trp Val Pro Ser Leu Asn Val Arg Gly Gly Arg Asp Ala Ile Ile Leu
            35                  40                  45

CTC ACG TGC GCA GTC TAC CCA GAG CTG ATC TTT GAC ATC ACC AAA CTC     192
Leu Thr Cys Ala Val Tyr Pro Glu Leu Ile Phe Asp Ile Thr Lys Leu
    50                  55                  60

TTG CTT GCC ACA CTC GGC CCG CTC ATG GTG CTC CAG GCT GGC TTA ACT     240
Leu Leu Ala Thr Leu Gly Pro Leu Met Val Leu Gln Ala Gly Leu Thr
65                  70                  75                  80

AGA GTG CCG TAC TTT GTG CGC GCC CAG GGG CTC ATT CGT GCG TGC ATG     288
Arg Val Pro Tyr Phe Val Arg Ala Gln Gly Leu Ile Arg Ala Cys Met
                85                  90                  95

TTG GTG CGG AAA GTT GCT GGG GGC CAT TAT                             318
Leu Val Arg Lys Val Ala Gly Gly His Tyr
            100                 105
```

(2) INFORMATION FOR SEQ ID NO: 109

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
    (D) OTHER INFORMATION: NS2-LBC29, Fig. 16

(xi) SEQUENCE DESCRIPTION: SEQ ID NO: 109

| | | | | | | | | | | | | | | | | |
|---|---|---|---|---|---|---|---|---|---|---|---|---|---|---|---|---|
|CTC|TTG|ACC|TTG|TCA|CCA|TAC|TAT|AAA|GTG|TTC|CTC|GCT|AGG|CTC|ATA|48|
|Leu|Leu|Thr|Leu|Ser|Pro|Tyr|Tyr|Lys|Val|Phe|Leu|Ala|Arg|Leu|Ile| |
|1| | |  |5| | | |10| | | | |15| | | |

| | | | | | | | | | | | | | | | | |
|---|---|---|---|---|---|---|---|---|---|---|---|---|---|---|---|---|
|TGG|TGG|TTG|CAA|TAT|TTT|ATC|ACC|AGA|GCC|GAA|GCG|CAC|TTG|CAA|GTG|96|
|Trp|Trp|Leu|Gln|Tyr|Phe|Ile|Thr|Arg|Ala|Glu|Ala|His|Leu|Gln|Val| |
| | | | |20| | | |25| | | |30| | | | |

| | | | | | | | | | | | | | | | | |
|---|---|---|---|---|---|---|---|---|---|---|---|---|---|---|---|---|
|TGG|GTC|CCC|CCT|CTC|AAC|GTT|CGA|GGA|GGC|CGT|GAT|GCT|ATC|ATC|CTC|144|
|Trp|Val|Pro|Pro|Leu|Asn|Val|Arg|Gly|Gly|Arg|Asp|Ala|Ile|Ile|Leu| |
| | |35| | | | |40| | | | |45| | | | |

| | | | | | | | | | | | | | | | | |
|---|---|---|---|---|---|---|---|---|---|---|---|---|---|---|---|---|
|CTC|ACG|TGC|GCA|GTC|TAC|CCA|GAG|CTA|ATC|TTT|GAC|ATC|ACC|AAA|CTC|192|
|Leu|Thr|Cys|Ala|Val|Tyr|Pro|Glu|Leu|Ile|Phe|Asp|Ile|Thr|Lys|Leu| |
|50| | | | |55| | | | |60| | | | | | |

| | | | | | | | | | | | | | | | | |
|---|---|---|---|---|---|---|---|---|---|---|---|---|---|---|---|---|
|TTG|CTT|GCC|ATA|CTC|GGT|CCG|CTC|ATG|GTG|CTC|CAG|GCT|AGC|ATA|ATT|240|
|Leu|Leu|Ala|Ile|Leu|Gly|Pro|Leu|Met|Val|Leu|Gln|Ala|Ser|Ile|Ile| |
|65| | | | |70| | | | |75| | | | |80| |

| | | | | | | | | | | | | | | | | |
|---|---|---|---|---|---|---|---|---|---|---|---|---|---|---|---|---|
|CGA|GTG|CCG|TAC|TTC|GTA|CGC|GCT|CAA|GGC|CTC|ATT|CGT|GCA|TGC|ATG|288|
|Arg|Val|Pro|Tyr|Phe|Val|Arg|Ala|Gln|Gly|Leu|Ile|Arg|Ala|Cys|Met| |
| | | | |85| | | | |90| | | | |95| | |

| | | | | | | | | | |
|---|---|---|---|---|---|---|---|---|---|
|TTG|GTG|CGG|AAA|GCC|GCC|GGG|GTC|AAT|TAT|
|Leu|Val|Arg|Lys|Ala|Ala|Gly|Val|Asn|Tyr|
| | | |100| | | | |105| |

318

(2) INFORMATION FOR SEQ ID NO: 110

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC30, Fig. 17

(xi) SEQUENCE DESCRIPTION: SEQ ID NO: 110

| | | | | | | | | | | | | | | | | |
|---|---|---|---|---|---|---|---|---|---|---|---|---|---|---|---|---|
|CTC|TTT|ACC|CTG|TCA|CCA|CAC|TGC|AAA|GTG|TTC|CTC|GCT|AGG|CTC|ATA|48|
|Leu|Phe|Thr|Leu|Ser|Pro|His|Cys|Lys|Val|Phe|Leu|Ala|Arg|Leu|Ile| |
|1| | | |5| | | |10| | | | |15| | | |

| | | | | | | | | | | | | | | | | |
|---|---|---|---|---|---|---|---|---|---|---|---|---|---|---|---|---|
|TGG|TGG|TTA|CAG|TAT|TTT|ATC|ACC|AGG|GCC|GAA|GCG|CAC|CTG|CAA|GTG|96|
|Trp|Trp|Leu|Gln|Tyr|Phe|Ile|Thr|Arg|Ala|Glu|Ala|His|Leu|Gln|Val| |
| | | | |20| | | |25| | | |30| | | | |

| | | | | | | | | | | | | | | | | |
|---|---|---|---|---|---|---|---|---|---|---|---|---|---|---|---|---|
|TGG|ATC|CCC|CCC|CTC|AAC|GTT|CGG|GGG|GGC|CGT|GAT|GCC|ATC|ATC|CTC|144|
|Trp|Ile|Pro|Pro|Leu|Asn|Val|Arg|Gly|Gly|Arg|Asp|Ala|Ile|Ile|Leu| |
| | |35| | | | |40| | | | |45| | | | |

| | | | | | | | | | | | | | | | | |
|---|---|---|---|---|---|---|---|---|---|---|---|---|---|---|---|---|
|CTC|GCA|TGT|GCG|GTC|CAC|CCA|GAG|CTG|ATC|TTC|GAC|ATC|ACC|AAA|CTC|192|
|Leu|Ala|Cys|Ala|Val|His|Pro|Glu|Leu|Ile|Phe|Asp|Ile|Thr|Lys|Leu| |
|50| | | | |55| | | | |60| | | | | | |

| | | | | | | | | | | | | | | | | |
|---|---|---|---|---|---|---|---|---|---|---|---|---|---|---|---|---|
|TTG|CTC|GCC|ATA|CTC|GGT|CCG|CTC|ATG|GTG|CTC|CAG|GCT|AGC|ATA|ATT|240|
|Leu|Leu|Ala|Ile|Leu|Gly|Pro|Leu|Met|Val|Leu|Gln|Ala|Ser|Ile|Ile| |
|65| | | | |70| | | | |75| | | | |80| |

| | | | | | | | | | | | | | | | | |
|---|---|---|---|---|---|---|---|---|---|---|---|---|---|---|---|---|
|CGA|GTG|CCG|TAC|TTG|TAC|CGC|GCT|CAA|GGC|CTC|ATT|CGT|GCA|TGC|ATG|288|
|Arg|Val|Pro|Tyr|Leu|Tyr|Arg|Ala|Gln|Gly|Leu|Ile|Arg|Ala|Cys|Met| |
| | | | |85| | | | |90| | | | |95| | |

| | | | | | | | | | |
|---|---|---|---|---|---|---|---|---|---|
|TTG|GTG|CGG|AAA|GCC|GCC|GGG|GGT|CAT|TAT|
|Leu|Val|Arg|Lys|Ala|Ala|Gly|Gly|His|Tyr|
| | | |100| | | | |105| |

318

(2) INFORMATION FOR SEQ ID NO: 111

(i) SEQUENCE CHARACTERISTICS:
    (A) LENGTH: 318 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: NS2-LBC31, Fig. 18

(xi) SEQUENCE DESCRIPTION: SEQ ID NO: 111

| | | | | | | | | | | | | | | | | |
|---|---|---|---|---|---|---|---|---|---|---|---|---|---|---|---|---|
| CTC | TTT | AAC | CTG | TCA | CCA | CAC | TAC | AAA | GTG | TTC | CTC | GCT | AGG | CTC | ATA | 48 |
| Leu | Phe | Asn | Leu | Ser | Pro | His | Tyr | Lys | Val | Phe | Leu | Ala | Arg | Leu | Ile | |
| 1 | | | | 5 | | | | | 10 | | | | | 15 | | |

| TGG | TGG | TTA | CAG | TAT | TTT | ATC | ACC | AGG | GCC | GAA | GCG | CAC | CTG | CAA | GTG | 96 |
|---|---|---|---|---|---|---|---|---|---|---|---|---|---|---|---|---|
| Trp | Trp | Leu | Gln | Tyr | Phe | Ile | Thr | Arg | Ala | Glu | Ala | His | Leu | Gln | Val | |
| | | | 20 | | | | | 25 | | | | | 30 | | | |

| TGG | ATC | CCC | CCC | CTC | AAC | GTT | CAG | GGG | GGC | CGT | GAT | GCC | ATC | ATC | CTC | 144 |
|---|---|---|---|---|---|---|---|---|---|---|---|---|---|---|---|---|
| Trp | Ile | Pro | Pro | Leu | Asn | Val | Gln | Gly | Gly | Arg | Asp | Ala | Ile | Ile | Leu | |
| | | 35 | | | | | 40 | | | | | 45 | | | | |

| CTC | GCA | TGT | GCG | GTC | CAC | CCA | GAG | CTG | ATC | TTT | GAC | ATC | ACC | AAA | CTC | 192 |
|---|---|---|---|---|---|---|---|---|---|---|---|---|---|---|---|---|
| Leu | Ala | Cys | Ala | Val | His | Pro | Glu | Leu | Ile | Phe | Asp | Ile | Thr | Lys | Leu | |
| 50 | | | | | 55 | | | | | 60 | | | | | | |

| TTG | CTC | GCC | ATA | CTC | GGT | CCG | CTC | ATG | GTG | CTC | CAG | GCT | AGC | ATA | ATT | 240 |
|---|---|---|---|---|---|---|---|---|---|---|---|---|---|---|---|---|
| Leu | Leu | Ala | Ile | Leu | Gly | Pro | Leu | Met | Val | Leu | Gln | Ala | Ser | Ile | Ile | |
| 65 | | | | 70 | | | | | 75 | | | | | 80 | | |

| CGA | GTG | CCG | TAC | TTC | GTA | CGC | GCT | CAA | GGC | CTC | ATT | CGT | GCA | TGC | ATG | 288 |
|---|---|---|---|---|---|---|---|---|---|---|---|---|---|---|---|---|
| Arg | Val | Pro | Tyr | Phe | Val | Arg | Ala | Gln | Gly | Leu | Ile | Arg | Ala | Cys | Met | |
| | | | | 85 | | | | | 90 | | | | | 95 | | |

| TTG | GTG | CGG | AAA | GCC | GCC | GGG | GGT | CAT | TAT | | | | | | | 318 |
|---|---|---|---|---|---|---|---|---|---|---|---|---|---|---|---|---|
| Leu | Val | Arg | Lys | Ala | Ala | Gly | Gly | His | Tyr | | | | | | | |
| | | | 100 | | | | | 105 | | | | | | | | |

(2) INFORMATION FOR SEQ ID NO: 112

(i) SEQUENCE CHARACTERISTICS:
    (A) LENGTH: 318 base pairs
    (B) TYPE: nucleic acid
    (C) STRANDEDNESS: single
    (D) TOPOLOGY: linear (ii) MOLECULE TYPE: DNA (ix) FEATURE:
    (D) OTHER INFORMATION: NS2-LBC32, Fig. 19

(xi) SEQUENCE DESCRIPTION: SEQ ID NO: 112

| CTC | TTG | ACC | TTG | TCA | CCA | CAC | TAT | AAA | GTG | TTC | CTT | GCC | AGG | TTC | GTA | 48 |
|---|---|---|---|---|---|---|---|---|---|---|---|---|---|---|---|---|
| Leu | Leu | Thr | Leu | Ser | Pro | His | Tyr | Lys | Val | Phe | Leu | Ala | Arg | Phe | Val | |
| 1 | | | | 5 | | | | | 10 | | | | | 15 | | |

| TGG | TGG | CTA | CAA | TAT | CTC | ATC | ACC | AGA | ACC | GAA | GCG | CAT | CTG | CAA | GTG | 96 |
|---|---|---|---|---|---|---|---|---|---|---|---|---|---|---|---|---|
| Trp | Trp | Leu | Gln | Tyr | Leu | Ile | Thr | Arg | Thr | Glu | Ala | His | Leu | Gln | Val | |
| | | | 20 | | | | | 25 | | | | | 30 | | | |

| TGG | GTC | CCC | CCT | CTC | AAC | GTT | CGG | GGG | GGT | CGC | GAT | GCC | ATC | ACC | CTC | 144 |
|---|---|---|---|---|---|---|---|---|---|---|---|---|---|---|---|---|
| Trp | Val | Pro | Pro | Leu | Asn | Val | Arg | Gly | Gly | Arg | Asp | Ala | Ile | Thr | Leu | |
| | | 35 | | | | | 40 | | | | | 45 | | | | |

| CTC | ACA | TGC | GTG | GTC | CAC | CCA | GAG | CTA | ATC | TTC | GAC | ATC | ACA | AAA | TAT | 192 |
|---|---|---|---|---|---|---|---|---|---|---|---|---|---|---|---|---|
| Leu | Thr | Cys | Val | Val | His | Pro | Glu | Leu | Ile | Phe | Asp | Ile | Thr | Lys | Tyr | |
| 50 | | | | | 55 | | | | | 60 | | | | | | |

| TTG | CTC | GCC | ATA | TTC | GGC | CCG | CTC | ATG | GTG | CTC | CAG | GCC | GGC | ATA | ACT | 240 |
|---|---|---|---|---|---|---|---|---|---|---|---|---|---|---|---|---|
| Leu | Leu | Ala | Ile | Phe | Gly | Pro | Leu | Met | Val | Leu | Gln | Ala | Gly | Ile | Thr | |
| 65 | | | | 70 | | | | | 75 | | | | | 80 | | |

| AGA | GTG | CCG | TAC | TTC | GTG | CGC | GCA | CAA | GGG | CTC | ATT | CGT | GCA | TGC | ATG | 288 |
|---|---|---|---|---|---|---|---|---|---|---|---|---|---|---|---|---|

```
Arg Val Pro Tyr Phe Val Arg Ala Gln Gly Leu Ile Arg Ala Cys Met
                85                  90                  95

TTG GTG CGG AAA GTT GCT GGG GGC CAT TAT                              318
Leu Val Arg Lys Val Ala Gly Gly His Tyr
            100                 105

(2) INFORMATION FOR SEQ ID NO: 113

(i) SEQUENCE CHARACTERISTICS:
        (A) LENGTH: 313 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS5-LBC20, Fig. 20

(xi) SEQUENCE DESCRIPTION: SEQ ID NO: 113

C CGT GTT GAG GAG TCA ATT TAC CAA TGT TGT GAC TTG GCC CCC GAA          46
  Arg Val Glu Glu Ser Ile Tyr Gln Cys Cys Asp Leu Ala Pro Glu
  1               5                  10                  15

GCC AAA CTG GCC ATA AAG TCG CCC ACA GAG CGG CTC TAT ATC GGG GGT        94
Ala Lys Leu Ala Ile Lys Ser Pro Thr Glu Arg Leu Tyr Ile Gly Gly
                20                  25                  30

CCC CTG ACT AAT TCA AAA GGG CAG AAC TGC GGT TAC TGC CGG TGC CGC       142
Pro Leu Thr Asn Ser Lys Gly Gln Asn Cys Gly Tyr Cys Arg Cys Arg
            35                  40                  45

GCG AGC CTG CTG ACG ACT AGC TGC GGT AAT ACC CTC ACA TGT CAC CTG       190
Ala Ser Leu Leu Thr Thr Ser Cys Gly Asn Thr Leu Thr Cys His Leu
        50                  55                  60

AAA GCC ACT GCG GCC TGT CGA GCT GCG AAG CTC CAG GAC TGC ACG ATG       238
Lys Ala Thr Ala Ala Cys Arg Ala Ala Lys Leu Gln Asp Cys Thr Met
65                  70                  75

CTC GTG AAC GGA GAC GAC CTT GTC GTT ATC TGT GAA AGC GCG GGG ACC       286
Leu Val Asn Gly Asp Asp Leu Val Val Ile Cys Glu Ser Ala Gly Thr
80                  85                  90                  95

CAG GAG GAC GCG GCG AGC CTA CGA GTC                                   313
Gln Glu Asp Ala Ala Ser Leu Arg Val
                100

(2) INFORMATION FOR SEQ ID NO: 114

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS5-LBC21, Fig. 21 , NS5B-LBC24,
            Fig. 29

(xi) SEQUENCE DESCRIPTION: SEQ ID NO: 114

C CGT GTT GAG GAG TCA ATT TAC CAA TAT TGT GAC TTG GCC CCC GAA          46
  Arg Val Glu Glu Ser Ile Tyr Gln Tyr Cys Asp Leu Ala Pro Glu
  1               5                  10                  15

GCC AAA CTG GCC ATA AAG TCG CTC ACA GAG CGG CTC TAT ATC GGG GGT        94
Ala Lys Leu Ala Ile Lys Ser Leu Thr Glu Arg Leu Tyr Ile Gly Gly
                20                  25                  30

CCC CTG ACT AAT TCA AAA GGG CAG AAC TGC GGT TAC CGC CGG TGC CGC       142
Pro Leu Thr Asn Ser Lys Gly Gln Asn Cys Gly Tyr Arg Arg Cys Arg
            35                  40                  45
```

```
GCG ACC GTG CTG ACG ACT AGC TGC GGT AAT ACC CTC ACA TGT CAC CTG       190
Ala Thr Val Leu Thr Thr Ser Cys Gly Asn Thr Leu Thr Cys His Leu
         50                  55                  60

AAA GCC ACT GCG GCC TGT CGA GCT GCG AAA CTC CGG GAC TGC ACG ATG       238
Lys Ala Thr Ala Ala Cys Arg Ala Ala Lys Leu Arg Asp Cys Thr Met
         65                  70                  75

CTC GTG AAC GGA GAC GAC CTT GTG CTT ATC TGT GAA AGC GCG GG            282
Leu Val Asn Gly Asp Asp Leu Val Leu Ile Cys Glu Ser Ala
 80                  85                  90

(2) INFORMATION FOR SEQ ID NO: 115

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS5-LBC23, Fig. 22

(xi) SEQUENCE DESCRIPTION: SEQ ID NO: 115

C CGT GTT GAG GAG TCA ATT TAC CAA TGT TGT GAC TTG GCC CCC GAA          46
  Arg Val Glu Glu Ser Ile Tyr Gln Cys Cys Asp Leu Ala Pro Glu
   1               5                  10                  15

GCC AAA CTG GCC ATA AAG TCG CTC ACA GAG CGG CTC TAT ATC GGG GGT        94
Ala Lys Leu Ala Ile Lys Ser Leu Thr Glu Arg Leu Tyr Ile Gly Gly
                 20                  25                  30

CCC CTG ACT AAT TCA AAA GGG CAG AAC TGC GGT TAC CGC CGG TGC CAC       142
Pro Leu Thr Asn Ser Lys Gly Gln Asn Cys Gly Tyr Arg Arg Cys His
         35                  40                  45

GCG AGC GGC GTG CTG ACG ACT AGC TGC GGT AAT ACC CTC ACA TGT CAC       190
Ala Ser Gly Val Leu Thr Thr Ser Cys Gly Asn Thr Leu Thr Cys His
         50                  55                  60

CTG AAA GCC ACT GCG GCC TGT CGA GCT GCG AAG CTC CGG GAC TGC ACG       238
Leu Lys Ala Thr Ala Ala Cys Arg Ala Ala Lys Leu Arg Asp Cys Thr
         65                  70                  75

ATG CTC GTG AAC GGA GAT GAC CTT GTC GTT ATC TGT GAA AGC GCG GG        285
Met Leu Val Asn Gly Asp Asp Leu Val Val Ile Cys Glu Ser Ala
 80                  85                  90

(2) INFORMATION FOR SEQ ID NO: 116

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS5-LBC25, Fig. 23

(xi) SEQUENCE DESCRIPTION: SEQ ID NO: 116

C CGT GTT GAG GAG TCA ATT TAC CAA TGT TGT GAC TTG GCC CCC GAA          46
  Arg Val Glu Glu Ser Ile Tyr Gln Cys Cys Asp Leu Ala Pro Glu
   1               5                  10                  15

GCC AAA CTG GCC ATA AAG TCG CTC ACA GAG CGG CTC TAT ATC GGG GGT        94
Ala Lys Leu Ala Ile Lys Ser Leu Thr Glu Arg Leu Tyr Ile Gly Gly
                 20                  25                  30

CCC CTG ACT AAT TCA AAA GGG CAG AAC TGC GGT TAC CGC CGG TGC CGC       142
Pro Leu Thr Asn Ser Lys Gly Gln Asn Cys Gly Tyr Arg Arg Cys Arg
```

```
                     35                      40                      45
GCG AGC CTG CTG ACG ACT AGC TGC GGT AAT ACC CTC ACA TGT CAC CTG             190
Ala Ser Leu Leu Thr Thr Ser Cys Gly Asn Thr Leu Thr Cys His Leu
            50                      55                      60

AAA GCC ACT GCG GCC TGT CGA GCT GCG AAG CTC CGG GAC TGC ACG ATG             238
Lys Ala Thr Ala Ala Cys Arg Ala Ala Lys Leu Arg Asp Cys Thr Met
    65                      70                      75

CTC GTG AAC GGA GAC GAC CTT GTC GTT ATC TGT GAA AGC GCG GG                  282
Leu Val Asn Gly Asp Asp Leu Val Val Ile Cys Glu Ser Ala
80                      85                      90

(2) INFORMATION FOR SEQ ID NO: 117

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS5-LBC27, Fig. 24

(xi) SEQUENCE DESCRIPTION: SEQ ID NO: 117

C CGT GTT GAG GAG TCA ATT TAC CAA TGT TGT GAC TTG GCC CCC GAA               46
  Arg Val Glu Glu Ser Ile Tyr Gln Cys Cys Asp Leu Ala Pro Glu
  1               5                      10                     15

GCC AAA CTG GCC ATA AAG TCG CTC ACA GAG CGG CTC TAT ATC GGG GGT             94
Ala Lys Leu Ala Ile Lys Ser Leu Thr Glu Arg Leu Tyr Ile Gly Gly
                20                      25                      30

CCC CTG ACT AAT TCA AAA GGG CAG AAC TGC GGT TAC CGC CGG TGC CAC             142
Pro Leu Thr Asn Ser Lys Gly Gln Asn Cys Gly Tyr Arg Arg Cys His
            35                      40                      45

GCG AGC GGC GTG CTG ACG ACT AGC TGC GGT AAT ACC CTC ACA TGT CAC             190
Ala Ser Gly Val Leu Thr Thr Ser Cys Gly Asn Thr Leu Thr Cys His
            50                      55                      60

CTG AAA GCC ACT GCG GCC                                                     208
Leu Lys Ala Thr Ala Ala
    65

(2) INFORMATION FOR SEQ ID NO: 118

(i) SEQUENCE CHARACTERISTICS:
        (A) LENGTH: 316 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS5-LBC28, Fig.25

(xi) SEQUENCE DESCRIPTION: SEQ ID NO: 118

C CGT GTT GAG GAG TCA ATT TAC CAA TGT TGT GAC TTG GCC CCC GAA               46
  Arg Val Glu Glu Ser Ile Tyr Gln Cys Cys Asp Leu Ala Pro Glu
  1               5                      10                     15

GCC AAA CTG GCC ATA AAG TCG CTC ACA GAG CGG CTC TAT ATC GGG GGT             94
Ala Lys Leu Ala Ile Lys Ser Leu Thr Glu Arg Leu Tyr Ile Gly Gly
                20                      25                      30

CCC CTG ACT AAT TCA AAA GGG CAG AAC TGC GGT TAC CGC CGG TGC CAC             142
Pro Leu Thr Asn Ser Lys Gly Gln Asn Cys Gly Tyr Arg Arg Cys His
            35                      40                      45

GCG AGC GGC GTG CTG ACG ACT AGC TGC GGT AAT ACC CTC ACA TGT CGC             190
```

```
Ala Ser Gly Val Leu Thr Thr Ser Cys Gly Asn Thr Leu Thr Cys Arg
         50                  55                  60

CTG AAA GCC ACT GCG GCC TGT CGA GCT GCG AAG CTC CGG GAC TGC ACG        238
Leu Lys Ala Thr Ala Ala Cys Arg Ala Ala Lys Leu Arg Asp Cys Thr
 65                  70                  75

ATG CTC GTG AAC GGA GAT GAC CTT GTC GTT ATC TGT GAA AGC GCG GGG        286
Met Leu Val Asn Gly Asp Asp Leu Val Val Ile Cys Glu Ser Ala Gly
 80                  85                  90                  95

ACC CAG GAG GAC GCG GCG AGC CTA CGA GTC                                316
Thr Gln Glu Asp Ala Ala Ser Leu Arg Val
                100                 105

(2) INFORMATION FOR SEQ ID NO: 119

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: NS2-LBC1

(xi) SEQUENCE DESCRIPTION: SEQ ID NO: 119

CTC TTG ACC TTG TCA CCA CAC TAT AAA GTG TTC CTT GCC AGG TTC ATA         48
Leu Leu Thr Leu Ser Pro His Tyr Lys Val Phe Leu Ala Arg Phe Ile
  1                  5                  10                  15

TGG TGG CTA CAA TAT CTC ATC ACC AGA ACC GAA GCG CAT CTG CAA GTG         96
Trp Trp Leu Gln Tyr Leu Ile Thr Arg Thr Glu Ala His Leu Gln Val
                 20                  25                  30

TGG GTC CCC CCT CTC AAC GTT CGG GGG GGT CGC GAT GCC ATC ATC CTC        144
Trp Val Pro Pro Leu Asn Val Arg Gly Gly Arg Asp Ala Ile Ile Leu
             35                  40                  45

CTC ACA TGC GTG GTC CAC CCA GAG CTA ATC TTT GAC ATC ACA AAA TAT        192
Leu Thr Cys Val Val His Pro Glu Leu Ile Phe Asp Ile Thr Lys Tyr
 50                  55                  60

TTG CTC GCC ATA TTC GGC CCG CTC ATG GTG CTC CAG GCC GGC ATA ACT        240
Leu Leu Ala Ile Phe Gly Pro Leu Met Val Leu Gln Ala Gly Ile Thr
 65                  70                  75                  80

AGA GTG CCG TAC TTC GTG CGC GCA CAA GGG CTC ATT CGT GCA TGC ATG        288
Arg Val Pro Tyr Phe Val Arg Ala Gln Gly Leu Ile Arg Ala Cys Met
                 85                  90                  95

TTG GCG CGG AAA GTC GTG GGG GGT CAT TAC                                318
Leu Ala Arg Lys Val Val Gly Gly His Tyr
                100                 105

(2) INFORMATION FOR SEQ ID NO: 120

(i) SEQUENCE CHARACTERISTICS:
        (A) LENGTH: 106 amino acids
        (B) TYPE: amino acid
        (D) TOPOLOGY: linear (ii) MOLECULE TYPE: protein (ix) FEATURE:
        (D) OTHER INFORMATION: JHCV-NCI (xi) SEQUENCE DESCRIPTION: SEQ ID NO: 120

Leu Leu Thr Leu Ser Pro Tyr Tyr Lys Val Phe Leu Ala Arg Leu
  1                  5                  10                  15

Ile Trp Trp Leu Gln Tyr Phe Ile Thr Arg Ala Glu Ala His Leu
                 20                  25                  30
```

```
Gln Val Trp Val Pro Pro Leu Asn Val Arg Gly Gly Arg Asp Ala
            35                  40                  45

Ile Ile Leu Leu Thr Cys Ala Val His Pro Glu Leu Ile Phe Asp
            50                  55                  60

Ile Thr Lys Leu Leu Leu Ala Ile Leu Gly Pro Leu Met Val Leu
            65                  70                  75

Gln Ala Gly Ile Thr Arg Val Pro Tyr Phe Val Arg Ala Gln Gly
            80                  85                  90

Leu Ile Arg Ala Cys Met Leu Val Arg Lys Val Ala Gly Gly His
            95                  100                 105

Tyr (2) INFORMATION FOR SEQ ID NO: 121

(i) SEQUENCE CHARACTERISTICS:
        (A) LENGTH: 106 amino acids
        (B) TYPE: amino acid
        (D) TOPOLOGY: linear (ii) MOLECULE TYPE: protein (ix) FEATURE:
         (D) OTHER INFORMATION: JHCV-OSAKA (xi) SEQUENCE DESCRIPTION: SEQ ID NO: 121

Leu Leu Thr Leu Ser Pro Tyr Tyr Lys Val Phe Leu Ala Arg Leu
1           5                   10                  15

Ile Trp Trp Leu Gln Tyr Phe Thr Thr Arg Ala Glu Ala Asp Leu
            20                  25                  30

His Val Trp Ile Pro Pro Leu Asn Ala Arg Gly Gly Arg Asp Ala
            35                  40                  45

Ile Ile Leu Leu Met Cys Ala Val His Pro Glu Leu Ile Phe Asp
            50                  55                  60

Ile Thr Lys Leu Leu Ile Ala Ile Leu Gly Pro Leu Met Val Leu
            65                  70                  75

Gln Ala Gly Ile Thr Arg Val Pro Tyr Phe Val Arg Ala Gln Gly
            80                  85                  90

Leu Ile His Ala Cys Met Leu Val Arg Lys Val Ala Gly Gly His
            95                  100                 105

Tyr (2) INFORMATION FOR SEQ ID NO: 122

(i) SEQUENCE CHARACTERISTICS:
        (A) LENGTH: 106 amino acids
        (B) TYPE: amino acid
        (D) TOPOLOGY: linear (ii) MOLECULE TYPE: protein (ix) FEATURE:
         (D) OTHER INFORMATION: HCPT-CHIRON (xi) SEQUENCE DESCRIPTION: SEQ ID NO: 122

Ala Leu Thr Leu Ser Pro Tyr Tyr Lys Arg Tyr Ile Ser Trp Cys
1           5                   10                  15

Leu Trp Trp Leu Gln Tyr Phe Leu Thr Arg Val Glu Ala Gln Leu
            20                  25                  30

His Val Trp Ile Pro Pro Leu Asn Val Arg Gly Gly Arg Asp Ala
            35                  40                  45
```

```
Val Ile Leu Leu Met Cys Ala Val His Pro Thr Leu Val Phe Asp
                50                  55                  60

Ile Thr Lys Leu Leu Ala Val Phe Gly Pro Leu Trp Ile Leu
                65                  70                  75

Gln Ala Ser Leu Leu Lys Val Pro Tyr Phe Val Arg Val Gln Gly
                80                  85                  90

Leu Leu Arg Phe Cys Ala Leu Ala Arg Lys Met Ile Gly Gly His
                95                  100                 105

Tyr (2) INFORMATION FOR SEQ ID NO: 123

(i) SEQUENCE CHARACTERISTICS:
         (A) LENGTH: 316 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: NS5B-LBC1

(xi) SEQUENCE DESCRIPTION: SEQ ID NO: 123

C CGT GTT GAG GAG TCA ATT TAC CAA TGT TGT GAC TTG GCC CCC GAA         46
  Arg Val Glu Glu Ser Ile Tyr Gln Cys Cys Asp Leu Ala Pro Glu
  1               5                   10                  15

GCC AAA CTG GCC ATA AAG TCG CTC ACA GAG CGG CTC TAT ATC GGG GGT       94
Ala Lys Leu Ala Ile Lys Ser Leu Thr Glu Arg Leu Tyr Ile Gly Gly
                20                  25                  30

CCC CTG ACT AAT TCA AAA GGG CAG AAC TGC GGT TAC CGC CGG TGC CGC      142
Pro Leu Thr Asn Ser Lys Gly Gln Asn Cys Gly Tyr Arg Arg Cys Arg
                35                  40                  45

GCG AGC GGC GTG CTG ACG ACT AGC TGC GGT AAT ACC CTC ACA TGT TAC      190
Ala Ser Gly Val Leu Thr Thr Ser Cys Gly Asn Thr Leu Thr Cys Tyr
                50                  55                  60

CTG AAA GCC ACT GCG GCC TGT CGA GCT GCG AAG CTC CGG GAC TGC ACG      238
Leu Lys Ala Thr Ala Ala Cys Arg Ala Ala Lys Leu Arg Asp Cys Thr
      65                  70                  75

ATG CTC GTG AAC GGA GAC GAC CTT GTC GTT ATC TGT GAA AGC GCG GGA      286
Met Leu Val Asn Gly Asp Asp Leu Val Val Ile Cys Glu Ser Ala Gly
80              85                  90                  95

ACC CAA GAG GAT GCG GCG AGC CTA CGA GTC                              316
Thr Gln Glu Asp Ala Ala Ser Leu Arg Val
                100                 105

(2) INFORMATION FOR SEQ ID NO: 124

(i) SEQUENCE CHARACTERISTICS:
         (A) LENGTH: 228 base pairs
         (B) TYPE: nucleic acid
         (C) STRANDEDNESS: single
         (D) TOPOLOGY: linear (ii) MOLECULE TYPE: DNA (ix) FEATURE:
         (D) OTHER INFORMATION: UBIQUITINE (xi) SEQUENCE DESCRIPTION: SEQ ID NO: 124

ATG CAA ATT TTC GTC AAA ACT CTA ACA GGG AAG ACT ATA ACC CTA GAG       48
Met Gln Ile Phe Val Lys Thr Leu Thr Gly Lys Thr Ile Thr Leu Glu
1               5                   10                  15
```

```
GTT GAA TCT TCC GAC ACT ATT GAC AAC GTC AAA AGT AAA ATT CAA GAT        96
Val Glu Ser Ser Asp Thr Ile Asp Asn Val Lys Ser Lys Ile Gln Asp
         20                  25                  30

AAA GAA GGT ATC CCT CCG GAT CAG CAG AGA TTG ATT TTT GCT GGT AAG       144
Lys Glu Gly Ile Pro Pro Asp Gln Gln Arg Leu Ile Phe Ala Gly Lys
         35                  40                  45

CAA CTA GAA GAT GGT AGA ACC TTG TCT GAC TAC AAC ATC CAA AAG GAA       192
Gln Leu Glu Asp Gly Arg Thr Leu Ser Asp Tyr Asn Ile Gln Lys Glu
     50                  55                  60

TCT ACT CTT CAC TTG GTG TTG AGA CTC CGC GGT GGT                       228
Ser Thr Leu His Leu Val Leu Arg Leu Arg Gly Gly
65                  70                  75
```

(2) INFORMATION FOR SEQ ID NO: 125

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer A (xi) SEQUENCE DESCRIPTION: SEQ ID NO: 125

CATAGTGGTC TGCGGAACCG                                                     20

(2) INFORMATION FOR SEQ ID NO: 126

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer B (xi) SEQUENCE DESCRIPTION: SEQ ID NO: 126

TTGAGGTTTA GGATTCGTGC                                                     20

(2) INFORMATION FOR SEQ ID NO: 127

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: primer C (xi) SEQUENCE DESCRIPTION: SEQ ID NO: 127

TACACCGGAA TTGCCAGGAC                                                     20

(2) INFORMATION FOR SEQ ID NO: 128

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued

```
    (ii) MOLECULE TYPE: DNA (ix) FEATURE:
         (D) OTHER INFORMATION: primer D (xi) SEQUENCE DESCRIPTION: SEQ ID NO: 128

TCATGGTGCA CGGTCTACGA G                                              21
```

What is claimed is:

1. A Korean type hepatitis C virus (KHCV) cDNA which has the nucleotide sequence of SEQ ID NO: 96.

2. A polynucleotide encoding a KHCV polypeptide, selected from the group consisting of: the 301st–726th, 301st–855th, 343rd–726th, 343rd–852nd, 343rd–915th, 814th–1326th, 916th–1509th, 1201st–2016th, 1510th–2010th, 1945th–2742nd, 2011th–2529th, 3208th–3960th, 3475th–3744th, 3916th–4713th, 3925th–4563rd, 5422nd–5547th, 6649th–7050th, 7612th–8184th, 7642nd–8136th and 8722nd–9216th nucleotides in the KHCV cDNA of claim 1, and a combination thereof.

3. A recombinant expression vector comprising an open reading frame comprising the polynucleotide of claim 2, wherein the open reading frame is operably linked to a regulatory sequence compatible with a desired host organism.

4. The vector of claim 3 wherein the open reading frame comprises a polynucleotide encoding ubiquitin fused with the polynucleotide of claim 2.

5. The vector of claim 4 which is a yeast expression vector selected from the group consisting of pYLBC-A/G-UB-CORE 14(ATCC 74081), pYLBC-A/G-UB-CORE 17, pYLBC-A/G-UB-CORE 22, pYLBC-A/G-UB-KHCV 897, pYLBC-A/G-UB-KHCV 403(ATCC 74079), pYLBC-A/G-UB-KHCV 573, pYLBC-A/G-UB-E2N and pYLBC-A/G-UB-E2C(ATCC 74117).

6. A Saccharomyces sp. cell transformed with the vector of claim 5.

7. The vector of claim 4 which is an *E. coli* expression vector selected from the group consisting of ptrpH-UB-CORE14(ATCC 68642), ptrpH-UB-CORE17(ATCC 68641), ptrpH-UB-CORE22, ptrpH-UB-KHCV 897(ATCC 68640), ptrpH-UB-E1(ATCC 68878), ptrpH-UB-E2N (ATCC 68966) and ptrpH-UB-E2C.

8. An *E. coli* cell transformed with the vector of claim 7.

9. The vector of claim 4 which is an *E. coli* expression vector of pMAL-KHCV 426, pMAL-KHCV 555(ATCC 68639), pMAL-KHCV 513, pMAL-KHCV 810, pMAL-KHCV 798, pMAL-KHCV 754, pMAL-KHCV 652, pMAL-KHCV 403, pMAL-KHCV 271, pMAL-KHCV 495 or pMAL-KHCV 494.

10. A recombinant expression vector comprising an open reading frame comprising a polynucleotide encoding a maltose binding protein fused with the polynucleotide of claim 2, wherein the open reading frame is operably linked to a regulatory sequence compatible with a desired host organism.

11. An *E. coli* cell transformed with the vector of claim 10.

12. A polypeptide encoded by the polynucleotide of claim 2.

13. A fused polypeptide wherein the polypeptide of claim 12 is fused with ubiquitin or a maltose binding protein.

14. The polypeptide of claim 13 which is produced by a Saccharomyces sp. cell transformed with an expression vector selected from the group consisting of: pYLBC-A/G-UB-CORE 14(ATCC 74081), pYLBC-A/G-UB-CORE 17, pYLBC-A/G-UB-CORE 22, pYLBC-A/G-UB-KHCV 897, pYLBC-A/G-UB-KHCV 403(ATCC 74079), pYLBC-A/G-UB-KHCV 573, pYLBC-A/G-UB-E2N and pYLBC-A/G-UB-E2C(ATCC 74117).

15. The polypeptide of claim 14 which is selected from the group consisting of: KHCV UB 897 protein, KHCV UB E1 protein, KHCV UB 403 protein, KHCV UB CORE 14 protein, KHCV UB 573 protein, KHCV UB CORE 17 protein, KHCV UB CORE 22 protein, KHCV UB-E2N protein, and KHCV UB-E2C protein.

16. The polypeptide of claim 13 which is produced by an *E. coli* cell transformed with an expression vector selected from the group consisting of: ptrpH-UB-CORE14(ATCC 68642), ptrpH-UB-CORE17(ATCC 68641), ptrpH-UB-CORE22, ptrpH-UB-KHCV 897(ATCC 68640), ptrpH-UB-E1(ATCC 68878), ptrpH-UB-E2N(ATCC 68966) and ptrpH-UB-E2C.

17. The polypeptide of claim 16 which is selected from the group consisting of: KHCV UB CORE14, KHCV UB CORE17, KHCV UB CORE22, KHCV UB 897, KHCV UB E1, KHCV UB E2N and KHCV UB E2C.

18. The polypeptide of claim 13 which is produced by an *E. coli* cell transformed with a recombinant expression vector comprising an open reading frame containing a polynucleotide encoding a maltose binding protein fused with a KHCV polynucleotide, wherein said open reading frame being operably linked to a regulatory sequence compatible with an *E. coli* cell and said KHCV polynucleotide being selected from the group consisting of: the 301st–726th, 301st–855th, 343rd–726th, 343rd–852nd, 343rd–915th, 814th–1326th, 916th–1509th, 1201st–2016th, 1510th–2010th, 1945th–2742nd, 2011th–2529th, 3208th–3960th, 3475th–3744th, 3916th–4713th, 3925th–4563rd, 5422nd–5547th, 6649th–7050th, 7612th–8184th, 7642nd–8136th and 8722nd–9216th nucleotides in the KHCV cDNA of SEQ ID NO: 96, and a combination thereof.

19. The polypeptide of claim 18 wherein the expression vector is selected from the group consisting of: pMAL-KHCV 426, pMAL-KHCV 555, pMAL-KHCV 513, pMAL-KHCV 810, pMAL-KHCV 798, pMAL-KHCV 754, pMAL-KHCV 652, pMAL-KHCV 403, pMAL-KHCV 271, PMAL-KHCV 495 and pMAL-KHCV 494.

20. The polypeptide of claim 18 which is selected from the group consisting of: KHCV 426 protein, KHCV 555 protein, KHCV 513 protein, KHCV 810 protein, KHCV 798 protein, KHCV 271 protein, KHCV 754 protein, KHCV 652 protein, KHCV 403 protein, KHCV 495 protein and KHCV 494 protein.

21. A diagnostic reagent for detecting an antibody directed against a KHCV antigen in a sample which comprises the polypeptide of claim 12 as an active ingredient.

22. A diagnostic kit comprising the diagnostic reagent of claim 21.

23. A diagnostic reagent for detecting an antibody directed against a KHCV antigen in a sample, which comprises two or more polypeptides of claim 12 as an active ingredient.

24. A monoclonal antibody having an immunoreactivity with the polypeptide of claim 12, which is useful for the purification and detection of a KHCV epitope.

25. The monoclonal antibody of claim 24 which is included in an IgG subclass.

26. The monoclonal antibody of claim 24 which is immunoreactive with a KHCV polypeptide encoded by the 3916th to 4713th nucleotides in the KHCV cDNA of claim 1.

27. The antibody of claim 26 which is immunoreactive with a polypeptide having the amino acid sequence of SEQ ID NO: 94.

28. The antibody of claim 26 which is immunoreactive with a polypeptide having the amino acid sequence of SEQ ID NO: 95.

29. A diagnostic reagent for detecting a KHCV epitope in a sample comprising one or more of the monoclonal antibodies according to any one of claims 24 to 28 as an active ingredient.

30. A cell line producing a monoclonal antibody having a immunoreactivity with a KHCV epitope, which is produced by the steps of:

(a) immunizing an animal with the polypeptide of claim 12;

(b) separating a spleen cell from the immunized animal; and (c) fusing the spleen cell with a myeloma cell.

31. The cell line of claim 30 which is Lucky 1.1(ATCC 10949) or Lucky 1.2(ATCC 10950).

32. The polypeptide of claim 12, which is selected from the group consisting of: KHCV 426 protein, KHCV 555 protein, KHCV CORE 14 protein, KHCV CORE 17 protein, KHCV CORE 22 protein, KHCV 513 protein, KHCV E1 protein, KHCV 810 protein, KHCV E2N protein, KHCV 798 protein, KHCV E2C protein, KHCV 271 protein, KHCV 754 protein, KHCV 897 protein, KHCV 652 protein, KHCV NS4E protein, KHCV 403 protein, KHCV 573 protein, KHCV 495 protein and KHCV 494 protein.

33. A kit for detecting a polynucleotide derived from KHCV in a sample comprising an oligonucleotide of 8 or more nucleotides which binds complementarily to the KHCV cDNA of SEQ ID NO: 96.

34. A KHCV cDNA coding for a KHCV wherein the amino acid sequence encoded in the 2824th to 3141st nucleotide of the KHCV cDNA of SEQ ID NO: 96 is substituted by any one of the amino acid sequences of SEQ ID NO's: 101 to 112.

35. A KHCV cDNA coding for a KHCV wherein the amino acid sequence encoded in the 2824th to 3098th nucleotides of the KHCV cDNA of SEQ ID NO: 96 is substituted by the amino acid sequence of SEQ ID NO: 97.

36. A kit for detecting a polynucleotide originating from KHCV in a sample comprising a nucleotide sequence of 8 or more nucleotides which binds complementarily to the KHCV cDNA of claim 34 or 35.

* * * * *